Figure 1B:
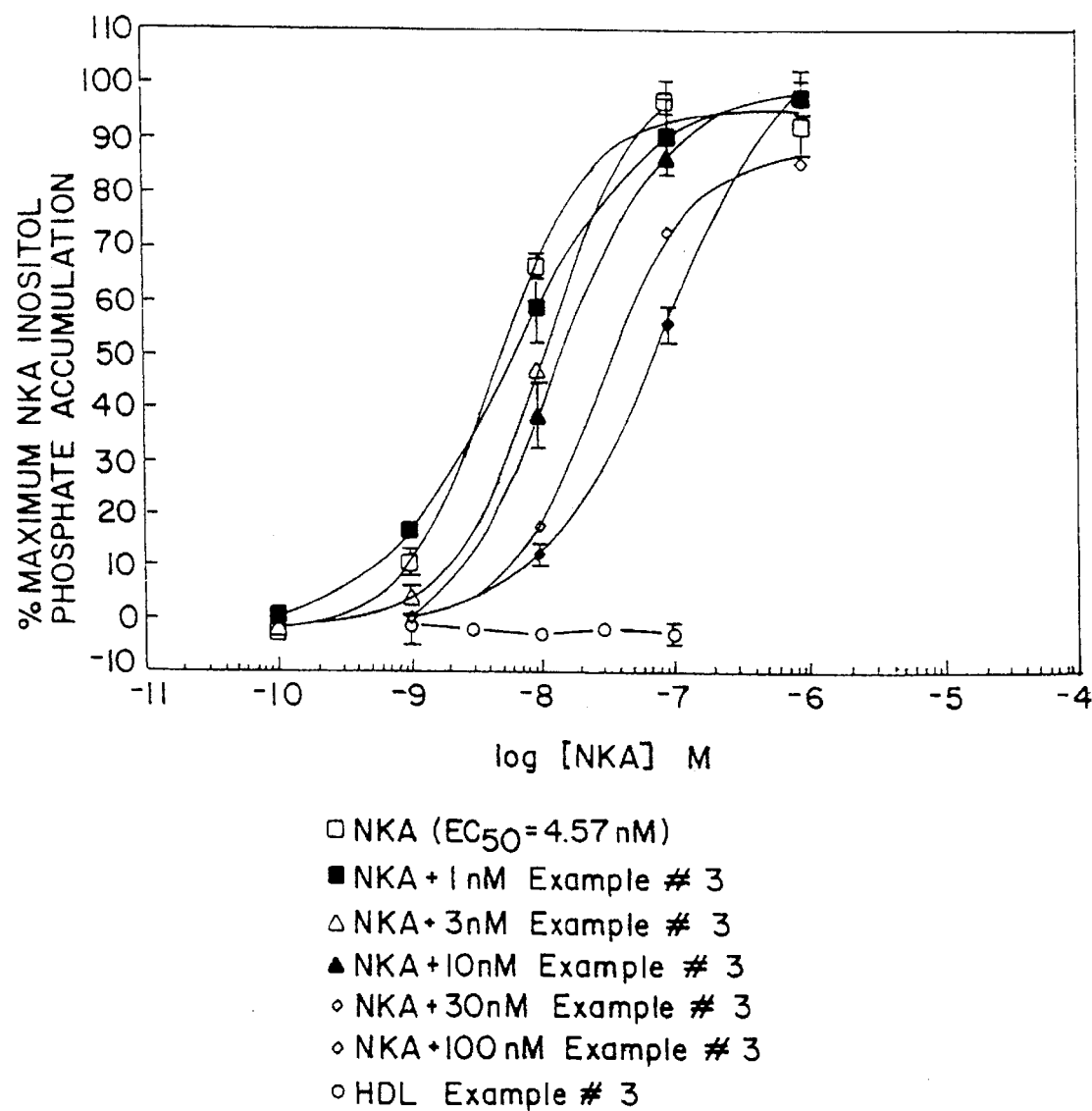

United States Patent [19]

Burkholder et al.

[11] Patent Number: 5,648,366
[45] Date of Patent: Jul. 15, 1997

[54] SUBSTITUTED PYRROLIDIN-3-YL-ALKYL-PIPERIDINES

[75] Inventors: Timothy P. Burkholder, Fairfield; Tieu-Binh Le, Cincinnati; Elizabeth M. Kudlacz, Cincinnati; George D. Maynard, Cincinnati, all of Ohio

[73] Assignee: Merrell Pharmaceuticals Inc., Cincinnati, Ohio

[21] Appl. No.: 477,167

[22] Filed: Jun. 7, 1995

Related U.S. Application Data

[60] Division of Ser. No. 332,027, Oct. 31, 1994, which is a continuation-in-part of Ser. No. 225,371, Apr. 19, 1994, abandoned, which is a continuation-in-part of Ser. No. 58,606, May 6, 1993, abandoned.

[51] Int. Cl.$^6$ .................... A61K 31/445
[52] U.S. Cl. .................. 514/326; 514/278; 546/20; 546/208
[58] Field of Search .................. 546/20, 208; 514/278, 514/326

[56] References Cited

U.S. PATENT DOCUMENTS

| | | | |
|---|---|---|---|
| 3,282,947 | 11/1966 | Grogan et al. | 546/15 |
| 5,166,136 | 11/1992 | Ward et al. | 514/19 |
| 5,212,187 | 5/1993 | Grogan et al. | 546/283 |
| 5,340,822 | 8/1994 | Edmonds-Alt et al. | 514/316 |
| 5,446,052 | 8/1995 | Emonds-Alt | 514/318 |

FOREIGN PATENT DOCUMENTS

| | | |
|---|---|---|
| 1591692 | 5/1991 | Australia. |
| 0428434 | 5/1991 | European Pat. Off.. |
| 0517589 | 6/1991 | European Pat. Off.. |
| 0474561 | 9/1991 | European Pat. Off.. |
| 0482539 | 4/1992 | European Pat. Off.. |
| 0512902 | 11/1992 | European Pat. Off.. |
| 05129001 | 11/1992 | European Pat. Off.. |
| 9300330 | 1/1993 | European Pat. Off.. |
| 0559538 | 3/1993 | European Pat. Off.. |
| 2601262 | 7/1976 | Germany. |
| 9222569 | 6/1991 | Japan. |
| 4297492 | 10/1991 | Japan. |
| 93/14113 | 1/1992 | WIPO. |

OTHER PUBLICATIONS

Barnes, et al., TIPS 11:185–189 (May 1990).
Ichinose, et al., *The Lancet* 340:1248–1251 (Nov. 21, 1992).
Hagiwara, et al., *J. Med. Chem.* 35(17):3184–3191 (1992).
Hagiwara, et al., *J. Med. Chem.* 35(11):2015–2025 (1992).
Van Parys, et al., *Bull. Soc. Chim. Beig.* 90(7):757–65 (1981).
Kametani, et al., *Chemical Abstracts* 72:55212n (1970).
Clark, et al., *J. Med. Chem.* 26)6):855–861 (1983).
Somers, et al., *J. Med. Chem.* 7:784–89 (1964).
Van Parys, et al., *Bull Soc. Chim. Beig* 90(7):749–55 (1981).
Kametani, et al., *Yakugaku Zasshi* 89(11)1482–7 (1969). (In Japanese).
Melloni, et al., *Eur. J. Med. Chem.* 26, 207–213 (1991).
Edmonds,–Alt, et al., *Life Sciences*, vol. 56(1), 27–32, (1995).
Daijiro Hagiwara et. al., "Design of a Novel Dipeptide Substance P Antagoinst FK888 and Its Pharmacological Profile", Fujisawa Pharmacological Profile, Fujisawa Pharmacetucial Co., Ltd. May 31, 1995.
T. Yamashita, et al., *Makromol. Chem.* 191, 1261–1268 (1990).
J. DiMaio, et al., *J. Chem. Soc., Perkin Trans*, 1989 pp. 1687–1689 pp. 1687–1689.
CA 107(23):217900f, Takase, et al., *Tetrahedron*, 42(21), 5887–5894, 1986.
CA 103(3):22829z, Takase, et al, *Tetrahedron*, 26(7), 847–850 (1987).
Schilling, et al., C.2., "Approaches towards the Design and Synthesis of Nonpeptidic Substance–P Antagonists", Ciba–Geigy Ltd., (15)207–220. (Dec. 15, 1993).
Logan, et al., "Recent Advances in Neurokinin Receptor Antagonists", *Annual Reports in Medicinal Chemistry* (26)43–51. (1983).
Hagiwara, et al., *J. Pharmacobio–Dyn.*, s–104 (1991).
Roubini, et al., "1,4–Piperazine–derived... of Substance p", Hebrew University of Jerusalem, pp. 161–162. (1991).
Chorev, et al., "Toward Nonpeptidal Substance P . . . Biological Activity", Hebrew Un of Jerusalem, 725–732, vol. 31 (1991).
Hagiwara, et al., *J. Med. Chem*, 36,2266–2278, 1993.
Clark, et al., *"Principles of Phychopharmacology"*, Academic Press, pp. 166–167 (1970).
CA 122:105675, Miller et al. (1994).
CA 124:117093, Bichon et al. (1995).
Rubini et al. "Synthesis of isosteric methylene–oxy pseudo–dipeptide analogues as novel amide bond surrogate units" *Tetrahedron* v42 pp. 6039–6045 1986.

*Primary Examiner*—Ceila Chang
*Attorney, Agent, or Firm*—David M. Stemerick; Kenneth J. Collier

[57] ABSTRACT

The present invention relates to substituted pyrrolidinyl-3-yl-alkyl-piperidines, their stereoisomers, and pharmaceutically acceptable salts thereof and processes for preparation of the same. The compounds of the present invention are useful in their pharmacological activities such as tachykinin antagonism, especially substance P and neurokinin A antagonism, and the like. Compounds having the property of tachykinin antagonism are indicated for conditions associated with neurogenic inflammation and other diseases described herein.

15 Claims, 3 Drawing Sheets

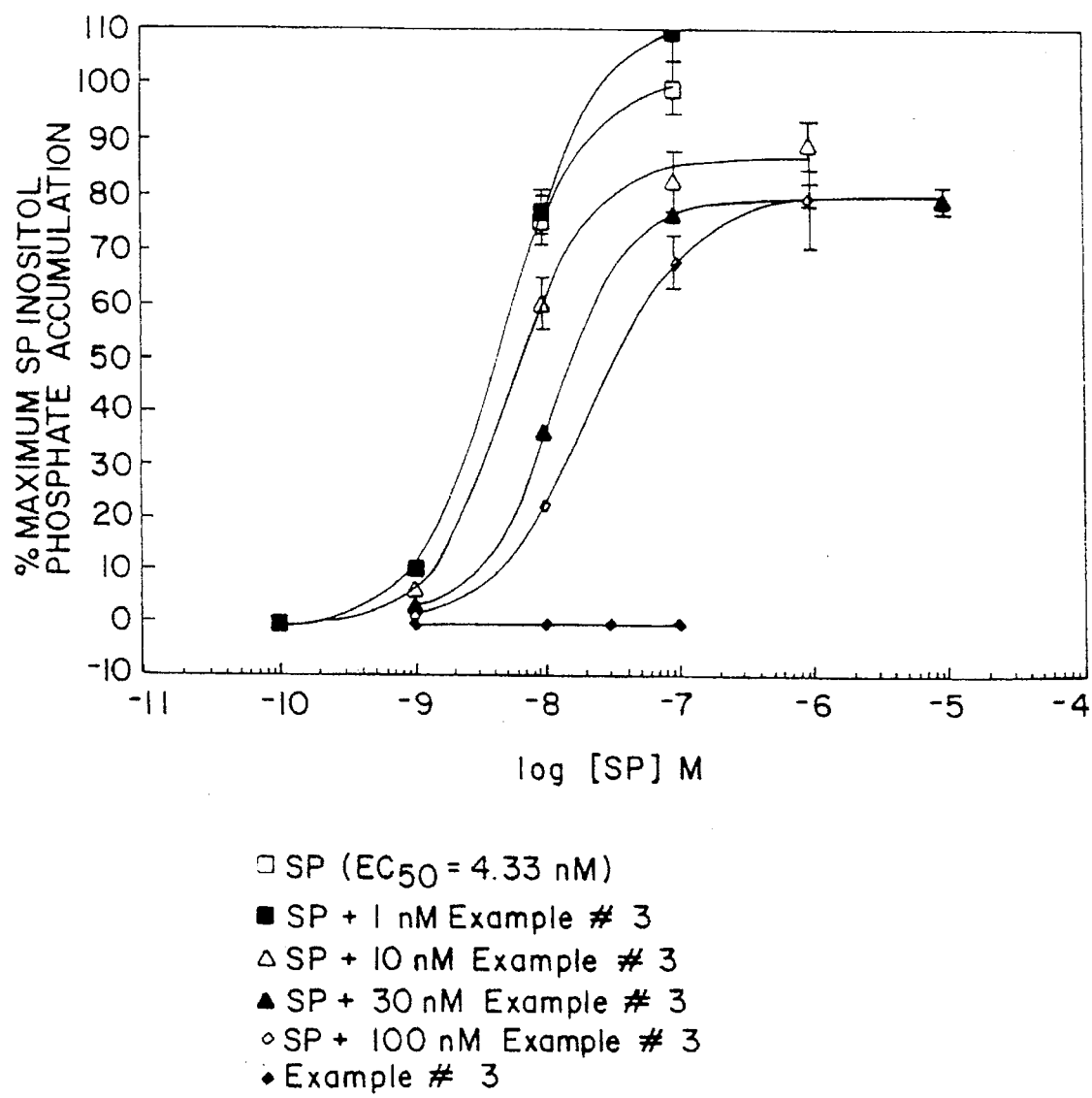

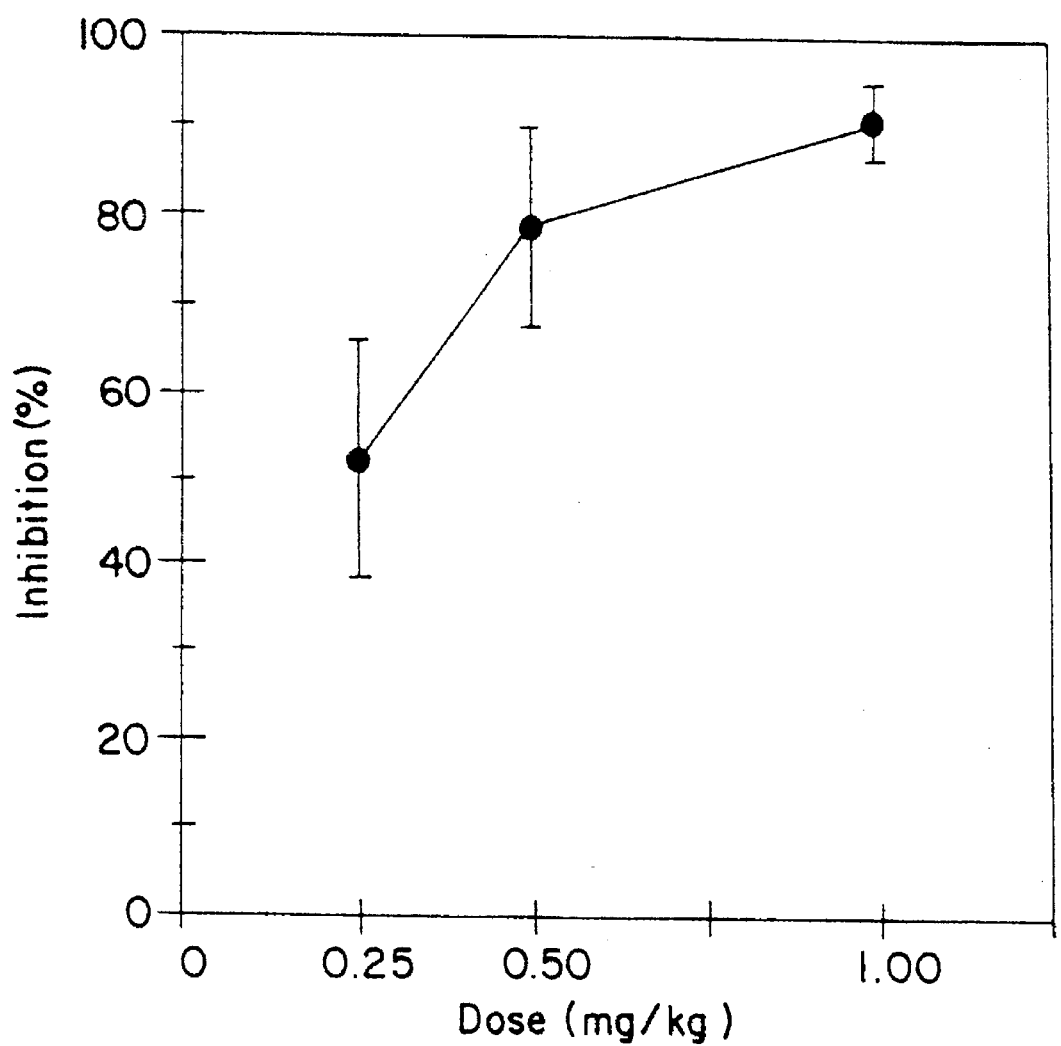

SUBSTITUTED PYRROLIDIN-3-YL-ALKYL-PIPERIDINES

This application is a Divisional of application Ser. No. 08/332,027, filed Oct. 31, 1994; which is a Continuation-in-Part of application Ser. No. 08/225,371, filed Apr. 19, 1994, now abandoned; which is a Continuation-in-Part of application Ser. No. 08/058,606, filed May 6, 1993, now abandoned.

The present invention relates to substituted pyrrolidin-3-yl-alkyl-piperidines, isomers, and pharmaceutically acceptable salts thereof (herein also referred to as compounds or compounds of formula (1)) and processes for preparation of the same. It is an object of the present invention, therefore, to provide new and useful compounds and pharmaceutically acceptable salts thereof, and processes for their preparation.

The compounds of the present invention are useful in their pharmacological activities such as tachykinin antagonism, especially substance P and neurokinin A antagonism, and the like. Antagonism of tachykinin responses can be elicited through blocking of tachykinin receptors. Three general classes of tachykinin receptors have been defined by their binding preference to substance P (neurokinin 1 receptors ($NK_1$)), neurokinin A (neurokinin 2 receptors ($NK_2$)), and neurokinin B (neurokinin 3 receptors ($NK_3$)). One object of the present invention is to provide new and useful antagonists of tachykinins, especially substance P and neurokinin A (NKA). Similarly, antagonism of neurokinin B (NKB) activities may be important. A particular object of the present invention are those compounds that exhibit both $NK_1$ and $NK_2$ receptor antagonism.

Compounds having the property of tachykinin antagonism are indicated for conditions associated with neurogenic inflammation. Neuropeptides, including the tachykinins substance P and neurokinin A, are released from capsaicin-sensitive sensory C-fiber neurons. These peptides produce local effects which may be tissue specific including vasodilation, microvascular leakage, mucus secretion, inflammatory cell recruitment and priming, smooth muscle contraction and neuronal modulation. Generally, antagonism of the effects of substance P on its preferred receptor, i.e. $NK_1$, will not prevent the effects of NKA on its preferred receptor, i.e. $NK_2$. Therefore, the potential benefits of having an antagonist at both $NK_1$ and $NK_2$ receptors would be to reduce or prevent clinical manifestations of a disease which are mediated through both receptors.

A further object of the present invention is to provide compounds, or pharmaceutically acceptable salts thereof, for the treatment and prevention of various diseases in a patient in need thereof. Because the compounds of the present invention are tachykinin antagonists, they are potentially useful in the treatment of conditions associated with neurogenic inflammation, including asthma, allergies, bronchitis, rhinitis, Crohn's disease, ulcerative colitis, rheumatoid arthritis, osteoarthritis, migraine, cystitis and hypersensitivity reactions. Tachykinin antagonism may also be appropriate therapy for the treatment of pain, peripheral neuropathy, cough, emesis, post-herpetic neuralgia, adverse immunological reactions, blood flow disorders due to vasodilation, ophthalmic diseases, such as conjuctivitis and cutaneous diseases such as contact dermatitis, atopic dermatitis, urticaria and the like. Various central nervous system disorders including anxiety, depression, psychosis, schizophrenia and dementia may also be amenable to treatment with tachykinin antagonists.

Asthma is a particular condition which may be treated with tachykinin antagonists. In experimental studies, sensory neuropeptides, especially tachykinins such as substance P and neurokinin A, can bring about many of the pathophysiological features of asthma. Neurokinin A produces contraction of airway smooth muscle and increases airway responsiveness to other bronchoconstrictive stimuli. Although also contributing to bronchoconstriction in some species, substance P is more potent in its ability to cause mucus secretion, microvascular leakage and vasodilation. Both tachykinins, substance P and neurokinin A, have been implicated in modulation of immune cells including mast cells, T lymphocytes, macrophages, eosinophils and neutrophils. The effectiveness of the combined $NK_1+NK_2$ receptor antagonist, FK 224, has been demonstrated in asthmatic patients undergoing bradykinin-induced bronchoconstriction by Ichinose et al. (Lancet (1992) Vol. 340: 1248–1251).

The compounds of the present invention are novel. The compounds of the present invention act as tachykinin antagonists and are thus potentially useful in the treatment of a number of diseases and conditions as described herein. A further object of the present invention is to provide a use for compounds, stereoisomers, or pharmaceutically acceptable salts thereof, for the treatment or prevention of conditions and diseases in a patient in need thereof.

List of Figures

Reaction Scheme A

Reaction Scheme B

Reaction Scheme C

Reaction Scheme D

Reaction Scheme E

Reaction Scheme E.1

Reaction Scheme F

Reaction Scheme G

Reaction Scheme H

Reaction Scheme I

Reaction Scheme J

Reaction Scheme K

Reaction Scheme K.1

Reaction Scheme L

Reaction Scheme M

FIG. 1a—PI TURNOVER IN UC11 CELLS

FIG. 1b—PI TURNOVER IN SKLKB82#3 CELLS

FIG. 2—INHIBITION OF SP-INDUCED PPE BY EXAMPLE 3

SUMMARY OF THE INVENTION

The present invention relates to compounds of formula (1), their stereoisomers, their N-oxides, and their pharmaceutically acceptable salts, and processes for preparing the same:

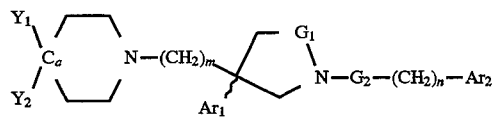

wherein $G_1$ is —$CH_2$— or —C(O)—;

$G_2$ is —$CH_2$— or —C(O)—;

m is 2 or 3;

n is 0 or 1;

Ar₁ is a radical chosen from the group:

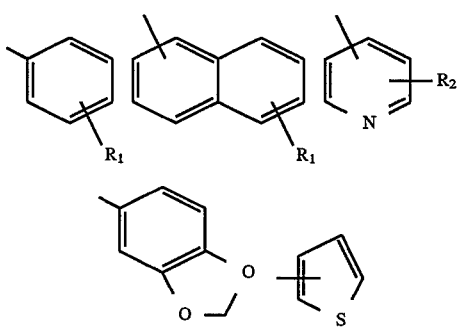

wherein $R_1$ is from 1 to 3 substituents each independently chosen from the group consisting of hydrogen, halogen, hydroxy, $CF_3$, $C_1$-$C_6$ alkyl, and $C_1$-$C_6$ alkoxy;

$R_2$ is from 1 to 2 substituents each independently chosen from the group consisting of hydrogen, halogen, $C_1$-$C_6$ alkyl, and $C_1$-$C_6$ alkoxy;

Ar₂ is a radical chosen from the group

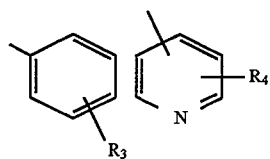

wherein $R_3$ is from 1 to 3 substituents each independently chosen from the group consisting of hydrogen, halogen, $C_1$-$C_6$ alkoxy, hydroxy, —O—C(O)O—CH₂—CH₃, —OC(O)CH₃, —CF₂H, —(CH₂)$_q$NR₆R₇, and —(CH₂)$_q$NR₈R₉ wherein q is 2 or 3, $R_6$ is $C_1$-$C_6$ alkyl, $R_7$ is $C_1$-$C_6$ alkyl, $R_8$ and $R_9$ taken together with the bonded nitrogen form a morpholine ring, piperidine ring, 4-methylpiperazine ring, or pyrrolidine ring;

$R_4$ is from 1 to 2 substituents each independently chosen from the group consisting of hydrogen, halogen, $C_1$-$C_6$ alkyl, and $C_1$-$C_6$ alkoxy;

$Y_1$ when selected individually is —C(O)NHR₅, —C(O)NR₆R₇, or —C(O)NR₈R₉ wherein $R_5$ is chosen from the group consisting of hydrogen, $C_1$-$C_6$ alkyl, 3-hydroxy-2-butyryl-$C_1$-$C_6$ alkyl ester, 2-glutaryl-$C_1$-$C_6$ alkyl ester, —(CH₂)$_q$NR₆R₇, and —(CH₂)$_q$NR₈R₉;

q is 2 or 3;

$R_6$ is $C_1$-$C_6$ alkyl;

$R_7$ is $C_1$-$C_6$ alkyl;

$R_8$ and $R_9$ taken together with the bonded nitrogen form a morpholine ring, piperidine ring, 4-methylpiperazine ring, or pyrrolidine ring;

$Y_2$ when selected individually is a radical chosen from the group

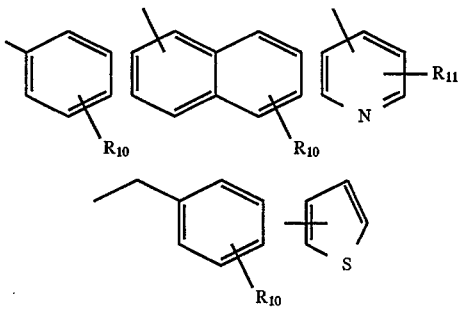

wherein $R_{10}$ is from 1 to 3 substituents each independently chosen from the group consisting of hydrogen, halogen, $CF_3$, $C_1$-$C_6$ alkyl, and $C_1$-$C_6$ alkoxy;

$R_{11}$ is from 1 to 2 substituents each independently chosen from the group consisting of hydrogen, halogen, $C_1$-$C_6$ alkyl, and $C_1$-$C_6$ alkoxy; or $Y_1$ and $Y_2$ together with their attached carbon form a spirocyclic ring chosen from the group

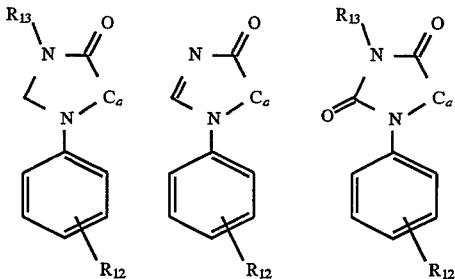

wherein the attached carbon is $C_a$;

$R_{12}$ is from 1 to 3 substituents each independently chosen from the group consisting of hydrogen, halogen, $CF_3$, $C_1$-$C_6$ alkyl, and $C_1$-$C_6$ alkoxy;

$R_{13}$ is hydrogen, $C_1$-$C_6$ alkyl, or benzyl;

or stereoisomers, or an N-oxide, or a pharmaceutically acceptable salt thereof.

The present invention also provides a method of using the compounds of formula (1) therapeutically in a patient in need thereof, comprising administering a therapeutically effective amount of a compound of formula (1).

As is appreciated by one of ordinary skill in the art the compounds of the formula (1) may exist as stereoisomers depending on the nature of the substituents present. Any reference in this application to one of the compounds of the formula (1) is meant to encompass either specific stereoisomers or a mixture of stereoisomers. Where indicated, the compounds follow the designation of (+)- and (−)- for the stereochemistry of compounds represented by formula (1). It is also understood that the use of the term compounds of the formula (1) and the preferred embodiment thereof is also inclusive of all its stereoisomers, radicals, salts, and pharmaceutical formulations and compositions thereof. It is specifically recognized that in the substituted 2-(pyrrolidinyl-3-yl)alkyl-piperidines the three position of the pyrrolidine is asymmetric, and may be in the (+)- or (−)- configuration, or may be a mixture thereof. The specific stereoisomers can be prepared by stereospecific synthesis or can be separated and recovered by techniques known in the art, such as chromatography on chiral stationary phases, enzymatic resolution, or fractional recrystallization of addition salts formed by reagents used for that purpose, as described in "Enantiomers, Racemates, and Resolutions", J. Jacques, A. Collet, and S. H. Wilen, Wiley (1981).

As used in this application:

a) the term "halogen" refers to a fluorine atom, chlorine atom, bromine atom, or iodine atom;

b) the term "$C_1$–$C_6$ alkyl" refer to a branched or straight chained alkyl radical containing from 1 to 4 carbon atoms, such as methyl, ethyl, n-propyl, isopropyl, n-butyl, isobutyl, t-butyl, pentyl, cyclopentyl, hexyl, cyclohexyl, etc;

c) the term "$C_1$–$C_6$ alkoxy" refer to a straight or branched alkoxy group containing from 1 to 4 carbon atoms, such as methoxy, ethoxy, n-propoxy, isopropoxy, n-butoxy, isobutoxy, t-butoxy, etc;

d) the designations —C(O)— and —CO— refer to a carbonyl group of the formula:

e) the designation "⌇" refers to a bond for which the stereochemistry is not designated;

f) the designations —$CO_2R$ and —C(O)OR refer to a group of the formula:

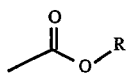

g) the designation —C(O)NRR refer to a group of the formula:

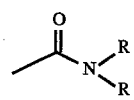

h) as used in the examples and preparations, the following terms have the meanings indicated: "g" refers to grams, "mg" refers to milligrams, "mmol" refers to millimoles, "mL" refers to milliliters, "cm" refers to centimeters, "L" refers to liters, "° C." refers to degrees Celsius, "$R_f$" refers to retention factor, "mp" refers to melting point, "dec" refers to decomposition, "$[\alpha]_D^{20}$" refers to specific rotation of the D line of sodium at 20° C. obtained in a 1 decimeter cell, "c" refers to concentration in g/mL, "TFA" refers to trifluoroacetic acid, "THF" refers to tetrahydrofuran, "DMF" refers to dimethylformamide, "M" refers to molar, "µL" refers to microliters, "HPLC" refers to high performance liquid chromatography, "eq." refers to equivalents; h refers to hours; "N" refers to normal, "X" refers to times, "NaHMDS" refers to sodium hexamethyldisilazide or sodium bis-(trimethylsilyl)amide, "EBA" refers to ethyl bromoacetate, "LiAlH$_4$" refers to lithium aluminum hydride, "NMM" refers to 4-methylmorpholine, "aryl$_1$" refers to Ar$_1$, "aryl$_2$" refers to Ar$_2$, "Boc" or "t-BOC" refers to t-butyloxycarbonyl; "EDC" refers to 1-(3-dimethyl aminopropyl)-3-ethylcarbodiimide hydrochloride; "HOBT" or "HOBt" refers to 1-hydroxybenzotriazole hydrate, "R$_t$" refers to retention time, "K$_2$CO$_3$" refers to potassium carbonate, "Na$_2$SO$_4$" refers to sodium sulfate, "MgSO$_4$" refers to magnesium sulfate, "H$_2$O" refers to water, "SOCl$_2$" refers to thionyl chloride, "NaOH" refers to sodium hydroxide, "CH$_3$CN" refers to acetonitrile, "KOH" refers to potassium hydroxide;

i) the designation

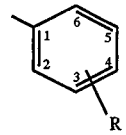

refers to a phenyl or substituted phenyl and it is understood that the radical is attached at the 1-position and the substituent or substituents represented by R can be attached in any of the 2, 3, 4, 5, or 6 positions;

j) the designation

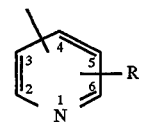

refers to a pyridine, substituted pyridine, pyridinyl, or substituted pyridinyl and it is understood that the radical can be attached at the either the 2-position, the 3-position, or the 4-position, it is further understood that when the radical is attached at the 2-position the substituent or substituents represented by R can be attached in any of the 3, 4, 5, or 6, positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

k) the designation

refers to a thienyl, thiophene, or thiophenyl and it is understood that the radical is attached at the 2- or the 3-positions;

l) the designation

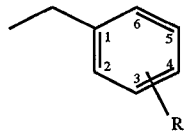

refers to a benzyl or substituted benzyl and it is understood that the substituent or substituents represented by R can be attached in any of the 2, 3, 4, 5, or 6 positions;

m) the designation

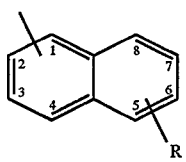

refers to a naphthyl, substituted naphthyl, naphthalenyl, substituted naphthalenyl and it is understood that the radical can be attached at the either the 1-position or the 2-position, it is further understood that when the radical is attached at the 1-position the substituent or substituents represented by R can be attached in any of the 2, 3, 4, 5, 6, 7, or 8 positions and that when the radical is attached at the 2-position the substituent or substituents represented by R can be attached in any of the 1, 3, 4, 5, 6, 7, or 8 positions;

n) the term "pharmaceutically acceptable salts thereof refers to either an acid addition salt or a basic addition salt.

o) the term "enantiomeric excess" or "ee" refers to the percent by which one enantiomer, E1, is in excess in a mixture of the two enantiomers, E1 plus E2, such that;

$$\frac{(E1-E2)}{(E1+E2)} \times 100\% = ee$$

The term (+)- refers to the plus enantiomer, (−)- refers to the minus enantiomer.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

p) the term "N-oxide" refers to the situation where the piperidine nitrogen is additionally bonded to an oxygen atom:

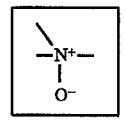

Preferred embodiments of formula (1) are given below:

1) When $Y_1$ and $Y_2$ are chosen independently, a preferred embodiment is where $Y_1$ is chosen to be —C(O)NHR$_5$;
2) When $Y_1$ and $Y_2$ are chosen independently a preferred embodiment is where $Y_2$ is chosen to be phenyl or substituted phenyl;
3) A preferred embodiment is when m is 2;
4) A preferred embodiment is when n is 0;
5) A preferred embodiment is when $G_1$ is —CH$_2$— and $G_2$ is —C(O)—;
6) A preferred embodiment is when $G_1$ is —C(O)— and $G_2$ is —CH$_2$—.

It is understood that further preferred embodiments of formula (1) can be selected by requiring one or more of the preferred embodiments above.

Nomenclature of the titled compounds of the invention were generated in part with the AUTONOM program, Version 1.0, of the Beilstein Institute, distributed by Springer-Verlag, Heidelberg (Copyright 1990, 1991) which are illustrated in Table 1 with their AUTONOM generated name and corresponding example number for several of the examples.

TABLE 1

| Example # | General Nomenclature |
|---|---|
| 9 | 8-[2-[3-(3,4-dichloro-phenyl)-1-(2,6-dimethoxy-benzoyl)-pyrrolidin-3-yl]-ethyl]-1-phenyl-1,3,8-triaza-spiro[4.5]decane-4-one |
| 3 | 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide |
| 5 | 1-[2-[3-(3,4-dichloro-phenyl)-1-(2,6-dimethoxy-benzoyl)-pyrrolidin-3-yl]-ethyl]-4-phenyl-piperidine-4-carboxylic acid amide |
| 4 | 1-(2-[3-(3,4-dichloro-phenyl)-1-[2-(2-methoxy-phenyl)-acetyl]-pyrrolidin-3-yl]-ethyl)-4-phenyl-piperidine-4-carboxylic acid amide |
| 13 | 1-[2-[3-(3,4-dichloro-phenyl)-1-(2-methoxy-benzoyl)-pyrrolidin-3-yl]-ethyl]-4-phenyl-piperidine-4-carboxylic acid amide |
| 2 | 1-[2-[3-(3,4-dichloro-phenyl)-1-(2,4-dimethoxy-benzoyl)-pyrrolidin-3-yl]-ethyl]-4-phenyl-piperidine-4-carboxylic acid amide |
| 6 | 2-[(2-[1-benzoyl-3-(3,4-dichloro-phenyl)-pyrrolidin-3-yl]-ethyl]-4-phenyl-piperidine-4-carbonyl)-amino]-pentanedioic acid dimethyl ester |
| 11 | 1-[2-[1-benzyl-3-(3,4-dichloro-phenyl)-5-oxo-pyrrolidin-3-yl]-ethyl]-4-phenyl-piperidine-4-carboxylic acid amide |
| 1 | 1-[2-[3-(3,4-dichloro-phenyl)-1-benzoyl-pyrrolidin-3-yl]-ethyl]-4-phenyl-piperidine-4-carboxylic acid amide |
| 10 | 8-[2-[3-(3,4-dichloro-phenyl)-1-benzoyl-pyrrolidin-3-yl]-ethyl]-1-phenyl-1,3,8-triaza-spiro[4.5]-decane-4-one |
| 7 | 2-[(1-(2-[1-benzoyl-3-(3,4-dichloro-phenyl)-pyrrolidin-3-yl]-ethyl)-4-phenyl-piperidine-4-carboxyl)-amino]-3-hydroxy butyric acid methyl ester |
| 12 | 1-[1-benzyl-3-naphthalen-2-yl-5-oxo-pyrrolidin-3-yl)-ethyl]-4-phenyl-piperidine-4-carboxylic acid amide |
| 8 | 1-[2-(1-benzoyl-3-napthalen-2-yl-pyrrolidin-3-yl)-ethyl]-4-phenyl-piperidine-4-carboxylic acid amide |
| 20 | (+)-1-[2-[3-(3,4-dichloro-phenyl)-1-(3,4,5-trimethoxy-benzoyl)-pyrrolidin-3-yl]-ethyl]-4-phenyl- |

TABLE 1-continued

| Example # | General Nomenclature |
|---|---|
| | piperidine-4-carboxylic acid amide |
| 21 | (−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide |
| 23 | 1-[2-[3-(3,4-dimethoxy-phenyl)-1-(3,4,5-trimethoxy-benzoyl)-pyrrolidin-3-yl)-ethyl]-4-phenyl-piperidine-4-carboxylic acid amide |
| 24 | 1-[2-[3-(3,4-dichloro-phenyl)-1-(3,5-bis-(trifluoromethyl)-pyrrolidin-3-yl]-ethyl]-4-phenyl-piperidine-4-carboxylic acid amide |
| 25 | 1-[2-[3-(3,4-dichloro-phenyl)-1-(3,5-dimethoxy-benzoyl)-pyrrolidin-3-yl]-ethyl]-4-phenyl-piperidine-4-carboxylic acid amide |
| 26 | 1-[2-[3-(3,4-dichloro-phenyl)-1-(3,4,5-trimethoxy-benzoyl)-pyrrolidin-3-yl]-ethyl]-4-phenyl-piperdine-4-carboxylic acid (2-dimethylamino-ethyl)-amide |
| 27 | 1-[2-[3-(3,4-dichloro-phenyl)-1-(3-methoxy-benzoyl)-pyrrolidin-3-yl]-ethyl]-4-phenyl-piperidine-4-carboxylic acid amide |
| 22 | 1-[2-[3-phenyl-1-(3,4,5-trimethoxy-benzoyl)-pyrrolidin-3-yl]-ethyl]-4-phenyl-piperidine-4-carboxylic acid amide |

Illustrative Examples of compounds encompassed by the present invention include:

8-[2-[3-(3,4-dichloro-phenyl)-1-(2,6-dimethoxy-benzoyl)-pyrrolidin-3-yl]-ethyl]-1-phenyl-1,3,8-triaza-spiro[4.5]decane-4-one;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide;

1-[2-[3-(3,4-dichloro-phenyl)-1-(2,6-dimethoxy-benzoyl)-pyrrolidin-3-yl]-ethyl]-4-phenyl-piperidine-4-carboxylic acid amide;

1-(2-[3-(3,4-dichloro-phenyl)-1-[2-(2-methoxy-phenyl)acetyl]-pyrrolidin-3-yl]-ethyl)-4-phenyl-piperidine-4-carboxylic acid amide;

1-[2-[3-(3,4-dichloro-phenyl)-1-(2-methoxy-benzoyl)pyrrolidin-3-yl]-ethyl]-4-phenyl-piperidine-4-carboxylic acid amide;

1-[2-[3-(3,4-dichloro-phenyl)-1-(2,4-dimethoxy-benzoyl)pyrrolidin-3-yl]-ethyl]-4-phenyl-piperidine-4-carboxylic acid amide;

2-[(2-[1-benzoyl-3-(3,4-dichloro-phenyl)-pyrrolidin-3-yl]-ethyl]-4-phenyl-piperidine-4-carbonyl)-amino]-pentanedioic acid dimethyl ester;

1-[2-[1-benzyl-3-(3,4-dichloro-phenyl)-5-oxo-pyrrolidin-3-yl]-ethyl]-4-phenyl-piperidine-4-carboxylic acid amide;

1-[2-[3-(3,4-dichloro-phenyl)-1-benzoyl-pyrrolidin-3-yl]-ethyl]-4-phenyl-piperidine-4-carboxylic acid amide;

8-[2-[3-(3,4-dichloro-phenyl)-1-benzoyl-pyrrolidin-3-yl]-ethyl]-1-phenyl-1,3,8-triaza-spiro[4.5]-decane-4-one;

2-[(1-(2-[1-benzoyl-3-(3,4-dichloro-phenyl)-pyrrolidin-3-yl]-ethyl)-4-phenyl-piperidine-4-carboxyl)-amino]-3-hydroxy butyric acid methyl ester;

1-[1-benzyl-3-naphthalen-2-yl-5-oxo-pyrrolidin-3-yl]-ethyl]-4-phenyl-piperidine-4-carboxylic acid amide;

1-[2-(1-benzoyl-3-napthalen-2-yl-pyrrolidin-3-yl)-ethyl]-4-phenyl-piperidine-4-carboxylic acid amide;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide;

1-[2-[3-phenyl-1-(3,4,5-trimethoxy-benzoyl)-pyrrolidin-3-yl]-ethyl]-4-phenyl-piperidine-4-carboxylic acid amide;

1-[2-[3-(3,4-dimethoxy-phenyl)-1-(3,4,5-trimethoxy-benzoyl)-pyrrolidin-3-yl]-ethyl]-4-phenyl-piperidine-4-carboxylic acid amide;

1-[2-[3-(3,4-dichloro-phenyl)-1-(3,5-bis-(trifluoromethyl)-benzoyl)-pyrrolidin-3-yl]-ethyl]-4-phenyl-piperidine-4-carboxylic acid amide;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-dimethylamino-ethyl)-amide;

1-[2-[3-(3,4-dichloro-phenyl)-1-(3-methoxy-benzoyl)-pyrrolidin-3-yl]-ethyl]-4-phenyl-piperidine-4-carboxylic acid amide;

1-[2-[3-(benzo[1,3]dioxol-5-yl)-1-(3,4,5-trimethoxy-benzoyl)-pyrrolidin-3-yl]-ethyl]-4-phenyl-piperidine-4-carboxylic acid amide;

1-[2-[3-(3,4-dimethoxy-phenyl)-1-(3,4,5-triethoxy-benzoyl)-pyrrolidin-3-yl]-ethyl]-4-phenyl-piperidine-4-carboxylic acid amide;

1-[2-[3-(3,4-dichloro-phenyl)-1-(3,4,5-trimethoxy-benzoyl)-pyrrolidin-3-yl]-ethyl]-4-(naphth-2-yl)-piperidine-4-carboxylic acid amide;

1-[2-[3-(3,4-dichloro-phenyl)-1-(3,4,5-trimethoxy-benzoyl)-pyrrolidin-3-yl]-ethyl]-4-(pyridin-4-yl)-piperidine-4-carboxylic acid amide;

1-[2-[3-(3,4-dichloro-phenyl)-1-(3,4,5-trimethoxy-benzoyl)-pyrrolidin-3-yl]-ethyl]-4-(pyridin-3-yl)-piperidine-4-carboxylic acid amide;

1-[2-[3-(3,4-dichloro-phenyl)-1-(3,4,5-trimethoxy-benzoyl)-pyrrolidin-3-yl]-ethyl]-4-(pyridin-2-yl)-piperidine-4-carboxylic acid amide;

1-[2-[3-(3,4-dichloro-phenyl)-1-(3,4,5-trimethoxy-benzoyl)-pyrrolidin-3-yl]-ethyl]-4-benzyl-piperidine-4-carboxylic acid amide;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid pyrrolidine-amide;

1-[2-[3-(3,4-dichloro-phenyl)-1-(3,5-dimethoxy-benzoyl)-pyrrolidin-3-yl]-ethyl]-4-phenyl-piperidine-4-carboxylic acid amide;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid piperidine-amide;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid methyl-amide;

1-[2-[3-(3,4-dichloro-phenyl)-1-(3,4,5-trimethoxy-benzoyl)-pyrrolidin-3-yl]-ethyl]-4-phenyl-piperidine-4-carboxylic acid dimethyl-amide;

1-[2-[3-(3,4-dichloro-phenyl)-1-(4-chloro-benzoyl)-pyrrolidin-3-yl]-ethyl]-4-phenyl-piperidine-4-carboxylic acid amide;

1-[2-[3-(3,4-dichloro-phenyl)-1-(4-tert-butyl-benzoyl)-pyrrolidin-3-yl]-ethyl]-4-phenyl-piperidine-4-carboxylic acid amide;

1-[2-[3-(3,4-dichloro-phenyl)-1-(4-tert-butyl-phenacyl)-pyrrolidin-3-yl]-ethyl]-4-phenyl-piperidine-4-carboxylic acid amide;

1-[2-[3-(3,4-dichloro-phenyl)-1-(3-isopropoxy-phenacyl)
-pyrrolidin-3-yl]-ethyl]-4-phenyl-piperidine-4-
carboxylic acid amide;

1-[2-[3-(3,4-dichloro-phenyl)-1-(3,4,5-trimethoxy-
phenacyl)-pyrrolidin-3-yl]-ethyl]-4-phenyl-piperidine-
4-carboxylic acid amide;

1-[2-[3-(3,4-dichloro-phenyl)-1-(pyridine-2-carbonyl)-
pyrrolidin-3-yl]-ethyl]-4-phenyl-piperidine-4-
carboxylic acid amide;

8-[2-[3-(3,4-dichloro-phenyl)-1-(3,4,5-trimethoxy-
benzoyl)-pyrrolidin-3-yl]-ethyl]-1-phenyl-1,3,8-triaza-
spiro[4.5]decan-4-one;

8-[2-[3-(3,4-dichloro-phenyl)-1-(3,4,5-trimethoxy-
benzoyl)-pyrrolidin-3-yl]-ethyl]-1-(4-fluoro-phenyl)-
1,3,8-triaza-spiro[4.5]dec-2-en-4-one;

8-[2-[3-(3,4-dichloro-phenyl)-1-(3,4,5-trimethoxy-
benzoyl)-pyrrolidin-3-yl]-ethyl]-1-(4-fluoro-phenyl)-
1,3,8-triaza-spiro[4.5]decan-4-one 3-benzyl-8-[2-[3-(3,4-dichloro-phenyl)-1-(3,4,5-
trimethoxy-benzoyl)-pyrrolidin-3-yl]-ethyl]-1-(4-
fluoro-phenyl)-1,3,8-triaza-spiro[4.5]decan-4-one;

3-benzyl-8-[2-[3-(3,4-dichloro-phenyl)-1-(3,4,5-
trimethoxy-benzoyl)-pyrrolidin-3-yl]-ethyl]-1-(4-
fluoro-phenyl)-1,3,8-triaza-spiro[4.5]decane-2,4-
dione;

8-[2-[3-(3,4-dichloro-phenyl)-1-(3,4,5-trimethoxy-
benzoyl)-pyrrolidin-3-yl]-ethyl]-1-(4-fluoro-phenyl)-
1,3,8-triaza-spiro[4.5]decane-2,4-dione;

1-[2-[3-(3-trifluoromethyl-phenyl)-1-(3,4,5-trimethoxy-
benzoyl)-pyrrolidin-3-yl]-ethyl]-4-phenyl-piperidine-
4-carboxylic acid amide;

1-[2-[3-(thiophen-2-yl)-1-(3,4,5-trimethoxy-benzoyl)-
pyrrolidin-3-yl]-ethyl]-4-phenyl-piperidine-4-
carboxylic acid amide;

1-[2-[3-(pyridin-3-yl)-1-(3,4,5-trimethoxy-benzoyl)-
pyrrolidin-3-yl]-ethyl]-4-phenyl-piperidine-4-
carboxylic acid amide;

1-[2-[3-(2-fluoro-phenyl)-1-(3,4,5-trimethoxy-benzoyl)-
pyrrolidin-3-yl]-ethyl]-4-phenyl-piperidine-4-
carboxylic acid amide;

1-[2-[3-(4-hydroxy-phenyl)-1-(3,4,5-trimethoxy-
benzoyl)-pyrrolidin-3-yl]-ethyl]-4-phenyl-piperidine-
4-carboxylic acid amide;

1-[2-[3-(4-trifluoromethyl-phenyl)-1-(3-isopropoxy-
benzoyl)-pyrrolidin-3-yl]-ethyl]-4-phenyl-piperidine-
4-carboxylic acid amide;

1-[2-[3-(3,4-dichloro-phenyl)-1-(3,4,5-trimethoxy-
benzoyl)-pyrrolidin-3-yl]-ethyl]-4-(thiophen-2-yl)-
piperidine-4-carboxylic acid amide;

1-[2-[3-(3,4-dichloro-phenyl)-5-oxo-1-(3,4,5-
trimethoxy-benzoyl)-pyrrolidin-3-yl]-ethyl]-4-phenyl-
piperidine-4-carboxylic acid amide;

1-[2-[3-(3,4-dichloro-phenyl)-1-(3,4,5-trimethoxy-
benzyl)-pyrrolidin-3-yl]-ethyl]-4-phenyl-piperidine-4-
carboxylic acid amide;

1-[3-[3-(3,4-dichloro-phenyl)-1-(3,4,5-trimethoxy-
benzoyl)-pyrrolidin-3-yl]-propyl]-4-phenyl-piperidine-
4-carboxylic acid amide;

1-[3-[3-(3,4-dichloro-phenyl)-1-(3,4,5-trimethoxy-
benzyl)-pyrrolidin-3-yl]-propyl]-4-phenyl-piperidine-
4-carboxylic acid amide;

1-[3-[3-(3,4-dichloro-phenyl)-1-(3,4,5-trimethoxy-
benzyl)-5-oxo-pyrrolidin-3-yl]-propyl]-4-phenyl-
piperidine-4-carboxylic acid amide;

1-[3-[3-(3,4-dichloro-phenyl)-1-(3,4,5-trimethoxy-
benzoyl)-5-oxo-pyrrolidin-3-yl]-propyl]-4-phenyl-
piperidine-4-carboxylic acid amide;

1-[2-[3-(3,4-dichloro-phenyl)-1-(3,5-dimethoxy-benzoyl)
-pyrrolidin-3-yl]-ethyl]-4-phenyl-piperidine-4-
carboxylic acid amide;

1-[2-[3-(3,4-dichloro-phenyl)-1-(3,4,5-triethoxy-
benzoyl)-pyrrolidin-3-yl]-ethyl]-4-phenyl-piperidine-
4-carboxylic acid amide;

1-[2-[3-(3,4-dichloro-phenyl)-1-(3,4,5-trimethoxy-
benzoyl)-pyrrolidin-3-yl]-ethyl]-4-phenyl-piperidine-
4-carboxylic acid 4-methylpiperazine-amide;

1-[2-[3-(3,4-dichloro-phenyl)-1-(3,4,5-trimethoxy-
benzoyl)-pyrrolidin-3-yl]-ethyl]-4-phenyl-piperidine-
4-carboxylic acid (2-morpholino-ethyl)-amide;

1-[2-[3-(3,4-dichloro-phenyl)-1-(4-methoxy-benzoyl)-
pyrrolidin-3-yl]-ethyl]-4-phenyl-piperidine-4-
carboxylic acid amide;

1-[2-[3-(3,4-dichloro-phenyl)-1-(3,4,5-trifluoro-benzoyl)
-pyrrolidin-3-yl]-ethyl]-4-phenyl-piperidine-4-
carboxylic acid amide;

1-[2-[3-(3,4-dichloro-phenyl)-1-(3,5-dibromo-4-
methoxy-benzoyl)-pyrrolidin-3-yl]-ethyl]-4-phenyl-
piperidine-4-carboxylic acid amide;

1-[2-[3-(3,4-dichloro-phenyl)-1-(3,5-dimethoxy-4-
(ethoxy-carboxyloxy)-benzoyl)-pyrrolidin-3-yl]-ethyl]
-4-phenyl-piperidine-4-carboxylic acid amide;

1-[2-[3-(3,4-dichloro-phenyl)-1-(3,5-dimethoxy-4-
methyl-benzoyl)-pyrrolidin-3-yl]-ethyl]-4-phenyl-
piperidine-4-carboxylic acid amide;

1-[2-[3-(3,4-dichloro-phenyl)-1-(3,5-di-tert-butyl-4-
hydroxy-benzoyl)-pyrrolidin-3-yl]-ethyl]-4-phenyl-
piperidine-4-carboxylic acid amide;

1-[2-[3-(3,4-dichloro-phenyl)-1-(3,4,5-trimethoxy-
benzoyl)-pyrrolidin-3-yl]-ethyl]-4-(4-fluoro-phenyl)-
piperidine-4-carboxylic acid amide;

1-[2-[3-(3,4-dichloro-phenyl)-1-(3,4,5-trimethoxy-
benzoyl)-pyrrolidin-3-yl]-ethyl]-4-(4-methoxy-phenyl)
-piperidine-4-carboxylic acid amide;

1-[2-[3-(3,4-dichloro-phenyl)-1-(3,4,5-trimethoxy-
benzoyl)-pyrrolidin-3-yl]-ethyl]-4-(4-methyl-phenyl)-
piperidine-4-carboxylic acid amide;

1-[2-[3-(3,4-dichloro-phenyl)-1-(3,4,5-trimethoxy-
benzoyl)-pyrrolidin-3-yl]-ethyl]-4-(4-chloro-phenyl)-
piperidine-4-carboxylic acid amide;

1-[2-[3-(3,4-dichloro-phenyl)-1-(3,4,5-trimethoxy-
benzoyl)-pyrrolidin-3-yl]-ethyl]-4-(4-trifluoromethyl-
phenyl)-piperidine-4-carboxylic acid amide;

1-[2-[3-(3,4-dichloro-phenyl)-1-(3,5-dimethoxy-4-
difuloromethoxy-benzoyl)-pyrrolidin-3-yl]-ethyl]-4-
phenyl-piperidine-4-carboxylic acid amide;

1-[2-[3-(3,4-dichloro-phenyl)-1-(3,5-dimethoxy-4-(2-
diethylamino-ethyl)-benzoyl)-pyrrolidin-3-yl]-ethyl]-
4-phenyl-piperidine-4-carboxylic acid amide;

1-[2-[3-(3,4-dichloro-phenyl)-1-(3,4,5-trimethoxy-
benzoyl)-pyrrolidin-3-yl]-ethyl]-4-phenyl-piperidine-
4-carboxylic acid amide N-oxide;

1-[2-[3-(3,4-dichloro-phenyl)-1-(3,5-dimethoxy-4-
hydroxy-benzoyl)-pyrrolidin-3-yl]-ethyl]-4-phenyl-
piperidine-4-carboxylic acid amide.

Examples of compounds of the (+) isomer encompassed by the present invention include:

(+)8-[2-[3-(3,4-dichloro-phenyl)-1-(2,6-dimethoxy-
benzoyl)-pyrrolidin-3-yl]-ethyl]-1-phenyl-1,3,8-triaza-
spiro[4.5]decan-4-one and the hydrochloride salt
thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(2,6-dimethoxy-benzoyl)-pyrrolidin-3-yl]-ethyl]-4-phenyl-piperidine-4-carboxylic acid amide and the hydrochloride salt thereof;

(+)-1-(2-[3-(3,4-dichloro-phenyl)-1-[2-(2-methoxy-phenyl)-acetyl]-pyrrolidin-3-yl]-ethyl)-4-phenyl-piperidine-4-carboxylic acid amide and the hydrochloride salt thereof;

(+)-1-[2-[3-(3,4-dichloro-phenyl)-1-(2-methoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(2,4-dimethoxy-benzoyl)-pyrrolidin-3-yl]-ethyl]-4-phenyl-piperidine-4-carboxylic acid amide and the hydrochloride salt thereof;

(+)-2-[(2-[1-benzoyl-3-(3,4-dichloro-phenyl)-pyrrolidin-3-yl]-ethyl]-4-phenyl-piperidine-4-carbonyl)-amino]-pentanedioic acid dimethyl ester and the hydrochloride salt thereof;

(+)-1-[2-[1-benzyl-3-(3,4-dichloro-phenyl)-5-oxo-pyrrolidin-3-yl]-ethyl]-4-phenyl-piperidine-4-carboxylic acid amide and the hydrochloride salt thereof;

(+)-1-[2-[3-(3,4-dichloro-phenyl)-1-benzoyl-pyrrolidin-3-yl]-ethyl]-4-phenyl-piperidine-4-carboxylic acid amide and the hydrochloride salt thereof;

(+)-8-[2-[3-(3,4-dichloro-phenyl)-1-benzoyl-pyrrolidin-3-yl]-ethyl]-1-phenyl-1,3,8-triaza-spiro[4.5]-decane-4-one and the hydrochloride salt thereof;

(+)-2-[(1-(2-[1-benzoyl-3-(3,4-dichloro-phenyl)-pyrrolidin-3-yl]-ethyl)-4-phenyl-piperidine-4-carboxyl)-amino]-3-hydroxy butyric acid methyl ester and the hydrochloride salt thereof;

(+)-1-[1-benzyl-3-naphthalen-2-yl-5-oxo-pyrrolidin-3-yl-ethyl]-4-phenyl-piperidine-4-carboxylic acid amide and the hydrochloride salt thereof;

(+)-1-[2-(1-benzoyl-3-napthalen-2-yl-pyrrolidin-3-yl)-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-phenyl-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(3,4-dimethoxy-phenyl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,5-bis-(trifluoromethyl)-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-dimethylamino-ethyl)-amide and the hydrochloride salt thereof;

(+)-1-[2-[3-(3,4-dichloro-phenyl)-1-(3-methoxy-benzoyl)-pyrrolidin-3-yl]-ethyl]-4-phenyl-piperidine-4-carboxylic acid amide and the hydrochloride salt thereof;

(+)-1-[2-[3-(benzo[1,3]dioxol-5-yl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(3,4-dimethoxy-phenyl)-1-(3,4,5-triethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(naphth-2-yl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(pyridin-4-yl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(pyridin-3-yl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(pyridin-2-yl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-benzyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid pyrrolidine-amide and the hydrochloride salt thereof;

(+)-1-[2-[3-(3,4-dichloro-phenyl)-1-(3,5-dimethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid piperidine-amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid methyl-amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid dimethyl-amide and the hydrochloride salt thereof;

(+)-1-[2-[3-(3,4-dichloro-phenyl)-1-(4-chloro-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(4-tert-butyl-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(4-tert-butyl-phenacyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3-isopropoxy-phenacyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-phenacyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(pyridine-2-carbonyl)-pyrrolidin-3-yl]-ethyl]-4-phenyl-piperidine-4-carboxylic acid amide and the hydrochloride salt thereof;

(+)-8-[2-[3-(3,4-dichloro-phenyl)-1-(3,4,5-trimethoxy-benzoyl)-pyrrolidin-3-yl]-ethyl]-1-phenyl-1,3,8-triaza-spiro[4.5]decan-4-one and the hydrochloride salt thereof;

(+)-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]dec-2-en-4-one and the hydrochloride salt thereof;

(+)-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one and the hydrochloride salt thereof;

(+)-3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one and the hydrochloride salt thereof;

(+)-3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione and the hydrochloride salt thereof;

(+)-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione and the hydrochloride salt thereof;

(+)-1-[2-[3-(3-trifluoromethyl-phenyl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(thiophen-2-yl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(pyridin-3-yl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(2-fluoro-phenyl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(4-hydroxy-phenyl)-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(4-trifluoromethyl-phenyl)-1-(3-isopropoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(thiophen-2-yl)-piperidine-4-carboxylic acid amide and the hydrochloride salt thereof;

(+)-1-[2-[3-(3,4-dichloro-phenyl)-5-oxo-1-(3,4,5-trimethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzyl)-pyrrolidin-3-yl]-ethyl]-4-phenyl-piperidine-4-carboxylic acid amide and the hydrochloride salt thereof;

(+)-1-[3-[3-(3,4-dichloro-phenyl)-1-(3,4,5-trimethoxy-benzoyl)-pyrrolidin-3-yl]-propyl]-4-phenyl-piperidine-4-carboxylic acid amide and the hydrochloride salt thereof;

(+)-1-[3-[3-(3,4-dichloro-phenyl)-1-(3,4,5-trimethoxy-benzyl)-pyrrolidin-3-yl]-propyl]-4-phenyl-piperidine-4-carboxylic acid amide and the hydrochloride salt thereof;

(+)-1-[3-[3-(3,4-dichloro-phenyl)-1-(3,4,5-trimethoxy-benzyl)-5-oxo-pyrrolidin-3-yl]-propyl]-4-phenyl-piperidine-4-carboxylic acid amide and the hydrochloride salt thereof;

(+)-1-[3-[3-(3,4-dichloro-phenyl)-1-(3,4,5-trimethoxy-benzoyl)-5-oxo-pyrrolidin-3-yl]-propyl]-4-phenyl-piperidine-4-carboxylic acid amide and the hydrochloride salt thereof;

(+)-1-[2-[3-(3,4-dichloro-phenyl)-1-(3,5-dimethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-triethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-morpholino-ethyl)-amide and the hydrochloride salt thereof;

(+)-1-[2-[3-(3,4-dichloro-phenyl)-1-(4-methoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trifluoro-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,5-dibromo-4-methoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,5-dimethoxy-4-(ethoxy-carboxyloxy)-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,5-dimethoxy-4-methyl-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,5-di-tert-butyl-4-hydroxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(4-fluoro-phenyl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(4-methoxy-phenyl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(4-methyl-phenyl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(4-chloro-phenyl)-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-(4-trifluoromethyl-phenyl)-piperidine-4-carboxylic acid amide and the hydrochloride salt thereof;

(+)-1-[2-[3-(3,4-dichloro-phenyl)-1-(3,5-dimethoxy-4-difuloromethoxy-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,5-dimethoxy-4-(2-diethylamino-ethyl)-benzoyl)-pyrrolidin-3-yl]-ethyl]-4-phenyl-piperidine-4-carboxylic acid amide and the hydrochloride salt thereof;

(+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide N-oxide and the hydrochloride salt thereof;

(+)-1-[2-[3-(3,4-dichloro-phenyl)-1-(3,5-dimethoxy-4-hydroxy-benzoyl)-pyrrolidin-3-yl]-ethyl]-4-phenyl-piperidine-4-carboxylic acid amide and the hydrochloride salt thereof.

Examples of compounds of the (−) isomer encompassed by the present invention include:

(−)-8-[2-[3-(3,4-dichloro-phenyl)-1-(2,6-dimethoxy-benzoyl)-pyrrolidin-3-yl]-ethyl]-1-phenyl-1,3,8-triaza-spiro[4.5]decane-4-one and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(2,6-dimethoxy-benzoyl)-pyrrolidin-3-yl]-ethyl]-4-phenyl-piperidine-4-carboxylic acid amide and the hydrochloride salt thereof;

(−)-1-(2-[3-(3,4-dichloro-phenyl)-1-[2-(2-methoxy-phenyl)-acetyl]-pyrrolidin-3-yl]-ethyl)-4-phenyl-piperidine-4-carboxylic acid amide and the hydrochloride salt thereof;

(−)-1-[2-[3-(3,4-dichloro-phenyl)-1-(2-methoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(2,4-dimethoxy-benzoyl)-pyrrolidin-3-yl]-ethyl]-4-phenyl-piperidine-4-carboxylic acid amide and the hydrochloride salt thereof;

(−)-2-[(2-[1-benzoyl-3-(3,4-dichloro-phenyl)-pyrrolidin-3-yl]-ethyl]-4-phenyl-piperidine-4-carbonyl)-amino]-pentanedioic acid dimethyl ester and the hydrochloride salt thereof;

(−)-1-[2-[1-benzyl-3-(3,4-dichloro-phenyl)-5-oxo-pyrrolidin-3-yl]-ethyl]-4-phenyl-piperidine-4-carboxylic acid amide and the hydrochloride salt thereof;

(−)-1-[2-[3-(3,4-dichloro-phenyl)-1-benzoyl-pyrrolidin-3-yl]-ethyl]-4-phenyl-piperidine-4-carboxylic acid amide and the hydrochloride salt thereof;

(−)-8-[2-[3-(3,4-dichloro-phenyl)-1-benzoyl-pyrrolidin-3-yl]-ethyl]-1-phenyl-1,3,8-triaza-spiro[4.5]-decane-4-one and the hydrochloride salt thereof;

(−)-2-[(1-(2-[1-benzoyl-3-(3,4-dichloro-phenyl)-pyrrolidin-3-yl]-ethyl)-4-phenyl-piperidine-4-carboxyl)-amino]-3-hydroxy butyric acid methyl ester and the hydrochloride salt thereof;

(−)-1-[1-benzyl-3-naphthalen-2-yl-5-oxo-pyrrolidin-3-yl-ethyl]-4-phenyl-piperidine-4-carboxylic acid amide and the hydrochloride salt thereof;

(−)-1-[2-(1-benzoyl-3-napthalen-2-yl-pyrrolidin-3-yl)-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-phenyl-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(3,4-dimethoxy-phenyl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,5-bis-(trifluoromethyl)-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-dimethylamino-ethyl)-amide and the hydrochloride salt thereof;

(−)-1-[2-[3-(3,4-dichloro-phenyl)-1-(3-methoxy-benzoyl)-pyrrolidin-3-yl]-ethyl]-4-phenyl-piperidine-4-carboxylic acid amide and the hydrochloride salt thereof;

(−)-1-[2-[3-(benzo[1,3]dioxol-5-yl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(3,4-dimethoxy-phenyl)-1-(3,4,5-triethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(naphth-2-yl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(pyridin-4-yl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(pyridin-3-yl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(pyridin-2-yl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-benzyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid pyrrolidine-amide and the hydrochloride salt thereof;

(−)-1-[2-[3-(3,4-dichloro-phenyl)-1-(3,5-dimethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid piperidine-amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid methyl-amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid dimethyl-amide and the hydrochloride salt thereof;

(−)-1-[2-[3-(3,4-dichloro-phenyl)-1-(4-chloro-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(4-tert-butyl-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(4-tert-butyl-phenacyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3-isopropoxy-phenacyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-phenacyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(pyridine-2-carbonyl)-pyrrolidin-3-yl]-ethyl]-4-phenyl-piperidine-4-carboxylic acid amide and the hydrochloride salt thereof;

(−)-8-[2-[3-(3,4-dichloro-phenyl)-1-(3,4,5-trimethoxy-benzoyl)-pyrrolidin-3-yl]-ethyl]-1-phenyl-1,3,8-triaza-spiro[4.5]decan-4-one and the hydrochloride salt thereof;

(−)-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]dec-2-en-4-one and the hydrochloride salt thereof;

(−)-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one and the hydrochloride salt thereof;

(−)-3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one and the hydrochloride salt thereof;

(−)-3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione and the hydrochloride salt thereof;

(−)-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione and the hydrochloride salt thereof;

(−)-1-[2-[3-(3-trifluoromethyl-phenyl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(thiophen-2-yl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(pyridin-3-yl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(2-fluoro-phenyl)-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(4-hydroxy-phenyl)-1-(3,4,5-trimethoxy-benzoyl )-pyrrolidin-3-yl]-ethyl]-4-phenyl-piperidine-4-carboxylic acid amide and the hydrochloride salt thereof;

(−)-1-[2-[3-(4-trifluoromethyl-phenyl)-1-(3-isopropoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(thiophen-2-yl)-piperidine-4-carboxylic acid amide and the hydrochloride salt thereof;

(−)-1-[2-[3-(3,4-dichloro-phenyl)-5-oxo-1-(3,4,5-trimethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzyl)-pyrrolidin-3-yl]-ethyl]-4-phenyl-piperidine-4-carboxylic acid amide and the hydrochloride salt thereof;

(−)-1-[3-[3-(3,4-dichloro-phenyl)-1-(3,4,5-trimethoxy-benzoyl)-pyrrolidin-3-yl]-propyl]-4-phenyl-piperidine-4-carboxylic acid amide and the hydrochloride salt thereof;

(−)-1-[3-[3-(3,4-dichloro-phenyl)-1-(3,4,5-trimethoxy-benzyl)-pyrrolidin-3-yl]-propyl]-4-phenyl-piperidine-4-carboxylic acid amide and the hydrochloride salt thereof;

(−)-1-[3-[3-(3,4-dichloro-phenyl)-1-(3,4,5-trimethoxy-benzyl)-5-oxo-pyrrolidin-3-yl]-propyl]-4-phenyl-piperidine-4-carboxylic acid amide and the hydrochloride salt thereof;

(−)-1-[3-[3-(3,4-dichloro-phenyl)-1-(3,4,5-trimethoxy-benzoyl)-5-oxo-pyrrolidin-3-yl]-propyl]-4-phenyl-piperidine-4-carboxylic acid amide and the hydrochloride salt thereof;

(−)-1-[2-[3-(3,4-dichloro-phenyl)-1-(3,5-dimethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-triethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-morpholino-ethyl)-amide and the hydrochloride salt thereof;

(−)-1-[2-[3-(3,4-dichloro-phenyl)-1-(4-methoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trifluoro-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,5-dibromo-4-methoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,5-dimethoxy-4-(ethoxy-carboxyloxy)-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,5-dimethoxy-4-methyl-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,5-di-tert-butyl-4-hydroxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(4-fluoro-phenyl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(4-methoxy-phenyl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(4-methyl-phenyl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(4-chloro-phenyl)-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-(4-trifluoromethyl-phenyl)-piperidine-4-carboxylic acid amide and the hydrochloride salt thereof;

(−)-1-[2-[3-(3,4-dichloro-phenyl)-1-(3,5-dimethoxy-4-difuloromethoxy-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,5-dimethoxy-4-(2-diethylamino-ethyl)-benzoyl)-pyrrolidin-3-yl]-ethyl]-4-phenyl-piperidine-4-carboxylic acid amide and the hydrochloride salt thereof;

(−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide N-oxide and the hydrochloride salt thereof;

(−)-1-[2-[3-(3,4-dichloro-phenyl)-1-(3,5-dimethoxy-4-hydroxy-benzoyl)-pyrrolidin-3-yl]-ethyl]-4-phenyl-piperidine-4-carboxylic acid amide and the hydrochloride salt thereof.

REACTION SCHEMES

Compounds of formula (1) and intermediates thereof can be prepared as described in the Reaction Schemes A through M below. All the substituents, unless otherwise indicated, are previously defined. The reagents and starting materials are readily available to one of ordinary skill in the art.

Reaction Scheme A

Reaction Scheme A may be used to synthesize substituted 1-aralkyl-3-aryl-3-(2-hydroxyethyl)-5-oxo-pyrrolidine as shown in formula 5a (see scheme A on next page). The substituents of formula 5a, 1-aralkyl-3-aryl-3-(2-hydroxyethyl)-pyrrolidines, are defined such that $Ar_1$ and $Ar_2$ are as desired in the final product.

In reaction Scheme A, Step A1, alkylation of the aryl-acetonitrile may be accomplished with 2-(2-bromo-ethoxy)-tetrahydro-pyran to form the 2-aryl-4-(tetrahydro-pyran-2-yloxy)-butyronitrile which is then followed by a second alkylation with ethyl bromoacetate (step A2) to form the 3-cyano-3-aryl-5-(tetrahydro-pyran-2-yloxy)-pentanoic acid ethyl ester (compound 2).

The 3-cyano-3-aryl-5-(tetrahydro-pyran-2-yloxy)-pentanoic acid ethyl ester is able to be converted to the corresponding lactam by reduction, as is illustrated by treatment with hydrogen and Raney nickel (step A3) to form the corresponding 4-aryl-4-[2-(tetrahydro-pyran-2-yloxy)ethyl]-pyrrolidin-2-one (compound 3).

The selected aralkyl group having the desired substituents previously defined for formula 5a, may be added to pyrrolidine ring nitrogen by alkylation with an aralkyl halide, such as benzyl bromide, (step A4) to form Reaction Scheme A

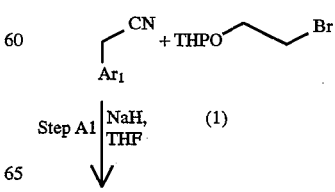

-continued
Reaction Scheme A

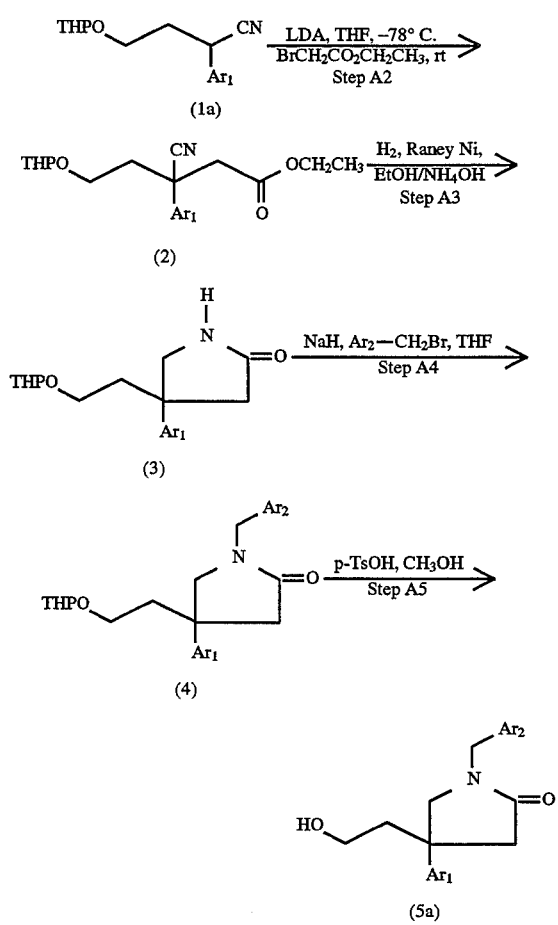

the corresponding 1-aralkyl-4-aryl-4-[2-(tetrahydro-pyran-2-yloxy)ethyl]-pyrrolidin-2-one.

The 5(a) intermediate corresponding to the 1-aralkyl-4-aryl-4-(2-hydroxyethyl)-pyrrolidin-2-one may be obtained by removal of the tetrahydropyran group by treatment of compound 4 with a suitable acid, such as p-toluenesulfonic acid in methanol.

Reaction Scheme B

Reaction Scheme B may be used to synthesize intermediate compounds wherein the structure is a substituted 1-aroyl-3-aryl-3-(2-hydroxyethyl)-pyrrolidine, as shown in formula 5b, or a substituted 1-arylacetyl-3-aryl-3-(2-hydroxyethyl)-pyrrolidine.

Reaction Scheme B
Reaction Scheme B may be used to synthesize
intermediate compounds wherein the structure is a
substituted 1-aroyl-3-aryl-3-(2-hydroxyethyl)-pyrrolidone,
as shown in formula 5b, or a substituted 1-arylacetyl-3-
aryl-3-(2-hydroxyethyl)-pyrrolidine.

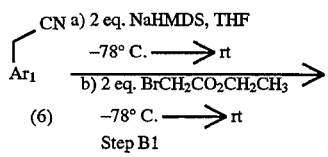

-continued
Reaction Scheme B
Reaction Scheme B may be used to synthesize
intermediate compounds wherein the structure is a
substituted 1-aroyl-3-aryl-3-(2-hydroxyethyl)-pyrrolidone,
as shown in formula 5b, or a substituted 1-arylacetyl-3-
aryl-3-(2-hydroxyethyl)-pyrrolidine.

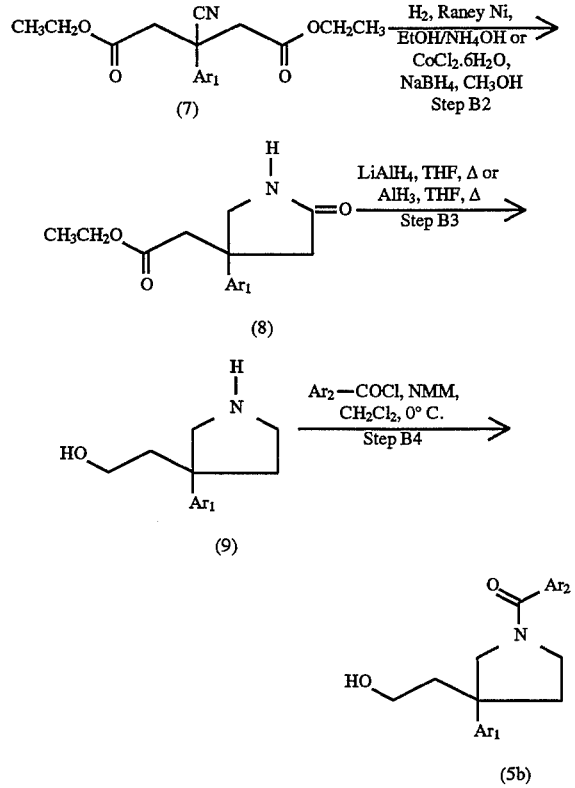

The compounds of formula 5b, 1-aroyl-3-aryl-3-(2-hydroxy-ethyl)-pyrrolidines and 1-phenylacetyl-3-aryl-3-(2-hydroxyethyl)-pyrrolidines are defined such $Ar_1$ and $Ar_2$ are as desired in the final product.

In reaction Scheme B, Step B1, the aryl-acetonitrile is treated with a base, for example, sodium bis (trimethylsily) amide), followed by addition of ethyl bromoacetate to produce the 3-cyano-3-aryl-pentanedioic diethyl ester (compound 7).

The 3-cyano group of the 3-cyano-3-aryl-pentanedioic diethyl ester may then subsequently be reduced with an appropriate reducing reagent (step B2), for example Raney nickel and hydrogen or with cobalt (II) chloride and sodium borohydride to give the corresponding 3-aryl-5-oxo-pyrrolidin-3-yl]-acetic acid ethyl ester (compound 8).

The 3-aryl-5-oxo-pyrrolidin-3-yl-acetic acid ethyl ester (compound 8) may subsequently be used in Scheme C or the 5-oxo-pyrrolidine ring may be reduced (step B3) with an appropriate reducing reagent, such as lithium aluminum hydride or aluminum hydride, to form the corresponding 3-aryl-3-(2-hydroxyethyl)-pyrrolidine (compound 9).

The pyrrolidine of compound 9 may subsequently be aroylated with an appropriately substituted benzoyl chloride in the presence of base such as 4-methylmorpholine to form the corresponding 1-aroyl-3-aryl-3-(2-hydroxyethyl)-pyrrolidine (Compound 5b) or substituted with an approprately substituted with a substituted arylacetyl chloride or aroyl chloride to form the corresponding 1-arylacetyl-3-aryl-3-(2-hydroxyethyl)-pyrrolidine or 1-aroyl-3-aryl-3-(2-hydroxyethyl)-pyrrolidine.

Reaction Scheme C

Reaction Scheme C is an alternative route which may be used to synthesize intermediate compounds wherein the structure is a substituted 1-aralkyl-3-aryl-3-(2-hydroxyethyl)-5-oxo-pyrrolidine as shown in formula 5a.

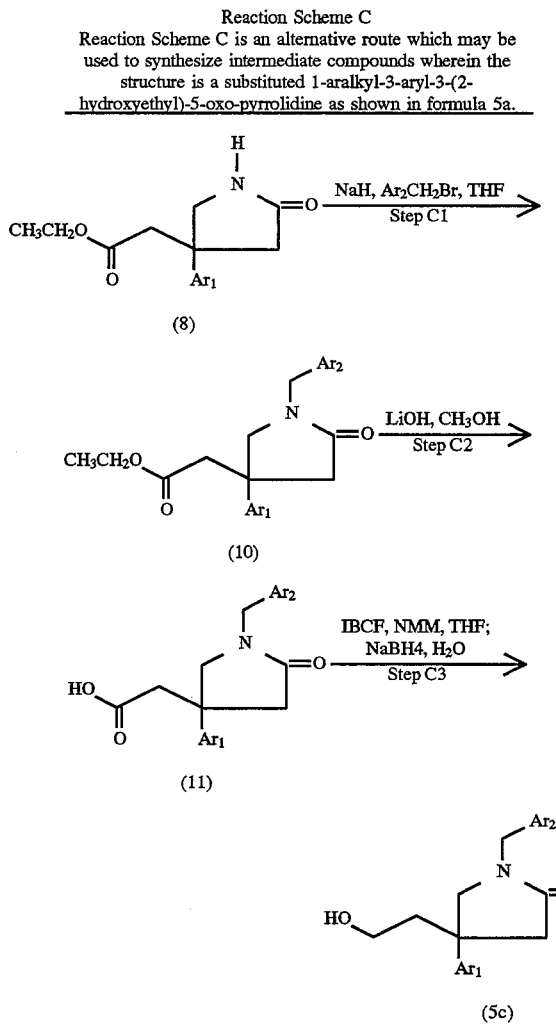

The substituents of formula 5a, 1-aralkyl-3-aryl-3-(2-hydroxyethyl)-pyrrolidines, have been previous defined wherein $Ar_1$ and $Ar_2$ are as desired in the final product.

A selected group from aryl may be added to the pyrrolidine ring of the (3-aryl-5-oxo-pyrrolidin-3-yl)-acetic acid ethyl ester (compound 8) by alkylation (step C1) of the nitrogen of pyrrolidine with an aralkyl halide, such as benzyl bromide, for example, to form the corresponding 1-aralkyl-3-aryl-5-oxo-pyrrolidin-3-yl-acetic acid ethyl ester (compound 10).

Conversion of the ethyl ester of compound 10 to the corresponding acid of compound 11 may be accomplished by base hydrolysis, for example lithium hydroxide in methanol, to form the 1-aralkyl-3-aryl-5-oxo-pyrrolidin-3-yl-acetic acid (compound 11).

The acetic acid of compound 11 is subsequently able to be reduced, for example, via the corresponding mixed anhydride in the presence of sodium borohydride to form the 1-aralkyl-4-aryl-4-(2-hydroxyethyl)-pyrrolidin-2-ones shown (compound 5c).

Reaction Scheme D

Reaction Scheme D may be used to synthesize the aryl substituted 2-(pyrrolidin-3-yl)-ethyl-piperidines of the invention.

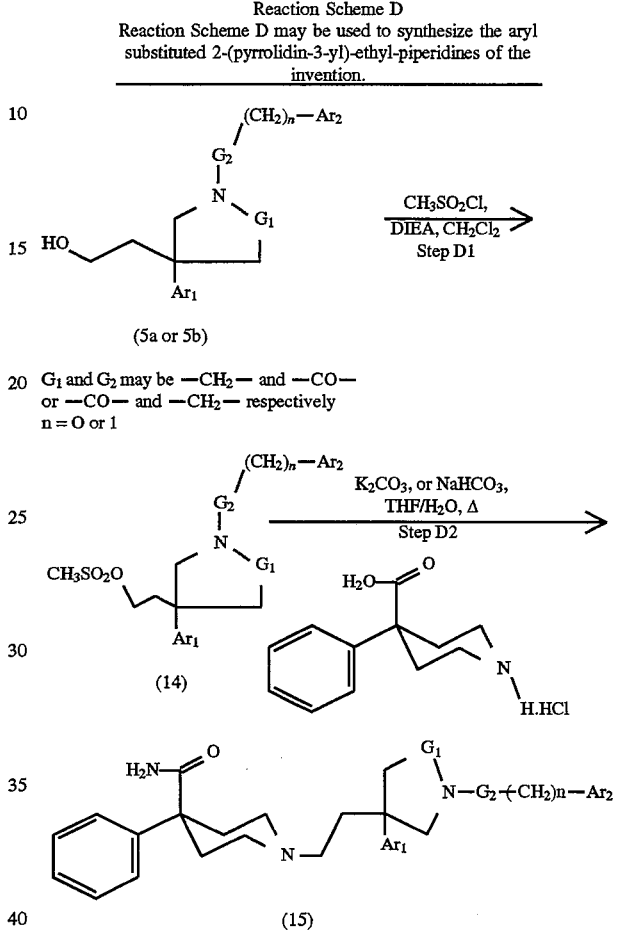

Scheme D is a general type procedure for condensation of substituted piperidines with substituted 1-aralkyl-3-aryl-3-(2-hydroxyethyl)-pyrrolidines, substituted 1-aroyl-3-arylacetyl-3-(2-hydroxyethyl)-pyrrolidine, or substituted 1-aroyl-3-aryl-3-(hydroxyethyl)-pyrrolidines previously discussed in Schemes A (Compound 5a), B (Compound 5b), or C (Compound 5c). The compounds of formula 15 are derived from the starting compounds described for Compounds 5a, 5b, and 5c, wherein the $Ar_1$ and $Ar_2$ is as desired in the final product.

Conversion of 1-aralkyl-3-aryl-3-(2-hydroxyethyl)-pyrrodidines, 1-arylacetyl-3-aryl-3-(2-hydroxyethyl)-pyrrolidines, or 1-aroyl-3-aryl-3-(2-hydroxyethyl)-pyrrolidines of intermediates 5a, 5b, or 5c may be accomplished by converting the 2-hydroxyethyl group to the corresponding mesylate by allowing 5a or 5b to react with methanesulfonyl chloride (step D1) and then allowing the mesylate derivative to react with a piperidine derivative to form the titled aryl substituted 2-(pyrrolidin-3-yl)-ethyl-piperidines of formula 15. It is realized that although the 4-phenyl-piperidine-4-carboxylic acid amide is shown as the substituted piperidine it may be replaced by a number of other piperidines or substituted piperidines. For instance, the piperidine derivatives may be condensed with the 1-aroyl-3-aryl-3-(2-hydroxy-ethyl)-pyrrolidine by refluxing the compounds in THF/water with a weak base, such as sodium bicarbonate or potassium carbonate. Suitable piperidine derivatives for condensation include, but are not limited to 4-phenyl-piperidine-4-carboxylic acid amide (4-phenyl isonipecotamide), 1-phenyl-1,3,8-triaza-spiro[4.5]decan-4-one, and the like.

The piperidine derivative can be further reacted following condensation with the mesylate. For example, one can use the 4-phenyl-piperidine-4-carboxylic acid methyl ester in the condensation with the mesylate derived from a 3-hydroxy-ethyl-pyrrolidine. After condensation of the piperidine derivative with the mesylate the 4-carboxylic acid ester protecting group may be removed to afford an intermediate acid derivative and further reacted to form the appropriate alkyl amides.

Reaction Scheme E

Reaction Scheme E is a general scheme for preparing the compounds of formula (1).

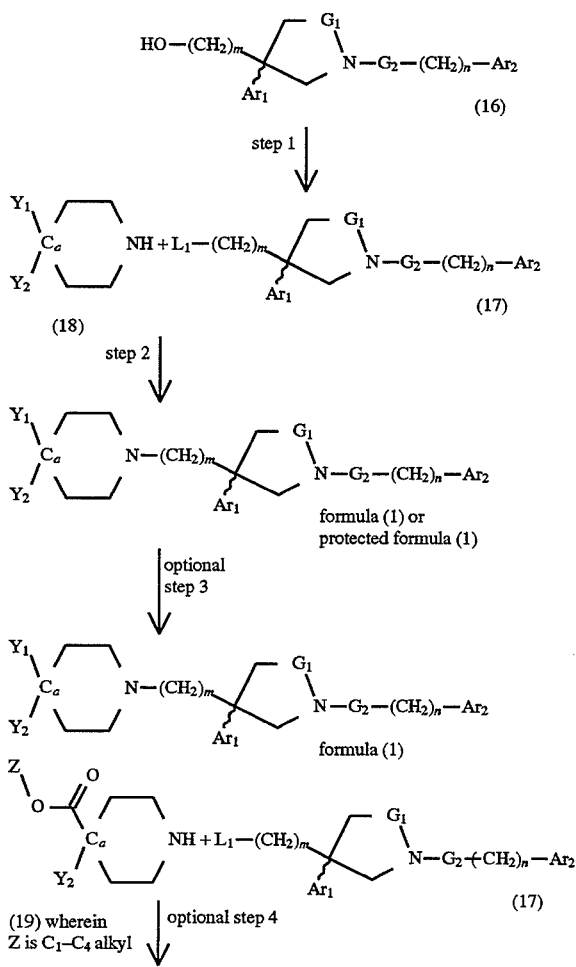

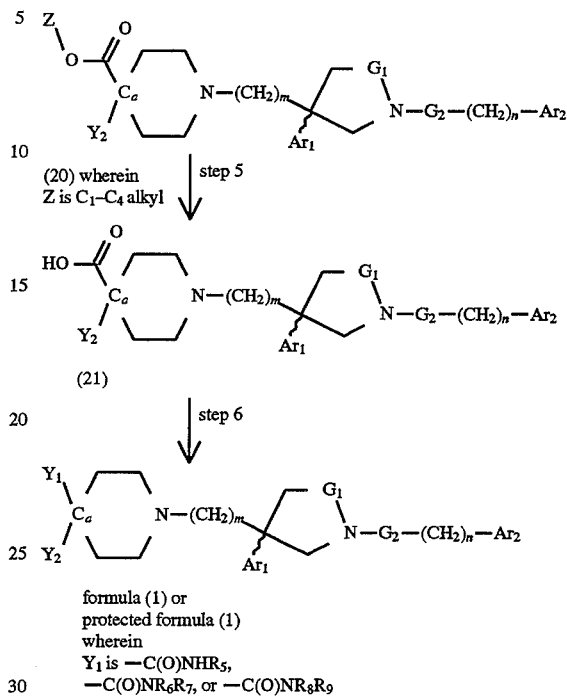

In Reaction Scheme E, step 1, the hydroxy group of an appropriate 3-(ω-hydroxyalkyl)pyrrolidine compound of formula 16 is converted to an appropriate leaving group. An appropriate 3-(ω-hydroxyalkyl)pyrrolidine compound of formula 16 is one in which m, n, $G_1$, $G_2$, $Ar_1$ and $Ar_2$ are as desired in the final product of formula (1) or can be one in which $Ar_1$ gives rise after deprotection to a group $Ar_1$ as desired in the final product of formula (1). An appropriate leaving group, $L_1$, is one which can be displaced by a piperidine of formula 18 to give a compound of formula (1). Appropriate leaving groups, $L_1$, include but are not limited to chloro, bromo, iodo, mesylate, tosylate, benzenesulfonate, trifluoromethanesulfonate, and the like. The conversion of hydroxy groups to leaving groups such as chloro, bromo, iodo, mesylate, tosylate, benzenesulfonate, and trifluoromethanesulfonate is well known and appreciated in the art.

For example, compounds in which $L_1$ is bromo are formed by contacting an appropriate 3-(ω-hydroxyalkyl)pyrrolidine compound of formula 16 with 1.0 to 1.5 molar equivalents of carbon tetrabromide and 1.0 to 1.75 molar equivalents triphenylphosphine. (P. J. Kocienski et al. *JOC* 42, 353–355 (1977)). The reaction is carried out by combining the 3-(ω-hydroxyalkyl)pyrrolidine compound of formula 16 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the reactions require from 5 minutes to 24 hours. The product can be isolated and purified by techniques well known in the art, such as extraction, evaporation, trituration, chromatography, and recrystallization.

Compounds in which $L_1$ is bromo are also formed by contacting an appropriate 3-(ω-hydroxyalkyl)pyrrolidine compound of formula 16 with a slight molar excess of triphenylphosphine dibromide. (R. F Borch et al. *JACS* 99, 1612–1619 (1977)). The reaction may be carried out by contacting an appropriate, 3-(ω-hydroxyalkyl)pyrrolidine compound of formula 16 with preformed triphenylphosphine dibromide. The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trituration, chromatography, and recrystallization.

Alternately, for example, compounds in which $L_1$ is mesylate are formed by contacting an appropriate 3-(ω-hydroxyalkyl)pyrrolidine compound of formula 16 with a molar excess of methanesulfonyl chloride. The reaction is carried out in a suitable solvent, such as dichloromethane, chloroform, toluene, benzene, or pyridine. The reaction is carried out in the presence of a suitable base, such as triethylamine, diisopropylethyl amine, or pyridine. Generally the reaction is carried out at temperatures of from –20° C. to 50° C. Generally, the reactions require from 1 hour to 24 hours. The product can be isolated and purified by techniques well known in the art, such as extraction, evaporation, trituration, chromatography, and recrystallization.

Compounds of formula 17 in which $L_1$ is iodo can be prepared from compounds of formula 17 in which $L_1$ is mesylate, chloro, or bromo by an exchange reaction, such as the Finkelstein reaction.

For example, a compound of formula 17 in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone or butanone. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme E, step 2, an appropriate 3-(ω-$L_1$-alkyl)pyrrolidine compound of formula 17 reacts with an appropriate piperidine compound of formula 18 or salt of an appropriate piperidine of formula 18 to give a protected compound of formula (1) or a compound of formula (1). An appropriate compound of formula 17 is one in which the leaving group, $L_1$, is one which can be displaced by a piperidine of formula 18, m, n, $G_1$, $G_2$, $Ar_1$ and $Ar_2$ are as desired in the final product of formula (1) or can be one in which $Ar_1$ gives rise after deprotection to a group $Ar_1$ as desired in the final product of formula (1). An appropriate piperidine of formula 18 or salt of an appropriate piperidine of formula 18 is one in which $Y_1$ and $Y_2$ are as desired in the final product of formula (1).

For example, an appropriate 3-(ω-$L_1$-alkyl)pyrrolidine compound of formula 17 is contacted with an appropriate piperidine compound of formula 18 or salt of an appropriate piperidine of formula 18 to give a protected compound of formula (1) or a compound of formula (1). The reaction is carried out in a suitable solvent, such as tetrahydrofuran, tetrahydrofuran/water mixtures, pyridine, acetonitrile, toluene, toluene/water mixtures, or dimethylformamide. The reaction is carried out in the presence of from 1.0 to 6.0 molar equivalents of a suitable base, such as sodium carbonate, sodium bicarbonate, potassium carbonate, potassium bicarbonate, triethylamine, pyridine, or diisopropylethylamine. When a salt of an appropriate piperidine of formula 18 is used, an additional molar excess of a suitable base is used. The reaction may be facilitated by the addition of a catalytic amount, 0.1 to 0.5 molar equivalents, of an iodide salt, such as sodium iodide or potassium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme E, optional step 3, a protected compound of formula (1) is deprotected to give a compound of formula (1). A deprotection reaction, such as the removal of hydroxy protecting groups utilizing suitable protecting groups such as those described in *Protecting Groups in Organic Synthesis* by T. Greene is well known and appreciated in the art.

Alternately, the compounds of formula (1) can be prepared by forming the amide group after the formation of an appropriate carboxylic acid derivative as generally taught below.

In Reaction Scheme E, optional step 4, an appropriate compound of formula 17, as defined above is contacted with an appropriate piperidine ester of formula 19 or salt of an appropriate piperidine ester of formula 19. An appropriate piperidine ester of formula 19 or salt of an appropriate piperidine ester of formula 19 is one in which $Y_2$ is as desired in the final product of formula (1) and Z is a $C_1$–$C_4$ alkyl group. This step is carried out as generally taught in Reaction Scheme E, step 2.

In Reaction Scheme E, step 5, an appropriate ester of formula 20 is hydrolyzed to give an acid of formula 21.

For example, an appropriate ester of formula 20 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme E, step 6, an appropriate acid of formula 21 undergoes an amidation reaction with an appropriate amine to give a compound of formula (1). An appropriate amine, $NH_2R_5$, $NHR_6R_7$, or $NHR_8R_9$, is one which $R_5$, $R_6$ and $R_7$, and $R_8$ and $R_9$ are as desired in the final compound of formula (1).

An amidation reaction may proceed through the acid of formula 21 or the acid function of a compound of formula 21 may be first converted to an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; an activated ester, such as phenol ester, p-nitrophenol ester, 2,4-dinitrophenol ester, pentafluorophenol ester, pentachlorophenol ester, N-hydroxysuccinimide ester, N-hydroxyphthalimide ester, 1-hydroxy-1H-benztriazole ester, and the like; activated amide, such as imidazole, dimethylpyrazole, triazole, or tetrazole; or the intermediate formed in the presence of coupling agents, such as dicyclohexylcarbodiimide or 1-(3-dimethylaminopropyl)-3-ethylcarbodiimide. Activated intermediates may be prepared and used directly, or are prepared and isolated before the addition of an appropriate amine, $NH_2R_5$, $NHR_6R_7$, or $NHR_8R_9$. Alternately, activated intermediates may be prepared isolated and purified before the addition of an appropriate amine, $NH_2R_5$, $NHR_6R_7$, or $NHR_8R_9$. The use and formation of activated intermediates is well known and appreciated in the art.

For example, an acid compound of formula 21 is contacted with a slight molar excess of an appropriate amine, $NH_2R_5$, $NHR_6R_7$, or $NHR_8R_9$, or a salt of an appropriate amine and 1-hydroxybenzotriazole hydrate in the presence of a slight molar excess of a coupling agent, such as dicyclohexylcarbodiimide or 1-(3-dimethylaminopropyl)-3-ethylcarbodiimide. The reaction is carried out in the presence of a suitable base, such as diisopropylethyl amine, N-methylmorpholine, or triethylamine. If the salt of an amine is used an additional equimolar of a suitable base is added. The reaction is carried out in a suitable solvent, such as dichloromethane or chloroform. The product can be isolated and purified by techniques well known in the art, such as extraction, evaporation, chromatography, and recrystallization.

Alternatively, for example, an acid of formula 21 is contacted with 1.2 to 1.7 equivalents of a suitable base, such as N-methylmorpholine, in a suitable solvent, such as tetrahydrofuran. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 24 hours to allow for the formation of the mixed anhydride, an activated intermediate. While maintaining the temperature at between −50° C. and 0° C. an appropriate amine, $NH_2R_5$, $NHR_6R_7$, or $NHR_8R_9$, is added, if the salt an appropriate amine is used an additional equimolar amount of a suitable base is added. The reaction may, after the addition of amine is complete, be warmed to room temperature. Generally, the reaction requires from 2 to 48 hours. The product can be isolated and purified by techniques well known in the art, such as extraction, evaporation, chromatography, and recrystallization.

The protected compounds of formula (1) prepared as described in Reaction Scheme E, optional step 4, step 5, and step 6 can be deprotected as required as described in Reaction Scheme E, optional step 3.

The N-oxide and pharmaceutically acceptable salt of compounds of formula (1) are readily prepared from compounds of formula (1) by methods and techniques well known and appreciated in the art.

Reaction Scheme E.1

Reaction Scheme E.1 is a general scheme for preparing the compounds of formula (1) in which $G_1$ is —$CH_2$—.

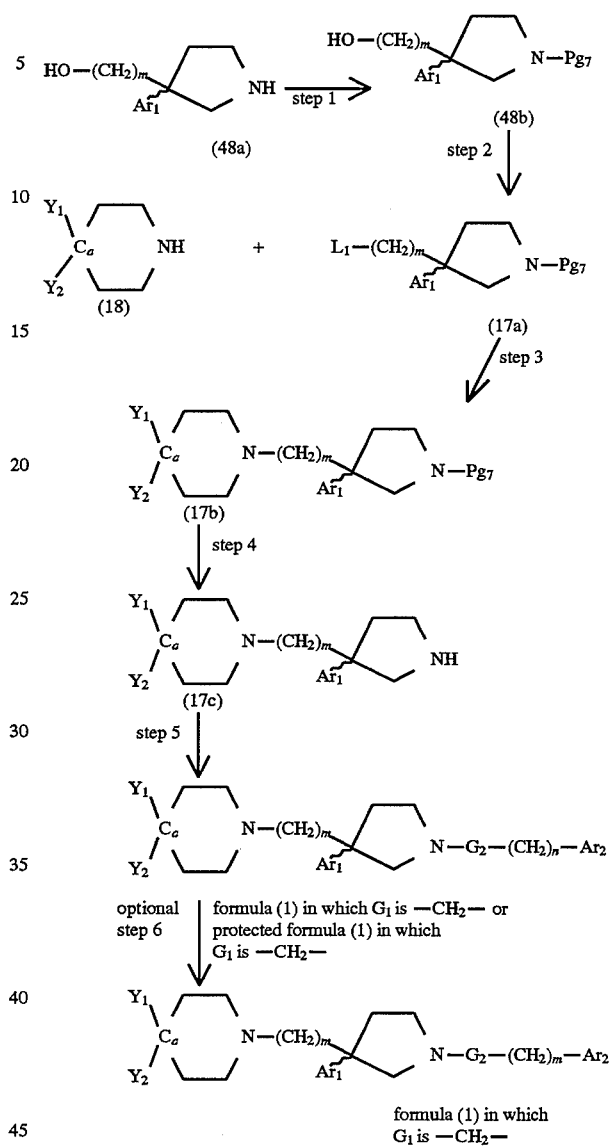

Reaction Scheme E.1

In Reaction Scheme E.1, step 1, the amino group of an appropriate 3-aryl-3-(ω-hydroxyethyl)-pyrrolidine of formula 48a is protected to give an appropriate protected 3-aryl-3-(ω-hydroxyethyl)-pyrrolidine of formula 48b. An appropriate 3-aryl-3-(ω-hydroxyethyl)-pyrrolidine of formula 48a is one in which the m and $Ar_1$ are as desired in the final product of formula (1) or can be one in which $Ar_1$ gives rise after deprotection to a group $Ar_1$ as desired in the final product of formula (1). Compounds of formula 48a are readily prepared as described in Reaction Scheme J for the preparation of compounds of formula 48 or by deprotection of tetrahydropyran ethers of compounds of formula 44 prepared in Reaction Scheme I or compounds of formula 31 prepared in Reaction Scheme F.

The selection and use of suitable amino protecting groups such as, t-BOC and those described in *Protecting Groups in Organic Synthesis* by T. Greene is well known and appreciated in the art.

In Reaction Scheme E.1, step 2, the hydroxy group of an appropriate protected 3-aryl-3-(ω-hydroxyethyl)- pyrrolidine of formula 48b is converted to an appropriate leaving group as generally taught in Reaction Scheme E, step 1 to give an appropriate protected 3-aryl-3-(ω-L₁-alkyl) pyrrolidine compound of formula 17a.

In Reaction Scheme E.1, step 3, an appropriate protected 3-aryl-3-(ω-L₁-alkyl)pyrrolidine compound of formula 17a reacts with an appropriate piperidine compound of formula 18 or salt of an appropriate piperidine of formula 18 to give a protected compound of formula (1) as generally taught in Reaction Scheme E, step 2 to give an appropriate protected 3-aryl-3-(ω-piperidino-alkyl)pyrrolidine compound of formula 17b.

In Reaction Scheme E.1, step 4, an appropriate protected 3-aryl-3-(ω-piperidino-alkyl)pyrrolidine compound of formula 17b is deprotected to give an appropriate 3-aryl-3-(ω-piperidino-alkyl)pyrrolidine compound of formula 17c or a salt of an appropriate 3-aryl-3-(ω-piperidino-alkyl) pyrrolidine compound of formula 17c. The removal of suitable amino protecting groups such as, t-BOC and those described in *Protecting Groups in Organic Synthesis* by T. Greene is well known and appreciated in the art.

In Reaction Scheme E.1, step 5, an appropriate 3-aryl-3-(ω-piperidino-alkyl)pyrrolidine compound of formula 17c is alkylated as generally taught in Reaction Scheme I, optional step 2, to give a compound of formula (1) or a protected compound of formula (1) in which $G_2$ is —$CH_2$— or is aroylated as generally taught in Reaction Scheme I, optional step 3, to give a compound of formula (1) or a protected compound of formula (1) in which $G_2$ is —$CH_2$—.

In Reaction Scheme E.1, optional step 6, a protected compound of formula (1) is deprotected to give a compound of formula (1) as generally taught in Reaction scheme E, optional step 3.

Reaction Scheme F

Reaction Scheme F is a general scheme for preparing intermediates of formula 16 useful for preparing compounds of formula (1).

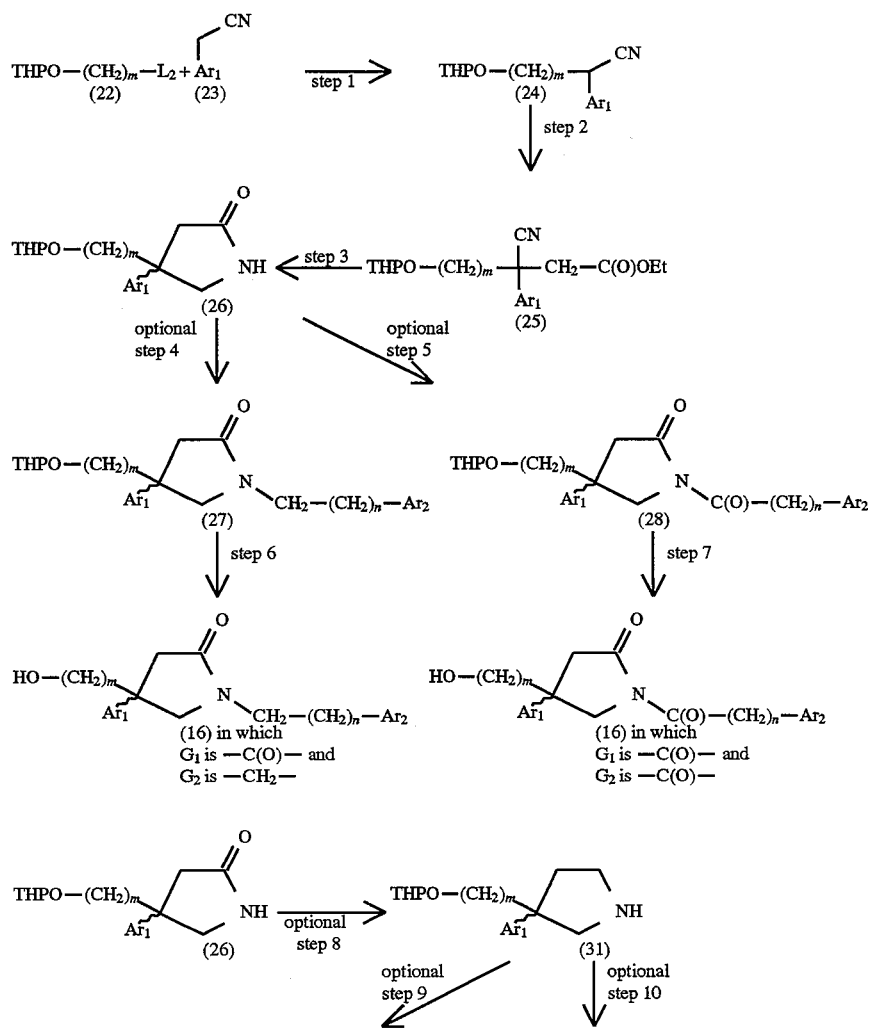

-continued
Reaction Scheme F

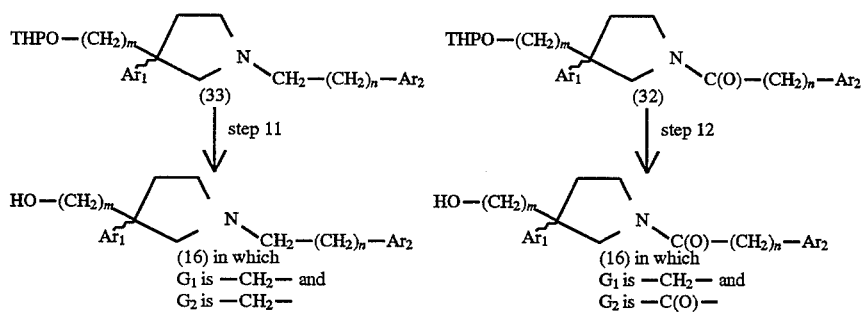

In Reaction Scheme F, step 1, an appropriate aryl-acetonitrile of formula 23 is alkylated with an appropriate ω-leaving group-THP-protected alcohol of formula 22 to give an ω-THP-protected-hydroxyalkyl-aryl-acetonitrile of formula 24. An appropriate aryl-acetonitrile of formula 23 is one in which $Ar_1$ is as desired in the final product of formula (1) or gives rise after deprotection to an $Ar_1$ as desired in the final product of formula (1). An appropriate ω-leaving group-THP-protected alcohol of formula 22 in one in which m is 2 or 3 as desired in the final product of formula (1) and the leaving group, $L_2$, is one which can be displaced by an anion derived from an appropriate aryl-acetonitrile of formula 23. Suitable leaving groups include but are not limited to chloro, bromo, iodo, and mesylate with bromo being preferred.

For example, an appropriate aryl-acetonitrile of formula 23 is contacted with an equimolar amount of an appropriate ω-leaving group-THP-protected alcohol of formula 22. The reaction is carried out in the presence of a base, such as sodium hydride, sodium hexamethyldisilazide, potassium t-butoxide, and lithium diisopropylamide with sodium hydride and sodium hexamethyldisilazide being preferred. The reaction is carried out in a solvent, such as dimethylformamide or tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme F, step 2, an appropriate ω-THP-protected-hydroxyalkyl-aryl-acetonitrile of formula 24 is alkylated with ethyl bromoacetate to give a nitrile ester compound of formula 25.

For example, an appropriate ω-THP-protected-hydroxyalkyl-aryl-acetonitrile of formula 24 is contacted with approximately a molar equivalent of ethyl bromoacetate. The reaction is carried out in the presence a suitable base, such as, sodium hexamethyldisilazide or lithium diisopropylamide. The reaction is carried out in a suitable solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme F, step 3, an appropriate nitrile ester compound of formula 25 is reduced and cyclized to give a 5-oxo-3-aryl-3-(ω-THP-protected-hydroxyalkyl) pyrrolidine of formula 26.

For example, an appropriate nitrile ester compound of formula 25 is contacted with an appropriate reducing agent, such as sodium borohydride in the presence of cobalt (II) chloride hexahydrate or hydrogen in the presence of a suitable catalyst, such as Raney nickel. For compounds of formula 25 in which $Ar_1$ is thienyl, sodium borohydride in the presence of cobalt (II) chloride hexahydrate is preferred.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. The product can be isolated and purified by techniques well known in the art, such as extraction with aqueous acid, evaporation, trituration, chromatography, and recrystallization.

When Raney nickel is used, the reaction is carried out in a suitable solvent containing ammonia, such as ethanol/ammonium hydroxide. The reaction is generally carried out at temperatures of from ambient temperature to 50° C. The reaction is carried out at pressures of from 15 psi to 120 psi in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization.

In Reaction Scheme F, optional step 4, an appropriate 5-oxo-3-aryl-3-(ω-THP-protected-hydroxyalkyl) pyrrolidine of formula 26 is alkylated with an appropriate alkyl halide, X—CH$_2$—(CH$_2$)$_n$—Ar$_2$, to an N-arylaklyl-5-oxo-3-aryl-3-(ω-THP-protected-hydroxyalkyl) pyrrolidine of formula 27. An appropriate alkyl halide, X—CH$_2$—(CH$_2$)$_n$—Ar$_2$, is one in which X is chloro, bromo, or iodo; n is as desired in the final product of formula (1), and $Ar_2$ is as desired in formula (1).

For example, an appropriate 5-oxo-3-aryl-3-(ω-THP-protected-hydroxyalkyl) pyrrolidine of formula 26 is contacted with from 1 to 5 molar equivalents of an appropriate alkyl halide, X—CH$_2$—(CH$_2$)$_n$—Ar$_2$. The reaction is carried out in a suitable solvent, such as tetrahydrofuran, dimethyl sulfoxide, or dimethylformamide. The reaction is carried out in the presence of a base, such as sodium hydride, potassium t-butoxide, or lithium diisopropylamide with sodium hydride being preferred. The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme F, optional step 5, an appropriate 5-oxo-3-aryl-3-(ω-THP-protected-hydroxyalkyl) pyrrolidine of formula 26 is aroylated with an appropriate aroyl halide, aryl anhydride, or aryl mixed anhydride, A—C(O)—$(CH_2)_n$—$Ar_2$, to an N-aroyl-5-oxo-3-aryl-3-(ω-THP-protected-hydroxyalkyl) pyrrolidine of formula 28. An appropriate aroyl halide, aryl anhydride, or aryl mixed anhydride, A—C(O)—$(CH_2)_n$—$Ar_2$, is one in which A is an activated leaving group, such as chloro or bromo, an anhydride, or mixed anhydride, n is as desired in the final product of formula (1), and $Ar_2$ is as desired in formula (1).

For example, an appropriate 5-oxo-3-aryl-3-(ω-THP-protected-hydroxyalkyl) pyrrolidine of formula 26 is contacted with 1 to 1.5 molar equivalents of an appropriate aroyl halide, aryl anhydride, or aryl mixed anhydride, A—C(O)—$(CH_2)_n$—$Ar_2$. The reaction is carried out in a suitable solvent, such as tetrahydrofuran, N,N-dimethylaniline, or diethyl ether. The reaction is carried out in the presence of a base, such as sodium hydride, N,N-dimethylaniline, potassium t-butoxide, or lithium diisopropylamide with sodium hydride being preferred. The reaction is generally carried out at temperatures of from −20° C. to the reflux temperature of the solvent. Generally, the reactions require 1 to 24 hours. The product can be isolated and purified by techniques well known in the art, such as extraction, evaporation, trituration, chromatography, and recrystallization.

In Reaction Scheme F, step 6, an N-arylaklyl-5-oxo-3-aryl-3-(ω-THP-protected-hydroxyalkyl) pyrrolidine of formula 27 is deprotected to give an N-arylaklyl-5-oxo-3-aryl-3-(ω-hydroxyalkyl) pyrrolidine of formula 16 which gives rise to compounds of formula (1) in which $G_1$ is —C(O)— and $G_2$ is —$CH_2$— and m, n, $Ar_1$, and $Ar_2$ are as desired in the final product of formula (1) or give rise after deprotection to $Ar_1$ as desired in the final product of formula (1).

For example, an N-arylaklyl-5-oxo-3-aryl-3-(ω-THP-protected-hydroxyalkyl) pyrrolidine of formula 27 is treated with a suitable acid, such as p-toluenesulfonic acid. The reaction is carried out in a suitable solvent, such as methanol or ethanol. The product is isolated by evaporation and purified by techniques well known in the art, such as extraction, evaporation, trituration, chromatography, and recrystallization.

In Reaction Scheme F, step 7, an N-aroyl-5-oxo-3-aryl-3-(ω-THP-protected-hydroxyalkyl) pyrrolidine of formula 28 is deprotected, as taught above for Reaction Scheme F, step 6, to give an an N-aroyl-5-oxo-3-aryl-3-(ω-hydroxyalkyl) pyrrolidine of formula 16 of which gives rise to compounds of formula (1) in which $G_1$ is —C(O)— and $G_2$ is —C(O)— and m, n, $Ar_1$, and $Ar_2$ are as desired in the final product of formula (1) or give rise after deprotection to $Ar_1$ as desired in the final product of formula (1).

In Reaction Scheme F, optional step 8, an appropriate 5-oxo-3-aryl-3-(ω-THP-protected-hydroxyalkyl) pyrrolidine of formula 26 is reduced to give a 3-aryl-3-(ω-THP-protected-hydroxyalkyl) pyrrolidine of formula 31.

For example, an appropriate 5-oxo-3-aryl-3-(ω-THP-protected-hydroxyalkyl) pyrrolidine of formula 26 is contacted with a suitable reducing agent, such as lithium aluminum hydride, aluminum hydride, or borane dimethyl sulfide complex. The reaction is carried out in a suitable solvent, such as tetrahydrofuran. The reaction is generally carried out at temperature of from 0° C. to the refluxing temperature of the solvent. Generally, the reactions require 1 to 72 hours. The product can be isolated and purified by techniques well known in the art, such as quenching of borane or aluminum complexes, extraction, evaporation, trituration, chromatography, and recrystallization.

In Reaction Scheme F, optional step 9, an appropriate 3-aryl-3-(ω-THP-protected-hydroxyalkyl) pyrrolidine of formula 31 is alkylated with an appropriate alkyl halide, X—$CH_2$—$(CH_2)_n$—$Ar_2$, to an N-arylaklyl-3-aryl-3-(ω-THP-protected-hydroxyalkyl) pyrrolidine of formula 33. An appropriate alkyl halide, X—$CH_2$—$(CH_2)_n$—$Ar_2$, is one in which X is chloro or bromo, n is as desired in the final product of formula (1), and $Ar_2$ is as desired in formula (1).

For example, an appropriate 3-aryl-3-(ω-THP-protected-hydroxyalkyl) pyrrolidine of formula 31 is contacted with from 1.0 to 1.2. molar equivalents of an appropriate alkyl halide, X—$CH_2$—$(CH_2)_n$—$Ar_2$. The reaction is carried out in a suitable solvent, such as tetrahydrofuran, dimethyl sulfoxide, acetonitrile, tetrahydrofuran/water, toluene, toluene/water, or dimethylformamide. The reaction is carried out in the presence of a base, such as sodium carbonate, sodium bicarbonate, potassium carbonate, triethylamine diisopropylethylamine, or pyridine. The reaction is generally carried out at temperatures of from 0° C. to reflux temperature of solvent. Generally, the reactions require 1 to 72 hours. The product can be isolated and purified by techniques well known in the art, such as extraction, evaporation, trituration, chromatography, and recrystallization.

In Reaction Scheme F, optional step 10, an appropriate 3-aryl-3-(ω-THP-protected-hydroxyalkyl) pyrrolidine of formula 31 is aroylated with an appropriate aroyl halide, aryl anhydride, or aryl mixed anhydride, A—C(O)—$(CH_2)_n$—$Ar_2$, to an N-aroyl-3-aryl-3-(ω-THP-protected-hydroxyalkyl) pyrrolidine of formula 32. An appropriate aroyl halide, aryl anhydride, or aryl mixed anhydride, A—C(O)—$(CH_2)_n$—$Ar_2$, is one in which A is an activated leaving group, such as chloro or bromo, an anhydride, or mixed anhydride, n is as desired in the final product of formula (1), and $Ar_2$ is as desired in formula (1).

For example, an appropriate 3-aryl-3-(ω-THP-protected-hydroxyalkyl) pyrrolidine of formula 31 is contacted with 1 to 1.5 molar equivalents of an appropriate aroyl halide, aryl anhydride, or aryl mixed anhydride, A—C(O)—$(CH_2)_n$—$Ar_2$. The reaction is carried out in a suitable solvent, such as tetrahydrofuran, acetonitrile, dimethylformamide, or pyridine. The reaction is carried out in the presence of a base, such as sodium carbonate, sodium bicarbonate, triethylamine, diisopropylethylamine, or pyridine. The reaction is generally carried out at temperatures of from −20° C. to 50° C. Generally, the reactions require 1 to 24 hours. The product can be isolated and purified by techniques well known in the art, such as extraction, evaporation, trituration, chromatography, and recrystallization.

In Reaction Scheme F, step 11, an N-arylaklyl-3-aryl-3-(ω-THP-protected-hydroxyalkyl) pyrrolidine of formula 33 is deprotected to give an N-arylaklyl-3-aryl-3-(ω-hydroxyalkyl) pyrrolidine of formula 16 which gives rise to compounds of formula (1) in which $G_1$ is —$CH_2$—, $G_2$ is —$CH_2$—, m, n, $Ar_1$, and $Ar_2$ are as desired in the final product of formula (1) or give rise after deprotection to $Ar_1$ as desired in the final product of formula (1).

For example, an N-arylaklyl-3-aryl-3-(ω-THP-protected-hydroxyalkyl) pyrrolidine of formula 33 is treated with a suitable acid, such as p-toluenesulfonic acid. The reaction is carried out in a suitable solvent, such as methanol or ethanol. The product is isolated by evaporation and purified by techniques well known in the art, such as extraction, evaporation, trituration, chromatography, and recrystallization.

In Reaction Scheme F, step 12, an N-aroyl-3-aryl-3-(ω-THP-protected-hydroxyalkyl) pyrrolidine of formula 32 is deprotected, as taught above in Reaction Scheme F, step 11, to give an an N-aroyl-3-aryl-3-(ω-hydroxyalkyl) pyrrolidine of formula 16 which gives rise to compounds of formula (1) in which $G_1$ is —$CH_2$—, $G_2$ is —C(O)—, and m, n, $Ar_1$, and $Ar_2$ are as desired in the final product of formula (1) or give rise after deprotection to $Ar_1$ as desired in the final product of formula (1).

Reaction Scheme G

Reaction Scheme G is a general scheme for preparing intermediates giving rise to compounds of formula (1) wherein m is 2.

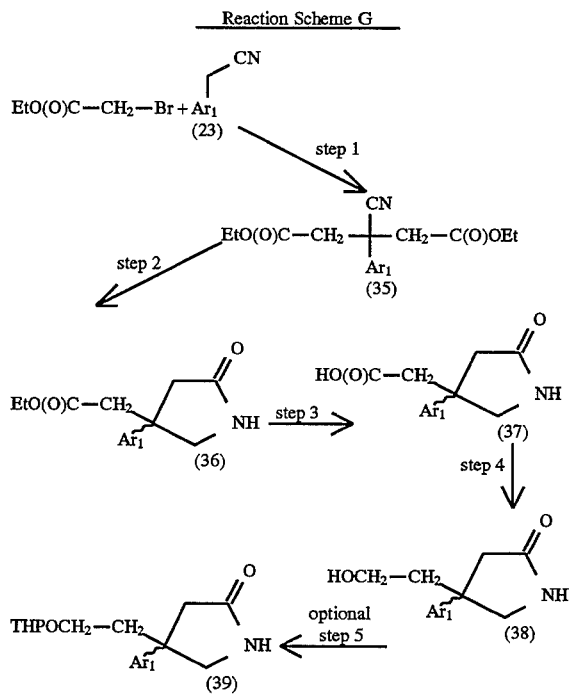

In Reaction Scheme G, step 1, an appropriate aryl acetonitrile of formula 23 is alkylated twice with ethyl bromoacetate to give a nitrile bis-ester compound of formula 35. An appropriate aryl acetonitrile of formula 23 is one in which $Ar_1$ is as is desired in the final product of formula (1) or gives rise after deprotection to an $Ar_1$ as desired in the final product of formula (1).

For example, an appropriate aryl acetonitrile of formula 23 is contacted with 2.0 to 3.0 molar equivalents of ethyl bromoacetate. The reaction is carried out in the presence of approximately 2.0 to 3.0 molar equivalents of a suitable base, such as sodium hexamethyldisilazide or lithium diisopropylamide. The reaction is carried out in a suitable solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme G, step 2, an appropriate nitrile bis-ester compound of formula 35 is reduced and cyclized to give a 5-oxo-3-aryl-3-acetic acid ester pyrrolidine of formula 36.

For example, an appropriate nitrile bis-ester compound of formula 35 is contacted with an appropriate reducing agent, such as sodium borohydride in the presence of cobalt II chloride hexahydrate or hydrogen in the presence of a suitable catalyst, such as Raney nickel. For compounds of formula 35 in which $Ar_1$ is thienyl, sodium borohydride in the presence of cobalt II chloride hexahydrate is preferred.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. The product can be isolated and purified by techniques well known in the art, such as extraction with aqueous acid, evaporation, trituration, chromatography, and recrystallization.

When Raney nickel is used, the reaction is carried out in a suitable solvent containing ammonia, such as ethanol/ammonium hydroxide. The reaction is generally carried out at temperatures of from ambient temperature to 50° C. The reaction is carried out at pressures of from 15 psi to 120 psi in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization.

In Reaction Scheme G, step 3, an appropriate 5-oxo-3-aryl-3-acetic acid ester pyrrolidine of formula 36 is hydrolyzed to give a 5-oxo-3-aryl-3-acetic acid pyrrolidine of formula 37.

For example, an appropriate 5-oxo-3-aryl-3-acetic acid ester pyrrolidine of formula 36 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme G, step 4, an appropriate 5-oxo-3-aryl-3-acetic acid pyrrolidine of formula 37 is reduced to give a 5-oxo-3-aryl-3-(2-hydroxyethyl) pyrrolidine of formula 38.

For example, an appropriate 5-oxo-3-aryl-3-acetic acid pyrrolidine of formula 37 is contacted with a suitable borane reagent, such as borane dimethyl sulfide complex or sodium borohydride reduction of a mixed anhydride intermediate formed by methods well known in the art. The reaction is carried out in a suitable solvent, such as tetrahydrofuran. The reaction is generally carried out at a temperature of from 0° C. to the refluxing temperature of the solvent. When complete the reaction is quenched by the careful addition of a suitable aqueous acid solution, such as 1M hydrochloric acid solution. The product can be isolated and purified by techniques well known in the art, such as extraction, evaporation, trituration, chromatography, and recrystallization.

In Reaction Scheme G, step 5, an appropriate 5-oxo-3-aryl-3-(2-hydroxyethyl) pyrrolidine of formula 38 is protected using dihydropyran to give a 5-oxo-3-aryl-3-(2-THP-protected-hydroxyethyl) pyrrolidine of formula 39.

For example, an appropriate 5-oxo-3-aryl-3-(2-hydroxyethyl) pyrrolidine of formula 38 is contacted with dihydropyran. The reaction is carried out in the presence of a catalytic amount of a suitable acid, such as p-toluenesulfonic acid, pyridinium p-toluenesulfonic acid, or a sulfonic acid containing resin, such as Amberlyst H-15.

The reaction is carried out in a suitable solvent, such as dichloromethane. The reaction is generally carried out at ambient temperature. The product can be isolated and purified by techniques well known in the art, such as extraction, evaporation, trituration, chromatography, and recrystallization.

Reaction Scheme H

Reaction Scheme H is a general Scheme H for preparing intermediates for preparing compounds of formula (1) wherein m is 2 and $G_1$ is —C(O)—.

protected-hydroxyethyl) pyrrolidine of formula 41. An appropriate aroyl halide, aryl anhydride, or aryl mixed anhydride, A—C(O)—$(CH_2)_n$—$Ar_2$, is one in which A is an activated leaving group, such as chloro or bromo, an anhydride, or mixed anhydride, n is as desired in the final product of formula (1), and $Ar_2$ is as desired in formula (1).

For example, an appropriate 5-oxo-3-aryl-3-(ω-THP-protected-hydroxyethyl) pyrrolidine of formula 39 is contacted with 1 to 1.5 molar equivalents of an appropriate aroyl halide, aryl anhydride, or aryl mixed anhydride, A—C(O)—$(CH_2)_n$—$Ar_2$. The reaction is carried out in a suitable solvent, such as tetrahydrofuran, N,N-dimethylaniline, or

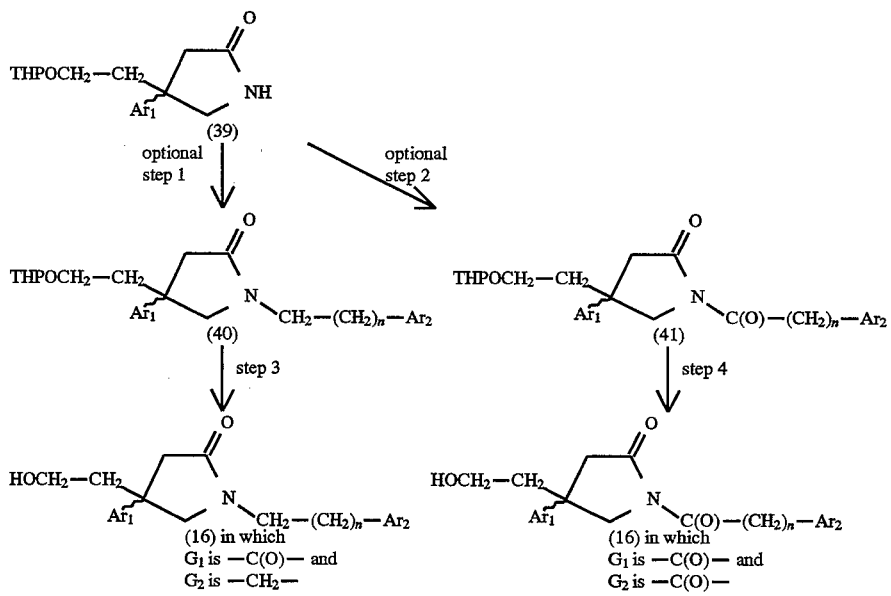

In Reaction Scheme H, optional step 1, an appropriate 5-oxo-3-aryl-3-(ω-THP-protected-hydroxyethyl) pyrrolidine of formula 39 is alkylated with an appropriate alkyl halide, X—$CH_2$—$(CH_2)_n$—$Ar_2$, to an N-arylalkyl-5-oxo-3-aryl-3-(ω-THP-protected-hydroxyethyl) pyrrolidine of formula 40. An appropriate alkyl halide, X—$CH_2$—$(CH_2)_n$—$Ar_2$, is one in which X is chloro, bromo, or iodo; n is as desired in the final product of formula (1), and $Ar_2$ is as desired in formula (1).

For example, an appropriate 5-oxo-3-aryl-3-(ω-THP-protected-hydroxyethyl) pyrrolidine of formula 39 is contacted with from 1 to 5 molar equivalents of an appropriate alkyl halide, X—$CH_2$—$(CH_2)_n$—$Ar_2$. The reaction is carried out in a suitable solvent, such as tetrahydrofuran, dimethyl sulfoxide, or dimethylformamide. The reaction is carried out in the presence of a base, such as sodium hydride, sodium hexamethyldisilazide, potassium t-butoxide, or lithium diisopropylamide with sodium hydride being preferred. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme H, optional step 2, an appropriate 5-oxo-3-aryl-3-(ω-THP-protected-hydroxyethyl) pyrrolidine of formula 39 is aroylated with an appropriate aroyl halide, aryl anhydride, or aryl mixed anhydride, A—C(O)—$(CH_2)_n$—$Ar_2$, to an N-aroyl-5-oxo-3-aryl-3-(ω-THPdiethyl ether. The reaction is carried out in the presence of a base, such as sodium hydride, N,N-dimethylaniline, potassium t-butoxide, or lithium diisopropylamide with sodium hydride being preferred. The reaction is generally carried out at temperatures of from −20° C. to 50° C. Generally, the reactions require 1 to 24 hours. The product can be isolated and purified by techniques well known in the art, such as extraction, evaporation, trituration, chromatography, and recrystallization.

In Reaction Scheme H, step 3, an N-arylalkyl-5-oxo-3-aryl-3-(ω-THP-protected-hydroxyethyl) pyrrolidine of formula 40 is deprotected to give an N-arylalkyl-5-oxo-3-aryl-3-(ω-hydroxyethyl) pyrrolidine of formula 16 which gives rise to compounds of formula (1) in which $G_1$ is —C(O)—, $G_2$ is —$CH_2$—, m is 2, and n, $Ar_1$, and $Ar_2$ are as desired in the final product of formula (1) or give rise after deprotection to $Ar_1$ as desired in the final product of formula (1).

For example, an N-arylalkyl-5-oxo-3-aryl-3-(ω-THP-protected-hydroxyethyl) pyrrolidine of formula 40 is treated with a suitable acid, such as p-toluenesulfonic acid. The reaction is carried out in a suitable solvent, such as methanol or ethanol. The product is isolated by evaporation and purified by techniques well known in the art, such as extraction, evaporation, trituration, chromatography, and recrystallization.

In Reaction Scheme H, step 4, an N-aroyl-5-oxo-3-aryl-3-(ω-THP-protected-hydroxyethyl) pyrrolidine of formula 41 is deprotected, as taught above, to give an an N-aroyl- 5-oxo-3-aryl-3-(ω-hydroxyalkyl) pyrrolidine of formula 16 which gives rise to compounds of formula (1) in which $G_1$ is —C(O)—, $G_2$ is —C(O)—, m is 2, and n, $Ar_1$, and $Ar_2$ are as desired in the final product of formula (1) or give rise after deprotection to $Ar_1$ as desired in the final product of formula (1).

Reaction Scheme I

Reaction Scheme I is a general scheme for preparing intermediates for preparing compounds of formula (1) wherein m is 2 and $G_1$ is —CH$_2$—.

from 1.0 to 1.2 molar equivalents of an appropriate alkyl halide, X—CH$_2$—(CH$_2$)$_n$—Ar$_2$. The reaction is carried out in a suitable solvent, such as tetrahydrofuran, dimethyl sulfoxide, acetonitrile, tetrahydrofuran, toluene, tetrahydrofuran/water mixtures, toluene/water mixtures, or dimethylformamide. The reaction is carried out in the presence of a base, such as sodium carbonate, potassium carbonate, sodium bicarbonate, triethylamine diisopropylethylamine, or pyridine. The reaction is generally carried out at temperatures of from 0° C. to the refluxing temperature of the solvent. Generally, the reactions require 1 to 72 hours. The product can be isolated and purified by

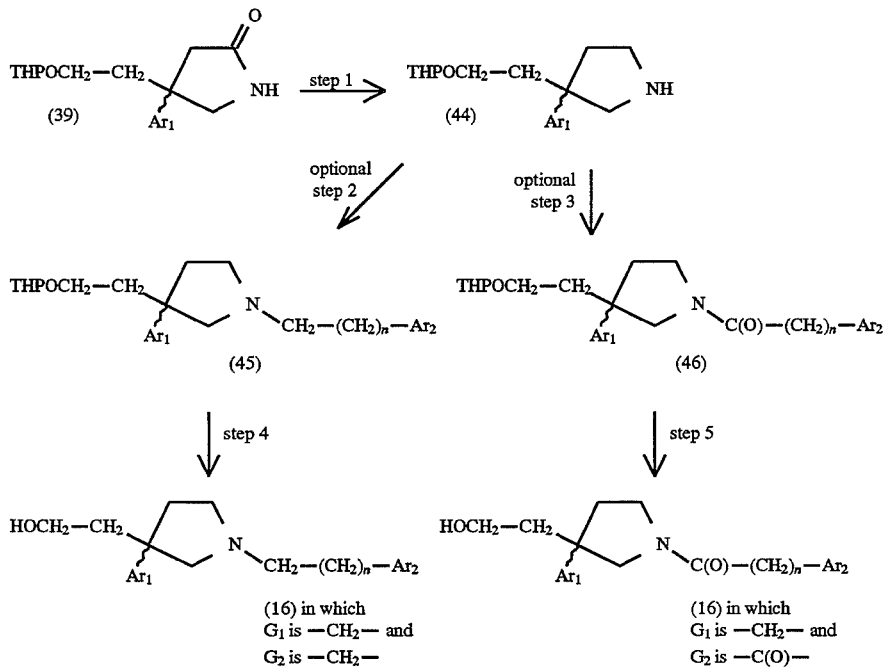

In Reaction Scheme I, step 1, an appropriate 5-oxo-3-aryl-3-(ω-THP-protected-hydroxyethyl)-pyrrolidine of formula 39 is reduced to give a 3-aryl-3-(ω-THP-protected-hydroxyethyl) pyrrolidine of formula 44.

For example, an appropriate 5-oxo-3-aryl-3-(ω-THP-protected-hydroxyethyl) pyrrolidine of formula 39 is contacted with a suitable reducing agent, such as lithium aluminum hydride, aluminum hydride, or borane dimethyl sulfide complex. The reaction is carried out in a suitable solvent, such as tetrahydrofuran. The reaction is generally carried out at temperature of from 0° C. to the refluxing temperature of the solvent. Generally, the reactions require 1 to 72 hours. The product can be isolated and purified by techniques well known in the art, such as quench of borane or aluminum complexes, extraction, evaporation, trituration, chromatography, and recrystallization.

In Reaction Scheme I, optional step 2, an appropriate 3-aryl-3-(ω-THP-protected-hydroxyethyl)-pyrrolidine of formula 44 is alkylated with an appropriate alkyl halide, X—CH$_2$—(CH$_2$)$_n$—Ar$_2$, to an N-arylalkyl-3-aryl-3-(ω-THP-protected-hydroxyethyl)-pyrrolidine of formula 45. An appropriate alkyl halide, X—CH$_2$—(CH$_2$)$_n$—Ar$_2$, is one in which X is chloro, bromo, or iodo; n is as desired in the final product of formula (1), and $Ar_2$ is as desired in formula (1).

For example, an appropriate 3-aryl-3-(ω-THP-protected-hydroxyethyl) pyrrolidine of formula 45 is contacted with techniques well known in the art, such as extraction, evaporation, trituration, chromatography, and recrystallization.

In Reaction Scheme I, optional step 3, an appropriate 3-aryl-3-(ω-THP-protected-hydroxyethyl) pyrrolidine of formula 44 is aroylated with an appropriate aroyl halide, aryl anhydride, or aryl mixed anhydride, A—C(O)—(CH$_2$)$_n$—Ar$_2$, to an N-aroyl-3-aryl-3-(ω-THP-protected-hydroxyethyl) pyrrolidine of formula 46. An appropriate aroyl halide, aryl anhydride, or aryl mixed anhydride, A—C(O)—(CH$_2$)$_n$—Ar$_2$, is one in which A is an activated leaving group, such as chloro or bromo, an anhydride, or mixed anhydride, n is as desired in the final product of formula (1), and $Ar_2$ is as desired in formula (1).

For example, an appropriate 3-aryl-3-(ω-THP-protected-hydroxyethyl) pyrrolidine of formula 44 is contacted with 1 to 1.5 molar equivalents of an appropriate aroyl halide, aryl anhydride, or aryl mixed anhydride, A—C(O)—(CH$_2$)$_n$—Ar$_2$. The reaction is carried out in a suitable solvent, such as tetrahydrofuran, dichloromethane, acetonitrile, dimethylformamide, or pyridine. The reaction is carried out in the presence of a base, such as sodium carbonate, potassium carbonate, sodium bicarbonate, triethylamine diisopropylethylamine, or pyridine. The reaction is generally carried out at temperatures of from −20° C. to 50° C.

Generally, the reactions require 1 to 24 hours. The product can be isolated and purified by techniques well known in the art, such as extraction, evaporation, trituration, chromatography, and recrystallization.

In Reaction Scheme I, step 4, an N-arylalkyl-3-aryl-3-(ω-THP-protected-hydroxyethyl) pyrrolidine of formula 45 is deprotected to give an N-arylalkyl-3-aryl-3-(ω-hydroxyethyl) pyrrolidine of formula 16 which gives rise to compounds of formula (1) in which $G_1$ is —$CH_2$—, $G_2$ is —$CH_2$—, m is 2, n, $Ar_1$, and $Ar_2$ are as desired in the final product of formula (1) or give rise after deprotection to $Ar_1$ as desired in the final product of formula (1).

For example, an N-arylalkyl-3-aryl-3-(ω-THP-protected-hydroxyethyl) pyrrolidine of formula 16 is treated with a in the final product of formula (1) or give rise after deprotection to $Ar_1$ as desired in the final product of formula (1).

Reaction Scheme J

Reaction Scheme J is an alternate scheme for preparing some intermediates giving rise to compounds of formula (1) wherein m is 2 and $G_1$ is —$CH_2$— and $G_2$ is —$C(O)$— and for preparing some intermediates giving rise to compounds of formula (1) wherein m is 2 and $G_1$ is —$C(O)$— and $G_2$ is —$CH_2$—.

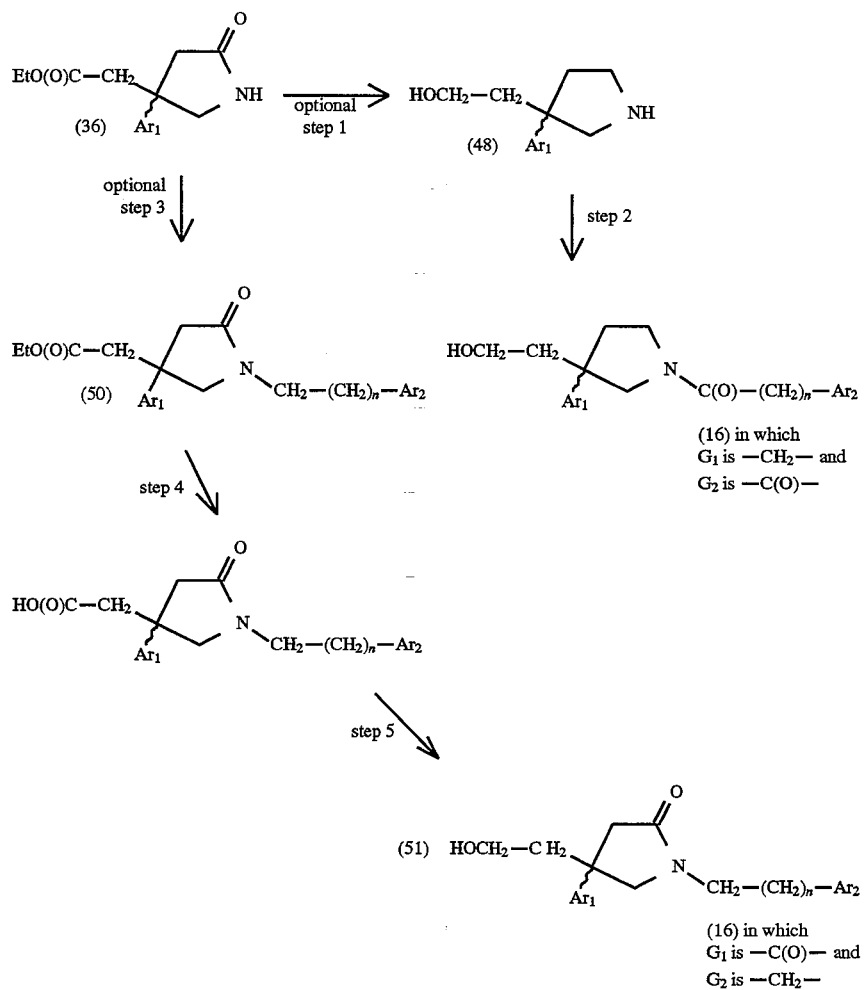

suitable acid, such as p-toluenesulfonic acid. The reaction is carried out in a suitable solvent, such as methanol or ethanol. The product is isolated by evaporation and purified by techniques well known in the art, such as extraction, evaporation, trituration, chromatography, and recrystallization.

In Reaction Scheme I, step 4, an N-aroyl-3-aryl-3-(ω-THP-protected-hydroxyethyl) pyrrolidine of formula 46 is deprotected, as taught above, to give an an N-aroyl-3-aryl-3-(ω-hydroxyethyl) pyrrolidine of formula 16 which gives rise to compounds of formula (1) in which $G_1$ is —$CH_2$—, $G_2$ is —$C(O)$—, and m is 2, n, $Ar_1$, and $Ar_2$ are as desired In Reaction Scheme J, optional step 1, an appropriate 5-oxo-3-aryl-3-acetic acid ester pyrrolidine of formula 36 is reduced to give a 3-aryl-3-(ω-hydroxyethyl) pyrrolidine of formula 48.

For example, an appropriate 5-oxo-3-aryl-3-acetic acid ester pyrrolidine of formula 36 is contacted with a suitable reducing agent, such as lithium aluminum hydride, aluminum hydride, or borane dimethyl sulfide complex. The reaction is carried out in a suitable solvent, such as tetrahydrofuran. The reaction is generally carried out at temperature of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme J, step 2, an appropriate 3-aryl-3-(ω-hydroxyethyl)-pyrrolidine of formula 48 is aroylated with an appropriate aroyl halide, aryl anhydride, or aryl mixed anhydride, A—C(O)—(CH$_2$)$_n$—Ar$_2$, to an N-aroyl-3-aryl-3-(ω-hydroxyethyl)-pyrrolidine of formula 16. An appropriate aroyl halide, aryl anhydride, or aryl mixed anhydride, A—C(O)—(CH$_2$)$_n$—Ar$_2$, is one in which A is an activated leaving group, such as chloro, bromo, or iodo; an anhydride, or mixed anhydride, n is as desired in the final product of formula (1), and Ar$_2$ is as desired in formula (1).

For example, an appropriate 3-aryl-3-(ω-hydroxyethyl) pyrrolidine of formula 48 is contacted with 1 to 1.1 molar equivalents of an appropriate aroyl halide, aryl anhydride, or aryl mixed anhydride, A—C(O)—(CH$_2$)$_n$—Ar$_2$. The reaction is carried out in a suitable solvent, such as tetrahydrofuran, N,N-dimethylaniline, or diethyl ether. The reaction is carried out in the presence of a base, such as N,N-dimethylaniline, sodium hydride, potassium t-butoxide, or lithium diisopropylamide. The reaction is generally carried out at temperatures of from –20° C. to 50° C. Generally, the reactions require 1 to 24 hours. The product can be isolated and purified by techniques well known in the art, such as extraction, evaporation, trituration, chromatography, and recrystallization.

In Reaction Scheme J, optional step 3, an appropriate 5-oxo-3-aryl-3-acetic acid ester pyrrolidine of formula 36 is alkylated with an appropriate alkyl halide, X—CH$_2$—(CH$_2$)$_n$—Ar$_2$, to an N-arylalkyl-5-oxo-3-aryl-3-acetic acid ester pyrrolidine of formula 50. An appropriate alkyl halide, X—CH$_2$—(CH$_2$)$_n$—Ar$_2$, is one in which X is chloro, bromo, or iodo; n is as desired in the final product of formula (1), and Ar$_2$ is as desired in formula (1).

For example, an appropriate 5-oxo-3-aryl-3-acetic acid ester pyrrolidine of formula 36 is contacted with from 1.0 to 1.2 molar equivalents of an appropriate alkyl halide, X—CH$_2$—(CH$_2$)$_n$—Ar$_2$. The reaction is carried out in a suitable solvent, such as tetrahydrofuran, dimethyl sulfoxide, acetonitrile, or dimethylformamide. The reaction is carried out in the presence of a base, such as sodium hydride, sodium hexamethyldisilazide, potassium t-butoxide. The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme J, step 4, an appropriate N-arylalkyl-5-oxo-3-aryl-3-acetic acid ester pyrrolidine of formula 50 is hydrolyzed to give an N-arylalkyl-5-oxo-3-aryl-3-acetic acid pyrrolidine of formula 51.

For example, an appropriate N-arylalkyl-5-oxo-3-aryl-3-acetic acid ester pyrrolidine of formula 50 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme J, step 5, an appropriate N-arylalkyl-5-oxo-3-aryl-3-acetic acid pyrrolidine of formula 51 is reduced to give a 5-oxo-3-aryl-3-(2-hydroxyethyl) pyrrolidine of formula 16.

For example, an appropriate 5-oxo-3-aryl-3-acetic acid pyrrolidine of formula 51 is contacted with a suitable borane reagent, such as borane dimethyl sulfide complex. The reaction is carried out in a suitable solvent, such as tetrahydrofuran. The reaction is generally carried out at a temperature of from 0° C. to the refluxing temperature of the solvent. When complete, the reaction is quenched by the careful addition of a suitable aqueous acid solution, such as 1M hydrochloric acid solution. The product can be isolated and purified by techniques well known in the art, such as extraction, evaporation, triteration, chromatography, and recrystallization.

Alternately, an appropriate 5-oxo-3-aryl-3-acetic acid pyrrolidine of formula 51 can be reduced by formation of a mixed anhydride intermediate and contacting the mixed anhydride intermediate with a suitable mild reducing agent, such as sodium borohydride to give 5-oxo-3-aryl-3-(2-hydroxyethyl) pyrrolidine of formula 16.

For example, an appropriate 5-oxo-3-aryl-3-acetic acid pyrrolidine of formula 51 is contacted with 1.2 to 1.7 equivalents of a suitable base, such as N-methylmorpholine, in a suitable solvent, such as tetrahydrofuran or diethyl ether. The reaction mixture is cooled to a temperature of between –50° C. and 0° C. with –25° C. to –20° C being preferred, before the addition of 1.2 to 1.7 equivalents of isobutyl chloroformate. The reaction is allowed to stir for 30 minutes to 3 hours to allow for the formation of the mixed anhydride. After the formation of the mixed anhydride is complete, sodium borohydride is added. The product can be isolated and purified by techniques well known in the art, such as extraction, evaporation, chromatography, and recrystallization.

Reaction Scheme K

Reaction Scheme K is a general route for preparing some piperidine compounds of formula 18 which give rise to compounds of formula (1),in which Y$_1$ is —C(O)NHR$_5$, —C(O)NR$_6$R$_7$, or —C(O)NR$_8$R$_9$ and Y$_2$ is a radical chosen from the group

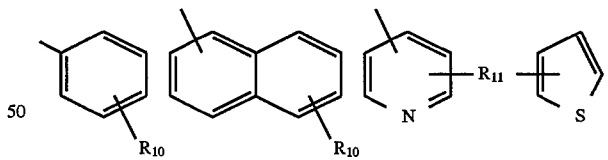

Reaction Scheme K

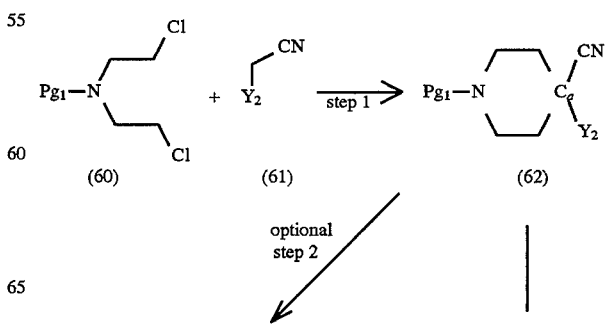

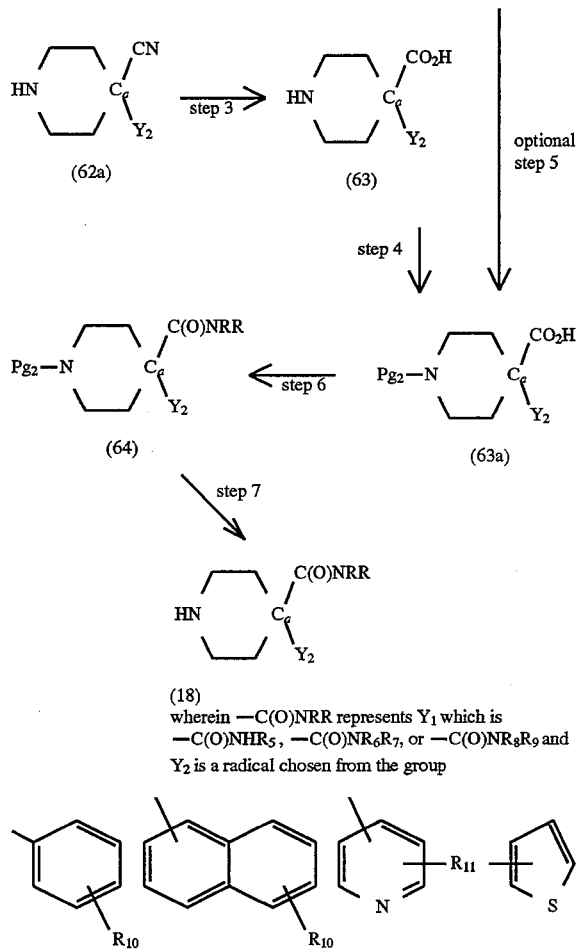

wherein —C(O)NRR represents Y₁ which is
—C(O)NHR₅, —C(O)NR₆R₇, or —C(O)NR₈R₉ and
Y₂ is a radical chosen from the group In Reaction Scheme K, step 1, an appropriate protected bis-(2-chloroethyl)-amine of formula 60 is alkylated with an appropriate aryl acetonitrile of formula 61 to give an protected 4-aryl-4-cyano-piperidine of of formula 62. An appropriate protected bis-(2-chloroethyl)-amine of formula 60 is one in which the protecting group, Pg₁, may be C₁–C₄ alkyl, benzyl, substituted benzyl, tosyl, benzenesulfonyl, or a carbamate, such as t-butoxycarbonyl or ethoxycarbonyl. An appropriate aryl acetonitrile of formula 61 is one in which Y₂ is as desired in the final product of formula (1). Alkylations of this type are well known and appreciated in the art, T. Cammack and P. C. Reeves, *J. Heterocyclic Chem.* 23, 73–75 (1986) and C. V. Bercz and R. D. Ice, *J. Pharmaceutical Sci.*, 61, 1316–1317 (1972).

For example, an appropriate protected bis-(2-chloroethyl)-amine of formula 60 is contacted with an appropriate aryl acetonitrile of formula 61. The reaction is carried out in the presence of a base, such as sodium amide, sodium hydride, sodium hexamethyldisilazide, potassium t-butoxide, and lithium diisopropylamide. The reaction is carried out in a solvent, such as dimethyl sulfoxide and tetrahydrofuran. The reaction can be carried out in the presence of 0.01 to 0.5 molar equivalents of a suitable catalyst, such as sodium iodide or potassium iodide. The reaction is generally carried out at temperatures of from 0° C. to 80° C. Generally, the reactions require 1 to 72 hours. The product can be isolated and purified by techniques well known in the art, such as extraction, evaporation, trituration, chromatography, and recrystallization.

Alternately, for example, an appropriate protected bis-(2-chloroethyl)-amine of formula 60 is contacted with an appropriate aryl acetonitrile of formula 61 under phase transfer conditions. The reaction is carried out in a solvent system consisting of an organic phase and an aqueous phase. The reaction is carried out in the presence of a hydroxide base, such as sodium hydroxide or potassium hydroxide. The reaction is carried out in the presence of a suitable catalyst including quaternary ammonium and phosphonium salts, such as tetrabutylammonium bromide, tetrabutylammonium hydrogen sulfate, benzyltrimethylammonium chloride, hexadecyltributylphosphonium bromide, and the like. The reaction is vigorously stirred and is generally carried out at temperatures of between 0° C. and 100° C. Generally, the reactions require 1 to 24 hours. The product can be isolated and purified by techniques well known in the art, such as extraction, evaporation, trituration, chromatography, and recrystallization.

In Reaction Scheme K, optional step 2, a protected 4-aryl-4-cyano-piperidine of formula 62 is deprotected to give a 4-aryl-4-cyano-piperidine of formula 62a. The removal of amine protecting groups is well known and appreciated in the art and is described in *Protecting Groups in Organic Synthesis* by T. Greene, Wiley-Interscience (1981). The removal of the amine protecting group $P_{g1}$, in this step may be required when $Pg_1$ is benzyl to allow the hydrolysis of the nitrile to the acid in step 3.

In Reaction Scheme K, step 3, a 4-aryl-4-cyano-piperidine of formula 62a is hydrolyzed to a 4-aryl-4-carboxylic acid-piperidine of formula 63. The hydrolysis of nitriles to acids may be carried out under acidic or basic conditions as is well known and appreciated in the art.

In Reaction Scheme K, step 4, a 4-aryl-4-carboxylic acid-piperidine of of formula 63 is protected to give a protected 4-aryl-4-carboxylic acid-piperidine of formula 63a. The selection and use of amine protecting groups, $P_{g2}$, is well known and appreciated in the art and is described in *Protecting Groups in Organic Synthesis* by T. Greene, Wiley-Interscience (1981).

In Reaction Scheme K, optional step 5, a protected 4-aryl-4-cyano-piperidine of of formula 62 is hydrolyzed to a a protected 4-aryl-4-carboxylic acid-piperidine of of formula 63a. The hydrolysis of nitriles to acids may be carried out under acidic or basic conditions as is well known and appreciated in the art. The selection and use of hydrolysis conditions which are compatible with the protecting groups, $P_{g1}$, is well known and appreciated in the art. For protected 4-aryl-4-carboxylic acid-piperidine of formula 63a prepared by Scheme K, optional step 5, the protecting groups $P_{g1}$ and $P_{g2}$ are necessarily the same protecting group.

In Reaction Scheme K, step 6, a protected 4-aryl-4-carboxylic acid-piperidine of formula 63a undergoes an amidation reaction with an appropriate amine, NHRR, to give a protected 4-aryl-4-carboxylic acid amide-piperidine of formula 64. An appropriate amine, NHRR, includes amines of the formulas $NH_2R_5$, $NHR_6R_7$, or $NHR_8R_9$, in which $R_5$, $R_6$ and $R_7$, and $R_8$ and $R_9$ are as desired in the final compound of formula (1).

An amidation reaction. may proceed through the acid of formula 63a or the acid function of a compound of formula 3a may be first converted to an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; an activated ester, such as phenol ester, p-nitrophenol ester, 2,4-dinitrophenol ester, pentafluorophenol ester, pentachlorophenol ester, N-hydroxysuccinimide ester, N-hydroxyphthalimide ester, 1-hydroxy-1H-benztriazole ester, and the like; activated amide, such as imidazole, dimethylpyrazole, triazole, or tetrazole; or the intermediate formed in the presence of coupling agents, such as dicyclohexylcarbodiimide or 1-(3-dimethylaminopropyl)-3-ethylcarbodiimide. Activated intermediates may be prepared and used directly, or are prepared and isolated before the addition of an appropriate amine, NHRR of the formulas NH$_2$R$_5$, NHR$_6$R$_7$, or NHR$_8$R$_9$. Alternately, activated intermediates may be prepared isolated and purified before the addition of an appropriate amine, NHRR of the formulas NH$_2$R$_5$, NHR$_6$R$_7$, or NHR$_8$R$_9$. The use and formation of activated intermediates is well known and appreciated in the art.

For example, an acid compound of formula 63a is contacted with a slight molar excess of an appropriate amine, NHRR of the formulas NH$_2$R$_5$, NHR$_6$R$_7$, or NHR$_8$R$_9$, or a salt of an appropriate amine and 1-hydroxybenzotriazole hydrate in the presence of a slight molar excess of a coupling agent, such as dicyclohexylcarbodiimide or 1-(3-dimethyaminopropyl)-3-ethylcarbodiimide. The reaction is carried out in the presence of a suitable base, such as diisopropylethyl amine, if the salt of an amine is used an additional equimolar molar amount of a suitable base is added. The reaction is carried out in a suitable solvent, such as dichloromethane or chloroform. The product can be isolated and purified by techniques well known in the art, such as extraction, evaporation, chromatography, and recrystallization.

Alternatively, for example, an acid of formula 63a is contacted with 1.2 to 1.7 equivalents of a suitable base, such as N-methylmorpholine, in a suitable solvent, such as tetrahydrofuran. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between −50° C. and 0° C. an appropriate amine, NHRR of the formulas NH$_2$R$_5$, NHR$_6$R$_7$, or NHR$_8$R$_9$, is added, if the salt of an appropriate amine is used an additional equimolar molar amount of a suitable base is added. The reaction may, after the addition of amine is complete, be warmed to room temperature. Generally, the reaction requires from 2 to 48 hours. The product can be isolated and purified by techniques well known in the art, such as extraction, evaporation, chromatography, and recrystallization.

In Reaction Scheme K, step 7 a protected 4-aryl-4-carboxylic acid amide-piperidine of formula 64 is deprotected to give a piperidine of formula 18. The removal of amine protecting groups is well known and appreciated in the art and is described in *Protecting Groups in Organic Synthesis* by T. Greene, Wiley-Interscience (1981).

Reaction Scheme K.1

Reaction Scheme K.1 is a general route for preparing some piperidine compounds of formula 18 which give rise to compounds of formula (1) in which Y$_1$ is —C(O)NHR$_5$ in which R$_5$ is hydrogen and Y$_2$ is a radical chosen from the group

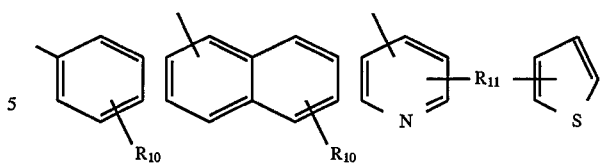

Reaction Scheme K.1

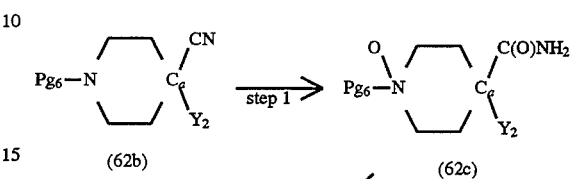

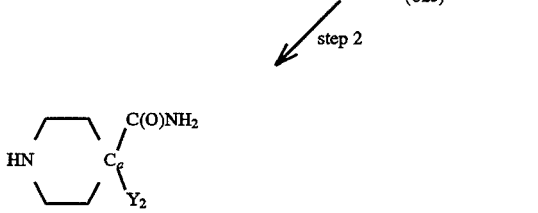

(18)
wherein Y$_1$ which is —C(O)NHR$_5$ in which R$_5$ is hydrogen and Y$_2$ is a radical chosen from the group

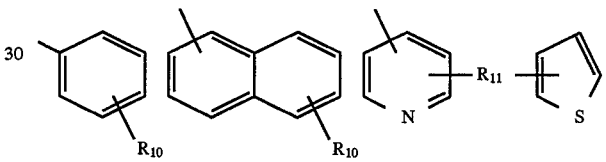

In Reaction Scheme K.1, step 1, an appropriate 4-aryl-4-cyano-piperidine of formula 62b is hydrolyzed to a 4-aryl-4-carboxylic acid amide-piperidine N-oxide of formula 62c.

An appropriate 4-aryl-4-cyano-piperidine of formula 62b is one in which the protecting group, Pg6 is benzyl or substituted benzyl and Y$_2$ is as desired in the final product of formula (1). Appropriate 4-aryl-4-cyano-piperidines of formula 62b are readily available as described in Reaction Scheme K and may also be obtained by benzylation of a 4-aryl-4-cyano-piperidine of formula 62a using a suitable benzyl halide or substituted benzyl halide as is well known in the art.

For example, an appropriate 4-aryl-4-cyano-piperidine of formula 62b is contacted with basic hydrogen peroxide. *Reagents for Organic Synthesis*, Fieser and Fieser, John Wiley and Sons, Inc. (1967). Alkali metal hydroxides, such as sodium hydroxide or potassium hydroxide are suitable bases for this reaction. The reaction is carried out in a suitable solvent, such as ethanol or methanol. The reaction is carried out at temperatures of from 0° C. to the refluxing temperature of the suitable solvent. Generally, the reaction requires from about 4 hours to 4 days. The product can be isolated and purified by techniques well known in the art, such as extraction, evaporation, trituration, chromatography, and recrystallization.

In Reaction Scheme K.1, step 2, an appropriate 4-aryl-4-carboxylic acid amide-piperidine N-oxide of formula 62c is deprotected and reduced to give a piperidine of formula 18 wherein Y$_1$ is —C(O)NHR$_5$ in which R$_5$ is hydrogen.

The removal of amine protecting groups, such as benzyl and substituted benzyl is well known and appreciated in the art and is described in *Protecting Groups in Organic Syn-*

*thesis* by T. Greene, Wiley-Interscience (1981). The reduction of amine oxides is also well known in the art. It is understood that the amine deprotection and amine oxide reduction may be carried out at the same time or may be carried out sequentially.

Reaction Scheme L

Reaction Scheme L is a general route for preparing some piperidine compounds of formula 18 which give rise to compounds of formula (1) in which $Y_1$ is —C(O)NHR$_5$, —C(O)NR$_6$R$_7$, or —C(O)NR$_8$R$_9$ and $Y_2$ is a radical chosen from the group desired in the final product of formula (1). For example, a protected piperidine-4-carboxylic acid ethyl ester of formula 67 is contacted with from 1.0 to 3.0 molar equivalents of benzyl halide or a substituted benzyl halide. The reaction is carried out in the presence of 1.0 to 1.5 molar equivalents of a suitable base, such as sodium hexamethyldisilazide, sodium hydride, potassium t-butoxide, or lithium diisopropylamide. The reaction is carried out in a suitable solvent, such as tetrahydrofuran, dimethylformamide, or dimethyl sulfoxide. The reaction is generally carried out at temperatures of from −78° C. to 0° C. Generally, the reactions require 1 to 24 hours. The product can be isolated and purified by techniques well known in the art, such as

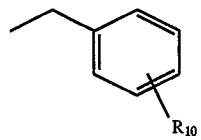

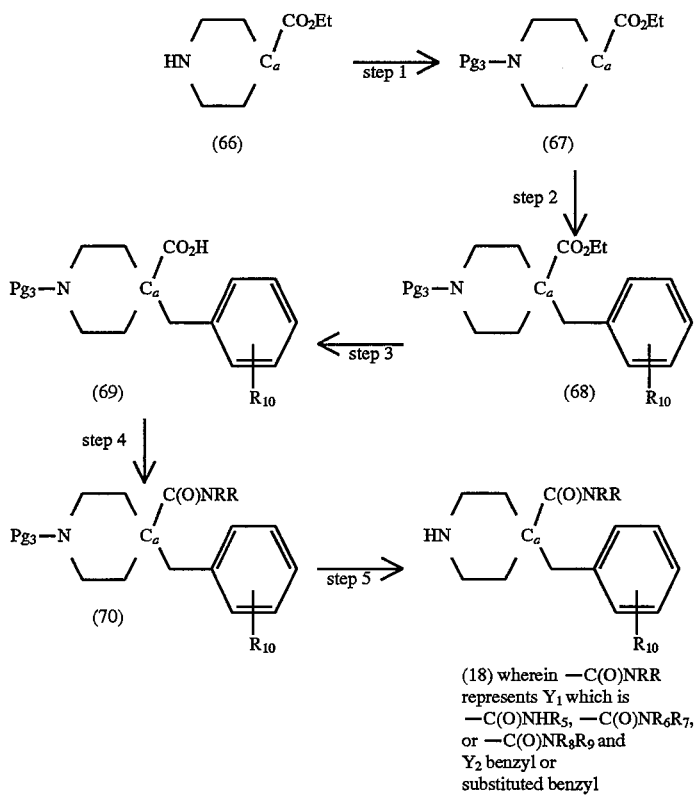

extraction, evaporation, trituration, chromatography, and recrystallization.

In Reaction Scheme L, step 1, piperidine-4-carboxylic acid ethyl ester, compound 66 is protected to give a protected piperidine-4-carboxylic acid ethyl ester of formula 67. The selection and use of amine protecting groups, Pg3, is well known and appreciated in the art and is described in *Protecting Groups in Organic Synthesis* by T. Greene, Wiley-Interscience (1981). The use of carbamate protecting groups, such as benzyloxycarbonyl and t-butoxycarbonyl is preferred.

In Reaction Scheme L, step 2, a protected piperidine-4-carboxylic acid ethyl ester of formula 67 is reacted with an appropriate benzylating agent to give a protected 4-benzylated-piperidine-4-carboxylic acid ethyl ester of formula 68. An appropriate benzylating agent is one which transfers an benzyl or substituted benzyl in which R10 is as Reaction Scheme L, step 3, a protected 4-benzylated-piperidine-4-carboxylic acid ethyl ester of formula 68 is hydrolyzed to give a protected 4-benzylated-piperidine-4-carboxylic acid of formula 69.

For example, a protected 4-benzylated-piperidine-4-carboxylic acid ethyl ester of formula 68 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme L, step 4, a protected 4-benzylated-piperidine-4-carboxylic acid of formula 69 undergoes an amidation reaction; as generally taught in Reaction Scheme K, step 6; with an appropriate amine, NHRR, to give a protected 4-benzylated-piperidine-4-carboxylic acid amide of formula 70. An appropriate amine, NHRR, includes amines of the formulas $NH_2R_5$, $NHR_6R_7$, or $NHRSR_9$, in which $R_5$, $R_6$ and $R_7$, and $R_8$ and $R_9$ are as desired in the final compound of formula (1).

In Reaction Scheme L, step 5, a protected 4-benzylated-piperidine-4-carboxylic acid amide of formula 70 is deprotected to give a 4-benzylated-piperidine-4-carboxylic acid amide of formula 18 in which Y1 is —$C(O)NHR_5$, -$C(O)NR_6R_7$, or —$C(O)NR_8R_9$ and $Y_2$ benzyl or substituted benzyl. The removal of amine protecting groups is well known and appreciated in the art and is described in Protecting Groups in Organic Synthesis by T. Greene, Wiley-Interscience (1981).

Reaction Scheme M

Reaction Scheme M is a general routes for preparing piperidine compounds of formula 18 which give rise to compounds of formula (1) in which $Y_1$ and $Y_2$ together with their attached carbon form a spirocyclic ring chosen from the group

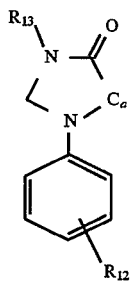

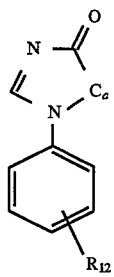

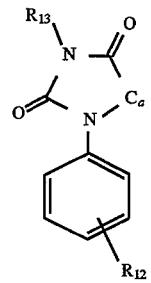

Some of the piperidine compounds of formula 18 in which $Y_1$ and $Y_2$ together with their attached carbon form a spirocyclic ring are known in the art or can be prepared by methods known analogously in the art. P. L. Feldman and M. F. Bracken JOC 55, 4207–4209 (1990); L. D. Wise et al. J. Med. Chem. 28, 1811–1817 (1985); and G. M. Carrera, Jr. and D. S. Garvey, J. Heterocyclic Chem. 29, 847–850 (1992).

Reaction Scheme M

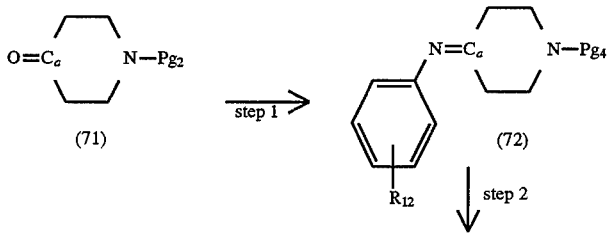

-continued
Reaction Scheme M
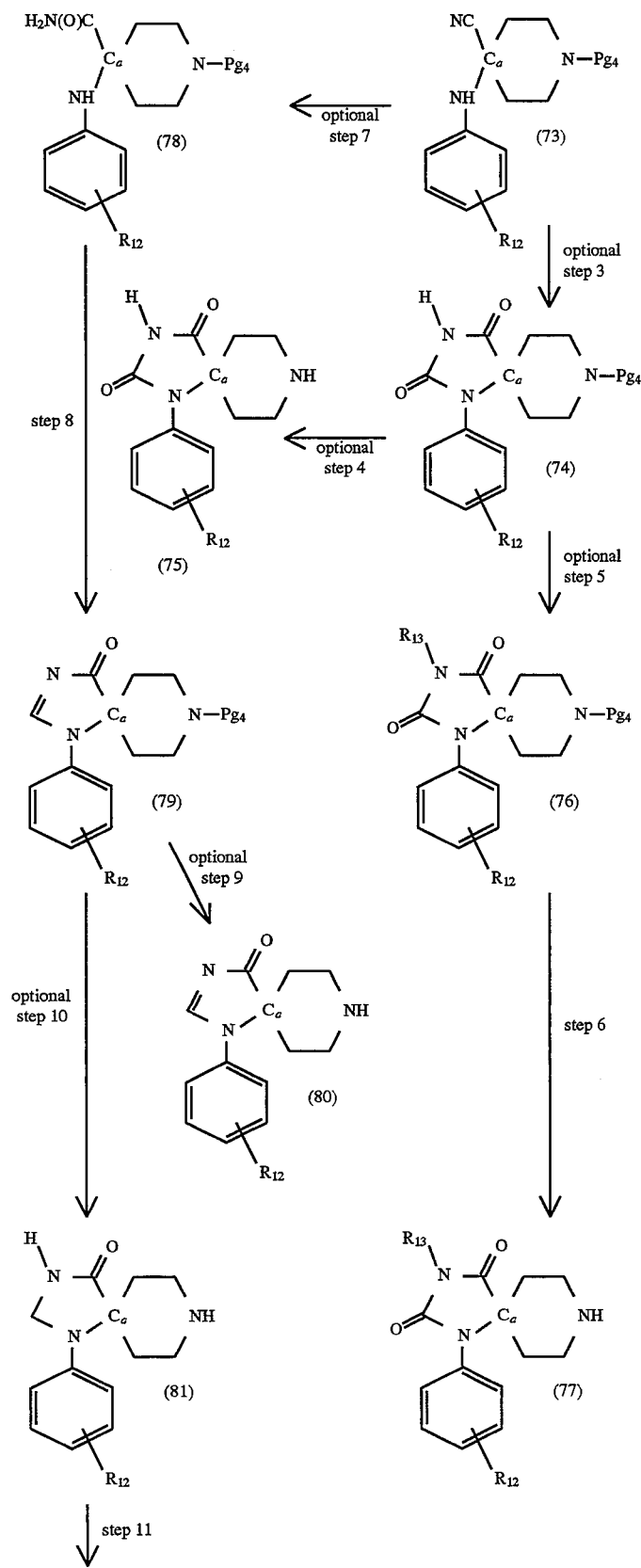

-continued
Reaction Scheme M

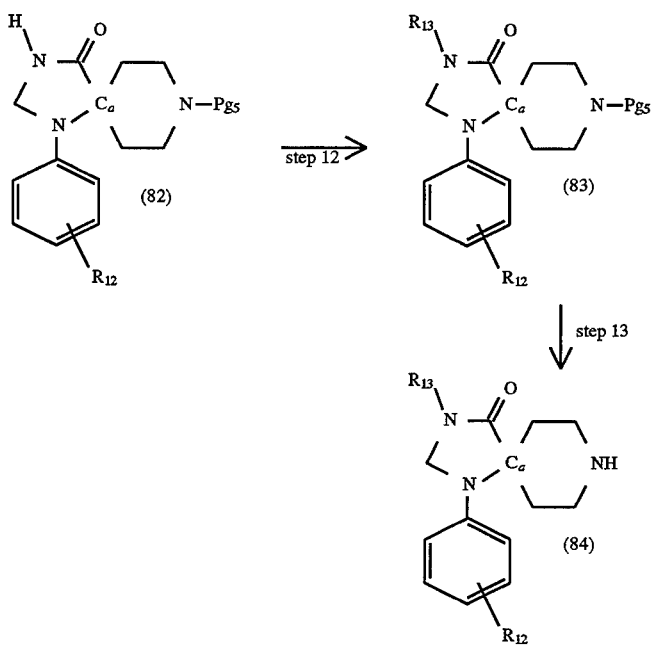

In Reaction Scheme M, step 1, a protected piperidin-4-one of formula 71 is condensed with the appropriate aniline to give a protected imine of formula 72. An appropriate aniline is one in which gives rise to an imine of formula in which $R_{12}$ is as is desired in the final compound of formula (1). Generally, the protected imine of formula 72 is not isolated before it is converted to the protected 4-cyano piperidine of formula 73. The formation of protected imines of formula 72 is well known and appreciated in the art.

In Reaction Scheme M, step 2, a protected imine of formula 72 is converted to a protected 4-cyano piperidine of formula 73. A protected imine of formula 72 is contacted with a reagent which causes it to undergo a Strecker reaction, such as hydrogen cyanide, potassium cyanide, sodium cyanide, acetone cyanohydrin, or trimethylsilyl cyanide. The conditions used depend on the method chosen for carrying out the Strecker reaction. The Strecker reaction and the choice of conditions for carrying out the Strecker reaction are well known and appreciated in the art.

In Reaction Scheme M, optional step 3, a protected 4-cyano piperidine of formula 73 is converted to a protected 1-phenyl-1,3,8-triazaspiro[4.5]decane-2,4-dione of formula 74.

For example, a protected 4-cyano piperidine of formula 73 is contacted with an equimolar amount of chlorosulfonyl isocyanate to give an unpurified intermediate. The reaction is carried out in a suitable solvent, such as dichloromethane. Generally, the reaction is carried out at temperatures of from 0° C. to 50° C. The reaction generally requires from 10 minutes to 3 hours. The unpurified intermediate is recovered by evaporation in vacuo. The unpurified intermediate is contacted with a suitable aqueous acid, such as 1M hydrochloric acid, and is heated to from 50° C. to the refluxing temperature of the suitable aqueous acid. The reaction generally requires from 30 minutes to 4 hours. The product can be isolated and purified by techniques well known in the art, such as cooling, adjusting of pH, extraction, evaporation, chromatography, and recrystallization.

In Reaction Scheme M, optional step 4, a protected 1-phenyl-1,3,8-triazaspiro[4.5]decane-2,4-dione of formula 74 is deprotected to give a 1-phenyl-1,3,8-triazaspiro[4.5]decane-2,4-dione of formula 75. The removal of amine protecting groups is well known and appreciated in the art and is described in Protecting Groups in Organic Synthesis by T. Greene, Wiley-Interscience (1981); R. A Olofson, JOC 49, 2936–2938 (1991); and Y-K. Shue et al., JOC 56, 2936–2938 (1991).

In Reaction Scheme M, optional step 5, a protected 1-phenyl-1,3,8-triazaspiro[4.5]decane-2,4-dione of formula 74 is benzylated or alkylated with an appropriate benzylating or alkylating agent to give a protected 3-substituted-1-phenyl-1,3,8-triazaspiro[4.5]decane-2,4-dione of formula 76. An appropriate benzylating or alkylating agent is one which transfers a benzyl, substituted benzyl, or $C_1$–$C_6$ alkyl as is required in $Rg_{13}$ in the final product of formula (1).

For example, a protected 1-phenyl-1,3,8-triazaspiro[4.5]decane-2,4-dione of formula 74 is contacted with 1.0 to 3.0 molar equivalents of an appropriate benzylating or alkylating agent, such as benzyl halide, a substituted benzyl halide, or a $C_1$–$C_6$ alkyl halide. The reaction is carried out in the presence of 1.0 to 1.5 molar equivalents a suitable base, such as sodium hydroxide, potassium hydroxide, sodium hexamethyldisilazide, sodium hydride, potassium t-butoxide, or lithium diisopropylamide. The reaction is carried out in a suitable solvent, such as tetrahydrofuran, ethanol, dimethylformamide, or dimethyl sulfoxide. The reaction is generally carried out at temperatures of from 0° C. to the refluxing temperature of the solvent. Generally, the reactions require 1 to 24 hours. The product can be isolated and purified by techniques well known in the art, such as extraction, evaporation, trituration, chromatography, and recrystallization.

In Reaction Scheme M, step 6, a protected 3-substituted-1-phenyl-1,3,8-triazaspiro[4.5]decane-2,4-dione of formula 76 is deprotected to give a 3-substituted-1-phenyl-1,3,8-triazaspiro[4.5]decane-2,4-dione of formula 77. The removal of amine protecting groups is well known and appreciated in the art and is described in Protecting Groups in Orqanic Synthesis by T. Greene, Wiley-Interscience (1981); R. A Olofson, JOC 49, 2936–2938 (1991); and Y-K. Shue et al., JOC 56, 2936–2938 (1991).

In Reaction Scheme M, optional step 7, a protected 4-cyano-piperidine of formula 73 is hydrolyzed to give a protected piperidine-4-carboxylic acid amide of formula 78. The hydrolysis of nitriles to carboxylic acid amides under acidic conditions is well known and appreciated in the art.

In Reaction Scheme M, step 8, a protected piperidine-4-carboxylic acid amide of formula 78 is converted to a protected 1-phenyl-1,3,8-triazaspiro[4.5]dec-2-en-4-one of formula 79.

For example, a protected piperidine-4-carboxylic acid amide of formula 78 is contacted with an excess of dimethoxy-N,N-dimethylmethanamine. The reaction is carried out in a suitable solvent, such as toluene. Generally, the reaction is carried out at temperatures of from ambient temperature to the refluxing temperature of the solvent. The reactions generally require from 12 to 72 hours. The product can be isolated and purified by techniques well known in the art, such as extraction, evaporation, trituration, chromatography, and recrystallization.

In Reaction Scheme M, optional step 9, a protected 1-phenyl-1,3,8-triazaspiro[4.5]dec-2-en-4-one of formula 79 is deprotected to give a 1-phenyl-1,3,8-triazaspiro[4.5]dec-2-en-4-one of formula 80. The removal of amine protecting groups is well known and appreciated in the art and is described in Protecting Groups in Organic Synthesis by T. Greene, Wiley-Interscience (1981); R. A Olofson, JOC 49, 2936–2938 (1991); and Y-K. Shue et al., JOC 56, 2936–2938 (1991). In Reaction Scheme M, optional step 10, a protected 1-phenyl-1,3,8-triazaspiro[4.5]dec-2-en-4-one of formula 79 is reduced to a 1-phenyl-1, 3,8-triazaspiro[4.5]decan-4-one of formula 81 or a protected 1-phenyl-1,3,8-triazaspiro[4.5]decan-4-one of formula 82. A 1-phenyl-1,3,8-triazaspiro[4.5]decan-4-one of formula 81 is the product of Reaction Scheme M, optional step 10, when $Pg_4$ is a protecting group which is removed be hydrogenation, such as benzyl or substituted benzyl. A protected 1-phenyl-1,3,8-triazaspiro[4.5]decan-4-one of formula 82 is the product of Reaction Scheme M, optional step 10, when a hydrogenation stable protecting group, such as methyl is used. For protected 1-phenyl-1, 3,8-triazaspiro[4.5]decan-4-one of formula 82 prepared by Scheme M, optional step 10, the protecting groups $Pg_4$ and $Pg_5$ are necessarily the same protecting group.

For example, a protected 1-phenyl-1, 3,8-triazaspiro[4.5]dec-2-en-4-one of formula 79 is contacted with hydrogen in the presence of a suitable catalyst, such as 5% platinum-on-carbon, 10% platinum-on-carbon, 5% palladium-on-carbon, 10% palladium-on-carbon, Pearlman's catalyst, platinum oxide, and palladium oxide. The reaction is carried out in a suitable solvent, such as ethanol, methanol, ethyl acetate, and water. The reaction is generally carried out at temperatures of from ambient temperature to 50° C. The reaction is carried out at pressures of from 15 psi to 120 psi in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization. In Reaction Scheme M, step 11, a 1-phenyl-1,3,8-triazaspiro[4.5]decan-4-one of formula 81 is protected to give a protected a 1-phenyl-1,3,8-triazaspiro[4.5]decan-4-one of formula 82. The selection and use of suitable amine protecting groups is well known and appreciated in the art and is described in Protecting Groups in Organic Synthesis by T. Greene, Wiley-Interscience (1981).

In Reaction Scheme M, step 12, a protected 1-phenyl-1,3, 8-triazaspiro[4.5]decan-4-one of formula 82 is benzylated or alkylated with an appropriate benzylating or alkylating agent to give a protected 3-substituted-1-phenyl-1,3,8-triazaspiro[4.5]decan-4-one of formula 83. An appropriate benzylating or alkylating agent is one which transfers a benzyl, substituted benzyl, or $C_1$–$C_6$ alkyl as is required in R13 in the final product of formula (1).

For example, a protected 1-phenyl-1,3,8-triazaspiro[4.5]decan-4-one of formula 82 is contacted with 1.0 to 3.0 molar equivalents of an appropriate benzylating or alkylating agent, such as benzyl halide, a substituted benzyl halide, or a $C_1$–$C_6$ alkyl halide. The reaction is carried out in the presence of 1.0 to 1.5 molar equivalents a suitable base, such as sodium hexamethyldisilazide, sodium hydride, potassium t-butoxide, or lithium diisopropylamide. The reaction is carried out in a suitable solvent, such as tetrahydrofuran, dimethylformamide, or dimethyl sulfoxide. The reaction is generally carried out at temperatures of from –10° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme M, step 13, a protected 3-substituted-1-phenyl-1,3,8-triazaspiro[4.5]decan-4-one of formula 83 is deprotected to give a 3-substituted-1-phenyl-1,3,8-triazaspiro[4.5]decan-4-one of formula 84. The removal of amine protecting groups is well known and appreciated in the art and is described in Protecting Groups in Organic Synthesis by T. Greene, Wiley-Interscience (1981).

EXAMPLE 1

Synthesis of 1-[2-[3-(3,4-dichloro-phenyl)-1-benzoyl-pyrrolidin-3-yl]-ethyl]-4-phenyl-piperidine-4-carboxylic acid amide 1.1 Synthesis of 3-cyano-3-(3,4-dichloro-phenyl)-pentanedioic diethyl ester (No.027F126)

3,4-Dichlorophenylacetonitrile (10 g, 53.75 mmol) was stirred mechanically in THF (50 mL) at –78° C. and treated dropwise with sodium bis-(trimethylsilyl)amide (108 mL, 1 M; 2 eq.). The reaction slurry was allowed to warm to 20° C. and stirred for 3 hours. The solution was cooled to –78° C. and the slurry was treated with ethyl bromoacetate (12 mL, 107 mmol, 2 eq.). The slurry was again allowed to warm to 20° C. and stirred 18 hours. The slurry was dissolved in ethyl ether and washed with water and brine. The organic phase was dried over magnesium sulfate, filtered, and concentrated in vacuo. The residue was chromatographed on silica gel (400 g) with 20% ethyl acetate to give 15.85 g (82%) of the title compound.

1.1.1 Synthesis of 3-cyano-3-(3,4-dichloro-phenyl)-pentanedioic diethyl ester

Sodium-bis-(trimethylsilyl)amide (7910 mL, 1M, 7910 mmol) was cooled to 0° C. A solution of 3,4-dichlorophenylacetonitrile (700 g, 3763 mmol) in THF (2.50L) was added maintianing the temperature of the reaction mixture between 0° and 20° C. After 1 hour, the above solution is added by candula to a solution of ethyl bromoacetate (910 mL) in THF (1.40L) cooled to 0° C. The addition is carried out at such a rate that the temperature Of the reaction mixture does not rise above 20° C. After 15 minutes, the reaction was quenched by the addition of t-butyl methyl ether (7.0 L) and water (3.5 L). The organic layer was separated and was extracted with water, 5% NaHCO₃, and brine. The organic layer was dried over MgSO₄, filtered, and concentrated in vacuo to obtain a residue. The residue was recrystallized from diethyl ether to give the title compound: mp=69°–71° C.

1.1.2 Synthesis of 3-cyano-3-(3,4-dichloro-phenyl)-pentanedioic acid diethyl ester 3,4-Dichlorophenylacetonitrile (30.0 g, 0.161 mol) and THF (100 mL) were combined and cooled in a dry-ice/acetone bath. Sodium bis-(trimethylsilyl)amide (324 mL, 1.0M in THF, 0.324 mol, 2 eq.) was added dropwise. After the addition was complete, the mixture was allowed to warm to ambient temperature. After 4 h, the mixture was cooled in a dry-ice/acetone bath. Ethyl bromoacetate (36 mL, 0.325 mol) was added dropwise. After the addition was complete, the mixture was allowed to warm to ambient temperature. The reaction mixture was partitioned between diethyl ether and water. The organic layer was extracted with H₂O(3×150 mL), 1N HCl (2×100 mL), 5% NaHCO₃ (2×100 mL), and brine (1×150 mL). The organic layer was dried over MgSO₄, filtered, and concentrated in vacuo to obtain a residue. The residue was recrystallized from diethyl ether to give the title compound:

$R_f$=0.28 (silica gel, 20% ethyl acetate in hexane), mp=68°–69° C.

Analysis: calculated for $C_{16}H_{17}Cl_2NO_4$ C 53.65; H 4.78; N 3.91; Found C 53.69; H 4.79; N 3.93.

1.2 Synthesis of [3-(3,4-dichloro-phenyl)-5-oxo-pyrrolidin-3-yl]-acetic acid ethyl ester (No.027F128)

3-Cyano-3-(3,4-dichloro-phenyl)-pentanedioic acid diethyl ester (10 g; 27.94 mmol) was dissolved in methanol (100 mL) and cobalt(II)chloride hexahydrate (13.2 g, 55.48 mmol) was added. The solution was then cautiously treated with one gram portions of. sodium borohydride (11 g, 290 mmol) over 45 minutes at 20°–30° C. The solution was allowed to stir an additional 1.5 hours and the solution was concentrated in vacuo. The residue was partitioned between dichloromethane and 1N HCl the organic phase was and washed with 1N HCl (700 mL). The organic phase was dried over magnesium sulfate, filtered, and concentrated in vacuo. The residue was chromatographed on silica gel (600 g) with a gradient of 3% to 6% methanol in dichloromethane to give 7.514 g (85%) of the title compound.

1.2.2 Synthesis of [3-(3,4-dichloro-phenyl)-5-oxo-pyrrolidin-3-yl]-acetic acid ethyl ester 3-Cyano-3-(3,4-dichloro-phenyl)-pentanedioic acid diethyl ester (32 g, 89.4 mmol) and ethanol (150 mL) were combined. The mixture was added to Raney nickel (100 g) in a Parr bottle and NH₄OH (40 mL) was added. The reaction was hydrogenated in a Parr shaker at 50 psi for 24 h. The slurry was filtered through a celite pad and the solids were rinsed with ethanol. The filtrate was concentrated in vacuo to obtain a residue. The residue was chromatographed on silica gel (400 g) eluting with 6% methanol in dichloromethane to give the title compound:

$R_f$=0.34 (silica gel, 6% methanol in dichloromethane), mp=87°–90° C.

Analysis: calculated for $C_{14}H_{15}Cl_2NO_3$ C 53.18; H 4.78; N 4.43; Found C 53.34; H 4.71; N 4.51.

1.3 Synthesis of [3-(3,4-dichloro-phenyl)-3-(2-hydroxy-ethyl)-pyrrolidine (No.027F129)

Lithium aluminum hydride (4.0 g, 105 mmol) was stirred in THF (20 mL) and [3-(3,4-dichloro-phenyl)-5-oxo-pyrrolidiny-3-yl]-acetic acid ethyl ester (7.51 g, 23.79 mmol) was added dropwise in THF (50 mL). The slurry was heated to reflux and allowed to stir for 21 hours. The slurry was cooled in an ice bath and sequentially treated dropwise with water (4 mL), 15% NaOH (4 mL), and water (12 mL). The slurry was allowed to stir for 3 hours at 20° C. The organic phase was dried over magnesium sulfate, filtered, and concentrated in vacuo to give 6.37 g of the title compound.

1.3.2 Synthesis of 2-[3-(3,4-dichloro-phenyl)-pyrrolidin-3-yl]-ethanol

A solution of LiAlH₄ (450 mL, 1M in THF, 450 mmol) was cooled in a ice/acetone bath (−10° C.). A solution of H₂SO₄ (99.999%) (12 mL, 225.3 mmol) in THF (35 mL) was added dropwise. (Use caution when adding the H₂SO₄ to the THF and also when adding the H₂SO₄/THF solution to the LiAlH₄.) After the addition was complete, the slurry was stirred for 1 h in an ice bath. The slurry was allowed to warm to ambient temperature and stir for 2 h. A solution of [3-(3,4-dichloro-phenyl)-5-oxo-pyrrolidin-3-yl]-acetic acid ethyl ester (23.2 g, 73.4 mmol) in THF (70 mL) was added dropwise. The slurry was heated to 45°–50° C. for 36 h. The slurry was cooled in an ice bath and a solution of THF:H₂O (1:1, 70 mL) was added dropwise. The slurry was filtered and the solids were rinsed with THF and dichloromethane. The salts were stirred with THF:H₂O:15% NaOH (1L :70 mL :20 mL) for 2 h. The slurry was filtered and the combined filtrates were concentrated in vacuo to obtain a residue. The residue was dissolved in dichloromethane and the solution was dried over MgSO₄, filtered, and concentrated in vacuo to obtain a residue. The residue was recrystallized from diethyl ether to give the title compound:

$R_f$=0.27 (silica gel, 9:1:0.2; dichloromethane:methanol:ammonium hydroxide), mp=91°–94° C.

Analysis: calculated for $Cl_2H_{15}Cl_2NO$ C 55.40; H 5.81; N 5.38; Found C 55.64; H 5.88; N 5.20.

1.4 Synthesis of 3-(3,4-dichloro-phenyl)-1-(benzoyl)-3-(2-hydroxy-ethyl)-pyrrolidine 3-(3,4-Dichloro-phenyl)-3-(2-hydroxy-ethyl)-pyrrolidine (6.37 g, 24.5 mmol) was dissolved in dichloromethane (100 mL) at −78° C. and treated with 4-methylmorpholine (5.5 mL, 50 mmol, 2.0 eq.) and benzoyl chloride (3.0 mL, 25.8 mmol, 1.05 eq.). The solution was allowed to warm to 0° C. and stir for 2 hours. The reaction mixture was washed with 1N HCl and 5% NaHCO₃, and the organic phase was dried over magnesium sulfate, filtered, and concentrated in vacuo. The residue was chromatographed on silica gel (300 g) with a gradient from ethyl acetate to 10% methanol in dichloromethane to give 6..32 g (71%) of the title compound.

1.5 Synthesis of 2-[1-benzoyl-3-(3,4-dichloro-phenyl)-pyrrolidin-3-yl]-ethyl-methanesulfonate (No.027F42)

3-(3,4-Dichloro-phenyl)-1-(benzoyl)-3-(2-hydroxy-ethyl)-pyrrolidine (220 mg, 0.6 mmol) was dissolved in dichloromethane (4 mL) and N,N-diisopropylethylamine (0.13 mL, 0.75 mmol, 1.24 eq.) and methanesulfonyl chloride (0.055 mL, 0.71 mmol, 1.18 eq.) were added at 0° C. The solution was allowed to stir at 0° C for 3 hours. The solution was diluted with dichloromethane and washed with 1 N HCl, 5% sodium bicarbonate and water. The organic phase was dried over magnesium sulfate, filtered, and concentrated in vacuo. The residue was chromatographed on silica gel (30 g), with a gradient of 50% ethyl acetate in hexane to 75% ethyl acetate in hexane to give 191 mg (72%) of the title compound.

1.6 Synthesis of 1-[2-[3-(3,4-dichloro-phenyl)-1-(benzoyl)-pyrrolidin-3-yl]-ethyl]-4-phenyl-piperidine-4-carboxylic acid amide (No.027F42)

2-[1-Benzoyl-3-(3,4-dichloro-phenyl)-pyrrolidin-3-yl] ethyl methanesulfonate (191 mg, 0.43 mmol) was treated with the 4-phenyl-piperidine-4-carboxylic acid amide hydrochloride (144 mg, 0,599 mmol) and NaHCO$_3$ (90 mg, 1.07 mmol, 2.5 eq.) in THF/H$_2$O (5 mL/1 mL) at reflux for 21 hours. The solution was concentrated in vacuo and the aqueous phase was extracted with dichloromethane. The organic phase was dried over magnesium sulfate, filtered, and concentrated in vacuo. The residue was chromatographed on silica gel (30 g) with 6% methanol in dichloromethane to give 146 mg (44%).

Exact mass (CI): calculated for C$_{31}$H$_{33}$Cl$_2$N$_3$O$_2$(M+): 549.1950.
Found 549.1920.

EXAMPLE 2

Synthesis of 1-[2-[3-(3,4-dichloro-phenyl)-1-(2,4-dimethoxy-benzoyl)-pyrrolidin-3-yl]-ethyl]-4-phenyl-piperidine-4-carboxylic acid amide 2.1 Synthesis of [3-(3,4-dichloro-phenyl)-1-(2,4-dimethoxy-benzoyl)-3-(2-hydroxy-ethyl)-pyrrolidine (No.027F108)

3-(3,4-Dichloro-phenyl)-3-(2-hydroxy-ethyl)-pyrrolidine (288 mg, 1.1 mmol) was dissolved in dichloromethane (3 mL) at −78° C. and treated with 4-methylmorpholine (0.25 mL, 2.27 mmol, 2.eq.) and 2,4-dimethoxy-benzoyl chloride (220 mg, 1.1 mmol, 1 eq.) dissolved in 3 mL of dichloromethane. The solution was allowed to warm to 0° C. and stirred for 1 hour. The solution was washed with 1N HCl, and 5% sodium bicarbonate. The organic phase was dried over magnesium sulfate, filtered, and concentrated in vacuo. The residue was chromatographed on silica gel (30 g) with a gradient of 50% ethyl acetate in hexane to 6% methanol in dichloromethane to give 324 mg (69%) of the title compound.

2.2 Synthesis of 2-[1-(2,4-dimethoxy-benzoyl)-3-(3,4-dichloro-phenyl)-pyrrolidin-3-yl]-ethyl-methanesulfonate (No.027F117)

3-(3,4-Dichloro-phenyl)-1-(2,4-dimethoxy-benzoyl)-3-(2-hydroxy-ethyl)-pyrrolidine (320 mg, 0.75 mmol) was dissolved in dichloromethane (5 mL) and N,N-diisopropylethylamine (0.35 mL, 2.0 mmol, 2.7 eq.) and methanesulfonyl chloride (0.080 mL, 1.0 mmol, 1.4 eq.) were added dropwise at 0° C. and allowed to stir for 3 hours. The solution was diluted with dichloromethane and washed with 1 N HCl and 5% sodium bicarbonate. The organic phase was dried over magnesium sulfate, filtered, and concentrated in vacuo. The residue was chromatographed on silica gel (30 g) with 6% methanol in dichloromethane to give 343 mg (91%) of the title compound.

2.3 Synthesis of 1-[2-[3-(3,4-dichloro-phenyl)-1-(2,4-dimethoxy-benzoyl)-pyrrolidin-3-yl]-ethyl]-4-phenyl-piperidine-4-carboxylic acid amide (No.027F117)

2-[1-(2,4-Dimethoxy-benzoyl)-3-(3,4-dichloro-phenyl)-pyrrolidin-3-yl]-ethyl-methanesulfonate (343 mg, 0.68 mmol) was dissolved in THF (8 mL) and the 4-phenyl-piperidine-4-carboxylic acid amide hydrochloride (170 mg, 0.71 mmol, 1.04 eq.), potassium carbonate (200 mg, 1.45 mmol, 2.1 eq.), and water (2 mL) were added and the solution was heated at reflux for 16 hours. The solution was concentrated in vacuo and the aqueous phase was extracted with dichloromethane, dried over magnesium sulfate, filtered, and concentrated in vacuo. The residue was chromatographed on silica gel (40 g) with a gradient of ethyl acetate to 6% methanol in dichloromethane to give 151 mg (36%) of the title compound.

Analysis: calculated for C$_{33}$H$_{37}$Cl$_2$N$_3$O$_4$·0.6 H$_2$O C 63.86; H 6.20; N 6.76. Found C 63.61; H 6.13; N 6.67.

EXAMPLE 3

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide 3.1 Synthesis of [3-(3,4-dichloro-phenyl)-1-(3,4,5-trimethoxy-benzoyl)-3-(2-hydroxy-ethyl)-pyrrolidine (No.027F109)

3-(3,4-Dichloro-phenyl)-3-(2-hydroxy-ethyl)-pyrrolidine (288 mg, 1.1 mmol) was dissolved in dichloromethane at −78° C. and treated with 4-methylmorpholine (0.25 mL, 2.27 mmol, 2 eq.) and 3,4,5-trimethoxy-benzoyl chloride (250 mg, 1.1 mmol, 1 eq) in dichloromethane (3 mL). The solution was allowed to warm to 0° C. and stir for 1 hour. The solution was washed with 1N HCl and 5% sodium bicarbonate and the organic phase was dried over magnesium sulfate, filtered, and concentrated in vacuo. The residue was chromatographed on silica gel (30 g) with a gradient of 50% ethyl acetate in hexane to 6% methanol in dichloromethane to give 353 mg (71%) of the title compound.

3.1.1 Synthesis of 2-[3-(3,4-dichloro-phenyl)-1-(3,4,5-trimethoxy-benzoyl)-pyrrolidin-3-yl]-ethanol 2-[3-(3,4-Dichloro-phenyl)-pyrrolidin-3-yl]-ethanol (5,885 g, 22.64 mmol) and dichloromethane (135 mL) were combined. 4-Methylmorpholine (5.0 mL , 45.48 mmol, 2 eq.) was added. The mixture was cooled in a dry-ice/acetone bath and a solution of 3,4,5-trimethoxy-benzoyl chloride (5.22 g, 22.63 mmol) in dichloromethane (100 mL) was added dropwise. After the addition was complete, the dry-ice/acetone bath was changed to an ice bath and the mixture was stirred for 1 h. The solution was extracted with 1N HCl (50 mL), 5% NaHCO$_3$ (50 mL), and H$_2$O (50 mL) . The organic phase was dried over MgSO$_4$, filtered, and concentrated in vacuo to obtain a residue. The residue was purified by chromatography on silica gel (400 g) eluting with ethyl acetate and then 6% methanol in dichloromethane to give the title compound:

Rf=0.38 (silica gel, 6% methanol in dichloromethane).

3.2 Synthesis of 2-[3,4-(dichloro-phenyl)-1-(3,4,5-trimethoxy-benzoyl)-pyrrolidin-3-yl]ethyl methanesulfonate (No.027F116)

3-(3,4-Dichloro-phenyl)-1-(3,4,5-trimethoxy-benzoyl)-3-(2-hydroxy-ethyl)-pyrrolidine (350 mg, 0.77 mmol), was dissolved in dichloromethane (5 mL) and N,N-diisopropylethylamine (0.35 mL, 2.0 mmol, 2.6 eq.) and methanesulfonyl chloride (0.080 mL, 1.03 mmol, 1.34 eq.) were added dropwise at 0° C. The solution was allowed to stir for 1 hour at 0° C. The solution was diluted with dichloromethane and washed with 1N HCl and 5% sodium bicarbonate. The organic phase was dried over magnesium sulfate, filtered, and concentrated in vacuo. The residue was chromatographed on silica gel (30 g) with a gradient of ethyl acetate to 6% methanol in dichloromethane to give 376 mg (92%) of the title compound.

3.2.1 Synthesis of 2-[3-(3,4-dichloro-phenyl)-1-(3,4,5-trimethoxy-benzoyl)-pyrrolidin-3-yl]-ethyl-methanesulfonate 2-[3-(3,4-Dichloro-phenyl)-1-(3,4,5-trimethoxy-benzoyl)-pyrrolidin-3-yl]-ethanol (3.5 g, 7.87 mmol) and dichloromethane (100 mL) were combined. N,N-diisopropylethylamine (3.0 mL , 17.22 mmol, 2.2 eq.) was added and the mixture was cooled in an ice bath. Methanesulfonyl chloride (0.82 mL, 10.59 mmol, 1.35 eq.) was added dropwise. After the addition, the mixture was stirred 1.5 h. Methanesulfonyl chloride (0.05 mL, 0.65 mmol, 0.08 eq.) was added dropwise. After the addition, the mixture was stirred 0.5 h. The solution was extracted with 1N HCl (2×100 mL) and 5% NaHCO$_3$ (100 mL). The organic phase was dried over MgSO$_4$, filtered, and concentrated in vacuo to obtain a residue. The residue was dried under high vacuum at ambient temperature for 18 h to give the title compound:

R$_f$=0.27 (silica gel, ethyl acetate).

3.3 Synthesis of 1-[2-[3-(3,4-dichloro-phenyl)-1-(3,4,5-trimethloxy-benzoyl)-pyrrolidin-3-yl]-ethyl]-4-phenyl-piperidine-4-carboxylic acid amide (No.027F116)

2-[3,4-(Dichloro-phenyl)-1-(3,4,5-trimethoxy-benzoyl)-pyrrolidin-3-yl]-ethyl-methanesulfonate, (376 mg, 0.707 mmol) was dissolved in THF (8 mL) and 4-phenyl-piperidine-4 carboxylic acid amide hydrochloride (170 mg, 0.707 mmol, 1 eq.), potassium carbonate (200 mg, 1.45 mmol, 2 eq.), and water (2 mL), were added and the solution was heated at reflux for 16 h. The solution was concentrated in vacuo and the aqueous phase was extracted with dichloromethane. The organic phase was dried over magnesium sulfate, filtered, and concentrated in vacuo. The residue was chromatographed on silica gel (40 g) with a gradient of ethyl acetate to 6% methanol in dichloromethane to isolate the the title compound. The residue was dissolved in dichloromethane and added dropwise into a saturated ether/HCl solution. The slurry was concentrated in vacuo and the residue was dried under high vacuum at 50° C. to give the hydrochloride salt of the title compound 321 mg (71%).

Analysis: calculated for C$_{34}$H$_{39}$Cl$_2$N$_3$O$_5$·HCl ·0.5 H$_2$O: C 62.93; H 6.21; N 6.48. Found C 62.86; H 6.19; N 6.30.

3.3.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide 2-[3-(3,4-Dichloro-phenyl)-1-(3,4,5-trimethoxy-benzoyl)-pyrrolidin-3-yl]-ethyl-methanesulfonate (7.87 mmol) and THF/H$_{20}$ (3/1, 80 mL) were combined. 4-Phenyl-piperidine-4-carboxylic acid amide hydrochloride (2.8 g, 11.64 mmol, 1.5 eq.) and potassium carbonate (3.3 g, 23.88 mmol, 3 eq.) were added. The mixture was heated to reflux for 72 h. The mixture was concentrated in in vacuo. The aqueous residue was extracted with dichloromethane. The organic phase was extracted with H$_2$O (50 mL). The organic phase was dried over MgSO$_4$, filtered, and concentrated in uacuo to obtain a residue. The residue was purified by chromatography on silica gel (350 g) eluting sequentially with ethyl acetate, 6% methanol in dichloromethane, and then 10% methanol in dichloromethane to give the title compound:

R$_f$=0.12 (silica gel, 6% methanol in dichloromethane).

Analysis: calculated for C$_{34}$H$_{39}$Cl$_2$N$_3$O$_5$·0.5 H$_2$O C 62.93; H 6.21; N 6.48; Found C 62.86; H 6.19; N 6.30.

3.3.2 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide Prepare by the method of example 70.5 using 1-[3-(3,4-dichloro-phenyl)-pyrrolidin-3-yl]-ethyl]-4-phenyl-piperidine-4-carboxylic acid amide hydrochloride (240 mg, 0.5 mmol) and 3,4,5-trimethoxy-benzoic acid to give the title compound: Rf=0.43 (silica gel, 10% methanol/dichloromethane).

Exact mass (FAB+): calculated for C$_{34}$H$_{40}$Cl$_2$N$_3$O$_4$ calculated 624.2395. Found 624.2393.

EXAMPLE 3A 3.3A.1 Synthesis of 1-[2-[3-(3,4-dichloro-phenyl)-1-(3,4,5-trimethoxy-benzoyl)-pyrrolidin-3-yl]-ethyl]- 4-phenyl-piperidine-4-carboxylic acid amide hydrochloride 1-[2-[3-(3,4-Dichloro-phenyl)-1-(3,4,5-trimethoxy-benzoyl)-pyrrolidin-3-yl]-ethyl]-4-phenyl-piperidine-4-carboxylic acid amide (4.13 g, 6.45 mmol) was dissolved in dichloromethane (20 mL) and treated with a solution of dichloromethane saturated with HCl(g) (20 mL). The solution was allowed to stir for 1 h. The solution was concentrated in vacuo to obtain a residue. The residue was dried under high vacuum at 56° C. for 18 h to give the title compound:

mp=175°–185° C. (slow dec. to glass)

Analysis: calculated for C$_{34}$H$_{40}$Cl$_3$N$_3$O$_5$ C 60.32; H 5.95; N 6.21; Found C 60.09; H 6.32; N 6.11.

EXAMPLE 4

Synthesis of 1-(2-[3-(3,4-dichloro-phenyl)-1-[2-(2-methoxy-phenyl)-acetyl]-pyrrolidin-3-yl]-ethyl)-4-phenyl-piperidine-4-carboxylic acid amide 4.1 Synthesis of [3-(3,4-dichloro-phenyl)-1-(2-methoxy-benzoyl)-3-(2-hydroxy-ethyl)-pyrrolidine (No.027F103)

3-(3,4-Dichloro-phenyl)-3-(2-hydroxy-ethyl)-pyrrolidine, (218 mg, 0.83 mmol) was dissolved in dichloromethane at −78° C. and treated with 4-methylmorpholine (0.19 mL, 1.73 mmol, 2 eq.) and 2-methoxybenzoyl chloride (155 mg, 0.84 mmol, 1 eq.) in dichloromethane (3×1 mL). The solution was allowed to warm to 0° C and stir for 4.5 hours. The solution was washed with 1N HCl and 5% sodium bicarbonate and the organic phase was dried over magnesium sulfate, filtered, and concentrated in vacuo. The residue was chromatographed on silica gel (30 g) with a gradient of 50% ethyl acetate in hexane to 6% methanol in dichloromethane to give 202 mg (60%) of the title compound.

4.2 Synthesis of 2-[3-(3,4-dichloro-phenyl)-1-[2-(2-methoxy-phenyl)-acetyl]-pyrrolidin-3-yl]-ethyl-methanesulfonate (No.027F104)

3-(3,4-Dichloro-phenyl)-1-(2-methoxy-benzoyl)-3-(2-hydroxy-ethyl)-pyrrolidine (No.027F103) (200 mg, 0.49 mmol) was dissolved in dichloromethane (5 mL) and diisopropylethylamine (0.17 mL, 0.976 mmol, 2 eq.) and methanesulfonyl chloride (0.050 mL, 0.646 mmol, 1.3 eq.) were added dropwise at 0° C. The solution was allowed to stir for 30 minutes at 0° C. The solution was diluted with dichloromethane and washed with 1N HCl and 5% sodium bicarbonate. The organic phase was dried over magnesium sulfate, filtered, and concentrated in vacuo. The residue was chromatographed on silica gel (25 g) with a gradient from 50% ethyl acetate in hexane to 6% methanol in dichloromethane to give 210 mg (88%) of the title compound.

4.3 Synthesis of 1-(2-[3-(3,4-dichloro-phenyl)-1-[2-(2-methoxy-phenyl)-acetyl]-pyrrolidin-3-yl]-ethyl)-4-phenyl-piperidine-4-carboxylic acid amide (No.027F104)

2-[3-(3,4-Dichloro-phenyl)-1-(2-methoxy-benzoyl)-pyrrolidin-3-yl]ethyl methanesulfonate (No.027F104)(210 mg, 0.43 mmol), was dissolved in THF (4 mL) and 4-phenyl-piperidine-4-carboxylic acid amide hydrochloride (105 mg, 0.44 mmol), sodium bicarbonate (75 mg, 0.89 mmol), and water (1 mL) , were added and the solution was heated at reflux for 22 hours. The solution was concentrated in vacuo and the aqueous phase was extracted with dichloromethane. The organic phase was dried over magnesium sulfate, filtered, and concentrated in vacuo. The residue was chromatographed on silica gel (30 g) with a gradient from ethyl acetate to 10% methanol in dichloromethane to give 05 mg (80%) of the title compound.

Analysis: calculated for C$_{33}$H$_{37}$Cl$_2$N$_3$O$_3$ 0.5 H$_{20}$ C 65.47; H 6.16; N 6.94. Found C 65.86; H 6.43; N 7.02.

EXAMPLE 5

Synthesis of 1-(2-[3-(3,4-dichloro-phenyl)-1-(2,6-dimethoxy-benzoyl-pyrrolidin-3-yl]-ethyl)-4-phenyl-piperidine-4-carboxylic acid amide 5.1 Synthesis of [3-(3,4-dichloro-phenyl)-1-(2,6-dimethoxy-benzoyl)-3-(2-hydroxy-ethyl)-pyrrolidine (No.027F130)

3-(3,4-Dichloro-phenyl)-3-(2-hydroxy-ethyl)-pyrrolidine (2 g, 7.695 mmol) was dissolved in dichloromethane at −78° C. and treated with 4-methylmorpholine (1.8 mL, 16.4 mmol, 2.1 eq.) and 2,6-dimethoxy-benzoyl chloride (1.55 g, 7.73 mmol) in dichloromethane (20 mL). The solution was allowed to warm to 0° C. and stirred for 1.5 hours. The solution was washed with 1N HCl and 5% sodium bicarbonate and the organic phase was dried over magnesium sulfate, filtered, and concentrated in vacuo. The residue was chromatographed on silica gel (200 g) with a gradient of 50% ethyl acetate in hexane to 6% methanol in dichloromethane to give 2.434 g (75%) of the title compound.

5.2 Synthesis of 2-[3-(3,4-dichloro-phenyl)-1-(2,6-dimethoxybenzoyl)-pyrrolidin-3-yl]-ethyl-methanesulfonate (No.027F130)

3-(3,4-Dichloro-phenyl)-1-(2,6-dimethoxy-benzoyl)-3-(2-hydroxy-ethyl)-pyrrolidine (2.434 g, 5.74 mmol), was dissolved in dichloromethane (30 mL) and treated with N,N-diisopropylethylamine (2.1 mL, 12.06 mmol, 2.1 eq.) and methanesulfonyl chloride (0.53 mL, 6.85 mmol, 1.2 eq.) at 0° C. for 1 hour. The solution was washed with 1N HCl, and 5% sodium bicarbonate. The organic phase was dried over magnesium sulfate, filtered, and concentrated in vacuo. The residue was chromatographed on silica gel (150 g) with a gradient of 50% ethyl acetate in hexane to 6% methanol in dichloromethane to give 2.8041 g (97%) of the title compound.

5.3 Synthesis of 1-(2-[3-(3,4-dichloro-phenyl)-1-(2,6-dimethoxy-benzoyl-pyrrolidin-3-yl]-ethyl)-4-phenyl-piperidine-4-carboxylic acid amide (No.027F131)

2-[3-(3,4-Dichloro-phenyl)-1-(2,6-dimethoxybenzoyl)-pyrrolidin-3-yl]ethyl methanesulfonate (2.0 g, 3.98 mmol) was dissolved in THF (40 mL) and 4-phenyl-piperidine-4-carboxylic acid amide hydrochloride (1 g, 4.16 mmol), water (10 mL), and potassium carbonate (1.2 g, 8.68 mmol) were added and the solution was heated at reflux for 18 hours. The solution was concentrated in vacuo. The aqueous phase was extracted with dichloromethane three times and the organic phase was washed with water, dried over magnesium sulfate, filtered, and concentrated in vacuo. The residue was chromatographed on silica gel (150 g) with a gradient from ethyl acetate to 10% methanol in dichloromethane to give 1.2515 g (52%) of a residue. CI/MS (m/e) 610 (M+H) for $C_{33}H_{37}Cl_2N_3O_4$.

The residue was dissolved in dichloromethane (5 mL) and filtered dropwise into a saturated ether/HCl solution. The slurry was concentrated in vacuo and the residue was dried under high vacuum at 55° C. to give 1.04 g (78%) of the title compound.

Analysis: calculated for $C_{33}H_{37}Cl_2N_3O_4 \cdot HCl$ C 61.26; H 5.92; N 6.49. Found C 61.19; H 6.22; N 6.57.

EXAMPLE 5A

Synthesis of 1-[2-[3-(3,4-dichloro-phenyl)-1-(2,6-dimethoxy-benzoyl)-pyrrolidin-3-yl]-ethyl]-4-phenyl-piperidine-4-carboxylic acid amide hydrochloride 5A.1 Synthesis of 1-[2.-[3-(3,4-dichloro-phenyl)-1-(2,6-dimethoxy-benzoyl)-pyrrolidin-3-yl]-ethyl]-4-phenyl-piperidine-4-carboxylic acid amide hydrochloride 1-[2-[3-(3,4-Dichloro-phenyl)-1-(2,6-dimethoxy-benzoyl)-pyrrolidin-3-yl]-ethyl]-4-phenyl-piperidine-4-carboxylic acid amide (1.8 mmol) was dissolved in dichloromethane (20 mL) and treated with a solution of dichloromethane saturated with HCl(g) (20 mL). The solution was allowed to stir for 1 h. The solution was concentrated in vacuo to obtain a residue. The residue was dried under high vacuum at 56° C. for 18 h to give the title compound.

Analysis: calculated for $C_{33}H_{38}Cl_3N_3O_4$ C 61.26; H 5.92; N 6.49; Found C 61.18; H 6.22; N 6.57.

EXAMPLE 6

Synthesis of 2-[(2-[1-benzoyl-3-(3,4-dichloro-phenyl)-pyrrolidin-3-yl]-ethyl]-4-phenyl-piperidine-4-carbonyl)-amino]-pentanedioic acid dimethyl ester 6.1 Synthesis of 1-tert-butyloxycarbonyl-4-phenyl-piperidine-4-carboxylic acid methyl ester (No.03F169)

1-tert-Butyloxycarbonyl-4-phenyl-piperidine-4-carboxylic acid (0.9162 g, 3 mmol) was allowed to react with methyl iodide (1.87 mL, 30 mmol, 10 eq.) in the presence of N,N-diisopropylethylamine (2.61 mL, 15 mmol, 5 eq.) in acetonitrile (30 mL) at 20° C. for 16 hours. The solution was diluted with ethyl acetate and washed with 1N HCl, 5 saturated sodium bicarbonate and saturated sodium chloride. The organic phase was dried over magnesium sulfate and the solvent was concentrated in vacuo to give 0.935 g (98%) of the title compound.

6.2 Synthesis of 4-phenyl-piperidine-4-acid methyl ester hydrochloride (No.03F170)

1-tert-Butyloxycarbonyl-4-phenyl-piperidine-4-acid methyl ester (0.9345 g, 2.93 mmol) was allowed to stir in 4N HCl in dioxane (10 mL) at 20° C. for 45 minutes. The solution was concentrated in vacuo and the residue was dried in vacuo to give 0.7143 g (95%) of the title compound.

6.3 Synthesis of 1-[2-[1-benzoyl-3-(3,4-dichloro-phenyl)-pyrrolidin-3-yl]-ethyl]-4-phenyl-piperidine-4-carboxylic acid methyl ester (003F171)

4-Phenyl-piperidine-4-carboxylic acid methyl ester hydrochloride (0.4143 g, 1.62 mmol) and 2-[1-benzoyl-3-(3,4-dichloro-phenyl)-pyrrolidin-3-yl]-ethyl-methanesulfonate (0.7165 g, 1.62 mmol) were dissolved in THF/$H_2O$ (20 mL/4 mL) and treated with sodium bicarbonate (0.2592 g, 3.24 mmol) at reflux for 16 hours. The solution was diluted with ethyl acetate and the aqueous phase was extracted with dichloromethane. The combined organic phases were dried over magnesium sulfate, filtered, and concentrated in vacuo. The residue was chromatographed on silica gel with 1% methanol in dichloromethane to give 0.2850 g (31%) of the title compound.

6.4 Synthesis of 1-[2-[1-benzoyl-3-(3,4-dichloro-phenyl)-pyrrolidin-3-yl]-ethyl]-4-phenyl-piperidine-4-carboxylic acid (003F172)

1-[2-[1-Benzoyl-3-(3,4-dichloro-phenyl)-pyrrolidin-3-yl]-ethyl]-4-phenyl-piperidine-4-carboxylic acid methyl ester (0.2850 g, 0.5 mmol) was dissolved in ethanol (10 mL) and treated with 1M sodium hydroxide (5 mL, 5 mmol) at 20° C. for 2 hours. The aqueous phase was washed with ethyl acetate. The aqueous phase was acidified with 1N hydrochloric acid, and then extracted with ethyl acetate. The organic phase was dried over magnesium sulfate, filtered, and concentrated in vacuo to give 0.117 g (43%) of the title compound.

6.5 Synthesis of 2-[(2-[1-benzoyl-3-(3,4-dichloro-phenyl)-pyrrolidin-3-yl]-ethyl]-4-phenyl-piperidine-4-carbonyl)-amino]-pentanedioic acid dimethyl ester (003F175)

A mixture of 1-[2-[1-benzoyl-3-(3,4-dichloro-phenyl)-pyrrolidin-3-yl]-ethyl]-4-phenyl-piperidine-4-carboxylic acid (49 mg, 0.11 mmol, 1.1 eq.), L-glutamic acid dimethyl ester hydrochloride (0.0260 g, 0.1 mmol), EDC (0.0236 g, 0.12 mmol, 1.2 eq.), HOBT (0.0180 g, 0.12 mmol, 1.2 eq.), and N,N-diisopropylethylamine (0.03 mL, 0.12 mmol, 1.2 eq.) were dissolved in dichloromethane (2 mL) and stirred 16 hours at 20° C. The solution was diluted with ethyl acetate and washed with 1N hydrochloric acid, saturated sodium bicarbonate, and saturated sodium chloride. The organic phase was dried over magnesium sulfate, filtered, and concentrated in vacuo. The residue was chromatographed on silica gel with 5% methanol in dichloromethane to give 63 mg (81%) of the title compound.

Analysis: calculated for $C_{38}H_{43}Cl_2N_3O_6$ C 64.40; H 6.11; N 5.93. Found C 64.07; H 6.28; N 5.87.

EXAMPLE 7

Synthesis of 2-[(1-(2-[1-benzoyl-3-(3,4-dichloro-phenyl)-pyrrolidin-3-yl]-ethyl)-4-phenyl-piperidine-4-carboxyl)-amino]-3-hydroxy butyric acid methyl ester (003F176).

7.1 Synthesis of 2-[(1-(2-[1-benzoyl-3-(3,4-dichloro-phenyl)-pyrrolidin-3-yl]-ethyl)-4-phenyl-piperidine-4-carboxyl)-amino]-3-hydroxybutyric acid methyl ester (003F176).

1-[2-[1-Benzoyl-3-(3,4-dichloro-phenyl)-pyrrolidin-3-yl]-ethyl]-4-phenyl-piperidine-4-carboxylic acid (61 mg, 0.1 mmol), L-threonine methyl ester hydrochloride (0.0187 g, 0.11 mmol, 1.1 eq.), EDC (0.0216 g, 0.11 mmol, 1.1 eq.), HOBT (0.0165 g, 0.11 mmol, 1.1 eq.), and N,N-diisopropylethylamine (0.0257 mL, 0.11 mmol, 1.1 eq.) were dissolved in dichloromethane (2 mL) and stirred 16 hours at 20° C. The solution was diluted with ethyl acetate and washed with 1N hydrochloric acid, saturated sodium bicarbonate, and saturated sodium chloride. The organic phase was dried over magnesium sulfate, filtered and concentrated in vacuo. The residue was chromatographed on silica gel with 5% methanol in dichloromethane to give 34.2 mg (51%) of the title compound.

Analysis: calculated for $C_{36}H_{41}Cl_2N_3O_5$ C 64.86; H 6.20; N 6.30. Found C 64.62; H 6.49; N 6.42.

EXAMPLE 8

Synthesis of 1-[2-[1-benzoyl-3-naphthylen-2-yl-pyrrolidin-3-yl]-ethyl]-4-phenyl-piperidine-4-carboxylic acid amide 8.1 Synthesis of 3-cyano-3-(2-naphthyl)-pentanedioic acid diethyl ester (03F106).

2-Naphthylacetonitrile (1.6721 g, 10 mmol) in THF (80 mL) at −78° C. was treated with sodium bis-(trimethylsilyl) amide (20 mL, 1M in THF; 20 mmol, 2 eq.). The solution was allowed to warm to 20° C. and stir for 2 hours. The solution was cooled to −78° C. and ethyl bromoacetate (2.2 mL, 20 .mmol, 2 eq.) was added. The solution was allowed to warm to 20° C. and stir 16 hours. The solution was diluted with dichloromethane and washed with water. The organic phase was dried over magnesium sulfate, filtered, and concentrated in vacuo. The residue was chromatographed on silica gel with a gradient from 5% ethyl acetate in hexane to 20% ethyl acetate in hexane to give 3.2124 g (95%) of the title compound.

8.2 Synthesis of [3-naphthalen-2-yl-5-oxo-pyrrolidin-3-yl]-acetic acid ethyl ester (003F115).

3-Cyano-3-(2-naphthyl-pentanedioic acid diethyl ester (3.2124 g, 9.47 mmol) was hydrogenated at 40 psi over Raney nickel (10 g) in ethanol (60 mL) and ammonium hydroxide (25 mL) for 8 hours. The slurry was filtered and the filtrate was concentrated in vacuo. The residue was chromatographed on silica gel with a gradient from 30% ethyl acetate in hexane to 2% methanol in dichloromethane to give 1.0337 g (68%) of the title compound.

8.3 Synthesis of 3-(2-naphthalen-2-yl-pyrrolidin-3-yl-ethanol (003F122).

3-(2-Naphthalen-2-yl-5-oxo-pyrrolidin-3-yl)-acetic acid ethyl ester (1.2636 g, 4.25 mmol) in THF (20 mL) was added slowly to a solution of LAH (0.6451 g, 17 mmol) in THF (20 mL) at room temperature. The slurry was heated at reflux for 12 hours and additional LAH (0.3225 g, 8.5 mmol) was added and then heated at reflux for an additional 8 hours. The slurry was treated dropwise with 0.98 mL of $H_2O$, 0.98 mL of 15% sodium hydroxide, and 2.94 mL of $H_2O$. The slurry was dried over magnesium sulfate, filtered, and concentrated in vacuo to give 0.9145 g (89%) of the title compound.

8.4 Synthesis of 1-benzoyl-3-(2-hydroxyethyl)-3-(2-naphthyl)pyrrolidine (003F129)

3-(2-Naphthylen-2-yl-pyrrolidin-3-yl)-ethanol (003F122) (0.1207 g, 0.5 mmol crude) was dissolved in dichloromethane and cooled to 0° C. Benzoyl chloride (0.06 mL, 0.5 mmol, 1 eq.) and N,N-diisopropylethylamine (0.09 mL, 0.5 mmol, 1 eq.) were added at 0° C. The solution was stirred at 0° C. for 4 hours and then diluted with ethyl acetate and washed with 1N HCl, saturated sodium bicarbonate, and saturated sodium chloride. The organic phase was dried over magnesium sulfate, filtered, and concentrated in vacuo. The residue was chromatographed on silica gel with a gradient from 35% ethyl acetate in hexane to 4% methanol in $CHCl_3$ to give 0.1061 g (61%) of the title compound.

8.5 Synthesis of 2-[1-benzoyl-3-napthylen-2-yl-pyrrolidin-3-yl]-ethyl-methanesulfonate (003F134).

1-Benzoyl-3-(2-hydroxyethyl)-3-(2-naphthyl)pyrrolidine 003F129 (1.0501 g, 3.04 mmol) in dichloromethane (30 mL) was cooled to 0° C., and treated with N,N-diisopropylethylamine (0.93 mL, 3.95 mmol, 1.3 eq.) and methanesulfonyl chloride (0.28 mL, 3.65 mmol, 1.2 eq.). The solution was allowed to stir at 0° C. for 2 hours and more N,N-diisopropylethylamine (0.93 mL, 3.95 mmol, 1.3 eq.) and methanesulfonyl chloride (0.28 mL, 3.65 mmol, 1.3 eq.) was added and the solution was allowed to stir for an additional 2 hours at 0° C. The solution was concentrated in vacuo and the residue was chromatographed on silica gel with 1% methanol in dichloromethane to give 1.297 g (97%) of the title compound.

8.6 Synthesis of 1-[2-[1-benzoyl-3-naphthylen-2-yl-pyrrolidin-3-yl]-ethyl]-4-phenyl-piperidine-4-carboxylic acid amide (003F136)

2-[1-Benzoyl-3-napthylen-2-yl-pyrrolidin-3-yl]-ethyl methanesulfonate (003F134), (1.1363 g, 2.58 mmol), 4-phenyl-piperidine-4-carboxylic acid amide hydrochloride (0.6846 g, 2.84 mmol, 1.1 eq.), sodium bicarbonate (0.4335 g, 5.16 mmol, 2 eq.) in THF/$H_{20}$ (25 mL/5 mL) was heated at reflux for 16 hours. The solution was concentrated in vacuo and the aqueous phase was extracted with dichloromethane. The organic phase was washed with water, dried over magnesium sulfate, filtered, and concentrated in vacuo. The residue was chromatographed on silica gel with a gradient from 3% methanol in dichloromethane to 5% methanol in dichloromethane to give 0.8325 g (61%) of the title compound.

Analysis: calculated for $C_{35}H_{37}N_3O_2$ $H_2O$ C 76.48; H 7.15; N 7.64. Found C 76.10; H 7.13; N 7.71.

EXAMPLE 9

Synthesis of 8-[2-[3-(3,4-dichloro-phenyl)-1-(2,6-dimethoxy-benzoyl)-pyrrolidin-3-yl]-ethyl]-1-phenyl-1,3,8-triaza-spiro[4.5]decane-4-one (027F145).

9.1 Synthesis of 8-[2-[3-(3,4-dichloro-phenyl)-1-(2,6-dimethoxy-benzoyl)-pyrrolidin-3-yl]-ethyl]-1-phenyl-1,3,8-triaza-spiro[4.5]decane-4-one (027F145).

2-[1-(2,6-Dimethoxy-benzoyl)-3-(3,4-dichloro-phenyl)-pyrrolidin-3-yl]-ethyl methanesulfonate (200 mg, 0.398 mmol), and 1-phenyl-1,3,8-triaza-spiro[4.5]decan-4-one (100 mg, 0.432 mmol) were dissolved in THF/H$_2$O (4 mL/1 mL) and treated with potassium carbonate (110 mg, 0.796 mmol, 2 eq.) at reflux for 22 hours. The solution was concentrated in vacuo and the aqueous phase was extracted (3x) with dichloromethane. The organic phase was dried over magnesium sulfate, filtered, and concentrated in vacuo. The residue was chromatographed on silica gel (40 g) with a gradient from ethyl acetate to 10% methanol in dichloromethane to give 130 mg (51%) of the title compound.

Exact mass (CI): calculated for C$_{34}$H$_{39}$Cl$_2$N$_4$O$_4$ (M+H): 637.2348. Found 637.2322.

EXAMPLE 10

Synthesis of 8-[2-[3-(3,4-dichloro-phenyl)-1-benzoyl-pyrrolidin-3-yl]-ethyl]-1-phenyl-1,3,8-triaza-spiro[4.5]-decane-4-one (027F60).

10.1 Synthesis of 2-[1-benzoyl-3-)3,4-dichloro-phenyl)-pyrrolidin-3-yl]-ethyl-methanesulfonate (027F60a).

1-Benzoyl-3-(2-hydroxyethyl)-3-(3,4-dichlorophenyl) pyrrolidine (350 mg, 0.962 mmol) was dissolved in dichloromethane (6 mL) at 0° C. and N,N-diisopropylethylamine (0.25 mL, 1.44 mmol, 1.5 eq.) and methanesulfonyl chloride (0,090 mL, 1.16 mmol, 1.2 eq.) were added. The solution was allowed to stir for 2 hours. Methanesulfonyl chloride (0,015 mL, 0.19 mmol, 0.2 eq.) was added and the solution was allowed to stir an additional 30 minutes. The solution was diluted with dichloromethane and washed with 1N HCl and 5% sodium bicarbonate. The organic phase was dried over magnesium sulfate, filtered, and concentrated in vacuo. The residue was chromatographed on silica gel (40g) with 2% methanol in dichloromethane to give 427 mg (99%) of the title compound.

0.2 Synthesis of 8-[2-[3-(3,4-dichloro-phenyl)-1-(benzoyl)-pyrrolidin-3-yl]-ethyl]-1-phenyl-1,3,8-triaza-spiro[4.5]-decane-4-one (027F60b).

2-[1-Benzoyl-3-(3,4-dichloro-phenyl)-pyrrolidin-3-yl]-ethyl-methanesulfonate (427 mg, 0.962 mmol) (027F60a), was dissolved in THF (6 mL) and 1-phenyl-1,3,8-triaza-spiro[4.5]decan-4-one (270 mg, 1,167 mmol, 1.2 eq.), water (1.5 mL) and sodium bicarbonate (150 mg, 1.79 mmol, 1.86 eq.) were added. The slurry has heated at reflux for 21 hours and then concentrated in vacuo. The aqueous phase was extracted with dichloromethane. The organic phase was washed with water, dried over magnesium sulfate, filtered, and concentrated in vacuo. The residue was chromatographed on silica gel (50 g) with a gradient from ethyl acetate to 0% methanol in dichloromethane to give 354 mg (64%). Analysis: calculated for C$_{32}$H$_{34}$Cl$_2$N4o$_2$ H$_{20}$ C 64.60; H 6.10; N 9.42. Found C 64.79; H 6.04; N 9.27.

EXAMPLE 11

Synthesis of 1-[2-[1-benzyl-3-(3,4-dichloro-phenyl)-5-oxo-pyrrolidin-3-yl]-ethyl]-4-phenyl-piperidine-4-carboxylic acid amide 11.1 Synthesis of 2-(3,4-dichloro-phenyl)-4-(tetrahydro-pyran-2-yl-oxy)-butyronitrile Sodium hydride (1.42 g, 59.2 mmol) in THF (25 mL) was treated with 3,4-dichlorophenylacetonitrile (10 g, 53.75 mmol) in THF (60 mL) at −78° C. and then the slurry was allowed to warm to 20° C. and stir for 2.5 hours. The solution was cooled to 0° C. and 2-(2-bromo-ethoxy)-tetrahydro-pyran in THF (25 mL) was added dropwise. The solution was allowed to warm to 20° C. and stir for 16 hours. The solution was poured into saturated ammonium chloride and extracted with diethyl ether. The organic phase was extracted with water and brine and the organic phase was dried over magnesium sulfate, filtered and concentrated in vacuo. The residue was chromatographed on silica gel (500 g) with a gradient from 5% ethyl acetate in hexane to 20% ethyl acetate in hexane to give 12.134 g (72%) of the title compound.

11.2 Synthesis of 3 cyano-3-(3,4-dichloro-phenyl)-5-(tetrahydro-pyran-2-yloxy) pentanoic acid ethyl ester (027F32–33).

2-(3,4-dichloro-phenyl)-4-(tetrahydro-pyran-2yloxy)-butyronitrile (10.8669 g, 34.62 mmol) was dissolved in THF (20 mL) at −78° C. and treated dropwise with LDA (27.2 mL, 40.8 mmol, 1.18 eq.) over 30 minutes. The solution was allowed to stir for 1.25 hour. Ethyl bromoacetate (4.2 mL, 37.87 mmol, 1.09 eq.) was added dropwise at −78° C. and the solution was allowed to warm to 20° C. and stir for 4 hours. The solution was partitioned between ammonium chloride and diethyl ether. The organic solution was extracted with water and brine and the organic phase was dried over magnesium sulfate, filtered, and concentrated in vacuo. The residue was chromatographed on silica gel (400 g) with a gradient from 20% ethyl acetate in hexane to 30% ethyl acetate in hexane to give 9.6243 g (69.5%) of the title compound.

11.3 Synthesis of 4-(3,4-dichloro-phenyl)-4-(tetrahydro-pyran-2-yloxy)ethyl)-pyrrolidin-2-one (027F34).

3-Cyano-3-(3,4-dichloro-phenyl)-5-(tetrahydro-pyran-2-yloxy) pentanoic acid ethyl ester (027F32a) (9.5 g, 23.76 mmol) was dissolved in ethanol/ammonium hydroxide (190 mL/38 mL) and hydrogenated in a Parr shaker at 45 psi for 7 hours over Raney nickel (30 g). The slurry was filtered and the filtrate was concentrated in vacuo. The residue was chromatographed on silica gel (30 g) with a gradient from 0% ethyl acetate in hexane to 10% methanol in dichloromethane to give 6.85 g (81%) of the title compound.

11.4 Synthesis of 1-benzyl-4-(3,4-dichloro-phenyl)-4-[2-(tetrahydro-pyran-2-yloxy)ethyl]-pyrrolidin-2-one (027F43).

4-(3,4-Dichloro-phenyl)-4-(tetrahydro-pyran-2-yloxy) ethyl)-pyrrolidin-2-one (027F34) (1 g, 2.79 mmol) was dissolved in THF (10 mL) and treated with sodium hydride (80 mg, 1.2 eq.) and benzyl bromide (0.7 mL, 5.89 mmol) at 20° C. The solution was allowed to stir 7.5 hours. The slurry was partitioned between diethyl ether and ammonium chloride and the solution was washed with water and brine. The organic phase was dried over magnesium sulfate, filtered, and concentrated in vacuo. The residue was chromatographed on silica gel (100 g) with 50% ethyl acetate in hexane to give 1,194 g (99%) of the title compound.

11.5 Synthesis of 1-benzyl-4-(3,4dichloro-phenyl)-4-(2-hydroxy-ethyl-pyrrolidin-2-one (027F44a).

1-Benzyl-4-(3,4-dichloro-phenyl)-4-[2-(tetrahydropyran-2-yloxy)ethyl]-pyrrolidin-2-one (027F43) (1.0 g, 2.79 mmol) was dissolved in methanol (6 mL) and treated with p-toluenesulfonic acid (200 mg) at room temperature for 5 hours. The solution was concentrated in vacuo and the residue was dissolved in dichloromethane and washed with 5% sodium bicarbonate and water. The organic phase was dried over magnesium sulfate, filtered, and concentrated in vacuo. The residue was purified on silica gel (100 g) with a gradient from 50% ethyl acetate in hexane to 10% methanol in dichloromethane to give 779 mg (77%) of the title compound.

11.6 Synthesis of 2-[4-benzyl-3-3,4-dichloro-phenyl)-5-oxo-pyrrolidin-3-yl]-ethyl methanesulfonate (027F44b).

1-Benzyl-4-(3,4-dichloro-phenyl)-4-(2-hydroxy-ethyl-pyrrolidin-2-one (027F44a) (779 mg, 2.14 mmol) was dissolved in dichloromethane (10 mL) and treated with N,N-diisopropylethylamine (0.5 mL, 2.87 mmol, 1.34 eq.) and methanesulfonyl chloride (0.2 mL, 2.58 mmol, 1.2 eq.) at 0° C for 2 hours. The solution was washed with 1N HCl, 5% sodium bicarbonate, and water, and the organic phase was dried over magnesium sulfate, filtered and concentrated in vacuo. The residue was chromatographed on silica gel (100 g) with a gradient from 50% ethyl acetate in hexane to ethyl acetate to give 815 mg (86%) of the title compound.

11.7 Synthesis of 1-[2-[1-benzyl-3-(3,4-dichloro-phenyl)-5-oxo-pyrrolidin-3-yl]-ethyl]-4-phenyl-piperidine-4-carboxylic acid amide (027F44c).

2-[4-Benzyl-3-3,4-dichloro-phenyl)-5-oxo-pyrrolidin-3-yl]-ethyl methanesulfonate (027F44b) (815 mg, 1.84 mmol) was dissolved in THF/water (15ml/4ml) and 4-phenyl-piperidine-4-carboxylic acid amide hydrochloride (520 mg, 2.16 mmol, 1.17 eq.) and sodium bicarbonate (320 mg, 3.8 mmol, 2.1 eq) were added. The solution was heated at reflux for 16 hours. The solvents were concentrated in vacuo. The aqueous phase was extracted with dichloromethane and the organic phase was washed with water. The organic phase was dried over magnesium sulfate, filtered, and concentrated in vacuo. The residue was chromatographed on silica gel (100 g) with 10% methanol in dichloromethane to give 389 mg (38%) of the title compound.

Exact mass (CI): calculated for $C_{31}H_{34}Cl_2N_3O_2$ (M+H) 550.2028. Found 550.2018.

EXAMPLE 12

Synthesis of 1-[1-benzyl-3-naphthalen-2-yl-5-oxo-pyrrolidin-3-yl)-ethyl]-4-phenyl-piperidine-4-carboxylic acid amide (003F112-113)

12.1 Synthesis of 2-(2-naphthyl)-4-(tetrahydro-pyran-2-yloxy)-butyronitrile (003F112) 2-Napthylacetonitrile (3.3442 g, 20 mmol) in THF (50 mL) was added to sodium hydride (0.528 g, 22 mmol, 1.1 eq.) in THF (50 mL) at −78° C. under nitrogen. The slurry was allowed to warm to 20° C. and stir for 2 hours. The slurry was cooled to 0° C. and 2-(2-bromo-ethoxy)-tetrahydro-pyran (4.1786 g, 20 mmol, 1 eq.) was added. The solution was allowed to stir at 20° C. for 16 hours and then diluted with dichloromethane and washed with water. The organic phase was dried over magnesium sulfate, filtered and concentrated in vacuo. The residue was chromatographed on silica gel with a gradient from 5% ethyl acetate in hexane to ethyl acetate to give 1.9774 g (66%) of the title compound.

12.2 Synthesis of 3-cyano-3-naphthalen-2-yl-5-(tetrahydro-pyran-2-yloxy)-pentanoic acid ethyl ester (003F143).

2-(2-Napthyl)-4-(tetrahydro-pyran-2-yloxy)-butyronitrile (003F112) (1.9 g, 6.45 mmol) in THF (60 mL) was cooled to −78° C. and treated dropwise with LDA (1.5M, 5.2 mL, 7.75 mmol, 1.2 eq.) and allowed to stir for 1 hour. Ethyl bromoacetate (0.86 mL, 7.75 mmol, 1.2 eq.) was added dropwise and the solution was allowed to warm to 20° C. and stir for 18 hours. The solution was partitioned between saturated aqueous ammonium chloride solution and ethyl acetate. The organic phase was dried over magnesium sulfate, filtered, and concentrated in vacuo. The residue was chromatographed on silica gel with a gradient from 20% ethyl acetate in hexane to 50% ethyl acetate in hexane to give 1,474 g (39%) of the title compound.

12.3 Synthesis of 4-naphthalen-2-yl-4-[2(tetrahydro-pyran-2-yloxy)-ethyl]-pyrrolidin-2-one (003F144). 3-Cyano-3-naphthalen-2-yl-5-(tetrahydro-pyran-2-yloxy)-pentanoic acid ethyl ester (003F143) (1.6154 g, 4.23 mmol) was hydrogenated at 40 psi over Raney nickel (10g) for 16 hours. The slurry was filtered and the filtrate was concentrated in vacuo. The residue was chromatographed on silica gel with a gradient from 50% ethyl acetate in hexane to 5% methanol in dichloromethane to give 0.8305 g (83%) of the title compound.

12.4 Synthesis of 1-benzyl-4-naphthalen-2-yl-4-[2-(tetrahydro-pyran-2-yloxy)-ethyl]pyrrolidin-2-one (003F145).

Sodium hydride (0.07 g, 2.94 mmol, 1.25 eq.) was added slowly to a solution of 4-naphthalen-2-yl-4-[2(tetrahydro-pyran-2-yloxy)-ethyl]-pyrrolidin-2-one (003F144) (0.81 g, 2.39 mmol). The solution was treated with benzyl bromide (0.6 mL, 4.9 mmol, 2 eq.) at 20° C. for 7 hours. The solution was partitioned between saturated aqueous ammonium chloride and ethyl acetate. The organic phase was dried over magnesium sulfate, filtered and concentrated in vacuo. The residue was chromatographed on silica gel with 50% ethyl acetate in hexane to give 1.1620 g (92%) of the title compound.

12.5 Synthesis of 1-benzyl-4-(2-hydroxy-ethyl)-4-napthalene-2-yl-pyrrolidin-2-one (003F146).

1-Benzyl-4-naphthalen-2-yl-4-[2-(tetrahydro-pyran-2-yloxy)-ethyl]pyrrolidin-2-one (003F145) (1.1620g, 2.71 mmol) was dissolved in methanol (2.7 mL) and treated with p-toluenesulfonic acid (0.0515 g, 0.27 mmol, 0.1 eq.). The solution was allowed to stir at 20° C. for 4 hours. The residue was chromatographed on silica gel with a gradient from 50% ethyl acetate in hexane to 5% methanol in dichloromethane to give the 0.6161 g (66%) of the title compound.

12.6 Synthesis of 2-[1-benzyl-3-naphthalene-2-yl-5-oxo-pyrrolidin-3-yl) ethyl methanesulfonate (003F147).

1-Benzyl-4-(2-hydroxyethyl)-4-napthalene-2-yl-pyrrolidin-2-one (003F146) (0.6161 g, 1.78 mmol) in dichloromethane (17 mL) at 0° C. was treated with N,N-diisopropylethylamine (0.84 mL, 3.56 mmol, 2 eq.) and methanesulfonyl chloride (0.27 mL, 3.56 mmol, 2 eq.). The solution was allowed to stir at 0° C. for 2 hours. The solution was concentrated and the residue was chromatographed on silica gel with 1% methanol in dichloromethane to give 0.7219 g (95%) of the title compound.

12.7 Synthesis of 1-[2-(1-benzyl)-3-naphthalen-2-yl-5-oxo-pyrrolidin-3-yl)-ethyl]-4-phenyl-piperidine-4-carboxylic acid amide (003F148).

2-[1-Benzyl-3-naphthalene-2-yl-5-oxo-pyrrolidin-3-yl)-ethyl-methanesulfonate (003F147) (0.5061 g, 1.19 mmol) was dissolved in THF/H$_{20}$ (12 mL/12 mL) and treated with 4-phenyl-piperidine-4-carboxylic acid amide hydrochloride (0.3155 g, 1.31 mmol, 1.1 eq.) and sodium bicarbonate (0.1999 g, 2.38 mmol) at reflux for 18 hours. The aqueous phase was extracted with dichloromethane and the organic phases were dried over magnesium sulfate, filtered and concentrated in vacuo. The residue was chromatographed on silica gel with 5% methanol in dichloromethane to give 0.5060 g (80%) of the title compound.

Exact mass (CI): calculated for $C_{35}C_{38}N_3O_2$ (M+H): 532.2964.

Found 532.2981.

EXAMPLE 13

Synthesis of 1-[2-[3-(3,4-dichloro-phenyl)-1-(2-methoxy-benzoyl)-pyrrolidin-3-yl]-ethyl]-4-phenyl-piperidine-4-carboxylic acid amide 13.1 Synthesis of [3-(3,4-dichloro-phenyl)-1-(2-methoxy-benzoyl)-3-(2-hydroxy-ethyl)-pyrrolidine (No.027F099)

3-(3,4-Dichloro-phenyl)-3-(2-hydroxy-ethyl)-pyrrolidine (200 mg, 0.76 mmol) was dissolved in dichloromethane (5 mL) at −78° C. and treated with 4-methylmorpholine (0.17 mL, 1.55 mmol, 2 eq.) and 2-methoxy-benzoyl chloride (0.11 mL, 0.74 mmol). The solution was allowed to warm to 0° C. and stir for 1 hour. The solution was washed with 1N HCl and 5% sodium bicarbonate and the organic phase was dried over magnesium sulfate, filtered, and concentrated in vacuo. The residue was chromatographed on silica gel (30 g) with a gradient of 50% ethyl acetate in hexane to 3% methanol in dichloromethane to give 268 mg (90%) of the title compound.

13.2 Synthesis of 2-[3-(3,4-dichloro-phenyl)-1-(2-methoxybenzoyl)-pyrrolidin-3-yl]-ethyl-methanesulfonate (No.027F100)

[3-(3,4-Dichloro-phenyl)-1-(2-methoxy-benzoyl)-3-(2-hydroxy-ethyl)-pyrrolidine (268 mg, 0.68 mmol) was dissolved in dichloromethane (5 mL) and treated with N,N-diisopropylethylamine (0.24 mL, 1.38 mmol, 2 eq.) and methanesulfonyl chloride (65 mL, 0.84 mmol, 1.2 eq.) at 0° C. for 1 hour. The solution was washed with 1N HCl, and 5% sodium bicarbonate. The organic phase was dried over magnesium sulfate, filtered, and concentrated in vacuo. The residue was chromatographed on silica gel (30g) with ethyl acetate to give 323 mg (99%) of the title compound.

13.3 Synthesis of 1-(2-[3-(3,4-dichloro-phenyl)-1-(2-methoxy-benzoyl)-pyrrolidin-3-yl]-ethyl)-4-phenyl-piperidine-4-carboxylic acid amide (No. 027F131)

2-[3-(3,4-Dichloro-phenyl)-1-(2-methoxybenzoyl)-pyrrolidin-3-yl]-ethyl-methanesulfonate (323 mg, 0.68 mmol) was dissolved in THF (4 mL) and 4-phenyl-piperidine-4-carboxylic acid amide hydrochloride (165 mg, 0.69 mmol), water (1 mL), and sodium bicarbonate (105 mg, 1.25 mmol) were added and the solution was heated at reflux for 21 hours. The solution was concentrated in vacuo. The aqueous phase was extracted with dichloromethane (3×) and the organic phase was washed with water, dried over magnesium sulfate, filtered, and concentrated in vacuo. The residue was chromatographed on silica gel (30 g) with a gradient from ethyl acetate to 6% methanol in dichloromethane to give 280 mg (73%) of the title compound.

Exact mass (Cl): calculated for $C_{32}H_{36}Cl_2N_3O_3$ (M+H): 580.2134. Found 580.2143.

EXAMPLE 20

Synthesis of (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide 20.2 Synthesis of ethyl-2-[3-(3,4-dichloro-phenyl)-1-(3,4,5-trimethoxy-benzoyl)-pyrrolidin-3-yl]-acetate 2-[3-(3,4-Dichloro-phenyl)-1-(3,4,5-trimethoxy-benzoyl)-pyrrolidin-3-yl]-ethanol (4.5 g, 9.9 mmol) was dissolved in dichloromethane/pyridine (70 mL, 6/1). The solution was treated with acetic anhydride (1.04 mL, 11.02 mmol, 1.1 eq.) and 4-dimethylaminopyridine (50 mg, 0.41 mmol, 0.04 eq.). The solution was allowed to stir for 2 h at ambient temperature. The organics were concentrated in vacuo and the residue was dissolved in ethyl acetate and washed with 1N HCl (2×200 mL), 5% NaHCO₃ (100 mL), brine (100 mL), dried over MgSO₄, filtered and concentrated in vacuo. The residue was chromatographed on silica gel (300 g) with ethyl acetate to afford the title compound:

$R_f$=0.38 (silica gel, ethyl acetate).

Analysis: calculated for $C_{24}H_{27}Cl_2NO_6$ C 58.07; H 5.48; N 2.82; Found C 57.67; H 5.46; N 2.84.

20.3 Synthesis of (+)-ethyl-2-[3-(3,4-dichloro-phenyl)-1-(3,4,5-trimethoxy-benzoyl)-pyrrolidin-3-yl]-acetate Ethyl-2-[3-(3,4-dichloro-phenyl)-1-(3,4,5-trimethoxy-benzoyl)-pyrrolidin-3-yl]-acetate (6.6 g, 13.31 mmol) was dissolved in dichloromethane (100 mL) and treated with silica gel (32 g). The slurry was concentrated in vacuo and the residue was added to a 2L three necked round-bottomed flask. The residue was suspended in phosphate buffer (800 mL, 0.1M, pH=7.5, the buffer was prepared with 11.5 g $H_3PO_4$ (85%) diluted to 1L with deionized $H_2O$ and then adjusting the pH with solid KOH pellets to 7.5). The slurry was treated with Lipase (13 g, EC 3.1.1.3, Type VII, from Candida cylindracea). The slurry was allowed to stir at ambient temperature for 84 h. The reaction was monitored by HPLC on a CHIRALPAK AD 25 cm×0.46 cm column eluting with pentane/ethanol/methanol (80/15/5) with a flow rate of 1.0 mL/minute. An aliquot (50 mL) was extracted with ethyl acetate (1 mL) in a centrifuge tube. The solution was centrifuged for 10 minutes at 14000 cm-¹. The supernatant was removed and concentrated under a nitrogen stream. The residue was dissolved in dichloromethane (ca. 1 mL) and 5 mL was injected on the column for analysis. When the enantiomeric excess (ee) was satisfactory (>95% ee) for the (+) acetate the reaction was filtered. The filtrate was extracted with dichloromethane (8×500 mL). The solids were rinsed with dichloromethane (8×500 mL, the same portion was then used to extract the filtrate). The solids were placed in a chromatography column and eluted with 6% methanol in dichloromethane until all the alcohol and acetate was eluted. The combined organics were concentrated in vacuo, dissolved in dichloromethane, dried over MgSO₄, filtered and concentrated in vacuo to give a residue. The residue was chromatographed on silica gel (400 g), eluting with ethyl acetate until the acetate was off and then eluting with 6% methanol in dichloromethane until the alcohols were off to give the title compound:

$R_f$=0.38 (silica gel, ethyl acetate).

Analysis: calculated for $C_{24}H_{27}Cl_2NO_6 \cdot 0.5\ H_2O$ C 57.14; H 5.59; N 2.78; Found C 57.37; H 5.45; N 2.87.

HPLC determination of enantiomeric excess was 99%.

$[\alpha]^{20}$=+36.4° (c=0.894, $CHCl_3$).

20.4 Synthesis of (+)-2-[3-(3,4-dichloro-phenyl)-1-(3,4,5-trimethoxy-benzoyl)-pyrrolidin-3-yl]-ethanol (+)-Ethyl-2-[3-(3,4-dichloro-phenyl)-1-(3,4,5-trimethoxy-benzoyl)-pyrrolidin-3-yl]-acetate (670 mg, 1,351 mmol, 99% ee) was dissolved in methanol (15 mL) and treated with LiOH (4.2 mL, 1N, 3.1 eq.) at ambient temperature for 3.5 h. The organics were concentrated in vacuo. The residue was dissolved in dichloromethane and washed with 1N HCl (50 mL), 5% NaHCO₃ (50 mL), dried over MgSO₄, filtered, and concentrated in vacuo to obtain a residue. The residue was dried under high vacuum for 18 h to give the title compound:

$R_f$=0.11 (silica gel, ethyl acetate).

20.4.1 Resolution of (+)-3-(3,4-dichloro-phenyl)-3-(2-hydroxy-ethyl)-pyrrolidine (R, R)-di-p-anisoyltartaric acid salt Combine 3-(3,4-dichloro-phenyl)-3-(2-hydroxy-ethyl)-pyrrolidine (1.0 g, 38.5 mmol) and butanone. Add a solution of (R, R)-di-p-anisoyltartaric acid (1.6 g, 38.0 mmol) in butanone (80 mL). Heat to reflux. After 15 minutes, cool to ambient temperature and then cool further in an ice-salt bath. Filter the solid that forms and rinse with butanone. Recrystallize the solid from water/methanol to give the title compound: mp; 201°–204° C. (dec). Analysis on HPLC, on an analytical sample of the free amine obtained by extraction, using a CHIRALPAK AD 25 cm×0.46 cm column eluting with pentane/methanol/triethylamine (90/10/0.1) with a flow rate of 1.0 mL/minute indicates an enantiomeric excess of 96%, (96% ee), retention time of the (+)-isomer 11.2 minutes, retention time of the (−)-isomer 14.5 minutes.

20.4.2 Resolution of (+)-3-(3,4-dichloro-phenyl)-3-(2-hydroxy-ethyl)-pyrrolidine (R, R)-di-p-anisoyltartaric acid salt Combine (R, R)-di-p-anisoyltartaric acid (354.1 g, 846 mmol) and aqueous 12M hydrochloric acid solution (70.5 mL, 846 mmol) in water/methanol (4.4L)/(4.4L). Heat to reflux. Add dropwise over 45 minutes, a solution of 3-(3,4-dichloro-phenyl)-3-(2-hydroxy-ethyl)-pyrrolidine (440 g, 1693 mmol) in methanol (3 L). After 20 minutes, slowly cool to ambient temperature. Filter the solid that forms and rinse with water to give the title compound: mp; 201°–204° C. (dec). Analysis by HPLC, as described in Example 20.4.1 indicates an enantiomeric excess of 97.5%, (97.5% ee).

20.4.3 Synthesis of (+)-1-(3,4,5-trimethoxy-benzoyl)-3-(3,4-dichloro-phenyl)-3-(2-hydroxy-ethyl)-pyrrolidine Combine (+)-3-(3,4-dichloro-phenyl)-3-(2-hydroxy-ethyl)-pyrrolidine (R, R)-di-p-anisoyltartaric acid salt (0.14 g, 0.21 mmol) ethyl acetate (15 mL, acetonitrile (6 mL), water, (6 mL) and sodium bicarbonate (0.09 g, 1.03 mmol). Cool to 0° C. in an ice-salt bath. Add trimethoxybenzoyl chloride (0.048 g, 0.21 mmol). After 30 minutes, warm to ambient temperature. After 30 minutes at ambient temperature, partition the reaction mixture between ethyl acetate and saturated aqueous sodium chloride solution. Extract the organic layer with 1M hydrochloric acid solution, then saturated aqueous sodium bicarbonate solution. Dry the organic layer over MgSO$_4$, filter, and evaporate in vacuo to give the title compound: R$_f$=0.11 (silica gel, ethyl acetate).

20.4.4 Synthesis of (+)-1-(3,4,5-trimethoxy-benzoyl)-3-(3,4-dichloro-phenyl)-3-(2-hydroxy-ethyl)-pyrrolidine Combine (+)-3-(3,4-dichloro-phenyl)-3-(2-hydroxy-ethyl)-pyrrolidine (R, R)-di-p-anisoyltartaric acid salt (772.7 g, 1140 mmol) and acetone (5 L). Cool in to 0°–10° C. and add aqueous sodium hydroxide solution (46 g, 1105 mmol, in 5L of water). Add sodium bicarbonate (479 g, 5700 mmol). While maintaining the temperature at 0°–10° C., add dropwise over 30 minutes, trimethoxy-benzoyl chloride (262.9 g, 1140 mmol). After 3 hours, add ethyl acetate (5L) and allow to warm to ambient temperature. Separate the layers and extract the aqueous layer 3 times with ethyl acetate. Combine the organic layers and extract 1M sodium hydroxide solution, 1M hydrochloric acid solution, and then saturated aqueous sodium bicarbonate solution. Dry the organic layer over MgSO$_4$, filter, and evaporate in vacuo to give a residue. Treat the residue with dichloromethane and evaporate in vacuo the title compound: R$_f$=0.36 (silica gel, 6% methanol/dichloromethane).

20.5 Synthesis of (+)-2-[3-(3,4-dichloro-phenyl)-1-(3,4,5-trimethoxy-benzoyl)-pyrrolidin-3-yl)-ethyl-methanesulfonate Prepare by the method of example 3.2 using (+)-2-[3-(3,4-dichloro-phenyl)-1-(3,4,5-trimethoxy-benzoyl)-pyrrolidin-3-yl]-ethanol (1,351 mmol) and methanesulfonyl chloride (0.14 mL, 1.81 mmol, 1.34 eq.) to obtain a residue. The residue was dried under high vacuum for 18 h to give the title compound: R$_f$=0.27 (silica gel, ethyl acetate).

20.6 Synthesis of 4-phenyl-piperidine-4-carboxylic acid hydrochloride

4-Cyano-4-phenylpiperidine hydrochloride (20.0 g, 89.8 mmol) and KOH (1.2 L, 3N, 3.6 mol, 40 eq.) were combined and heated at reflux for 15 h. The solution was cooled in an ice bath and treated dropwise with conc. HCl until the pH=2. The white precipitate was collected and dried under high vacuum at 56° C. for 15 h to give the title compound: R$_f$=0.2 (silica gel, 85:10:5, chloroform:methanol:acetic acid).

Analysis: calculated for C$_{12}$H$_{36}$ClNO$_2$ C 59.63; H 6.67; N 5.79; Found C 58.19; H 6.52; N 5.72.

20.7 Synthesis of 1-tert-butoxycarbonyl-4-phenyl-piperidine-4-carboxylic acid 4-phenyl-piperidine-4-carboxylic acid hydrochloride (2.42 g, 10 mmol) was combined with di-tert-butyl dicarbonate (2.4 g, 11 mmol) in DMF (100 mL). N,N-diisopropylethylamine (1.91 mL, 11 mmol) was added to the mixture and the mixture was allowed to stir at ambient temperature for 30 h. The mixture was diluted with ethyl acetate and extracted with 1N HCl. The organic phase was extracted with 1N NaOH (2×200 mL). The aqueous phase was cooled in an ice bath and treated with 1N HCl to pH=2. The aqueous phase was extracted with ethyl acetate. The organic phase was dried over MgSO$_4$, filtered, and concentrated in vacuo to give a residue. The residue was dried under high vacuum to give the title compound: R$_f$=0.48 (silica gel, 6% methanol in dichloromethane, stains brown with ninhydrin).

Analysis: calculated for C$_{17}$H$_{23}$NO$_4$ C 66.86; H 7.59; N 4.59; Found C 66.56; H 7.72; N 4.52.

20.8 Synthesis of 1-tert-butoxycarbonyl-4-phenyl-piperidine-4-carboxylic acid amide 1-tert-Butoxycarbonyl-4-phenyl-piperidine-4-carboxylic acid (1.22 g, 4 mmol) was combined with THF (40 mL) and cooled to −10° C. Triethylamine (0.61 mL, 4.4 mmol, 1.1 eq.) and isobutylchloroformate (0.57 mL, 4.4 mmol, 1.1 eq.) were added and the reaction was allowed to warm to ambient temperature and stir 15 h, The slurry was filtered and the solids were rinsed with THF. The filtrate was cooled to −10° C. and sparged with NH$_3$(gas) for 0.5 h. The slurry was allowed to warm to 20° C. and stir for 15 h. The slurry was filtered and the filtrate was diluted with ethyl acetate and washed with saturated NaHCO$_3$ (3×). The organic phase was dried over MgSO$_4$, filtered, and concentrated in vacuo to give a residue. The residue was recrystallized from diethyl ether to give the title compound:

R$_f$=0.48 (silica gel, 6% methanol in dichloromethane, stains blue with ninhydrin).

Analysis: calculated for C$_{17}$H$_{24}$N$_2$O$_3$ C 67.08; H 7.95; N 9.20; Found C 66.99; H 8.00; N 9.14. HPLC analysis R$_f$=30.16 min. using a Vydac C-18 column eluting with an acetonitrile:water (0.1% TFA) gradient (elution with CH$_3$CN/H$_2$O(0.1%TFA), flow rate=1.0 mL/min., 10% CH$_3$CN for 10 minutes, 30% CH$_3$CN for 15 minutes, 40% CH$_3$CN for 15 minutes, 50% CH$_3$CN for 10 minutes, and then 100% CH$_3$CN).

20.9 Synthesis of 1-tert-butoxycarbonyl-4-phenyl-piperidine-4-carboxylic acid amide 1-tert-Butoxycarbonyl-4-phenyl-piperidine-4-carboxylic acid (1.22 g, 4 mmol) was combined with dichloromethane (40 mL). N,N-diisopropylethylamine (0.77 mL, 4.4 mmol, 1.1 eq.), 1-ethyl-3-(3-dimethylaminopropyl)carbodiimide hydrochloride (EDC) (0.8435 g, 4.4 mmol, 1.1 eq.), and 1-hydroxybenzotriazole hydrate (HOBT) (0.5946 g, 4.4 mmol, 1.1 eq.) were added. The mixture was allowed to stir at ambient temperature for 15 h. The solution was sparged with NH$_3$(gas) for 0.5 h and then allowed to stir at ambient temperature for 15 h. The mixture was filtered and the filtrate was concentrated in vacuo to give a residue. The residue was dissolved in ethyl acetate and extracted with saturated NaHCO$_3$ (6×). The organic phase was dried over MgSO$_4$, filtered, and concentrated in vacuo to give a residue. The residue was recrystallized from diethyl ether to give the title compound:

R$_f$=0.48 (silica gel, 6% methanol in dichloromethane, stains blue with ninhydrin).

20.10 Synthesis of 4-phenyl-piperidine-4-carboxylic acid amide-hydrochloride 1-tert-Butoxycarbonyl-4-phenyl-piperidine-4-carboxylic acid amide (0.95 g, 3.12 mmol) was combined with HCl in dioxane (10 mL, 4N, 40 mmol, 13 eq.) at ambient temperature for 1 h. The solvent was concentrated in vacuo and ethyl acetate was added. The slurry was filtered and dried under high vacuum for 48 h to give the title compound:

HPLC analysis Rt=5.56 min. using a C-18 column eluting with a acetonitrile:water (0.1% TFA), flow rate =1.0 mL/min., gradient (elution with $CH_3CN/H_2O$ (0.1% TFA) 10% $CH_3CN$ for 10 minutes, 30% $CH_3CN$ for 15 minutes, 40% $CH_3CN$ for 15 minutes, 50% $CH_3CN$ for 10 minutes, and then 100% $CH_3CN$).

Analysis: calculated for $C_{12}H_{17}ClN_2O$ C 59.87; H 7.12; N 11.64; Found C 59.82; H 7.00; N 11.52.

20.11 Synthesis of (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide Prepare by the method of example 3.3 using (+)-2-[3-(3,4-dichloro-phenyl)-1-(3,4,5-trimethoxy-benzoyl)-pyrrolidin-3-yl]-ethyl-methanesulfonate (1,3,5mmol) and 4-phenyl-piperidine-4-carboxylic acid amide hydrochloride (480 mg, 1.99 mmol, 1.5 eq.) to obtain a residue. The residue was chromatographed on silica gel (70 g) packed with ethyl acetate, loaded with ethyl acetate, and eluted with ethyl acetate, 6% methanol in dichloromethane, and then 10% methanol in dichloromethane to give the title compound:

HPLC determination of enantiomeric excess was 96.8%.

$R_t$=13 minutes (with analytical column using a CHIRALPAK AD chiral HPLC column (25 cm×0.46 cm) with 15% methanol in penfane and a flow rate of 1.0 mL/minute.

20A.1 Synthesis of (+)-1-[2-[3-(3,4-dichloro-phenyl)-1-(3,4,-trimethoxy-benzoyl)-pyrrolidin-3-yl]-ethyl]-4-phenyl-piperidine-4-carboxylic acid amide hydrochloride (+)-1-[2-[3-(3,4-Dichloro-phenyl)-1-(3,4,5-trimethoxy-benzoyl)-pyrrolidin-3-yl]-ethyl]-4-phenyl-piperidine-4-carboxylic acid amide (1.17 g, 96.8% ee, 1.828 mmol) was dissolved in dichloromethane (20 mL) and treated with a solution of dichloromethane saturated with HCl(gas) (20 mL). The solution was allowed to stir for 1 h. The solution was concentrated in vacuo to obtain a residue. The residue was dried under high vacuum at 56° C. for 18 h to afford the title compound:

mp=173°–185° C. (slow dec. to glass)

HPLC determination of enantiomeric excess was 96.8%.

$R_t$=13 minutes (with analytical column using a CHIRALPAK AD chiral HPLC column (25 cm×0.46 cm) with 15% methanol in pentane and a flow rate of 1.0 mL/minute.

Analysis: calculated for $C_{34}H_{39}Cl_2N_3O_5 \cdot 0.77$ $H_2O$ C 59.11; H 6.06; N 6.08; Found C 59.50; H 6.11; N 6.07.

$[\alpha]^{20}$=+13.2° (c=0.851, $CH_3OH$).

20A. 2 Synthesis of (+)-1-[2-[3-(3,4-dichloro-phenyl)-1-(3,4,5-trimethoxy-benzoyl)-pyrrolidin-3-yl-ethyl]-4-phenyl-piperidine-4-carboxylic acid 5 amide hydrochloride (+)-1-[2-[3-(3,4-Dichloro-phenyl)-1-(3,4,5-trimethoxy-benzoyl)-pyrrolidin-3-yl]-ethyl]-4-phenyl-piperidine-4-carboxylic acid amide (54.0 g, 84.3 mmol) was dissolved in ethyl acetate (1 L) and the solution was cooled to 0° C. The mixture was treated with a solution of ethyl acetate ((167.7 g) containing HCl(gas) (7.8 g). When the addition was complete the solid which had formed was collected by filtration and rinsed with ethyl acetate and dried to give the title compound.

20B.1 Synthesis of (+)-1-[2-[3-(3,4-dichloro-phenyl)-1-(3,4,5-trimethoxy-benzoyl)-pyrrolidin-3-yl-ethyl]-4-phenyl-piperidine-4-carboxylic acid amide maleate (+)-1-[2-[3-(3,4-Dichloro-phenyl)-1-(3,4,5-trimethoxy-benzoyl)-pyrrolidin-3-yl]-ethyl]-4-phenyl-piperidine-4-carboxylic acid amide (0.5 g, 0.78 mm61) was dissolved in ethanol (3 mL) and was treated with a solution of maleic aid (0.10 g) in ethanol (2 mL). After 10 minutes, the reaction mixture was triturated with diethyl ether (100 mL) and the solid which formed was collected by filtration and dried to give the title compound.

Analysis: calculated for $C_{34}H_{39}Cl_2N_3O_5 \bullet 0.52$ $H_2O$ $\bullet C_4H_4O_4$ C 59.56; H 5.78; N 5.48; Found C 59.67; H 5.71; N 5.46.

20C.1 Synthesis of (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide citrate (+)-1-[2-[3-(3,4-Dichloro-phenyl)-1-(3,4,5-trimethoxy-benzoyl)-pyrrolidin-3-yl]-ethyl]-4-phenyl-piperidine-4-carboxylic acid amide (2.5 g) was dissolved in isopropanol (15 mL) and heated to reflux before the mixture was treated with a solution of citric aid (0.75 g) in isopropanol (13 mL). After 10 minutes, the reaction mixture was cooled to ambient temperature and the solid which had formed was collected by filtration and dried to give the title compound.

Analysis: calculated for $C_{34}H_{39}Cl_2N_3O_5 \bullet 1.0$ $H_2O \bullet C_6H_8O_7 \bullet 1.2$ $C_3H_8O$ (isopropanol) C 56.75; H 6.42; N 4.54; Found C 56.66; H 6.34; N 4.47.

EXAMPLE 21

Chromatographic Resolution of (−)-1-[2-[3-(3,4-dichlorophenyl)-1-(3,4,5-trimethoxy-benzoVl)-pyrrolidin-3-yl]-ethyl]-4-phenyl-piperidine-4-carboxylic acid amide Chromatographic Resolution of (+) and (−)-1-[2-[3-(3,4-Dichloro-and phenyl)-1-(3,4,5-trimethoxy-benzoyl)-pyrrolidin-3-yl]-ethyl]-4-phenyl-piperidine-4-carboxylic acid amide A racemic mixture of 1-[2-[3-(3,4-Dichloro-phenyl)-1-(3,4,5-trimethoxy-benzoyl)-pyrrolidin-3-yl]-ethyl]-4-phenyl-piperidine-4-carboxylic acid amide hydrochloride (120 mg, 0.18 mmol) was resolved into two enantiomers on a CHIRALPAK AD chiral HPLC column (25 cm×2 cm) using 15% methanol in pentane to give the title compound:

$R_t$=10 minutes for (−)-1-[2-[3-(3,4-Dichloro-and phenyl) -1-(3,4,5-trimethoxy-benzoyl)-pyrrolidin-3-yl]-ethyl]-4-phenyl-piperidine-4-carboxylic acid amide.

The (+)-isomer, (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide was also obtained, Rt=13 minutes for (+)-1-[2-[3-(3,4-Dichloro-and phenyl)-1-(3,4,5-trimethoxy-benzoyl)-pyrrolidin-3-yl]-ethyl]-4-phenyl-piperidine-4-carboxylic acid amide. (Retention times determined using an analytical CHIRALPAK AD chiral HPLC column (25 cm×0.46 cm) with 15% methanol in pentane and a flow rate of 1.0 mL/minute.

EXAMPLE 22

Synthesis of 1-[2-[3-phenyl-1-(3,4,5-trimethoxy-benzoyl)-pyrrolidin-3-yl]-ethyl]-4-phenyl-piperidine-4-carboxylic acid amide 2.1 Synthesis of 3-cyano-3-phenyl-pentanedioic acid diethyl ester Combined phenylacetonitrile (5.85 g, 50.0 mmol) and THF (30 mL). Cooled in a dry-ice/acetone bath. Added dropwise, sodium bis-(trimethylsilyl)amide (100 mL, 1.0M in THF, 100 mmol, 2 eq.). After the addition was complete, allowed to warm to ambient temperature. Cooled in a dry-ice/acetone bath. Added dropwise, ethyl bromoacetate (11 mL, 99 mmol). After the addition was complete, warmed to ambient temperature and stir for 3 h. Partitioned the reaction mixture between diethyl ether (200 mL) and water (200 mL). The organic layer was extracted with $H_2O$ (3×150 mL), 1N HCl (2×100 mL), 5% $NaHCO_3$ (2×100 mL), and brine (1×150 mL). Dried over $MgSO_4$, filtered, and concentrated in vacuo to obtain a residue. Chromatographed on silica gel eluting with 20% ethyl acetate in hexane to obtain the title compound:

$R_f$=0.23 (silica gel, 20% ethyl acetate in hexane).

22.2 Synthesis of [3-phenyl-5-oxo-pyrrolidin-3-yl]-acetic acid ethyl ester

Prepared by the method of example 1.2.2 using 3-cyano-3-phenyl-pentanedioic acid diethyl ester (37 mmol) and Raney nickel (70 g) to give the title compound: $R_f$=0.60 (silica gel, 6% methanol in dichloromethane).

22.3 Synthesis of 2-(3-phenyl-5-yl-pyrrolidin-3-yl)-ethanol

Combined (3-phenyl-5-oxo-pyrrolidin-3-yl)-acetic acid ethyl ester (8.71 g, 35 mmol) and $LiAlH_4$ (141 mL, 1M solution in THF, 141 mmol) in THF (20 mL). Heated to reflux for 19 h. Cooled in an ice bath. Added $H_2O$ (5 mL), NaOH (5 mL, 15%), and $H_2O$(15 mL). The slurry was filtered and the filtrate was concentrated to obtain a residue. Dissolved the residue in dichloromethane and dried it over $MgSO_4$, filtered, and concentrated the filtrate in vacuo to obtain a residue which was dried under high vacuum for 24 h to give the title compound:

$R_f$=0.03 (silica gel, 6% methanol in dichloromethane).

22.4 Synthesis of 2-[3-phenyl-1-(3,4,5-trimethoxy-benzoyl)-pyrrolidin-3-yl]-ethanol Prepared by the method of example 3.1 using 2-(3-phenyl-pyrrolidin-3-yl)-ethanol (10.47 mmol) and 3,4,5-trimethoxy-benzoyl chloride (10.49 mmol). Chromatographed on silica gel (200 g) eluting with ethyl acetate and then 3% methanol in dichloromethane to give the title compound:

$R_f$=0.38 (silica gel, 6% methanol in dichloromethane).

22.5 Synthesis of 2-[3-phenyl-1-(3,4,5-trimethoxy-benzoyl)-pyrrolidin-3-yl]-ethyl-methanesulfonate Prepared by the method of example 3.2 using 2-[3-phenyl-1-(3,4,5-trimethoxy-benzoyl)-pyrrolidin-3-yl]-ethanol (2.59 mmol) and methanesulfonyl chloride (3.62 mmol) to give the title compound:

$R_f$=0.70 (silica gel, 10% methanol in dichloromethane).

22.6 Synthesis of 1-[2-[3-phenyl-1-(3,4,5-trimethoxy-benzoyl)-pyrrolidin-3-yl]-ethyl]-4-phenyl-piperidine-4-carboxylic acid amide Prepared by the method of example 3.3 using -[3-phenyl-1-(3,4,5-trimethoxy-benzoyl)-pyrrolidin-3-yl]-ethyl-methanesulfonate (2.59 mmol) and 4-phenyl-piperidine-carboxylic acid amide hydrochloride (3.3 mmol). Chromatography on silica gel (100 g) eluting sequentially with ethyl acetate, 6% methanol in dichloromethane, and 10% methanol in dichloromethane gave the title compound:

$R_f$=0.41 (silica gel, 10% methanol in dichloromethane).

22A.7 Synthesis of 1-[2-[3-phenyl-1-(3,4,5-trimethoxy-benzoyl)-pyrrolidin-3-yl]-ethyl]-4-phenyl-piperidine-4-carboxylic acid amide hydrochloride Prepared by the method of example 3.3A using 1-[2-[3-phenyl-1-(3,4,5-trimethoxy-benzoyl)-pyrrolidin-3-yl]-ethyl]-4-phenyl-piperidine-4-carboxylic acid amide (710 mg, 1.24 mmol) and dichloromethane saturated with HCl (gas) (20 mL). The solution was concentrated in vacuo to obtain a residue. The residue was dried under high vacuum at 56° C. for 18 h to afford the title compound:

Analysis: calculated for $C_{34}H_{42}ClN_3O_5 \cdot 0.91$ $H_2O$ C 65.38; H 7.07; N 6.73; Found C 65.00; H 6.97; N 6.49.

EXAMPLE 23

Synthesis of 1-[2-[3-(3,4-dimethoxy-phenyl)-1-(3,4,5-trimethoxy-benzoyl)-pyrrolidin-3-yl]-ethyl]-4-phenyl-piperidine-4-carboxylic acid amide 23.1 Synthesis of 3-cyano-3-(3,4-dimethoxy-phenyl)-pentanedioic acid diethyl ester Combined 3,4-dimethoxy-phenyl-acetonitrile (20.0 g, 113 mmol) and THF (100 mL). Cooled in a dry-ice/acetone bath. Added dropwise, sodium bis(trimethylsilyl)amide (226 mL, 1.0M in THF, 226 mmol, 2 eq.). After the addition was complete, allowed to warm to 10° C. Cooled in a dry-ice/acetone bath. Added dropwise, ethyl bromoacetate (37.7 g, 226 mmol). After the addition was complete, the reaction mixture was allowed to warm to ambient temperature and maintained overnight. Filtered the reaction mixture and concentrated in vacuo to obtain a residue. The residue was partitioned between diethyl ether (600 mL) and water (200 mL). The organic layer was extracted with water (200 mL), saturated $NH_4Cl$ (2×100 mL), dried over $MgSO_4$, filtered, and concentrated in vacuo to obtain a residue. Chromatographed on silica gel eluting with ethyl acetate/hexane (1:2) to obtain the title compound:

$R_f$=0.42 (silica gel, 1:2 ethyl acetate/hexane).

Analysis: calculated for $C_{18}H_{23}NO_6$ C 61.88; H 6.64; N 4.01; Found C 61.79; H 6.62; N 3.91.

23.2 Synthesis of [3-(3,4-dimethoxy-phenyl)-5-oxo-pyrrolidin-3-yl]-acetic acid ethyl ester Combined 3-cyano-3-(3,4-dimethoxy-phenyl)-pentanedioic acid diethyl ester (16.8 g, 48.0 mmol), methanol (300 mL) and cobalt (II) chloride hexahydrate (22.8 g, 96.0 mmol). Cooled until the internal temperature reached 10° C. Added portionwise so as to maintain the reaction temperature below 20° C., sodium borohydride (44.2 g, 1.17 mol). After addition was complete, the reaction mixture was allowed to warm to ambient temperature and stirred over the weekend. Concentrated in vacuo to obtain a residue. Partitioned between 1N HCl (800 mL) and dichloromethane (800 mL). The organic layer was extracted with 1N HCl (2×200 mL). The combined aqueous layers were extracted with dichloromethane (3×100 mL). The organic layers were combined, dried over $Na_2SO_4$, filtered, and concentrated in vacuo to obtain a residue. The residue was chromatographed on silica gel eluting with ethyl acetate/methanol (20:1) to obtain the title compound:

$R_f$=0.27 (silica gel, 20:1 ethyl acetate/methanol), mp=116°–118° C.

Analysis: calculated for $C_{16}H_{21}NO_5$ C 62.53; H 6.89; N 4.56; Found C 62.52; H 6.85; N 4.50.

23.3 Synthesis of 2-[3-(3,4-dimethoxy-phenyl)-pyrrolidin-3-yl]-ethanol

Combined $LiAlH_4$ (4.80 g, 127 mmol, 4 eq) and anhydrous THF (200 mL). Added portionwise, a slurry of [3-(3,4-dimethoxy-phenyl)-5-oxo-pyrrolidin-3-yl]-acetic acid ethyl ester (9.72 g, 31.6 mmol) in THF (100 mL). After the addition was complete, the reaction was heated at reflux overnight. Cooled in an ice/NaCl bath. Cautiously added $H_2O$ (4.8 mL), NaOH (4.8 mL, 15%), and $H_2O$ (19.2 mL). Filtered. Concentrated the filtrate to obtain a residue. Dissolved the residue in dichloromethane and dried over $MgSO_4$, filtered, and concentrated the filtrate in vacuo to obtain a residue which was dried at 0.05 Torr overnight to give the title compound. This material was used without further purification.

23.4 Synthesis of 2-[3-(3,4-dimethoxy-phenyl)-1-(3,4,5-trimethoxy-benzoyl)-pyrrolidin-3-yl]-ethanol 2-[3-(3,4-Dimethoxy-phenyl)-pyrrolidin-3-yl]-ethanol (2.27 g, 9.03 mmol) and dichloromethane (100 mL) were combined. 4-Methylmorpholine (2.28 mL, 22.6 mmol, 2.5 eq.) was added. The mixture was cooled in a ice/NaCl bath and a solution of 3,4,5-trimethoxy-benzoyl chloride (2.19 g, 9.48 mmol) in dichloromethane (30 mL) was added dropwise. After the addition was complete, the dry-ice/acetone bath was changed to an ice bath and the mixture was allowed to warm to ambient temperature and maintained overnight. The solution was extracted with 1N HCl (3×100 mL), saturated $K_2CO_3$ (3×100 mL). The organic phase was dried over $Na_2SO_4$, filtered, and concentrated in vacuo to obtain a residue. The residue was purified by chromatography on silica gel eluting with ethyl acetate/methanol (20:1) to obtain a residue. The residue was dissolved in dichloromethane (50 mL), extracted with water (2×50 mL), dried over $Na_2SO_4$, filtered, and concentrated in vacuo to obtain a residue. Heated at 110° C./0.3 Torr for 16 h to obtain the title compound: $R_f$=0.14 (silica gel, 20:1 ethyl acetate/methanol), mp=60°–62° C.

Analysis: calculated for $C_{24}H_{31}NO_7$, C 64.70; E 7.01; N 3.14; Found C 64.40; H 7.21; N 2.85.

23.5 Synthesis of 2-[3-(3,4-dimethoxy-phenyl)-1-(3,4,5-trimethoxy-benzoyl)-pyrrolidin-3-yl]-ethyl-methanesulfonate Prepared by the method of example 3.2 using 2-[3-(3,4-dimethoxy-phenyl)-1-(3,4,5-trimethoxy-benzoyl)-pyrrolidin-3-yl]-ethanol (249 mg, 0.55 mmol) and methanesulfonyl chloride (0.76 mmol) to give the title compound:

$R_f$=0.73 (silica gel, 10% methanol in dichloromethane).

23.6 Synthesis of 1-[2-[3-(3,4-dimethoxy-phenyl)-1-(3,4,5-trimethoxy-benzoyl)-pyrrolidin-3-yl]-ethyl]-4-phenyl-piperidine-4-carboxylic acid amide Prepared by the methoB of example 3.3 using 2-[3-(3,4-dimethoxy-phenyl)-1-(3,4,5-trimethoxy-benzoyl)-pyrrolidin-3-yl]-ethyl-methanesulfonate (0.55 mmol) and 4-phenyl-piperidine-4-carboxylic acid amide hydrochloride (175 mg, 0.73 mmol). Chromatography on silica gel (30 g) eluting sequentially with ethyl acetate, 6% methanol in dichloromethane, and 10% methanol in dichloromethane gave the title compound:

$R_f$=0.39 (silica gel, 10% methanol in dichloromethane).

Analysis: calculated for $C_{36}H_{45}N_3O_7 \cdot 1.7 H_2O$ C 65.27; H 7.36; N 6.34; Found C 65.26; H 7.02; N 6.32.

EXAMPLE 24

Synthesis of 1-[2-[3-(3,4-dichloro-phenyl)-1-(3,5-bis-(trifluoromethyl)-benzoyl)-pyrrolidin-3-yl]-ethyl]-4-phenyl-piperidine-4-carboxylic acid amide 24.1 Synthesis of 2-[3-(3,4-dichloro-phenyl)-1-(3,5-bis-(trifluoromethyl)-benzoyl)-pyrrolidin-3-yl]-ethanol The method of example 3.1 was used with 2-[3-(3,4-dichloro-phenyl)-pyrrolidin-3-yl]-ethanol (1 mmol) and 3,5-bis(trifluoromethyl)-benzoyl chloride (1 mmol) to obtain a residue. Chromatography of the residue on silica gel eluting sequentially with 1% methanol in dichloromethane and then 6% methanol in dichloromethane gave the title compound.

$R_f$=0.53 (silica gel, 10% methanol in dichloromethane).

24.2 Synthesis of 2-[3-(3,4-dichloro-phenyl)-1-(3,5-bis-(trifluoromethyl)-benzoyl)-pyrrolidin-3-yl]-ethyl-methanesulfonate The method of example 3.2 was used with 2-[3-(3,4-dichloro-phenyl)-1-(3,5-bis-(trifluoromethyl)-benzoyl)-pyrrolidin-3-yl]-ethanol (0,924 mmol) and methanesulfonyl chloride (1.01 mmol) to obtain a residue. Drying the residue under high vacuum at ambient temperature 18h gave the title compound.

$R_f$=0.68 (silica gel, 10% methanol in dichloromethane).

24.3 Synthesis of 1-[2-[3-(3,4-dichloro-phenyl)-1-(3,5-bis-(trifluoromethyl)-pyrrolidin-3-yl)-ethyl]-4-phenyl-piperidine-4-carboxylic acid amide The method of example 3.3 was used with 2-[3-(3,4-dichloro-phenyl)-1-(3,5-bis-(trifluoromethyl)- pyrrolidin-3-yl]-ethyl-methanesulfonate (0.87 mmol) 4-phenyl-piperidine-4-carboxylic acid amide hydrochloride (1.04 mmol) to obtain a residue. Chromatography of the residue on silica gel eluting sequentially with 30% ethyl acetate in hexane, 50% ethyl acetate in hexane, 1% methanol in dichloromethane, 3% methanol in dichloromethane, and then 6% methanol in dichloromethane gave the title compound:

$R_f$=0.41 (silica gel, 10% methanol in dichloromethane).

EXAMPLE 25

Synthesis of 1-[2-[3-(3,4-dichloro-phenyl)-1-(3,5-dimethoxy-benzoyl)-pyrrolidin-3-yl]-ethyl]-4-phenyl-piperidine-4-carboxylic acid amide 25.1 Synthesis of 2-[3-(3(4-dichloro-phenyl)-1-(3,5-dimethoxy-benzoyl)-pyrrolidin-3-yl]-ethanol The method of example 3.1 was used with 2-[3-(3,4-dichloro-phenyl)-pyrrolidin-3-yl]-ethanol (1 mmol) and 3,5-dimethoxy-benzoyl chloride (1 mmol) to prepare the title compound. Chromatography on silica gel eluting sequentially with ethyl acetate and then 6% methanol in dichloromethane gave the title compound.

$R_f$=0.72 (silica gel, 10% methanol in dichloromethane).

25.2 Synthesis of 2-[3-(3,4-dichloro-phenyl)-1-(3,5-dimethoxy-benzoyl)-pyrrolidin-3-yl]-ethyl- methanesulfonate The method of example 3.2 was used with 2-[3-(3,4-dichloro-phenyl)-1-(3,5-dimethoxy-benzoyl)-pyrrolidin-3-yl]-ethanol (0.96 mmol) and methanesulfonyl chloride (1.06 mmol) to obtain a residue. Drying the residue under high vacuum at ambient temperature 18 h gave the title compound.

25.3 Synthesis of 1-[2-[3-(3,4-dichloro-phenyl)-1-(3,5-dimethoxy-benzoyl)-pyrrolidin-3-yl]-ethyl]-4-phenyl-piperidine-4-carboxylic acid amide The method of example 3.3 was used with 2-[3-(3,4-dichloro-phenyl)-1-(3,5-dimethoxy-benzoyl)-pyrrolidin-3-yl]-ethyl-methanesulfonate (0.96 mmol) and 4-phenyl-piperidine-4-carboxylic acid amide hydrochloride (1.06 mmol) to prepare the title compound. Chromatography on silica gel eluting sequentially with ethyl acetate, 6% methanol in dichloromethane, and then 10% methanol in dichloromethane gave the title compound:

$R_f$=0.55 (silica gel, 10% methanol in dichloromethane).

EXAMPLE 26

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-dimethylamino-ethyl)-amide 26.1 Synthesis of 4-phenyl-piperidine-4-carboxylic acid methyl-ester hydrochloride 4-Phenyl-piperidine-4-carboxylic acid hydrochloride (from example 20.6) (2.67 g, 11 mmol) and methanol (35 mL) were combined. $SOCl_2$ (0.9 mL, 12.34 mmol, 1.1 eq.)

was added dropwise. The reaction was heated at reflux for 18 h. The reaction was concentrated in vacuo to obtain a residue. The residue was slurried in diethyl ether, filtered, and the solids were rinsed with diethyl ether to give the title compound.

26.2 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid methyl-ester The method of example 3.3 was used with 2-[3-(3,4-dichloro-phenyl)-1-(3,4,5-trimethoxy-benzoyl) -pyrrolidin-3-yl]-ethyl-methanesulfonate (5 mmol) and 4-phenyl-piperidine-4-carboxylic acid methyl-ester hydrochloride (6 mmol, 1.2 eq.) to obtain a residue. The residue was chromatographed on silica gel eluting sequentially with 1% methanol in dichloromethane and then 2% methanol in dichloromethane to give the title compound:

$R_f$=0.57 (silica gel, 6% methanol in dichloromethane).

26.3 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 1-[2-[3-(3,4-Dichloro-phenyl)-1-(3,4,5-trimethoxy-benzoyl)-pyrrolidin-3-yl]-ethyl]-4-phenyl-piperidine-4-carboxylic acid methyl-ester (0.393 g, 0.60 mmol) and NaOH (6 mL, 1N, 6 mmol) were combined in ethanol (12 mL). The mixture was stirred for 48 h at ambient temperature. 1N HCl was added to adjust the pH to 1. The aqueous phase was extracted with ethyl acetate. The organic phase was dried over $MgSO_4$, filtered, and concentrated in vacuo to obtain a residue. The residue was chromatographed on silica gel eluting sequentially with 10% methanol in dichloromethane and then 20% methanol in dichloromethane. The fractions which contained the title compound were washed with $H_2O$, dried over $MgSO_4$, filtered, and concentrated in vacuo to give the title compound:

$R_f$=0.59 (silica gel, 85:10:5 $CHCl_3$:$CH_3OH$:$CH_3CO_2H$).

26FH.4 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-dimethylamino-ethyl)-amide bis-trifluoroacetate 1-[2-[3-(3,4-Dichloro-phenyl)-1-(3,4,5-trimethoxy-benzoyl)-pyrrolidin-3-yl]-ethyl]-4-phenyl-piperidine-4-carboxylic acid (0.2566 g, 0.4 mmol), N,N-dimethylethylene-diamine (0.05 mL, 0.48 mmol), HOBt (65 mg, 0.48 mmol), EDC (92 mg, 0.48 mmol), DIEA (0.08 mL, 0.48 mmol) were combined in dichloromethane (20 mL). The mixture was stirred for 72 h at ambient temperature. The mixture was extracted with $H_{2O}$. The organic phase was dried over $MgSO_4$, filtered, and concentrated in vacuo to obtain a residue. The residue was chromatographed using a Vydac (25×250 mm) C-18 HPLC column to give the title compound:

$R_t$=28 minutes (gradient elution with $CH_3CN$/$H_2O$(0.1% TFA; flow rate=1.0 ml/min.) 10% $CH_3CN$ for 10 minutes, 30% $CH_3CN$ for 15 minutes, 40% $CH_3CN$ for 15 minutes, 50% $CH_3CN$ for 10 minutes, and then 100% $CH_3CN$).

EXAMPLE 27

Synthesis of 1-[2-[3-(3,4-dichloro-phenyl)-1-(3-methoxy-benzoyl)-pyrrolidin-3-yl]-ethyl]-4-phenyl-piperidine-4-carboxylic acid amide 27.1 Synthesis of,2-[3-(3,4-dichloro-phenyl)-1-(3-methoxy-benzoyl)-pyrrolidin-3-yl]-ethanol The method of example 3.1 was used with 2-[3-(3,4-dichloro-phenyl)-pyrrolidin-3-yl]-ethanol (2 mmol) and 3-methoxy-benzoyl chloride (2 mmol) to obtain a residue. The residue was chromatographed on silica gel eluting sequentially with ethyl acetate and then 6% methanol in dichloromethane to give the title compound.

$R_f$=0.53 (silica gel, 10% methanol in dichloromethane).

27.2 Synthesis of 2-[3-(3,4-dichloro-phenyl)-1-(3-methoxy-benzoyl)-pyrrolidin-3-yl]-ethyl-methanesulfonate The method of example 3.2 was used with 2-[3-(3,4-dichloro-phenyl)-1-(3-methoxy-benzoyl)-pyrrolidin-3-yl]-ethanol (0.6 mmol) and methanesulfonyl chloride (0.66 mmol) to obtain a residue. Drying the residue under high vacuum at ambient temperature for 18 h gave the title compound:

$R_f$=0.69 (silica gel, 10% methanol in dichloromethane).

27.3 Synthesis of 1-[2-[3-(3,4-dichloro-phenyl)-1-(3-methoxy-benzoyl)-pyrrolidin-3-yl]-ethyl]-4-phenyl-piperidine-4-carboxylic acid amide The method of example 3.3 was used with 2-[3-(3,4-dichloro-phenyl)-1-(3-methoxy-benzoyl)-pyrrolidin-3-yl]-ethyl-methanesulfonate (0.6 mmol) 4-phenyl-piperidine-4-carboxylic acid amide hydrochloride (0.72 mmol) to prepare the title compound. Chromatography on silica gel eluting sequentially with ethyl acetate, 6% methanol in dichloromethane, and then 10% methanol in dichloromethane gave the title compound:

$R_f$=0.41 (silica gel, 10% methanol in dichloromethane).

27.3.1 Synthesis of,1-[2-[3-(3,4-dichloro-phenyl)-1-(3-methoxy-benzoyl)-pyrrolidin-3-yl]-ethyl]-4-phenyl-piperidine-4-carboxylic acid amide 2-[3-(3,4-Dichloro-phenyl)-1-(3-methoxy-benzoyl)-pyrrolidin-3-yl]-ethyl-methanesulfonate (0.54 g), 4-phenyl-piperidine-4-carboxylic acid amide hydrochloride (173 mg, 0.72 mmol) and potassium carbonate (0.25 g, 1.8 mmol) were combined in THF/$H_2O$ (20 mL/10 mL) and heated at reflux for 48 hours. The reaction mixture was diluted with ethyl acetate and extracted with water. The organic layer was separated, dried over $MgSO_4$, and evaporated in vacuo to give a residue. The residue was chromatographed on silica gel eluting sequentially with 1% methanol in dichloromethane, 2% methanol in dichloromethane, 3% methanol in dichloromethane, 6% methanol in dichloromethane, and 10% methanol in dichloromethane to give the title compound:

$R_f$=0.48 (silica gel, 10% methanol in dichloromethane).

Exact mass (FAB+): calculated for $C_{32}H_{36}Cl_2N_3O_3$ calculated 580.2133. Found 580.2131.

EXAMPLE 28

Synthesis of 1-[2-[3-(benzo[1,3]dioxol-5-yl)-1-(3,4,5-trimethoxy-benzoyl)-pyrrolidin-3-yl]-ethyl]-4-phenyl-piperidine-4-carboxylic acid amide 28.1 Synthesis of 3-cyano-3-(benzo[1,3]dioxol-5-yl)-pentanedioic acid diethyl ester Combined 3-(benzo[1,3]dioxol-5-yl)-phenylacetonitrile (25.7 g, 0,159 mol) and THF (200 mL). Cooled in a dry-ice/acetone bath. Added dropwise, sodium bis-(trimethylsilyl)amide (318 mL, 1.0M in THF, 0,318 mol, 2 eq.). After the addition was complete, allowed to warm to 10° C. Cooled in a dry-ice/acetone bath. Added dropwise, ethyl bromoacetate (35.3 mL, 0.318 mol). After the addition was complete, warmed to ambient temperature. Removed the THF by evaporation at reduced pressure. Partitioned the reaction mixture between diethyl ether (200 mL) and water (200 mL). Extracted the organic layer with saturated $NH_4Cl$ solution (2×200 mL). Dried over $MgSO_4$, filtered, and concentrated in vacuo to obtain a residue. Chromatographed on silica gel eluting with 25% ethyl acetate in hexane to obtain the title compound:

$R_f$=0.32 (silica gel, 25% ethyl acetate in hexane).

Analysis: calculated for $C_{17}H_{19}NO_6$ C 61.25; H 5.75; N 4.20; Found C 61.51; H 5.88; N 4.18.

28.2 Synthesis of [3-(benzo[1r3]dioxol-5-yl)-5-oxo-pyrrolidin-3-yl]-acetic acid ethyl ester Prepare by the method of example 1.2.2 using 3-cyano-3-(benzo[1,3]dioxol-5-yl)-pentanedioic acid diethyl ester (89 mmol). Chromatograph on silica gel to give the title compound.

28.3 Synthesis of 2-(3-benzo[1,3]dioxol-5-yl-pyrrolidin-3-yl)-ethanol

Prepare by the method of example 1.3.2 using [3-(benzo[1,3]dioxol-5-yl)-5-oxo-pyrrolidin-3-yl]-acetic acid ethyl ester (73 mmol). Chromatograph on silica gel to give the title compound.

28.4 Synthesis of 2-[3-(benzo[1,3]dioxol-5-yl)-1-(3,4,5-trimethoxy-benzoyl)-pyrrolidin-3-yl]-ethanol Prepare by the method of example 3.1 using 2-(3-benzo[1,3]dioxol-5-yl-pyrrolidin-3-yl)-ethanol (23 mmol) and 3,4,5-trimethoxy-benzoyl chloride (23 mmol). Chromatograph on silica gel to give the title compound.

28.5 Synthesis of 2-[3-(benzo[1,3]dioxol-5-yl)-1-(3,4,5-trimethoxy-benzoyl)-pyrrolidin-3-yl]-ethyl-methanesulfonate Prepare by the method of example 3.2 using 2-[3-(benzo[1,3]dioxol-5-yl)-1-(3,4,5-trimethoxy-benzoyl)-pyrrolidin-3-yl]-ethanol (8 mmol) and methanesulfonyl chloride (11 mmol) to give the title compound. $R_f$=0.60 (silica gel, 6% methanol/dichloromethane).

28.6 Synthesis of 1-[2-[3-(benzo[1,3]dioxol-5-yl)-1-(3,4,5-trimethoxy-benzoyl)-pyrrolidin-3-yl]-ethyl]-4-phenyl-piperidine-4-carboxylic acid amide Prepare by the method of example 3.3 using 2-[3-(benzo[1,3]dioxol-5-yl)-1-(3,4,5-trimethoxy-benzoyl)-pyrrolidin-3-yl]-ethyl-methanesulfonate (8 mmol) and 4-phenyl-piperidine-4-carboxylic acid amide hydrochloride (12 mmol). Chromatograph on silica gel to give the title compound.

28.6.1 Synthesis of 1-[2-[3-(benzo[1,31dioxol-5-yl)-1-(3,4,5-trimethoxy-benzoyl)-pyrrolidin-3-yl]-ethyl]-4-phenyl-piperidine-4-carboxylic acid amide Prepare by the method of example 27.3.1 using 2-[3-(benzo[1,3]dioxol-5-yl)-1-(3,4,5-trimethoxy-benzoyl)-pyrrolidin-3-yl]-ethyl-methanesulfonate (0.22 g, 0.43 mmol) and 4-phenyl-piperidine-4-carboxylic acid amide hydrochloride (0.21 g,0.86 mmol). Chromatograph on silica gel eluting sequentially with 50% ethyl acetate/hexane and then 6% methanol/dichloromethane to give the title compound: $R_f$=0.38 (silica gel, 10% methanol/ dichloromethane).

Exact mass (FAB+): calculated for $C_{35}H_{42}N_3O_7$ calculated 616.3023. Found 616.3027.

EXAMPLE 29

Synthesis of 1-[2-[3-(3,4-dimethoxy-phenyl)-1-(3,4,5-triethoxy-benzoyl)-pyrrolidin-3-yl]-ethyl]-4-phenyl-piperidine-4-carboxylic acid amide 29.1 Synthesis of 2-[3-(3,4-dimethoxy-phenyl)-1-(3,4,5-triethoxy-benzoyl)-pyrrolidin-3-yl]-ethanol 2-[3-(3,4-Dimethoxy-phenyl)-pyrrolidin-3-yl]-ethanol (405 mg, 1.61 mmol) and dichloromethane (20 mL) were combined. 4-Methylmorpholine (350L, 3.22 mmol, 2 eq.) was added. The mixture was cooled in a dry-ice/acetone bath and a solution of 3,4,5-triethoxy-benzoyl chloride (461 mg, 1.69 mmol) in dichloromethane (10 mL) was added dropwise. After the addition was complete, the dry-ice/acetone bath was changed to an ice bath and the mixture was stirred for 1 h. Allowed to warm to ambient temperature and maintained overnight. The solution was extracted with iN HCl (2×50 mL), saturated $NaHCO_3$ (50 mL), and $H_{2O}$ (50 mL). The organic phase was dried over $Na_2SO_4$, filtered, and concentrated in vacuo obtain a residue. The residue was purified by chromatography on silica gel eluting with ethyl acetate/methanol (20:1) to obtain a residue. The residue was dissolved in dichloromethane (50 mL), extracted with water (2×50 mL), dried over $Na_2SO_4$, filtered, and concentrated in vacuo to obtain a residue. Heated at 70° C./0.5 Torr for 16 h to obtain the title compound: $R_f$=0.31 (silica gel, 20:1 ethyl acetate/methanol), mp=139°–141° C.

29.2 Synthesis of 2-[3-(3,4-dimethoxy-phenyl)-1-(3,4,5-triethoxy-benzoyl)-pyrrolidin-3-yl]-ethyl-methanesulfonate Prepare by the method of example 3.2 using 2-[3-(3,4-methoxy-phenyl)-1-(3,4,5-triethoxy-benzoyl)-pyrrolidin-3-yl]-ethanol (8 mmol) and methanesulfonyl chloride (11 mmol) to give the title compound.

29.3 Synthesis of 1-[2-[3-(3,4-dimethoxy-phenyl)-1-(3,4,5-triethoxy-benzoyl)-pyrrolidin-3-yl]-ethyl]-4-phenyl-piperidine-4-carboxylic acid amide Prepare by the method of example 3.3 using 2-[3-(3,4-dimethoxy-phenyl)-1-(3,4,5-triethoxy-benzoyl)-pyrrolidin-3-yl]-ethyl-methanesulfonate (8 mmol) and 4-phenyl-piperidine-4-carboxylic acid amide hydrochloride (12 mmol). Chromatograph on silica gel to give the title compound.

EXAMPLE 30

Synthesis of 1-[2-[3-(3,4-dichloro-phenVl)-1-(3,4,5-trimethoxy-benzoyl)-pyrrolidin-3-yl]-ethyl]-4-(naphth-2-yl)-piperidine-4-carboxylic acid amide 30.1 Synthesis of 2-chloro-N-(2-chloroethyl)-N-tert-butoxycarbonyl-ethanamine Combine bis-(2-chloroethyl) amine hydrochloride (500 mmol) and dichloromethane (350 mL). Add dropwise, N,N-diisopropylethylamine (1.1 mol). Cool the mixture to −30° C. Add dropwise, a solution of di-tert-butyl dicarbonate (550 mmol) in dichloromethane (100 mL). Stir the mixture and allow it to warm to ambient temperature. Concentrate the mixture in vacuo to give a residue. Purify the residue to give the title compound.

30.2 Synthesis of 1-tert-butoxycarbonyl-4-cyano-4-(naphth-2-yl)-piperidine

Combine naphth-2-ylacetonitrile (10 mmol) and 2-chloro-N-(2-chloroethyl)-N-tert-Butoxycarbonyl-ethanamine (11 mmol) in DMSO (30 mL). Add portionwise, $NaNH_2$ (22 mmol). After the addition, stir for an additional 0.5 h. Pour the contents of the flask over ice (150 g). Extract the mixture with dichloromethane. Dry the organic phase over $MgSO_4$, filter, and concentrate in vacuo to give a residue. Purify to give the title compound.

30.3 Synthesis of 4-cyano-4-(naphth-2-yl)-piperidine hydrochloride

Combine 1-tert-butoxycarbonyl-4-cyano-4-(naphth-2-yl) -piperidine (3.12 mmol) and HCl in dioxane (10 mL, 40 mmol, 4N, 13 eq.) at ambient temperature for 1 h. Concentrate the solvent in vacuo and dry under high vacuum to give the title compound.

30.4 Synthesis of 4-(naphth-2-yl)-piperidine-4-carboxylic acid hydrochloride

Prepare by the method of example 20.6 using 4-cyano-4-(naphth-2-yl)-piperidine hydrochloride (10 mmol) and KOH (0.4 mol, 3N). Purify to give the title compound.

30.5 Synthesis of 1-tert-butoxycarbonyl-4-(naphth-2-yl)-piperidine-4-carboxylic acid Prepare by the method of example 20.7 using 4-(naphth-2-yl)-piperidine-4-carboxylic acid hydrochloride (10 mmol) and di-tert-butyl dicarbonate (11 mmol). Purify to give the title compound.

30.6 Synthesis of 1-tert-butoxycarbonyl-4-(naphth-2-yl)-piperidine-4-carboxylic acid amide Prepare by the method of example 20.8 using 1-tert-butoxycarbonyl-4-(naphth-2-yl)-piperidine-4-carboxylic acid (4 mmol) and $NH_3$(gas). Purify to give the title compound.

30.7 Synthesis of 4-(naphth-2-yl)-piperidine-4-carboxylic acid amide hydrochloride Prepare by the method of example 20.10 using 1-tert-butoxycarbonyl-4-(naphth-2-yl)-piperidine-4-carboxylic acid amide (3 mmol) and HCl in dioxane (40 mmol, 4N) to give the title compound.

30.8 Synthesis of 1-[2-[3-(3,4-dichloro-phenyl)-1-(3,4,5-trimethoxy-benzoyl)-pyrrolidin-3-yl]-ethyl]-4-(naphth-2-yl)-piperidine-4-carboxylic acid amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-(naphth-2-yl)-piperidine-4-carboxylic acid amide hydrochloride (7.5 mmol, 1.5 eq.). Chromatograph on silica gel to give the title compound.

EXAMPLE 31

Synthesis of 1-[2-[3-(3,4-dichloro-phenyl)-1-(3,4,5-trimethoxy-benzoyl)-pyrrolidin-3-yl]-ethyl]-4-(pyridin-4-y1)-piperidine-4-carboxylic acid amide 31.1 Synthesis of 1-tert-butoxycarbonyl-4-cyano-4-(pyridin-4-yl)-piperidine Prepare by the method of example 30.2 using 4-pyridylacetonitrile (10 mmol) and 2-chloro-N-(2-chloroethyl)-N-tert-butoxycarbonyl-ethanamine (11 mmol). Purify to give the title compound.

31.2 Synthesis of 4-cyano-4-(pyridin-4-yl)-piperidine hydrochloride

Prepare by the method of example 30.3 using 1-tert-butoxycarbonyl-4-cyano-4-(pyridin-4-yl)-piperidine (3 mmol) and HCl in dioxane (40 mmol, 4N). Concentrate the solvent in vacuo and dry under high vacuum to give the title compound.

31.3 Synthesis of 4-(pyridin-4-yl)-piperidine-4-carboxylic acid hydrochloride

Prepare by the method of example 20.6 using 4-cyano-4-(pyridin-4-yl)-piperidine hydrochloride (10 mmol) and KOH (0.4 mol, 3N). Purify to give the title compound.

31.4 Synthesis of 1-tert-butoxycarbonyl-4-(pyridin-4-yl)-piperidine-4-carboxylic acid Prepare by the method of example 20.7 using 4-(pyridin-4-yl)-piperidine-4-carboxylic acid hydrochloride (10 mmol) and di-tert-butyl dicarbonate (11 mmol). Purify to give the title compound.

31.5 Synthesis of 1-tert-butoxycarbonyl-4-(pyridin-4-yl)-piperidine-4-carboxylic acid amide Prepare by the method of example 20.8 using 1-tert-butoxycarbonyl-4-(pyridin-4-yl)-piperidine-4-carboxylic acid (4.0 mmol) and $NH_3$(gas). Purify to give the title compound.

31.6 Synthesis of 4-(pyridin-4-yl)-piperidine-4-carboxylic acid amide hydrochloride Prepare by the method of example 20.10 using 1-tert-butoxycarbonyl-4-(pyridin-4-yl)-piperidine-4-carboxylic acid amide (3 mmol) and HCl in dioxane (40 mmol, 4N) to give the title compound.

31.7 Synthesis of 1-[2-[3-(3,4-dichloro-phenyl)-1-(3,4,5-trimethoxy-benzoyl)-pyrrolidin-3-yl]-ethyl]-4-(pyridin-4-yl)-piperidine-4-carboxylic acid amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-(pyridin-4-yl)-piperidine-4-carboxylic acid amide hydrochloride (7.5 mmol, 1.5 eq.). Chromatograph on silica gel to give the title compound.

EXAMPLE 32

Synthesis of 1-[2-[3-(3,4-dichloro-phenyl)-1-(3,4,5-trimethoxy-benzoyl)-pyrrolidin-3-yl]-ethyl]-4-(pyridin-3-yl)-piperidine-4-carboxylic acid amide 32.1 Synthesis of 1-tert-Butoxycarbonyl-4-cyano-4-(pyridin-3-yl)-piperidine Prepare by the method of example 30.2 using 3-pyridylacetonitrile (10 mmol) and 2-chloro-N-(2-chloroethyl)-N-tert-butoxycarbonyl-ethanamine (11 mmol). Purify to give the title compound.

32.2 Synthesis of 4-cyano-4-(pyridin-3-yl)-piperidine hydrochloride

Prepare by the method of example 30.3 using 1-tert-butoxycarbonyl-4-cyano-4-(pyridin-3-yl)-piperidine (3 mmol) and HCl in dioxane (40 mmol, 4N). Concentrate the solvent in vacuo and dry under high vacuum to give the title compound.

32.3 Synthesis of 4-(pyridin-3-yl)-piperidine-4-carboxylic acid hydrochloride

Prepare by the method of example 20.6 using 4-cyano-4-(pyridin-3-yl)-piperidine hydrochloride (10 mmol) and KOH (0.4 mol, 3N). Purify to give the title compound.

32.4 Synthesis of 1-tert-butoxycarbonyl-4-(pyridin-3-yl)-piperidine-4-carboxylic acid Prepare by the method of example 20.7 using 4-(pyridin-3-yl)-piperidine-4-carboxylic acid hydrochloride (10 mmol) and di-tert-butyl dicarbonate (11 mmol). Purify to give the title compound.

32.5 Synthesis of 1-tert-butoxycarbonyl-4-(pyridin-3-yl)-piperidine-4-carboxylic acid amide Prepare by the method of example 20.8 using 1-tert-butoxycarbonyl-4-(pyridin-3-yl)-piperidine-4-carboxylic acid (4.0 mmol) and NH3(gas). Purify to give the title compound.

32.6 Synthesis of 4-(pyridin-3-yl)-piperidine-4-carboxylic acid amide hydrochloride Prepare by the method of example 20.10 using 1-tert-butoxycarbonyl-4-(pyridin-3-yl)-piperidine-4-carboxylic acid amide (3 mmol) and HCl in dioxane (40 mmol, 4N) to give the title compound.

32.7 Synthesis of 1-[2-[3-(3,4-dichloro-phenyl)-1-(3,4r5-trimethoxy-benzoyl)-pyrrolidin-3-yl]-ethyl₁-4-(pyridin-3-yl)-piperidine-4-carboxylic acid amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-(pyridin-3-yl)-piperidine-4-carboxylic acid amide hydrochloride (7.5 mmol, 1.5 eq.). Chromatograph on silica gel to give the title compound.

EXAMPLE 33

Synthesis of 1-[2-[3-(3,4-dichloro-phenyl)-1-(3,4,5-trimethoxy-benzoyl)-pyrrolidin-3-yl]-ethyl]-4-(pyridin-2-yl)-piperidine-4-carboxylic acid amide 33.1 Synthesis of 1-tert-butoxycarbonyl-4-cyano-4-(pyridin-2-yl)-piperidine Prepare by the method of example 30.2 using 2-pyridylacetonitrile (10 mmol) and 2-chloro-N-(2-chloroethyl)-N-tert-Butoxycarbonyl-ethanamine (11 mmol). Purify to give the title compound.

33.2 Synthesis of 4-cyano-4-(pyridin-2-yl)-piperidine hydrochloride

Prepare by the method of example 30.3 using 1-tert-butoxycarbonyl-4-cyano-4-(pyridin-2-yl)-piperidine (3 mmol) and HCl in dioxane (40 mmol, 4N). Concentrate the solvent in vacuo and dry under high vacuum to give the title compound.

33.3 Synthesis of 4-(pyridin-2-yl)-piperidine-4-carboxylic acid hydrochloride

Prepare by the method of example 20.6 using 4-cyano-4-(pyridin-2-yl)-piperidine hydrochloride (10 mmol) and KOH (0.4 mol, 3N). Purify to give the title compound.

33.4 Synthesis of 1-tert-butoxycarbonyl-4-(pyridin-2-yl)-piperidine-4-carboxylic acid Prepare by the method of example 20.7 using 4-(pyridin-2-yl)-piperidine-4-carboxylic acid hydrochloride (10 mmol) and di-tert-butyl dicarbonate (11 mmol). Purify to give the title compound.

33.5 Synthesis of 1-tert-butoxycarbonyl-4-(pyridin-2-yl)-piperidine-4-carboxylic acid amide Prepare by the method of example 20.8 using 1-tert-butoxycarbonyl-4-(pyridin-2-yl)-piperidine-4-carboxylic acid (4 mmol) and NH3(gas). Purify to give the title compound.

33.6 Synthesis of 4-(pyridin-2-yl)-piperidine-4-carboxylic acid amide hydrochloride Prepare by the method of example 20.10 using 1-tert-butoxycarbonyl-4-(pyridin-2-yl)-piperidine-4-carboxylic acid amide (3 mmol) and HCl in dioxane (40 mmol, 4N) to give the title compound.

3.7 Synthesis of 1-[2-[3-(3,4-dichloro-phenyl)-1-(3,4,5-trimethoxy-benzoyl)-pyrrolidin-3-yl]-ethyl)-4-(pyridin-2-yl)-piperidine-4-carboxylic acid amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-(pyridin-2-yl)-piperidine-4-carboxylic acid amide hydrochloride (7.5 mmol, 1.5 eq.). Chromatograph on silica gel to give the title compound.

EXAMPLE 34

Synthesis of 1-[2-[3-(3,4-dichloro-phenyl)-1-(3,4,5-trimethoxy-benzoyl)-pyrrolidin-3-yl]-ethyl]-4-benzyl-piperidine-4-carboxylic acid amide 34.1 Synthesis of ethyl-(1-tert-butoxycarbonyl-piperidine)-4-carboxylate Combine ethyl-piperidine-4-carboxylate (10 mmol) and dichloromethane (50 mL). Add dropwise, N,N-diisopropylethylamine (11 mmol). Add dropwise, a solution of di-tert-butyl dicarbonate (11 mmol) in dichloromethane (10 mL). Stir the mixture at ambient temperature. Extract the mixture with 1N HCl and $H_2O$. Dry the organic phase over $MgSO_4$, filter, and concentrate in vacuo to give a residue. Purify the residue to give the title compound.

34.2 Synthesis of ethyl-(4-benzyl-1-tert-butoxycarbonyl-piperidine)-4-carboxylate Combine lithium diisopropylamide (11 mmol) and THF (100 mL). Cool in a dry-ice/acetone bath. Add ethyl-(1-tert-butoxycarbonyl-piperidine)-4-carboxylate (10 mmol). Stir for 2 h. Add dropwise, benzyl bromide (12 mmol) in hexamethylphosphoramide (3 mmol). Stir and allow the mixture to warm slowly. Dilute with ethyl acetate and extract with $H_2O$. Dry the organic phase over $MgSO_4$, filter, and concentrate in vacuo to give a residue. Purify the residue to give the title compound.

34.3 Synthesis of 4-benzyl-1-tert-butoxycarbonyl-piperidine)-4-carboxylic acid

Combine ethyl-(4-benzyl-1-tert-butoxycarbonyl-piperidine)-4-carboxylate (0.60 mmol) and NaOH (6 mL, 1N, 6 mmol) in ethanol (12 mL). Stir the mixture at ambient temperature. Add 1N HCl to adjust the pH to 1. Extract the aqueous phase with ethyl acetate. Dry the organic phase over $MgSO_4$, filter, and concentrate in vacuo to obtain a residue. Purify the residue to give the title compound. 34.4 Synthesis of 4-benzyl-1-tert-butoxycarbonyl-piperidine)-4-carboxylic acid amide Prepare by the method of example 20.8 using 4-benzyl-1-tert-butoxycarbonyl-piperidine-4-carboxylic acid (4.0 mmol) and $NH_3$(gas). Purify to give the title compound.

34.5 Synthesis of 4-benzyl-piperidine-4-carboxylic acid amide

Prepare by the method of example 20.10 using 4-benzyl-1-tert-butoxycarbonyl-piperidine)-4-carboxylic acid amide (3 mmol) and HCl in dioxane (40 mmol, 4N) to give the title compound.

34.6 Synthesis of 1-[2-[3-(3,4-dichloro-phenyl)-1-(3,4,5-trimethoxy-benzoyl)-pyrrolidin-3-yl]-ethyl]-4-benzyl-piperidine-4-carboxylic acid amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-benzyl-piperidine-4-carboxylic acid amide hydrochloride (7.5 mmol, 1.5 eq.). Chromatograph on silica gel to give the title compound.

EXAMPLE 35

Synthesis of 1-[2-[3-(3,4-dichloro-phenyl)-1-(3,4,5-trimethoxy-benzoyl)-pyrrolidin-3-Vl]-ethyl]-4-phenyl-piperidine-4-carboxylic acid pyrrolidine-amide 35.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid pyrrolidine-amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-phenyl-piperidine-4-carboxylic acid pyrrolidine-amide hydrochloride (7.5 mmol, 1.5 eq.). Chromatograph on silica gel to give the title compound.

35.1.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid pyrrolidine-amide Prepare by the method of example 27.3.1 using 2-[3-(3,4-dichloro-phenyl)-1-(3,4,5-trimethoxy-benzoyl)-pyrrolidin- 3-yl]-ethyl-methanesulfonate (0.22 g, 0.42 mmol) and 4-phenyl-piperidine-4-carboxylic acid pyrrolidine-amide hydrochloride (0.13 mmol, 0.42 mmol). Chromatograph on silica gel eluting sequentially with 50% ethyl acetate/hexane, 2% methanol/dichloromethane, and then 4% methanol/dichloromethane.to give the title compound:

$R_f$=0.50 (silica gel, 6% methanol/dichloromethane).

Exact mass (FAB+): calculated for $C_{38}H_{46}Cl_2N_3O_5$ calculated 694.2830. Found 694.2814.

EXAMPLE 36

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide 36.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-phenyl-piperidine-4-carboxylic acid morpholine-amide hydrochloride (7.5 mmol, 1.5 eq.). Chromatograph on silica gel to give the title compound.

36.1.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (0.22 g, 0.42 mmol) and 4-phenyl-piperidine-4-carboxylic acid morpholine-amide hydrochloride (0.13 mmol, 0.42 mmol). Chromatograph on silica gel eluting sequentially with 50% ethyl acetate/hexane, 3% methanol/dichloromethane, and then 6% methanol/dichloromethane to give the title compound. Exact mass (FAB+): calculated for $C_{38}H_{46}Cl_2N_3O_6$ calculated 710.2764. Found 710.2762.

EXAMPLE 36A

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide hydrochloride 36A.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide hydrochloride Prepare by the method of example 66.4 using 1-[2-[3-(3,4-dichloro-phenyl)-1-(3,4,5-trimethoxy-benzoyl)pyrrolidin-3-yl]-ethyl]-4-phenyl-piperidine-4-carboxylic acid morpholine-amide (2.34 g, 3.3 mmol) and dichloromethane saturated with hydrochloric acid (100 mL) to give the title compound: $R_f$=0.58 (silica gel, 10% methanol/dichloromethane).

EXAMPLE 37

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid piperidine-amide 37.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid piperidine-amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-phenyl-piperidine-4-carboxylic acid piperidine-amide hydrochloride (7.5 mmol, 1.5 eq.). Chromatograph on silica gel to give the title compound.

37.1.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid piperidine-amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (0.21 g, 0.4 mmol) and 4-phenyl-piperidine-4-carboxylic acid piperidine-amide hydrochloride (0.12 mmol, 0.4 mmol). Chromatograph on silica gel eluting sequentially with 50% ethyl acetate/hexane, 2% methanol/dichloromethane, and then 4% methanol/dichloromethane to give the title compound: $R_f$=0.41 (silica gel, 5% methanol/dichloromethane). Exact mass (FAB+): calculated for $C_{39}H_{48}Cl_2N_3O_5$ calculated 708.2937. Found 708.2971.

EXAMPLE 38

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid methyl-amide 38.1 Synthesis of 1-tert-butoxycarbonyl-4-phenyl-piperidine-4-carboxylic acid methyl-amide Prepare by the method of example 20.8 using 1-tert-butoxycarbonyl-4-phenyl-piperidine-4-carboxylic acid (4.0 mmol) and $CH_3NH_2$. Purify to give the title compound.

38.2 Synthesis of 4-phenyl-piperidine-4-carboxylic acid methyl-amide

Prepare by the method of example 20.10 using 4-phenyl-1-tert-butoxycarbonyl-piperidine)-4-carboxylic acid methyl-amide (3 mmol) and HCl in dioxane (40 mmol, 4N) to give the title compound.

38.3 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid methyl-amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-phenyl-piperidine-4-carboxylic acid methyl-amide hydrochloride (7.5 mmol, 1.5 eq.). Chromatograph on silica gel to give the title compound.

EXAMPLE 39

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid dimethyl-amide 39.1 Synthesis of 1-tert-butoxycarbonyl-4-phenyl-piperidine-4-carboxylic acid dimethyl-amide Prepare by the method of example 20.8 using 1-tert-butoxycarbonyl-4-phenyl-piperidine-4-carboxylic acid (4.0 mmol) and $(CH_3)_2NH$. Purify to give the title compound.

39.2 Synthesis of 4-phenyl-piperidine-4-carboxylic acid dimethyl-amide

Prepare by the method of example 20.10 using 4-phenyl-1-tert-butoxycarbonyl-piperidine)-4-carboxylic acid dimethyl-amide (3 mmol) and HCl in dioxane (40 mmol, 4N) to give the title compound.

39.3 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid dimethyl-amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-phenyl-piperidine-4-carboxylic acid dimethyl-amide hydrochloride (7.5 mmol, 1.5 eq.). Chromatograph on silica gel to give the title compound.

EXAMPLE 40

Synthesis of 1-[2-[3-(3,4-dichloro-phenyl)-1-(4-chloro-benzoyl)-pyrrolidin-3-yl]-ethyl]-4-phenyl-piperidine-4-carboxylic acid amide 40.1 Synthesis of 2-[3-(3,4-dichloro-phenyl)-1-(4chloro-benzoyl)-pyrrolidin-3-yl]-ethanol Prepare by the method of example 3.1 using 2-[3-(3,4-dichloro-phenyl)-pyrrolidin-3-yl]-ethanol (2 mmol) and 4-chlorobenzoyl chloride (2 mmol). Chromatograph on silica gel to give the title compound.

40.2 Synthesis of 2-[3-(3,4-dichloro-phenyl)-1-(4-chloro-benzoyl)-pyrrolidin-3-yl]-ethyl-methanesulfonate Prepare by the method of example 3.2 using 2-[3-(3,4-dichloro-phenyl)-1-(4-chloro-benzoyl)-pyrrolidin-3-yl]-ethanol (0.6 mmol) and methanesulfonyl chloride (0.66 mmol). Dry the residue under high vacuum at ambient temperature 18 h to obtain the title compound.

40.3 Synthesis of 1-[2-[3-(3,4-dichloro-phenyl)-1-(4-chloro-benzoyl)-pyrrolidin-3-yl]-ethyl]-4-phenyl-piperidine-4-carboxylic acid amide Prepare by the method of example 3.3 using 2-[3-(3,4-dichloro-phenyl)-1-(4-chloro-benzoyl)-pyrrolidin-3-yl]-ethyl-methanesulfonate (0.6 mmol) and 4-phenyl-piperidine-4-carboxylic acid amide hydrochloride (0.72 mmol). Chromatograph on silica gel to give the title compound.

EXAMPLE 41

Synthesis of 1-[2-[3-(3,4-dichloro-phenyl)-1-(4-tert-butyl -benzoyl)-pyrrolidin-3-yl]-ethyl]-4-phenyl-piperidine-4-carboxylic acid amide 41.1 Synthesis of 2-[3-(3,4-dichloro-phenyl)-1-(4-tert-butyl-benzoyl)-pyrrolidin-3-yl]-ethanol Prepare by the method of example 3.1 using 2-[3-(3,4-dichloro-phenyl)-pyrrolidin-3-yl]-ethanol (2 mmol) and 4-tert-butyl-benzoyl chloride (2 mmol). Chromatograph on silica gel to give the title compound.

41.2 Synthesis of 2-[3-(3,4-dichloro-phenyl)-1-(4-tert-butyl-benzoyl)-pyrrolidin-3-yl]-ethyl-methanesulfonate Prepare by the method of example 3.2 using 2-[3-(3,4-dichloro-phenyl)-1-(4-tert-butyl-benzoyl)-pyrrolidin-3-yl]-ethanol (0.6 mmol) and methanesulfonyl chloride (0.66 mmol). Dry the residue under high vacuum at ambient temperature 18 h to obtain the title compound.

41.3 Synthesis of 1-[2-[3-(3,4-dichloro-phenyl)-1-(4-tert-butyl-benzoyl)-pyrrolidin-3-yl]-ethyl]-4-phenyl-piperidine-4-carboxylic acid amide Prepare by the method of example 3.3 using 2-[3-(3,4-dichloro-phenyl)-1-(4-tert-butyl-benzoyl)-pyrrolidin-3-yl]-ethyl-methanesulfonate (0.6 mmol) and 4-phenyl-piperidine-4-carboxylic acid amide hydrochloride (0.72 mmol). Chromatograph on silica gel to give the title compound.

EXAMPLE 42

Synthesis of 1-[2-[3-(3,4-dichloro-phenyl)-1-(4-tert-butyl-phenacyl)-pyrrolidin-3-yl]-ethyl]-4-phenyl-piperidine-4-carboxylic acid amide 42.1 Synthesis of 2-[3-(3,4-dichloro-phenyl)-1-(4-tert-butyl-phenacyl)-pyrrolidin-3-yl]-ethanol Prepare by the method of example 3.1 using 2-[3-(3,4-dichloro-phenyl)-pyrrolidin-3-yl]-ethanol (2 mmol) and 4-tert-butyl-phenacyl chloride (2 mmol). Chromatograph on silica gel to give the title compound.

42.2 Synthesis of 2-[3-(3,4-dichloro-phenyl)-1-(4-tert-butyl-phenacyl)-pyrrolidin-3-yl]-ethyl-methanesulfonate Prepare by the method of example 3.2 using 2-[3-(3,4-dichloro-phenyl)-1-(4-tert-butyl-phenacyl)-pyrrolidin-3-yl]-ethanol (0.6 mmol) and methanesulfonyl chloride (0.66 mmol). Dry the residue under high vacuum at ambient temperature for 18 h to obtain the title compound.

42.3 Synthesis of 1-[2-[3-(3,4-dichloro-phenyl)-1-(4-tert-butyl-phenacyl)-pyrrolidin-3-yl]-ethyl]-4-phenyl-piperidine-4-carboxylic acid amide Prepare by the method of example 3.3 using 2-[3-(3,4-dichloro-phenyl)-1-(4-tert-butyl-phenacyl)-pyrrolidin-3-yl]-ethyl-methanesulfonate (0.6 mmol) and 4-phenyl-piperidine-4-carboxylic acid amide hydrochloride (0.72 mmol). Chromatograph on silica gel to give the title compound.

PREPARATION 1

Synthesis of 3-Isopropoxy-phenyl-acetyl chloride

Combine 3-hydroxy-phenyl acetic acid (9.26 g, 60.9 mmol), isopropyl iodide (42.6 g, 250 mmol), and acetone (80 mL). Add portionwise, potassium carbonate (16.9 g, 122 mmol). Heat to reflux with vigorous mechanical stirring. After 20 hours, cool to ambient temperature and evaporate in vacuo to give a residue. Partition the residue between diethyl ether and 5% sodium hydroxide solution. Extract the organic layer with water and a saturated sodium chloride solution. Dry the organic layer over $MgSO_4$, filter and evaporate in vacuo to obtain a liquid. Bulb-to-bulb distillation gives 3-isopropoxy-phenyl-acetic acid isopropyl ester: bp; 125° C. at 0.2 mm of Hg.

Combine 3-isopropoxy-phenyl-acetic acid isopropyl ester 10.2 g, 43.2 mmol) and sodium hydroxide (2.08 g, 51.8 mmol) in 1/1 ethanol/water (80 mL). Heat to reflux. After 18 hours, remove the ethanol by evaporation in vacuo and acidify to pH=1 using an aqueous solution with 1M hydrochloric acid solution. Extract the aqueous solution 3 times with ethyl acetate. Extract the combined organic layers with water and saturated sodium chloride solution. Dry the organic layer over $MgSO_4$, filter, and evaporate in vacuo to obtain 3-isopropoxy-phenyl-acetic acid.

Combine 3-isopropoxy-phenyl-acetic acid (0.5 g, 2.6 mmol) and dichloromethane (5 mL). Cool to −5° C. using a ice-salt bath. Add 2 drops of dimethylformamide followed by dropwise addition of oxalyl chloride (0.34 g, 2.7 mmol). after 1 hour, warm the reaction mixture to ambient temperature. After 2 hours, evaporate the reaction mixture in vacuo to give the title compound as a liquid.

EXAMPLE 43

Synthesis of 1-[2-[3-(3,4-dichloro-phenyl)-1-(3-isopropoxy-phenacyl)-pyrrolidin-3-yl]-ethyl]-4-phenyl-piperidine-4-carboxylic acid amide 43.1 Synthesis of 2-[3-(3,4-dichloro-phenyl)-1-(3-isopropoxy-phenacyl)-pyrrolidin-3-yl]-ethanol Prepare by the method of example 3.1 using 2-[3-(3,4-dichloro-phenyl)-pyrrolidin-3-yl]-ethanol (2 mmol) and 3-isopropoxy-phenacyl chloride (2 mmol). Chromatograph on silica gel to give the title compound. $R_f$=0.44 (silica gel, 5% methanol/dichloromethane).

43.2 Synthesis 2-[3-(3,4-dichloro-phenyl)-1-(3-isopropoxy-phenacyl)-pyrrolidin-3-yl]-ethyl-methanesulfonate Prepare by the method of example 3.2 using 2-[3-(3,4-dichloro-phenyl)-1-(3-isopropoxy-phenacyl)-pyrrolidin-3-yl]-ethanol (0.6 mmol) and methanesulfonyl chloride (0.66 mmol). Dry the residue under high vacuum at ambient temperature 18 h to obtain the title compound. $R_f$=0.65 (silica gel, 10% methanol/dichloromethane).

43.3 Synthesis of 1-[2-[3-(3,4-dichloro-phenyl)-1-(3-isopropoxy-phenacyl)-pyrrolidin-3-yl]-ethyl]-4-phenyl-piperidine-4-carboxylic acid amide Prepare by the method of example 3.3 using 2-[3-(3,4-dichloro-phenyl)-1-(3-isopropoxy-phenacyl)-pyrrolidin-3-yl]-ethyl-methanesulfonate (0.6 mmol) and 4-phenyl-piperidine-4-carboxylic acid amide hydrochloride (0.72 mmol). Chromatograph on silica gel to give the title compound.

43.3.1 Synthesis of 1-[2-[3-(3,4-dichloro-phenyl)-1-(3-isopropoxy-phenacyl)-pyrrolidin-3-yl]-ethyl]-4-phenyl-piperidine-4-carboxylic acid amide Prepare by the method of example 27.3.1 using 2-[3-(3,4-dichloro-phenyl)-1-(3-isopropoxy-phenacyl)-pyrrolidin-3-yl]-ethyl-methanesulfonate (0.24 g, 0.5 mmol) and 4-phenyl-piperidine-4-carboxylic acid amide hydrochloride (0.24 g, 0.98 mmol). Chromatograph on silica gel to give the title compound: $R_f$=0.45 (silica gel, 6% methanol/dichloromethane).
Exact mass (FAB+): calculated for $C_{35}H_{42}Cl_2N_3O_3$ calculated 622.2603. Found 622.2597.

PREPARATION 2

Synthesis of 3,4,5-Trimethoxy-phenyl-acetyl chloride

Combine 3,4,5-trimethoxy-phenyl-acetic acid (2.26 g, 10 mmol) and dichloromethane (50 mL). Cool to −5° C. using a ice-salt bath. Add 2 drops of dimethylformamide followed by dropwise addition of oxalyl chloride (1.74 mL, 20 mmol). after 1 hour, warm the reaction mixture to ambient temperature. After 2 hours, evaporate the reaction mixture in vacuo to give the title compound as a liquid.

EXAMPLE 44

Synthesis of 1-[2-[3-(3,4-dichloro-phenyl)-1-(3,4,5-trimethoxy-phenacyl)-pyrrolidin-3-yl]-ethyl]-4-phenyl-piperidine-4-carboxylic acid amide

44.1 Synthesis of 2-[3-(3,4-dichloro-phenyl)-1-(3,4,5-trimethoxy-phenacyl)-pyrrolidin-3-yl]-ethanol Prepare by the method of example 3.1 using 2-[3-(3,4-dichloro-phenyl)-pyrrolidin-3-yl]-ethanol (2 mmol) and 3,4,5-trimethoxy-phenacyl chloride (2 mmol). Chromatograph on silica gel to give the title compound. $R_f$=0.45 (6% methanol/dichloromethane).

44.2 2-[3-(3,4-dichloro-phenyl)-1-(3,4,5-trimethoxy-phenacyl)-pyrrolidin-3-yl]-ethyl-methanesulfonate Prepare by the method of example 3.2 using 2-[3-(3,4-dichloro-phenyl)-1-(3,4,5-trimethoxy-phenacyl)-pyrrolidin-3-yl]-ethanol (0.6 mmol) and methanesulfonyl chloride (0.66 mmol). Dry the residue under high vacuum at ambient temperature 18 h to obtain the title compound. $R_f$=0.57 (6% methanol/dichloromethane).

44.3 Synthesis of 1-[2-[3-(3,4-dichloro-phenyl)-1-(3,4,5-trimethoxy-phenacyl)-pyrrolidin-3-yl]-ethyl]-4-phenyl-piperidine-4-carboxylic acid amide Prepare by the method of example 3.3 using 2-[3-(3,4-dichloro-phenyl)-1-(3,4,5-trimethoxy-phenacyl)-pyrrolidin-3-yl]-ethyl-methanesulfonate (0.6 mmol) and 4-phenyl-piperidine-4-carboxylic acid amide hydrochloride (0.72 mmol). Chromatograph on silica gel to give the title compound.

44.3.1 Synthesis of 1-[2-[3-(3,4-dichloro-phenyl)-1-(3,4,5-trimethoxy-phenacyl)-pyrrolidin-3-yl]ethyl]-4-phenyl-piperidine-4-carboxylic acid amide Prepare by the method of example 27.3.1 using 2-[3-(3,4-dichloro-phenyl)-1-(3,4,5-trimethoxy-phenacyl)-pyrrolidin-3-yl]-ethyl-methanesulfonate (0.22 g, 0.4 mmol) and 4-phenyl-piperidine-4-carboxylic acid amide hydrochloride (0.20 g, 0.8 mmol). Chromatograph on silica gel to give the title compound.
Exact mass (FAB+): calculated for $C_{35}H_{42}Cl_2N_3O_5$ calculated 654.2501. Found 654.2495.

EXAMPLE 45

Synthesis of 1-[2-[3-(3,4-dichloro-phenyl)-1-(pyridine-2-carbonyl)-pyrrolidin-3-yl]-ethyl]-4-phenyl-piperidine-4-carboxylic acid amide

45.1 Synthesis of 2-[3-(3,4-dichloro-phenyl)-1-(pyridine-2-carbonyl)-pyrrolidin-3-yl]-ethanol Prepare by the method of example 3.1 using 2-[3-(3,4-dichloro-phenyl)-pyrrolidin-3-yl]-ethanol (2 mmol) and 2-pyridinecarbonyl chloride (2 mmol). Chromatograph on silica gel to give the title compound.

45.2 Synthesis of 2-[3-(3,4-dichloro-phenyl)-1-(pyridine-2-carbonyl)-pyrrolidin-3-yl]-ethyl-methanesulfonate Prepare by the method of example 3.2 using 2-[3-(3,4-dichloro-phenyl)-1-(pyridine-2-carbonyl)-pyrrolidin-3-yl]-ethanol (0.6 mmol) and methanesulfonyl chloride (0.66 mmol). Dry the residue under high vacuum at ambient temperature 18 h to obtain the title compound.

45.3 Synthesis of 1-[2-[3-(3,4-dichloro-phenyl)-1-(pyridine-2-carbonyl)-pyrrolidin-3-yl]-ethyl]-4-phenyl-piperidine-4-carboxylic acid amide Prepare by the method of example 3.3 using 2-[3-(3,4dichloro-phenyl)-1-(pyridine-2-carbonyl)-pyrrolidin-3-yl]-ethyl-methanesulfonate (0.6 mmol) and 4-phenyl-piperidine-4-carboxylic acid amide hydrochloride (0.72 mmol). Chromatograph on silica gel to give the title compound.

EXAMPLE 46

Synthesis of 8-[2-[3-(3,4-dichloro-phenyl)-1-(3,4,5-trimethoxy-benzoyl)-pyrrolidin-3-yl]-ethyl]-1-phenyl-1,3,8-triaza-spiro[4.5]decan-4-one

46.1 Synthesis of 8-[2-[3-(3,4-dichloro-phenyl)-1-(3,4,5-trimethoxy-benzoyl)-pyrrolidin-3-yl]-ethyl]-1-phenyl-1,3,8-triaza-spiro[4.5]decan-4-one Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 1-phenyl-1,3,8-triaza-spiro[4.5]decan-4-one hydrochloride (7.5 mmol, 1.5 eq.). Chromatograph on silica gel to give the title compound.

EXAMPLE 47

Synthesis of 8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]dec-2-en-4-one

47.1 Synthesis of 1-benzyl-4-(4-fluoro-phenylamino)-piperidine-4-carbonitrile Combine 1-benzyl-4-oxo-piperidine (100 mmol), 4-fluorophenylamine (110 mmol), and toluene (300 mL). Heat at reflux for 3 h with azeotropic removal of water. Cool to 50° C. Add acetone cyanohydrin (277 mmol). Slowly distill away the acetone. Concentrate the solvent in vacuo to obtain a residue. Chromatograph on silica gel to obtain the title compound.

47.2 Synthesis of 1-benzyl-4-(4-fluoro-phenylamino)-piperidine-4-carboxylic acid amide Cautiously combine 1-benzyl-4-(4-fluoro-phenylamino)-piperidine-4-carbonitrile (60 mmol) and concentrated sulfuric acid (270 mL). Let stand for 24 h at ambient temperature. Cautiously pour the reaction mixture into excess dilute ammonium hydroxide solution/ice. Extract with dichloromethane (3×300 mL). Combine the dichloromethane extracts and extract them using saturated NaHCO$_3$ solution (3×300 mL). Dry the dichloromethane solution over magnesium sulfate, filter, and concentrate in vacuo to obtain a residue. Purify to obtain the title compound.

47.3 Synthesis of 8-benzyl-1-(4-fluoro-phenyl)-1,3,8-triaza-spiro[4.5]dec-2-en-4-one Mix 1-benzyl-4-(4-fluoro-phenylamino)-piperidine-4-carboxylic acid amide (20 mmol) and hot toluene (240 mL). Add dimethoxy-N,N-dimethylmethanamine (20 mL) and heat at reflux for 48 h. Concentrate in vacuo to obtain a residue. Purify to obtain the title compound.

47.4 Synthesis of 1-(4-fluoro-phenyl)-1,3,8-triaza-spiro[4.5] dec-2-en-4-one hydrochloride Combine 8-benzyl-1-(4-fluoro-phenyl)-1,3,8-triaza-spiro [4.5]dec-2-en-4-one (10 mmol) and 1,2-dichloroethane (70 mL). Cool using an ice bath. Add in dropwise fashion, 1-chloroethyl chloroformate (48.6 mmol). Warm to ambient temperature and maintain for 1 h. Extract using saturated $NaHCO_3$ (120 mL). Extract the aqueous phase using dichloromethane (120 mL). Combine the organic layers, extract with saturated NaCl, dry over $Na_2SO_4$, filter, and concentrate in vacuo to obtain a residue. Add anhydrous methanol (70 mL) and heat at reflux for 1 h. Concentrate in vacuo to obtain a residue and purify to obtain the title compound.

47.5 Synthesis of 8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]dec-2-en-4-one Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 1-(4-fluoro-phenyl)-1,3,8-triaza-spiro[4.5]dec-2-en-4-one hydrochloride (7.5 mmol, 1.5 eq.). Chromatograph on silica gel to give the title compound.

EXAMPLE 48

Synthesis of 8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one 48.1 1-(4-fluoro-phenyl)-1,3,8-triaza-spiro[4.5]decan-4-one Mix 8-benzyl-1-(4-fluoro-phenyl)-1,3,8-triaza-spiro[4.5] dec-2-en-4-one (20 mmol) and methanol (200 mL). Add to a catalytic amount of $PtO_2$ and hydrogenate at 50 psi. Remove the $PtO_2$ by filtration and concentrate in vacuo to obtain a residue. Purify to obtain the title compound.

48.2 Synthesis of 8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 1-(4-fluoro-phenyl)-1,3,8-triaza-spiro[4.5]decan-4-one (7.5 mmol, 1.5 eq.). Chromatograph on silica gel to give the title compound.

EXAMPLE 49

Synthesis of 3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one 49.1 Synthesis of 8-tert-butoxycarbonyl-1-(4-fluoro-phenyl)-4-oxo-1,3,8-triaza-spiro[4.5]decane Combine 1-2-(4-fluoro-phenyl)-1,3,8-triaza-spiro[4.5] decan-4-one (15 mmol), di-tert-butyl dicarbonate (16 mmol), and chloroform (100 mL). After 24 h, concentrate in vacuo to obtain a residue. Purify to obtain the title compound.

49.2 Synthesis of 8-tert-butoxycarbonyl-3-benzyl-1-(4-fluoro-phenyl)-4-oxo-1,3,8-triaza-spiro[4.5]decane Combine 8-tert-butoxycarbonyl-1-(4-fluoro-phenyl)-4-oxo-1,3,8-triaza-spiro[4.5]decane (12 mmol) and DMF (20 mL). Cool in an ice bath. Add NaH (18 mmol) in several portions. After the addition is complete, add benzyl bromide (18 mmol). Allow the reaction mixture to warm to ambient temperature. After 3 h, cool the reaction vessel using an ice bath and cautiously add 10% aqueous citric acid (20 mL). When gas evolution has ceased, pour into an additional 20 mL of 10% aqueous citric acid and extract using ethyl acetate (3×60 mL). Extract the combined organics with saturated aqueous NaCl, dry over $Na_2SO_4$, filter, and concentrate in vacuo to obtain a residue. Purify to obtain the title compound.

49.3 Synthesis of 3-benzyl-1-(4-fluoro-phenyl)-1,3,8-triaza-spiro[4.5]decan-4-one Cool trifluoroacetic acid (20 mL) using an ice bath and add 8-tert-butoxycarbonyl-3-benzyl-1-(4-fluoro-phenyl)-4-oxo-1,3,8-triaza-spiro[4.5]decane (10 mmol). After 1 h, dilute with diethyl ether (150 mL), filter to obtain a residue. Purify to obtain the title compound.

49.4 Synthesis of 3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decan-4-one Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 3-benzyl-1-(4-fluoro-phenyl)-1,3,8-triaza-spiro[4.5]decan-4-one trifluoroacetate (7.5 mmol, 1.5 eq.). Chromatograph on silica gel to give the title compound.

EXAMPLE 50

Synthesis of 3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione 50.1 Synthesis of 8-benzyl-1-(4-fluoro-phenyl)-1,3,8-triaza-spiro[4.5]decane-2,4-dione Combine -1-benzyl-4-(4-fluoro-phenylamino)-piperidine-4-carbonitrile (32 mmol) and dichloromethane (100 mL). Add chlorosulfonyl isocyanate (20 mmol) in dropwise fashion with water bath cooling so as to maintain the temperature of the reaction mixture between 20 and 30° C. After 30 minutes, concentrate the reaction mixture in vacuo to obtain a residue. Add 1N HCl (100 mL) and heat at reflux for 1 h. Cool in an ice bath and adjust the pH to 5.5 using 5N NaOH. Filter to obtain a residue. Wash with diethyl ether and dry in vacuo. Purify to obtain the title compound.

50.2 Synthesis of 3,8-dibenzyl-1-(4-fluoro-phenyl)-1,3,8-triaza-spiro[4.5]decane-2,4-dione Combine 8-benzyl-1-(4-fluoro-phenyl)-1,3,8-triaza-spiro [4.5]decane-2,4-dione (12 mmol) and DMF (20 mL). Cool in an ice bath. Add NaH (18 mmol) in several portions. After the addition is complete, add benzyl bromide (18 mmol). Allow the reaction mixture to warm to ambient temperature. After 3 h, cool the reaction vessel using an ice bath and cautiously add 10% aqueous citric acid (20 mL). When gas evolution has ceased, pour into an additional 20 mL of 10% aqueous citric acid and extract using ethyl acetate (3×60 mL). Extract the combined organics with saturated aqueous NaCl, dry over $Na_2SO_4$, filter, and concentrate in vacuo to obtain a residue. Purify to obtain the title compound.

50.3 Synthesis of 3-benzyl-1-(4-fluoro-phenyl)-1,3,8triaza-spiro[4.5]decane-2,4-dione Combine 3,8-dibenzyl-1-(4-fluoro-phenyl)-1,3,8-triaza-spiro[4.5]decane-2,4-dione (10 mmol) and 1,2-dichloroethane (70 mL). Cool using an ice bath. Add in dropwise fashion, 1-chloroethyl chloroformate (48.6 mmol). Warm to ambient temperature and maintain for 1 h. Extract using saturated $NaHCO_3$ (120 mL). Extract the aqueous phase using dichloromethane (120 mL). Combine the organic layers, extract with saturated NaCl, dry over $Na_2SO_4$, filter, and concentrate in vacuo to obtain a residue.

Add anhydrous methanol (70 mL) and heat at reflux for 1 h. Concentrate in vacuo to obtain a residue and purify to obtain the title compound.

50.4 Synthesis of 3-benzyl-8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 3-benzyl-1-(4-fluoro-phenyl)-1,3,8-triaza-spiro[4.5]decane-2,4-dione hydrochloride (7.5 mmol, 1.5 eq.). Chromatograph on silica gel to give the title compound.

EXAMPLE 51

Synthesis of 8-[2-[3-(3,4-dichloro-phenyl)-1-(3,4,5-trimethoxy-benzoyl)-pyrrolidin-3-yl]-ethyl]-1-(4-fluoro-phenyl)-1,3,8-triaza-spiro[4.5]decane-2,4-dione 51.1 Synthesis of 1-(4-fluoro-phenyl)-1,3,8-triaza-spiro[4.5]decane-2,4-dione Combine 8-benzyl-1-(4-fluoro-phenyl)-1,3,8-triaza-spiro[4.5]decane-2,4-dione (10 mmol) and 1,2-dichloroethane (70 mL). Cool using an ice bath. Add in dropwise fashion, 1-chloroethyl chloroformate (48.6 mmol). Warm to ambient temperature and maintain for 1 h. Extract using saturated NaHCO$_3$ (120 mL). Extract the aqueous phase using dichloromethane (120 mL). Combine the organic layers, extract with saturated NaCl, dry over Na$_2$SO$_4$, filter, and concentrate in vacuo to obtain a residue. Add anhydrous methanol (70 mL) and heat at reflux for 1 h. Concentrate in vacuo to obtain a residue and purify to obtain the title compound.

51.2 Synthesis of 8-[2-[3-(3,4-dichloro-phenyl)-1(3,4,5-trimethoxy-benzoyl)-pyrrolidin-3-yl]-ethyl]-1-(4-fluoro-phenyl)-1,3,8-triaza-spiro[4.5]decane-2,4-dione Combine the 2-[3-(3,4-dichloro-phenyl)-1-(3,4,5-trimethoxy-benzoyl)-pyrrolidin-3-yl]-ethyl-methanesulfonate (5.0 mmol), 1-(4-fluoro-phenyl)-1,3,8-triaza-spiro[4.5]decane-2,4-dione hydrochloride (7.5 mmol, 1.5 eq.), N,N-diisopropylethylamine (15 mmol), and DMF (8 mL). Heat the mixture at 85° C. for 48 h. Cool to ambient temperature and add ethyl acetate (100 mL). Extract with water (25 mL), 1N HCl (2×25 mL), saturated NaHCO$_3$ (25 mL), and saturated NaCl (25 mL). Dry over MgSO$_4$, filter, and concentrate in vacuo to obtain a residue. Purify to obtain the title compound.

EXAMPLE 52

Synthesis of 1-[2-[3-(3-trifluoromethyl-phenyl)-1-(3,4,5-trimethoxy-benzoyl)-pyrrolidin-3-yl]-ethyl]-4-phenyl-piperidine-4-carboxylic acid amide 52.1 Synthesis of 3-cyano-3-(3-trifluoromethyl-phenyl)-pentanedioic acid diethyl ester Prepare by the method of example 1.1.2 using 3-trifluoromethyl-phenylacetonitrile (0.161 mol) and ethyl bromoacetate (0.325 mol). Chromatograph on silica gel to give the title compound.

52.2 Synthesis of [3-(3-trifluoromethyl-phenyl)-5-oxo-pyrrolidin-3-yl]-acetic acid ethyl ester Prepare by the method of example 1.2.2 using 3-cyano-3-(3-trifluoromethyl-phenyl)-pentanedioic acid diethyl ester (89 mmol). Chromatograph on silica gel to give the title compound.

52.3 Synthesis of 2-[3-(3-trifluoromethyl-phenyl)-pyrrolidin-3-yl]-ethanol

Prepare by the method of example 1.3.2 using [3-(3-trifluoromethyl-phenyl)-5-oxo-pyrrolidin-3-yl]-acetic acid ethyl ester (73 mmol). Chromatograph on silica gel to give the title compound.

52.4 Synthesis of 2-[3-(3-trifluoromethyl-phenyl)-1-(3,4,5-trimethoxy-benzoyl)-pyrrolidin-3-yl]-ethanol Prepare by the method of example 3.1 using 2-[3-(3-trifluoromethyl-phenyl)-pyrrolidin-3-yl]-ethanol (23 mmol) and 3,4,5-trimethoxy-benzoyl chloride (23 mmol). Chromatograph on silica gel to give the title compound.

52.5 Synthesis of 2-[3-(3-trifluoromethyl-phenyl)-1-(3,4,5-trimethoxy-benzoyl)-pyrrolidin-3-yl]-ethyl-methanesulfonate Prepare by the method of example 3.2 using 2-[3-(3-trifluoromethyl-phenyl)-1-(3,4,5-trimethoxy-benzoyl)-pyrrolidin-3-yl]-ethanol (8 mmol) and methanesulfonyl chloride (11 mmol) to give the title compound.

52.6 Synthesis of 1-[2-[3-(3-trifluoromethyl-phenyl)-1-(3,4,5-trimethoxy-benzoyl)-pyrrolidin-3-yl]-ethyl]-4-phenyl-piperidine-4-carboxylic acid amide Prepare by the method of example 3.3 using 2-[3-(3-trifluoromethyl-phenyl)-1-(3,4,5-trimethoxy-benzoyl)-pyrrolidin-3-yl]-ethyl-methanesulfonate (8 mmol) and 4-phenyl-piperidine-4-carboxylic acid amide hydrochloride (12 mmol). Chromatograph on silica gel to give the title compound.

EXAMPLE 53

Synthesis of 1-[2-[3-(thiophen-2-yl)-1-(3,4,5-trimethoxy-benzoyl)-pyrrolidin-3-yl]-ethyl]-4-phenyl-piperidine-4-carboxylic acid amide 53.1 Synthesis of 3-cyano-3-(thiophen-2-yl)-pentanedioic acid diethyl ester Prepare by the method of example 1.1.2 using thiophen-2-yl-acetonitrile (0.161 mol) and ethyl bromoacetate (0.325 mol). Chromatograph on silica gel to give the title compound.

53.2 Synthesis of [3-(thiophen-2-yl)-5-oxo-pyrrolidin-3-yl]-acetic acid ethyl ester Prepare by the method of example 1.2 using 3-cyano-3-(thiophen-2-yl)-pentanedioic acid diethyl ester (28 mmol), cobalt (II) chloride hexahydrate (55.5 mmol), and NaBH$_4$ (290 mmol). Chromatograph on silica gel to give the title compound.

53.3 Synthesis of 2-[3-(thiophen-2-yl)-pyrrolidin-3-yl]-ethanol

Prepare by the method of example 1.3.2 using [3-(thiophen-2-yl)-5-oxo-pyrrolidin-3-yl]-acetic acid ethyl ester (73 mmol). Chromatograph on silica gel to give the title compound.

53.4 Synthesis of 2-[3-(thiophen-2-yl)-1-(3,4,5-trimethoxy-benzoyl)-pyrrolidin-3-yl]-ethanol Prepare by the method of example 3.1 using 2-[3-(thiophen-2-yl)-pyrrolidin-3-yl]-ethanol (23 mmol) and 3,4,5-trimethoxy-benzoyl chloride (23 mmol). Chromatograph on silica gel to give the title compound.

53.5 Synthesis of 2-[3-(thiophen-2-yl)-1-(3,4,5-trimethoxy-benzoyl)-pyrrolidin-3-yl]-ethyl-methanesulfonate Prepare by the method of example 3.2 using 2-[3-(thiophen-2-yl)-1-(3,4,5-trimethoxy-benzoyl)-pyrrolidin-3-yl]-ethanol (8 mmol) and methanesulfonyl chloride (11 mmol) to give the title compound.

53.6 Synthesis of 1-[2-[3-(thiophen-2-yl)-1-(3,4,5-trimethoxy-benzoyl)-pyrrolidin-3-yl]-ethyl]-4-phenyl-piperidine-4-carboxylic acid amide Prepare by the method of example 3.3 using 2-[3-(thiophen-2-yl)-1-(3,4,5-trimethoxy-benzoyl)-pyrrolidin-3- yl]-ethyl-methanesulfonate (8 mmol) and 4-phenyl-piperidine-4-carboxylic acid amide hydrochloride (12 mmol). Chromatograph on silica gel to give the title compound.

EXAMPLE 54

Synthesis of 1-[2-[3-(pyridin-3-yl)-1-(3,4,5-trimethoxy-benzoyl)-pyrrolidin-3-yl]-ethyl]-4-phenyl-piperidine-4-carboxylic acid amide 54.1 Synthesis of 3-cyano-3-(pyridin-3-yl)-pentanedioic acid diethyl ester Prepare by the method of example 1.1.2 using pyridin-3-yl-acetonitrile (0.161 mol) and ethyl bromoacetate (0.325 mol). Chromatograph on silica gel to give the title compound.

54.2 Synthesis of [3-(pyridin-3-yl)-5-oxo-pyrrolidin-3-yl]-acetic acid ethyl ester Prepare by the method of example 1.2.2 using 3-cyano-3-(pyridin-3-yl)-pentanedioic acid diethyl ester (89 mmol). Chromatograph on silica gel to give the title compound.

54.3 Synthesis of 2-[3-(pyridin-3-yl)-pyrrolidin-3-yl]-ethanol

Prepare by the method of example 1.3.2 using [3-(pyridin-3-yl)-5-oxo-pyrrolidin-3-yl]-acetic acid ethyl ester (73 mmol). Chromatograph on silica gel to give the title compound.

54.4 Synthesis of 2-[3-(pyridin-3-yl)-1-(3,4,5-trimethoxy-benzoyl)-pyrrolidin-3-yl]-ethanol Prepare by the method of example 3.1 using 2-[3-(pyridin-3-yl)-pyrrolidin-3-yl]-ethanol (23 mmol) and 3,4,5-trimethoxy-benzoyl chloride (23 mmol). Chromatograph on silica gel to give the title compound.

54.5 2-[3-(pyridin-3-yl)-1-(3,4,5-trimethoxy-benzoyl)-pyrrolidin-3-yl]-ethyl-methanesulfonate Prepare by the method of example 3.2 using 2-[3-(pyridin-3-yl)-1-(3,4,5-trimethoxy-benzoyl)-pyrrolidin-3-yl]-ethanol (8 mmol) and methanesulfonyl chloride (11 mmol) to give the title compound.

54.6 Synthesis of 1-[2-[3-(pyridin-3-yl)-1-(3,4,5-trimethoxy-benzoyl)-pyrrolidin-3-yl]-ethyl]-4-phenyl-piperidine-4-carboxylic acid amide Prepare by the method of example 3.3 using 2-[3-(pyridin-3-yl)-1-(3,4,5-trimethoxy-benzoyl)-pyrrolidin-3-yl]-ethyl-methanesulfonate (8 mmol) and 4-phenyl-piperidine-4-carboxylic acid amide hydrochloride (12 mmol). Chromatograph on silica gel to give the title compound.

EXAMPLE 55

Synthesis of 1-[2-[3-(2-fluoro-phenyl)-1-(3,4,5-trimethoxy-benzoyl)-pyrrolidin-3-yl]-ethyl]-4-phenyl-piperidine-4-carboxylic acid amide 55.1 Synthesis of 3-cyano-3-(2-fluoro-phenyl)-pentanedioic acid diethyl ester Prepare by the method of example 1.1.2 using 2-fluorophenylacetonitrile (0.161 mol) and ethyl bromoacetate (0.325 mol). Chromatograph on silica gel to give the title compound.

55.2 Synthesis of [3-(2-fluoro-phenyl)-5-oxo-pyrrolidin-3-yl]-acetic acid ethyl ester Prepare by the method of example 1.2.2 using 3-cyano-3-(2-fluoro-phenyl)-pentanedioic acid diethyl ester (89 mmol). Chromatograph on silica gel to give the title compound.

55.3 Synthesis of 2-[3-(2-fluoro-phenyl)-pyrrolidin-3-yl]-ethanol

Prepare by the method of example 1.3.2 using [3-(2-fluoro-phenyl)-5-oxo-pyrrolidin-3-yl]-acetic acid ethyl ester (73 mmol). Chromatograph on silica gel to give the title compound.

55.4 Synthesis of 2-[3-(2-fluoro-phenyl)-1-(3,4,5-trimethoxy-benzoyl)-pyrrolidin-3-yl]-ethanol Prepare by the method of example 3.1 using 2-[3-(2-fluoro-phenyl)-pyrrolidin-3-yl]-ethanol (23 mmol) and 3,4,5-trimethoxy-benzoyl chloride (23 mmol). Chromatograph on silica gel to give the title compound.

55.5 Synthesis of 2-[3-(2-fluoro-phenyl)-1-(3,4,5-trimethoxy-benzoyl)-pyrrolidin-3-yl]-ethyl-methanesulfonate Prepare by the method of example 3.2 using 2-[3-(2-fluoro-phenyl)-1-(3,4,5-trimethoxy-benzoyl)-pyrrolidin-3-yl]-ethanol (8 mmol) and methanesulfonyl chloride (11 mmol) to give the title compound.

55.6 Synthesis of 1-[2-[3-(2-fluoro-phenyl)-1-(3,4,5-trimethoxy-benzoyl)-pyrrolidin-3-yl]-ethyl]-4-phenyl-piperidine-4-carboxylic acid amide Prepare by the method of example 3.3 using 2-[3-(2-fluoro-phenyl)-1-(3,4,5-trimethoxy-benzoyl)-pyrrolidin-3-yl]-ethyl-methanesulfonate (8 mmol) and 4-phenyl-piperidine-4-carboxylic acid amide hydrochloride (12 mmol). Chromatograph on silica gel to give the title compound.

EXAMPLE 56

Synthesis of 1-[2-[3-(4-hydroxy-phenyl)-1-(3,4,5-trimethoxy-benzoyl)-pyrrolidin-3-yl]-ethyl]-4-phenyl-piperidine-4-carboxylic acid amide 56.1 Synthesis of 4-(tert-butyldimethylsilyloxy)-phenyl-acetonitrile Combine tert-butyldimethylsilyl chloride (0.460 mol), imidazole (0.600 mol) and. DMF (125 mL). Add 4-hydroxyphenylacetonitrile (0.400 mol) and maintain at ambient temperature for 16 h. Dilute with ether (500 mL), extract with water (4×75 mL), saturated sodium chloride (75 mL), dry over $MgSO_4$, filter, and concentrate in vacuo to obtain a residue. Chromatograph on silica gel to obtain the title compound.

56.2 Synthesis of 3-cyano-3-[4-(tert-butyldimethylsilyloxy)-phenyl]-pentanedioic acid diethyl ester Prepare by the method of example 1.1.2 using 4-(tert-butyldimethylsilyloxy)-phenyl-acetonitrile (0.161 mol) and ethyl bromoacetate (0.325 mol). Chromatograph on silica gel to give the title compound.

56.3 Synthesis of [3-[4-(tert-butyldimethylsilyloxy)-phenyl]-5-oxo-pyrrolidin-3-yl]-acetic acid ethyl ester Prepare by the method of example 1.2.2 using 3-cyano-3-[4-(tert-butyldimethylsilyloxy)-phenyl]-pentanedioic acid diethyl ester (89 mmol). Chromatograph on silica gel to give the title compound.

56.4 Synthesis of 2-[3-[4-(tert-butyldimethylsilyloxy)-phenyl]-5-oxo-pyrrolidin-3-yl]-ethanol Prepare by the method of example 1.3.2 using [3-[4-(tert-butyldimethylsilyloxy)-phenyl]-5-oxo-pyrrolidin-3-yl]-acetic acid ethyl ester (73 mmol). Chromatograph on silica gel to give the title compound.

56.5 Synthesis of 2-[3-[4-(tert-butyldimethylsilyloxy)-phenyl]-1-(3,4,5-trimethoxy-benzoyl)-pyrrolidin-3-yl]-ethanol Prepare by the method of example 3.1 using 2-[3-[4-(tert-butyldimethylsilyloxy)-phenyl]-5-oxo-pyrrolidin-3-yl]- ethanol (23 mmol) and 3,4,5-trimethoxy-benzoyl chloride (23 mmol). Chromatograph on silica gel to give the title compound.

56.6 Synthesis of 2-[3-[4-(tert-butyldimethylsilyloxy)-phenyl]-1-(3,4,5-trimethoxy-benzoyl)-pyrrolidin-3-yl]-ethyl-methanesulfonate Prepare by the method of example 3.2 using 2-[3-[4-(tert-butyldimethylsilyloxy)-phenyl]-1-(3,4,5-trimethoxy-benzoyl)-pyrrolidin-3-yl]-ethanol (8 mmol) and methanesulfonyl chloride (11 mmol) to give the title compound.

56.7 Synthesis of 1-[2-[3-[4-(tert-butyldimethylsilyloxy)-phenyl]-1-(3,4,5-trimethoxy-benzoyl)-pyrrolidin-3-yl]-ethyl]-4-phenyl-piperidine-4-carboxylic acid amide Prepare by the method of example 3.3 using 2-[3-[4-(tert-butyldimethylsilyloxy)-phenyl]-1-(3,4,5-trimethoxy-benzoyl)-pyrrolidin-3-yl]-ethyl-methanesulfonate (8 mmol) and 4-phenyl-piperidine-4-carboxylic acid amide hydrochloride (12 mmol). Chromatograph on silica gel to give the title compound.

56.8 Synthesis of 1-[2-[3-(4-hydroxy-phenyl)-1-(3,4,5-trimethoxy-benzoyl)-pyrrolidin-3-yl]-ethyl]-4-phenyl-piperidine-4-carboxylic acid amide Combine 1-[2-[3-[4-(tert-butyldimethylsilyloxy)-phenyl]-1-(3,4,5-trimethoxy-benzoyl)-pyrrolidin-3-yl]-ethyl]-4-phenyl-piperidine-4-carboxylic acid amide (6 mmol) and THF (20 mL). Cool using an ice bath. Add a 1M THF solution of tetrabutylammonium fluoride (7 mL) in dropwise fashion. After 30 minutes, concentrate in vacuo to obtain a residue. Add dichloromethane (50 mL) to the residue. Extract with water (3×15 mL), dry over $Na_2SO_4$, filter, and concentrate in vacuo to obtain a residue. Purify to obtain the title compound.

EXAMPLE 57

Synthesis of 1-[2-[3-(4-trifluoromethyl-phenyl)-1-(3-isopropoxy-benzoyl)-pyrrolidin-3-yl]-ethyl]-4-phenyl-piperidine-4-carboxylic acid amide 57.1 Synthesis of 3-cyano-3-(4-trifluoromethyl-phenyl)-pentanedioic acid diethyl ester Prepare by the method of example 1.1.2 using 4-trifluoromethyl-phenylacetonitrile (0.161 mol) and ethyl bromoacetate (0.325 mol). Chromatograph on silica gel to give the title compound.

57.2 Synthesis of [3-(4-trifluoromethyl-phenyl)-5-oxo-pyrrolidin-3-yl]-acetic acid ethyl ester Prepare by the method of example 1.2.2 using 3-cyano-3-(4-trifluoromethyl-phenyl)-pentanedioic acid diethyl ester (89 mmol). Chromatograph on silica gel to give the title compound.

57.3 Synthesis of 2-[3-(4-trifluoromethyl-phenyl)-pyrrolidin-3-yl]-ethanol

Prepare by the method of example 1.3.2 using [3-(4-trifluoromethyl-phenyl)-5-oxo-pyrrolidin-3-yl]-acetic acid ethyl ester (73 mmol). Chromatograph on silica gel to give the title compound.

57.4 Synthesis of 3-isopropoxybenzoic acid

Combine 3-hydroxybenzoic acid (100 mmol), 2-iodopropane (500 mmol), $K_2CO_3$ (300 mmol), and 2-butanone (300 mL). Heat at reflux for 72 h. Concentrate in vacuo to obtain a residue. Add water (500 mL) and cool in an ice bath. Adjust to pH 1 by dropwise addition of concentrated HCl. Extract with dichloromethane (3×200 mL). Extract the combined organic layers with water (200 mL), dry over $Na_2SO_4$, filter, and concentrate in vacuo to obtain a residue. Purify to obtain the title compound.

57.5 Synthesis of 3-isopropoxy-benzoyl chloride

Combine 3-isopropoxybenzoic acid (50 mmol) and dichloromethane (100 mL). Cool in an ice bath. Add in dropwise fashion, oxalyl chloride (55 mmol). Allow the reaction mixture to warm to ambient temperature. After 2 h, concentrate in vacuo to obtain a residue. Use the title compound without further purification.

57.6 Synthesis of 2-[3-(4-trifluoromethyl-phenyl)-1-(3-isopropoxy-benzoyl)-pyrrolidin-3-yl]-ethanol Prepare by the method of example 3.1 using 2-[3-(4-trifluoromethyl-phenyl)-pyrrolidin-3-yl]-ethanol (23 mmol) and 3-isopropoxy-benzoyl chloride (23 mmol). Chromatograph on silica gel to give the title compound.

57.7 Synthesis of 2-[3-(4-trifluoromethyl-phenyl)-1-(3-isopropoxy-benzoyl)-pyrrolidin-3-yl]-ethyl-bromide Combine 2-[3-(4-trifluoromethyl-phenyl)-1-(3-isopropoxy-benzoyl)-pyrrolidin-3-yl]-ethanol (10 mmol), carbon tetrabromide (12.5 mmol), and dichloromethane (15 mL). Cool in an ice bath. Add in portions, triphenylphosphine (15 mmol). After 1 h, concentrate in vacuo to obtain a residue. Purify to obtain the title compound.

57.8 Synthesis of 1-[2-[3-(4-trifluoromethyl-phenyl)-1-(3-isopropoxy-benzoyl)-pyrrolidin-3-yl]-ethyl]-4-phenyl-piperidine-4-carboxylic acid amide Combine 2-[3-(4-trifluoromethyl-phenyl)-1-(3-isopropoxy-benzoyl)-pyrrolidin-3-yl]-ethyl-bromide (8 mmol), 4-phenyl-piperidine-4-carboxylic acid amide hydrochloride (12 mmol), $K_2CO_3$ (36 mmol), KI (0.8 mmol), and $THF/H_2O$ (3/1, 80 mL). Heat at reflux for 72 h. Concentrate in vacuo to remove THF and extract with dichloromethane (2×50 mL). Extract the combined organic layers using water (50 mL). Dry over $MgSO_4$, filter, and concentrate in vacuo to obtain a residue. Chromatograph on silica gel to obtain the title compound.

EXAMPLE 58

Synthesis of 1-[2-[3-(3,4-dichloro-phenyl)-1-(3,4,5-trimethoxy-benzoyl)-pyrrolidin-3-yl]-ethyl]-4-(thiophen-2-yl)-piperidine-4-carboxylic acid amide 58.1 Synthesis of 1-tert-butoxycarbonyl-4-cyano-4-(thiophen-2-yl)-piperidine Prepare by the method of example 30.2 using 2-thiopheneacetonitrile (10 mmol) and 2-chloro-N-(2-chloroethyl)-N-tert-Butoxycarbonyl-ethanamine (11 mmol). Purify to give the title compound.

58.2 Synthesis of 4-cyano-4-(thiophen-2-yl)-piperidine hydrochloride

Prepare by the method of example 30.3 using 1-tert-butoxycarbonyl-4-cyano-4-(thiophen-2-yl)-piperidine (3 mmol) and HCl in dioxane (4N, 40 mmol). Concentrate the solvent in vacuo and dry under high vacuum to give the title compound.

58.3 Synthesis of 4-(thiophen-2-yl)-piperidine-4-carboxylic acid hydrochloride

Prepare by the method of example 20.6 using 4-cyano-4-(thiophen-2-yl)-piperidine hydrochloride (10 mmol) and KOH (0.4 mol, 3N). Purify to give the title compound.

58.4 Synthesis of 1-tert-butoxycarbonyl-4-(thiophen-2-yl)-piperidine-4-carboxylic acid Prepare by the method of example 20.7 using 4-(thiophen-2-yl)-piperidine-4-carboxylic acid hydrochloride (10 mmol) and di-tert-butyl dicarbonate (11 mmol). Purify to give the title compound.

58.5 Synthesis of 1-tert-butoxycarbonyl-4-(thiophen-2-yl)-piperidine-4-carboxylic acid amide Prepare by the method of example 20.8 using 1-tert-butoxycarbonyl-4-(thiophen-2-yl)-piperidine-4-carboxylic acid (4.0 mmol) and $NH_3$(gas). Purify to give the title compound.

58.6 Synthesis of 4-(thiophen-2-yl)-piperidine-4-carboxylic acid amide hydrochloride Prepare by the method of example 20.10 using 1-tert-butoxycarbonyl-4-(thiophen-2-yl)-piperidine-4-carboxylic acid amide (3 mmol) and HCl in dioxane (40 mmol, 4N) to give the title compound.

58.7 Synthesis of 1-[2-[3-(3,4-dichloro-phenyl)-1-(3,4,5-trimethoxy-benzoyl)-pyrrolidin-3-yl]-ethyl]-4-(thiophen-2-yl)-piperidine-4-carboxylic acid amide Prepare by the method of example 3.3 using 2-[3-(3,4-dichloro-phenyl)-1-(3,4,5-trimethoxy-benzoyl)-pyrrolidin-3-yl]-ethyl-methanesulfonate (5 mmol) and 4-(thiophen-2-yl)-piperidine-4-carboxylic acid amide hydrochloride (7.5 mmol, 1.5 eq.). Chromatograph on silica gel to give the title compound.

EXAMPLE 59

Synthesis of 1-[2-[3-(3,4-dichloro-phenyl)-5-oxo-1-(3,4,5-trimethoxy-benzoyl)-pyrrolidin-3-yl]-ethyl]-4-phenyl-piperidine-4-carboxylic acid amide 59.1 Synthesis of 4-(3,4-dichloro-phenyl)-4-[2-(tetrahydro-pyran-2-yloxy)-ethyl]-1-(3,4,5-trimethoxy-benzoyl)-pyrrolidin-2-one Combine 4-(3,4-dichloro-phenyl)-4-[2-(tetrahydro-pyran-2-yloxy)ethyl]-pyrrolidin-2-one (as prepared in example 11.3) (5 mmol) and 3,4,5-trimethoxy-benzoyl chloride (5.0 mmol) in N,N-dimethylaniline (20 mL). Heat to 90° C. and stir for 24 h. Concentrate in vacuo. Partition the reaction mixture between dichloromethane and $H_2O$. Separate the organic layer, dry over $MgSO_4$, filter, and concentrate in vacuo to obtain a residue. Purify to give the title compound.

59.2 Synthesis of 4-(3,4-dichloro-phenyl)-4-(2-hydroxy-ethyl)-1-(3,4,5-trimethoxy-benzoyl)-pyrrolidin-2-one Prepare according to the method of example 11.5 using 4-(3,4-dichloro-phenyl)-4-[2-(tetrahydro-pyran-2-yloxy)-ethyl]-1-(3,4,5-trimethoxy-benzoyl)-pyrrolidin-2-one (3 mmol) and p-toluenesulfonic acid (200 mg). Chromatograph on silica gel to give the title compound.

59.3 Synthesis of 2-[3-(3,4-dichloro-phenyl)-5-oxo-1-(3,4,5-trimethoxy-benzoyl)-pyrrolidin-3-yl]-ethyl-methanesulfonate Prepare according to the method of example 3.2 using 4-(3,4-dichloro-phenyl)-4-2-hydroxy-ethyl-1-(3,4,5-trimethoxy-benzoyl)-pyrrolidin-2-one (5 mmol) and methanesulfonyl chloride (6 mmol). Dry under high vacuum at ambient temperature for 18 h to give the title compound.

59.4 Synthesis of 1-[2-[3-(3,4-dichloro-phenyl)-5-oxo-1-(3,4,5-trimethoxy-benzoyl)-pyrrolidin-3-yl]-ethyl]-4-phenyl-piperidine-4-carboxylic acid amide Prepare according to the method of example 3.3 using 2-[3-(3,4-dichloro-phenyl)-5-oxo-1-(3,4,5-trimethoxy-benzoyl)-pyrrolidin-3-yl]-ethyl-methanesulfonate (5 mmol) and 4-phenyl-piperidine-4-carboxylic acid amide hydrochloride (7.5 mmol, 1.5 eq.). Chromatograph on silica gel to give the title compound.

EXAMPLE 60

Synthesis of 1-[2-[3-(3,4-dichloro-phenyl)-1-(3,4,5-trimethoxy-benzyl)-pyrrolidin-3-yl]-ethyl]-4-phenyl-piperidine-4-carboxylic acid amide 60.1 Synthesis of 4-(3,4-dichloro-phenyl)-4-[2-(tetrahydro-pyran-2-yloxy)-ethyl]-pyrrolidine Prepare according to the method of example 1.3.2 using 4-(3,4-dichloro-phenyl)-4-[2-(tetrahydro-pyran-2-yloxy) ethyl]-pyrrolidin-2-one (as prepared in example 11.3) (3 mmol), $LiAlH_4$ (18 mmol) $H_2SO_4$ (99,999%) (9 mmol). Purify to give the title compound.

60.2 Synthesis of 4-(3,4-dichloro-phenyl)-4-[2-(tetrahydro-pyran-2-yloxy)-ethyl]-1-(3,4,5-trimethoxy-benzyl)-pyrrolidine Combine 4-(3,4-dichloro-phenyl)-4-[2-(tetrahydro-pyran-2-yloxy) -ethyl]-pyrrolidine (10 mmol), $K_2CO_3$ (30 mmol), and 3,4,5-trimethoxy-benzyl bromide (10 mmol) in $THF/H_2O$ (4/1, 200 mL). Heat to reflux and stir for 16 h. Concentrate in vacuo to obtain a residue. Dilute the residue with ethyl acetate and extract with $H_2O$. Separate the layers, dry the organic layer over $MgSO_4$, filter, and concentrate in vacuo. Chromatograph on silica gel to give the title compound.

60.3 Synthesis of 4-(3,4-dichloro-phenyl)-4-2-hydroxy-ethyl-1-(3,4,5-trimethoxy-benzyl)-pyrrolidine Prepare according to the method of example (11.5) using 4-(3,4-dichloro-phenyl)-4-[2-(tetrahydro-pyran-2-yloxy)-ethyl]-1-(3,4,5-trimethoxy-benzyl)-pyrrolidine (3 mmol) and p-toluenesulfonic acid (200 mg). Chromatograph on silica gel to give the title compound.

60.4 Synthesis of 2-[3-(3,4-dichloro-phenyl)-1-(3,4,5-trimethoxy-benzyl)-pyrrolidin-3-yl]-ethyl-bromide Prepare according to the method of example 57.7 using 4-(3,4-dichloro-phenyl)-4-2-hydroxy-ethyl-1-(3,4,5-trimethoxy-benzyl)-pyrrolidine (5 mmol), carbon tetrabromide (6.3 mmol), and triphenylphosphine (7.5 mmol). Purify to obtain the title compound.

60.5 Synthesis of 1-[2-[3-(3,4-dichloro-phenyl)-1-(3,4,5-trimethoxy-benzyl)-pyrrolidin-3-yl]-ethyl]-4-phenyl-piperidine-4-carboxylic acid amide Prepare according to the method of example 57.8 using 2-[3-(3,4-dichloro-phenyl)-1-(3,4,5-trimethoxy-benzyl)-pyrrolidin-3-yl]-ethyl-bromide (5 mmol) and 4-phenyl-piperidine-4-carboxylic acid amide hydrochloride (7.5 mmol, 1.5 eq.). Chromatograph on silica gel to give the title compound.

EXAMPLE 61

Synthesis of 1-[3-[3-(3,4-dichloro-phenyl)-1-(3,4,5-trimethoxy-benzoyl)-pyrrolidin-3-yl]-propyl]-4-phenyl-piperidine-4-carboxylic acid amide 61.1 Synthesis of 2-(3,4-dichloro-phenyl)-5-(tetrahydro-pyran-2-yloxy)-pentanenitrile Prepare according to the method of example 11.1 using 3,4-dichlorophenylacetonitrile (50 mmol) and 2-(3-bromopropoxy)-tetrahydro-pyran (50 mmol). Chromatograph on silica gel to give the title compound.

61.2 Synthesis of ethyl-[3-cyano-3-(3,4-dichloro-phenyl)-6-(tetrahydro-pyran-2-yloxy)]-hexanoate Prepare according to the method of example 11.2 using 2-(3,4-dichloro-phenyl)-5-(tetrahydro-pyran-2-yloxy)-pentane nitrile (34 mmol) and ethyl bromoacetate (38 mmol, 1.1 eq.). Chromatograph on silica gel to give the title compound.

61.3 Synthesis of 4-(3,4-dichloro-phenyl)-4-[3-(tetrahydro-pyran-2-yloxy)-propyl]-pyrrolidin-2-one Prepare according to the method of example 11.3 using ethyl-[3-cyano-3-(3,4-dichloro-phenyl)-6-(tetrahydro-pyran-2-yloxy)]-hexanoate (24 mmol) and Raney nickel (30 g). Chromatograph on silica gel to give the title compound.

61.4 Synthesis of 4-(3,4-dichloro-phenyl)-4-[3-(tetrahydro-pyran-2-yloxy)-propyl]-pyrrolidine Prepare according to the method of example 1.3.2 using 4-(3,4-dichloro-phenyl)-4-[3-(tetrahydro-pyran-2-yloxy)-propyl]-pyrrolidin-2-one (3 mmol), LiAlH$_4$ (18 mmol) H$_2$SO$_4$ (99.999%) (9 mmol). Purify to give the title compound.

61.5 Synthesis of 4-(3,4-dichloro-phenyl)-4-[3-(tetrahydro-pyran-2-yloxy)-propyl]-1-(3,4,5-trimethoxy-benzoyl)-pyrrolidine Prepare by the method of example 3.1 using 4-(3,4-dichloro-phenyl)-4-[3-(tetrahydro-pyran-2-yloxy)-propyl]-pyrrolidine (2 mmol) and 3,4,5-trimethoxy-benzoyl chloride (2 mmol). Chromatograph on silica gel to give the title compound.

61.6 Synthesis of 4-(3,4-dichloro-phenyl)-4-(3-hydroxy-propyl)-1-(3,4,5-trimethoxy-benzoyl)-pyrrolidine Prepare according to the method of example 11.5 using 4-(3,4-dichloro-phenyl)-4-[3-(tetrahydro-pyran-2-yloxy)-propyl]-1-(3,4,5-trimethoxy-benzoyl)-pyrrolidine (3 mmol) and p-toluenesulfonic acid (200 mg). Chromatograph on silica gel to give the title compound.

61.7 Synthesis of 3-[3-(3,4-dichloro-phenyl)-1-(3,4,5-trimethoxy-benzoyl)-pyrrolidin-3-yl]-propyl-methanesulfonate Prepare according to the method of example 3.2 using 4-(3,4-dichloro-phenyl)-4-(3-hydroxy-propyl)-1-(3,4,5-trimethoxy-benzoyl)-pyrrolidine (5 mmol) and methanesulfonyl chloride (6 mmol). Dry under high vacuum at ambient temperature for 18 h to give the title compound.

61.8 Synthesis of 1-[3-[3-(3,4-dichloro-phenyl)-1-(3,4,5-trimethoxy-benzoyl)-pyrrolidin-3-yl]-propyl]-4-phenyl-piperidine-4-carboxylic acid amide Prepare according to the method of example 3.3 using 3-[3-(3,4-dichloro-phenyl)-1-(3,4,5-trimethoxy-benzoyl)-pyrrolidin-3-yl]-propyl-methanesulfonate (5 mmol) and 4-phenyl-piperidine-4-carboxylic acid amide hydrochloride (7.5 mmol, 1.5 eq.). Chromatograph on silica gel to give the title compound.

EXAMPLE 62

Synthesis of 1-[3-[3-(3,4-dichloro-phenyl)-1-(3,4,5-trimethoxy-benzyl)-pyrrolidin-3-yl]-propyl]-4-phenyl-piperidine-4-carboxylic acid amide 62.1 Synthesis of 4-(3,4-dichloro-phenyl)-4-[3-(tetrahydro-pyran-2-yloxy)-propyl]-1-(3,4,5-trimethoxy-benzyl)-pyrrolidine Combine 4-(3,4-dichloro-phenyl)-4-[3-(tetrahydro-pyran-2-yloxy)-propyl]-pyrrolidine (10 mmol), K$_2$CO$_3$ (30 mmol), and 3,4,5-trimethoxy-benzyl bromide (10 mmol) in THF/H$_2$O (4/1, 200 mL). Heat to reflux and stir for 16 h. Concentrate in vacuo to obtain a residue. Dilute the residue with ethyl acetate and extract with H$_2$O. Separate the layers, dry the organic layer over MgSO$_4$, filter, and concentrate in vacuo. Chromatograph on silica gel to give the title compound.

62.2 Synthesis of 4-(3,4-dichloro-phenyl)-4-(3-hydroxy-propyl)-1-(3,4,5-trimethoxy-benzyl)-pyrrolidine Prepare according to the method of example 11.5 using 4-(3,4-dichloro-phenyl)-4-[3-(tetrahydro-pyran-2-yloxy)-propyl]-1-(3,4,5-trimethoxy-benzyl)-pyrrolidine (3 mmol) and p-toluenesulfonic acid (200 mg). Chromatograph on silica gel to give the title compound.

62.3 Synthesis of 3-[3-(3,4-dichloro-phenyl)-1-(3,4,5-trimethoxy-benzyl)-pyrrolidin-3-yl]-propyl-bromide Prepare according to the method of example 57.7 using 4-(3,4-dichloro-phenyl)-4-(3-hydroxy-propyl)-1-(3,4,5-trimethoxy-benzyl)-pyrrolidine (5 mmol), carbon tetrabromide (6.3 mmol), and triphenylphosphine (7.5 mmol). Purify to obtain the title compound.

62.4 Synthesis of 1-[3-[3-(3,4-dichloro-phenyl)-1-(3,4,5-trimethoxy-benzyl)-pyrrolidin-3-yl]-propyl]-4-phenyl-piperidine-4-carboxylic acid amide Prepare according to the method of example 57.8 using 3-[3-(3,4-dichloro-phenyl)-1-(3,4,5-trimethoxy-benzyl)-pyrrolidin-3-yl]-propyl-bromide (5 mmol) and 4-phenyl-piperidine-4-carboxylic acid amide hydrochloride (7.5 mmol, 1.5 eq.). Chromatograph on silica gel to give the title compound.

EXAMPLE 63

Synthesis of 1-[3-[3-(3,4-dichloro-phenyl)-1-(3,4,5-trimethoxy-benzyl)-5-oxo-pyrrolidin-3-yl]-propyl]-4-phenyl-piperidine-4-carboxylic acid amide 63.1 Synthesis of 4-(3,4-dichloro-phenyl)-1-(3,4,5-trimethoxy-benzyl)-4-[3-(tetrahydro-pyran-2-yloxy)-propyl]-pyrrolidin-2-one Prepare according to the procedure of example 11.4 using 4-(3,4-dichloro-phenyl)-4-[3-(tetrahydro-pyran-2-yloxy)-propyl]-pyrrolidin-2-one (2.79 mmol) and 3,4,5-trimethoxy-benzyl bromide (5.9 mmol). Chromatograph on silica gel to give the title compound.

63.2 Synthesis of 4-(3,4-dichloro-phenyl)-4-(3-hydroxy-propyl)-1-(3,4,5-trimethoxy-benzyl)-pyrrolidin-2-one Prepare according to the method of example 11.5 using 4-(3,4-dichloro-phenyl)-4-[3-(tetrahydro-pyran-2-yloxy)-propyl]-1-(3,4,5-trimethoxy-benzyl)-pyrrolidin-2-one (3 mmol) and p-toluenesulfonic acid (200 mg). Chromatograph on silica gel to give the title compound.

63.3 Synthesis of 3-[3-(3,4-dichloro-phenyl)-1-(3,4,5-trimethoxy-benzyl)-5-oxo-pyrrolidin-3-yl]-propyl-methanesulfonate Prepare according to the method of example 3.2 using 4-(3,4-dichloro-phenyl)-4-(3-hydroxy-propyl)-1-(3,4,5-trimethoxy-benzyl)-pyrrolidin-2-one (5 mmol) and methanesulfonyl chloride (6 mmol). Dry under high vacuum at ambient temperature for 18 h to give the title compound.

63.4 Synthesis of 1-[3-[3-(3,4-dichloro-phenyl)-1-(3,4,5-trimethoxy-benzyl)-5-oxo-pyrrolidin-3-yl-]-propyl]-4-phenyl-piperidine-4-carboxylic acid amide Prepare according to the method of example 3.3 using 3-[3-(3,4-dichloro-phenyl)-1-(3,4,5-trimethoxy-benzyl)-5-oxo-pyrrolidin-3-yl]-propyl-methanesulfonate (5 mmol) and 4-phenyl-piperidine-4-carboxylic acid amide hydrochloride (7.5 mmol, 1.5 eq.). Chromatograph on silica gel to give the title compound.

EXAMPLE 64

Synthesis of 1-[3-[3-(3,4-dichloro-phenyl)-1-(3,4,5-trimethoxy-benzoyl)-5-oxo-pyrrolidin-3-yl]-propyl]-4-phenyl-piperidine-4-carboxylic acid amide 64.1 Synthesis of 4-(3,4-dichloro-phenyl)-1-(3,4,5-trimethoxy-benzoyl)-4-[3-(tetrahydro-pyran-2-yloxy)-propyl]-pyrrolidin-2-one Prepare according to the procedure of example 59.1 using 4-(3,4-dichloro-phenyl)-4-[3-(tetrahydro-pyran-2-yloxy)-propyl]-pyrrolidin-2-one (5.0 mmol) and 3,4,5-trimethoxy-benzoyl chloride (5.0 mmol). Chromatograph on silica gel to give the title compound.

64.2 Synthesis of 4-(3,4-Dichloro-phenyl)-4-(3-hydroxy-propyl)-1-(3,4,5-trimethoxy-benzoyl)-pyrrolidin-2-one Prepare according to the method of example 11.5 using 4-(3,4-dichloro-phenyl)-4-[3-(tetrahydro-pyran-2-yloxy)- propyl]-1-(3,4,5-trimethoxy-benzoyl)-pyrrolidin-2-one (3 mmol) and p-toluenesulfonic acid (200 mg). Chromatograph on silica gel to give the title compound.

64.3 Synthesis of 3-[3-(3,4-dichloro-phenyl)-1-(3,4,5-trimethoxy-benzoyl)-5-oxo-pyrrolidin-3-yl]-propyl-methanesulfonate Prepare according to the method of example 3.2 using 4-(3,4-dichloro-phenyl)-4-(3-hydroxy-propyl)-1-(3,4,5-trimethoxy-benzoyl)-pyrrolidin-2-one (5 mmol) and methanesulfonyl chloride (6 mmol). Dry under high vacuum at ambient temperature for 18 h to give the title compound.

64.4 Synthesis of 1-[3-[3-(3,4-dichloro-phenyl)-1-(3,4,5-trimethoxy-benzoyl)-5-oxo-pyrrolidin-3-yl]-propyl]-4-phenyl-piperidine-4-carboxylic acid amide Prepare according to the method of example 3.3 using 3-[3-(3,4-dichloro-phenyl)-1-(3,4,5-trimethoxy-benzoyl)-5-oxo-pyrrolidin-3-yl]-propyl-methanesulfonate (5 mmol) and 4-phenyl-piperidine-4-carboxylic acid amide hydrochloride (7.5 mmol, 1.5 eq.). Chromatograph on silica gel to give the title compound.

EXAMPLE 65

Synthesis of 1-[2-[3-(3,4-dichloro-phenyl)-1-(3,4,5-triethoxy-benzoyl)-pyrrolidin-3-yl]-ethyl]-4-phenyl-piperidine-4-carboxylic acid amide 65.1 Synthesis of 2-[3-(3,4-dichloro-phenyl)-1-(3,4,5-triethoxy-benzoyl)-pyrrolidin-3-yl]-ethanol Combine 3-(3,4-dichloro-phenyl)-3-(2-hydroxy-ethyl)-pyrrolidine (260 mg, 1 mmol) and and potassium carbonate (0.69 g, 5 mmol) in ethyl acetate/water (10 mL/10 mL). Cool in an ice-bath. Add a solution of triethoxy-benzoyl chloride (1.2 mmol) in ethyl acetate (10 mL). After 1 hour, dilute with ethyl acetate and extract with 1M hydrochloric acid solution, 5% sodium bicarbonate solution, and water. Dry the organic layer over $MgSO_4$, filter, and evaporate in vacuo to give the title compound: $R_f$=0.43 (silica gel, 6% methanol/dichloromethane).

65.2 Synthesis of 2-[3-(3,4-dichloro-phenyl)-1-(3,4,5-triethoxy-benzoyl)-pyrrolidin-3-yl]-ethyl-methanesulfonate Prepare by the method of Example 3.2 using 2-[3-(3,4-dichloro-phenyl)-1-(3,4,5-triethoxy-benzoyl)-pyrrolidin-3-yl]-ethanol (1 mmol) and methanesulfonyl chloride (0.09 mL, 1.1 mmol) to give the title compound: $R_f$=0.61 (silica gel, 6% methanol in dichloromethane).

65.3 Synthesis of 1-[2-[3-(3,4-dichloro-phenyl)-1-(3,4,5-triethoxy-benzoyl)-pyrrolidin-3-yl]-ethyl]-4-phenyl-piperidine-4-carboxylic acid amide Prepare by the method of example 27.3.1 using 2-[3-(3,4-dichloro-phenyl)-1-(3,4,5-triethoxy-benzoyl)-pyrrolidin-3-yl]-ethyl-methanesulfonate ((1 mmol) and 4-phenyl-piperidine-4-carboxylic acid amide hydrochloride (0.29 g, 1.2 mmol). Chromatograph on silica gel eluting sequentially with 50% ethyl acetate/hexane and then 6% methanol/dichloromethane to give the title compound: $R_f$=0.36 (silica gel, 10% methanol in dichloromethane). Exact mass (FAB+): calculated for $C_{37}H_{46}Cl_2N_3O_5$ calculated 682.2815. Found 682.2799.

EXAMPLE 66

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide hydrochloride 66.1 Synthesis of 1-tert-butoxycarbonyl-4-phenyl-piperidine-4-carboxylic acid 4-methylpiperazine-amide Prepare by the method of Example 20.9 using 1-tert-butoxycarbonyl-4-phenyl-piperidine-4-carboxylic acid (1.6 g, 5.2 mmol) and 4-methylpiperazine (1.2 mL, 10.5 mmol) to give the title compound: $R_f$=0.54 (silica gel, 10% methanol/dichloromethane).

66.2 Synthesis of 4-phenyl-piperidine-4-carboxylic acid 4-methylpiperazine-amide hydrochloride Prepare by the method of Example 20.10 using 1-tert-butoxycarbonyl-4-phenyl-piperidine-4-carboxylic acid 4-methylpiperazine-amide to give the title compound.

66.3.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (2.8 g, 5.24 mmol) and 4-phenyl-piperidine-4-carboxylic acid 4-methylpiperazine-amide hydrochloride (2.8 g, 3.9 mmol). Chromatograph on silica gel eluting sequentially with 50% ethyl acetate/hexane, 3% methanol/dichloromethane, and then 6% methanol/dichloromethane to give the title compound.

66.3.2 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide Prepare by the method of Example 26FH.5 using 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (0.18 g, 0.3 mmol) and 4-phenyl-piperidine-4-carboxylic acid 4-methylpiperazine-amide hydrochloride (0.7 mL, 0.6 mmol). Chromatograph on silica gel eluting with 6% methanol/dichloromethane to give the title compound. Exact mass (FAB+): calculated for $C_{39}H_{49}Cl_2N_4O_5$ calculated 723.3080. Found 723.3067.

66A.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide hydrochloride Dissolve 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide (1.96 g, 2.71 mmol) in dichloromethane (20 mL). This solution was combined with a saturated solution of hydrochloric acid in dichloromethane (20 mL) and the mixture was stirred for 1 hour. The reaction mixture was evaporated in vacuo and hexane was added. This mixture was evaporated in vacuo and diethyl ether was added. The diethyl ether mixture was evaporated in vacuo to give a solid. The solid was dried in vacuo to give the title compound.

Exact mass (FAB+): calculated for $C_{39}H_{49}Cl_2N_4O_5$ calculated 723.3080. Found 723.3073.

EXAMPLE 67

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-morpholino-ethyl)-amide hydrochloride 67.1 Synthesis of 1-tert-butoxycarbonyl-4-phenyl-piperidine-4-carboxylic acid (2-morpholino-ethyl)-amide Prepare by the method of Example 20.9 using 1-tert-butoxycarbonyl-4-phenyl-piperidine-4-carboxylic acid (7 mmol) and 2-morpholino-ethylamine (7 mmol) to give the title compound: $R_f$=0.49 (silica gel, 6% methanol/dichloromethane).

67.2 Synthesis of 4-phenyl-piperidine-4-carboxylic acid (2-morpholino-ethyl)-amide hydrochloride Prepare by the method of Example 20.10 using 1-tert-butoxycarbonyl-4-phenyl-piperidine-4-carboxylic acid (2-morpholino-ethyl)-amide to give the title compound.

67.3.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-morpholino-ethyl)-amide Prepare by the method of example 27.3.1 using 2-[3-(3, 4-dichloro-phenyl)-1-(3,4,5-triethoxy-benzoyl)-pyrrolidin-3-yl]-ethyl-methanesulfonate (2.8 g, 5.24 mmol) and 4-phenyl-piperidine-4-carboxylic acid (2-morpholino-ethyl) -amide hydrochloride (1.87 g, 35.2 mmol). Chromatograph on silica gel eluting sequentially with 50% ethyl acetate/hexane and then 6% methanol/dichloromethane to give the title compound.

67.3.2 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (2-morpholino-ethyl)-amide Prepare by the method of Example 26FH.5 using 1-[2-[3-(3,4-dichloro-phenyl)-1-(3,4,5-trimethoxy-benzoyl)-pyrrolidin-3-yl]-ethyl]-4-phenyl-piperidine-4-carboxylic acid (0.16 g, 0.625 mmol) and 4-phenyl-piperidine-4-carboxylic acid (2-morpholino-ethyl)-amide hydrochloride (0.07 mL, 0.5 mmol). Chromatograph on silica gel eluting with 6% methanol/dichloromethane to give the title compound: $R_f$=0.34 (silica gel, 10% methanol/dichloromethane).

Exact mass (FAB+): calculated for $C_{40}H_{51}Cl_2N_4O_6$ calculated 753.3191. Found 753.3186.

67A.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide hydrochloride Prepare by the method of example 66A.1 using 1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide to give the title compound: $R_f$=0.53 (silica gel, 10% methanol/dichloromethane).

EXAMPLE 68

Synthesis of 1-[2-[3-(3,4-dichloro-phenyl)-1-[4-methoxy-benzoyl)-pyrrolidin-3-yl]-ethyl]-4-phenyl-piperidine-4-carboxylic acid amide 68.1 Synthesis of 3-(3,4-dichloro-phenyl)-1-(4-methoxy-benzoyl)-3-(2-hydroxy-ethyl)-pyrrolidine Prepare by the method of Example 1.4 using 2-[3-(3,4-dichloro-phenyl)-pyrrolidin-3-yl]-ethanol (0.26 g, 1 mmol) and 4-methoxy-benzoyl chloride (2 mmol) to give the title compound: $R_f$=0.44 (silica gel, 6% methanol in dichloromethane).

68.2 Synthesis of 2-[3-(3,4-dichloro-phenyl)-1-(4-methoxy-benzoyl)-pyrrolidin-3-yl]-ethyl-methanesulfonate Prepare by the method of Example 1.5 using 3-(3,4-dichloro-phenyl)-1-(4-methoxy-benzoyl)-3-(2-hydroxy-ethyl)-pyrrolidine (0.24 g, 0.62 mmol) and methanesulfonyl chloride (0.62 mmol) to give the title compound: $R_f$=0.57 (silica gel, 6% methanol in dichloromethane).

68.3 Synthesis of 1-[2-[3-(3,4-dichloro-phenyl)-1-(4-methoxy-benzoyl)-pyrrolidin-3-yl]-ethyl]-4-phenyl-piperidine-4-carboxylic acid amide Prepare by the method of example 27.3.1 using 2-[3-(3, 4-dichloro-phenyl)-1-(4-methoxy-benzoyl)-pyrrolidin-3-yl] -ethyl-methanesulfonate (0.63 mmol) and 4-phenyl-piperidine-4-carboxylic acid amide hydrochloride (0.3 g). Purify by chromatographed on silica gel eluting sequentially with 50% ethyl acetate/hexane, 4% methanol/dichloromethane, and then 6% methanol/dichloromethane to give the title compound: $R_f$=0.58 (silica gel, 10% methanol in dichloromethane).

EXAMPLE 69

Synthesis of 1-[2-[3-(3,4-dichloro-phenyl)-1-(3,4,5-trifluoro-benzoyl)-pyrrolidin-3-yl]-ethyl]-4-phenyl-piperidine-4-carboxylic acid amide 69.1 Synthesis of 2-[3-(3,4-dichloro-phenyl)-1-(3,4,5-trifluoro-benzoyl)-pyrrolidin-3-yl]-ethanol Combine 3-(3,4-dichloro-phenyl)-3-(2-hydroxy-ethyl)-pyrrolidine (286 mg, 1.1 mmol), 3,4,5-trifluoro-benzoic acid (1 mmol), N,N-diisopropylethylamine (0.19 mL, 1.1 mmol), 1-ethyl-3-(3-dimethylaminopropyl) carbodiimide hydrochloride (EDC) (0.21 g, 1.1 mmol), and 1-hydroxybenzotriazole hydrate (HOBT) (0.15 g, 1.1 mmol) in dichloromethane (10 mL). After 18 hour, dilute with dichloromethane and extract with 1M hydrochloric acid solution, 5% sodium bicarbonate solution, and water. Dry the organic layer over $MgSO_4$, filter, and evaporate in vacuo to give the title compound: $R_f$=0.45 (silica gel, 10% methanol/dichloromethane).

69.2 Synthesis of 2-[3-(3,4-dichloro-phenyl)-1-(3,4,5-trifluoro-benzoyl)-pyrrolidin-3-yl]-ethyl-methanesulfonate Prepare by the method of Example 3.2 using 2-[3-(3, 4dichloro-phenyl)-1-(3,4,5-trifluoro-benzoyl)-pyrrolidin-3-yl]-ethanol (1 mmol) and methanesulfonyl chloride (0.09 mL, 1.1 mmol) to give the title compound: $R_f$=0.50 (silica gel, 6% methanol in dichloromethane).

69.3 Synthesis of 1-[2-[3-(3,4-dichloro-phenyl)-1-(3,4,5-trifluoro-benzoyl)-pyrrolidin-3-yl]-ethyl]-4-phenyl-piperidine-4-carboxylic acid amide Prepare by the method of example 27.3.1 using 2-[3-(3, 4-dichloro-phenyl)-1-(3,4,5-trifluoro-benzoyl)-pyrrolidin-3-yl]-ethyl-methanesulfonate (1 mmol) and 4-phenyl-piperidine-4-carboxylic acid amide hydrochloride (0.29 g, 1.2 mmol). Chromatograph on silica gel eluting sequentially with 50% ethyl acetate/hexane and then 6% methanol/dichloromethane to give the title compound: $R_f$=0.45 (silica gel, 10% methanol in dichloromethane). Exact mass (FAB+): calculated for $C_{37}H_{46}Cl_2N_3O_5$ calculated 682.2815. Found 682.2799.

EXAMPLE 70

Synthesis of 1-[2-[3-(3,4-dichloro-phenyl)-1-(3,5-dibromo-4-methoxy-benzoyl)-pyrrolidin-3-yl]-ethyl] -4-phenyl-piperidine-4-carboxylic acid amide 70.1 Synthesis of 2-[3-(3,4-dichloro-phenyl)-1-tert-butoxycarbonyl-pyrrolidin-3-yl]-ethanol 3-(3,4-Dichloro-phenyl)-3-(2-hydroxy-ethyl)-pyrrolidine (10.4 mg, 40 mmol) was combined with di-tert-butyl dicarbonate (8.7 g, 40 mmol) in DMF/ethyl acetate (200 mL/200 mL) and the mixture was allowed to stir at ambient temperature for 18 h. Dilute with ethyl acetate and extract with 1M hydrochloric acid solution, 5% sodium bicarbonate solution, and water. Dry the organic layer over $MgSO_4$, filter, and evaporate in vacuo to give the title compound: $R_f$=0.57 (silica gel, 10% methanol/dichloromethane).

70.2 Synthesis of 2-[3-(3,4-dichloro-phenyl)-1-tert-butoxycarbonyl-pyrrolidin-3-yl]-ethyl-methanesulfonate Prepare by the method of Example 3.2 using 2-[3-(3,4-dichloro-phenyl)-1-tert-butoxycarbonyl-pyrrolidin-3-yl]-ethanol (16.18 g) and methanesulfonyl chloride (3.41 mL, 44 mmol). Chromatograph on silica gel eluting with 6% methanol/dichloromethane to give the title compound: $R_f$=0.79 (silica gel, 10% methanol in dichloromethane).

70.3 Synthesis of 1-[3-(3,4-dichloro-phenyl)-1-tert-butoxycarbonyl-pyrrolidin-3-yl]-ethyl]-4-phenyl-piperidine-4-carboxylic acid amide Combine 2-[3-(3,4-dichloro-phenyl)-1-tert-butoxycarbonyl-pyrrolidin-3-yl]-ethyl-methanesulfonate (40 mmol), 4-phenyl-piperidine-4-carboxylic acid amide hydrochloride (19.26 g, 80 mmol), and potassium carbonate (33.2 g, 240 mmol) in THF/water (200 mL/200 mL). Heat at reflux for 18 hours. The reaction mixture is diluted with ethyl acetate and extracted with water. The organic layer is separated, dried over $MgSO_4$, and evaporated in vacuo to give a residue. The residue was chromatographed on silica gel eluting sequentially with 50% ethyl acetate/hexane and then 6% methanol in dichloromethane to give the title compound: $R_f$=0.41 (silica gel, 10% methanol in dichloromethane).

70.4 Synthesis of 1-[3-(3,4-dichloro-phenyl)-pyrrolidin-3-yl]-ethyl]-4-phenyl-piperidine-4-carboxylic acid amide hydrochloride Combine 1-[3-(3,4-dichloro-phenyl)-1-tert-butoxycarbonyl-pyrrolidin-3-yl]-ethyl]-4-phenyl-piperidine-4-carboxylic acid amide (17.78 g, 32.4 mmol) and a saturated solution of hydrochloric acid in dichloromethane (500 mL). After 1 hour, evaporate in vacuo to give the title compound.

70.5 Synthesis of 1-[2-[3-(3,4-dichloro-phenyl)-1-(3,5-dibromo-4-methoxy-benzoyl)-pyrrolidin-3-yl]-ethyl]-4-phenyl-piperidine-4-carboxylic acid amide Combine 1-[3-(3,4-dichloro-phenyl)-pyrrolidin-3-yl]-ethyl]-4-phenyl-piperidine-4-carboxylic acid amide hydrochloride (241 mg, 0.41 mmol), 3,5-dibromo-4-methoxy-benzoic acid (0.23 g, 0.75 mmol), N,N-diisopropylethylamine (0.75 mmol), 1-ethyl-3-(3-dimethylaminopropyl) carbodiimide hydrochloride (EDC) (0.75 mmol), and 1-hydroxybenzotriazole hydrate (HOBT) (0.75 g, 1.1 mmol) in dichloromethane (10 mL). After 18 hour, dilute with dichloromethane and extract with 1M hydrochloric acid solution, 5% sodium bicarbonate solution, and water. Dry the organic layer over $MgSO_4$, filter, and evaporate in vacuo to give a residue. Chromatograph the residue on silica gel eluting sequentially with 50% ethyl acetate/hexane and then 6% methanol/dichloromethane to give the title compound: $R_f$=0.35 (silica gel, 10% methanol/dichloromethane). Exact mass (FAB+): calculated for $C_{32}H_{34}Br_2Cl_2N_3O_3$ calculated 736.0344. Found 736.0330.

EXAMPLE 71

Synthesis of 1-[2-[3-(3,4-dichloro-phenyl)-1-(3,5-dimethoxy-4-(ethoxy-carboxyloxy)-benzoyl)-pyrrolidin-3-yl]-ethyl]-4-phenyl-piperidine-4-carboxylic acid amide 71.1 Synthesis of 1-[2-[3-(3,4-dichloro-phenyl)-1-(3,5-dimethoxy-4-(ethoxy-carboxyloxy)-benzoyl)-pyrrolidin-3-yl]-ethyl]-4-phenyl-piperidine-4-carboxylic acid amide Prepare by the method of example 70.5 using 1-[3-(3,4-dichloro-phenyl)-pyrrolidin-3-yl]-ethyl]-4-phenyl-piperidine-4-carboxylic acid amide hydrochloride (240 mg, 0.4 mmol) and 3,5-dimethoxy-4-(ethoxy-carboxyloxy)-benzoic acid (0.20 g, 0.75 mmol) to give a residue. Chromatograph the residue on silica gel eluting sequentially with 50% ethyl acetate/hexane and then 6% methanol/dichloromethane to give the title compound: $R_f$=0.35 (silica gel, 10% methanol/dichloromethane).

Exact mass (FAB+): calculated for $C_{36}H_{42}Cl_2N_3O_7$ calculated 698.2399. Found 698.2402.

EXAMPLE 72

Synthesis of 1-[2-[3-(3,4-dichloro-phenyl)-1-(3,5-di-tert-butyl-4-hydroxy-benzoyl)-pyrrolidin-3-yl]-ethyl] -4-phenyl-piperidine-4-carboxylic acid amide 72.1 Synthesis of 1-[2-[3-(3,4-dichloro-phenyl)-1-(3,5-di-tert-butyl-4-hydroxy-benzoyl)-pyrrolidin-3-yl]-ethyl]-4-phenyl-piperidine-4-carboxylic acid amide Prepare by the method of example 70.5 using 1-[3-(3,4-dichloro-phenyl)-pyrrolidin-3-yl]-ethyl]-4-phenyl-piperidine-4-carboxylic acid amide hydrochloride (480 mg, 1 mmol) and 3,5-di-tert-butyl-4-hydroxy-benzoic acid (0.25 g, 1 mmol) to give a residue. Chromatograph the residue on silica gel eluting sequentially with 50% ethyl acetate/hexane and then 6% methanol/dichloromethane to give the title compound: $R_f$=0.52 (silica gel, 10% methanol/dichloromethane).

Exact mass (FAB+): calculated for $C_{39}H_{50}Cl_2N_3O_3$ calculated 678.3229. Found 678.3201.

EXAMPLE 73

Synthesis of 1-[2-[3-(3,4-dichloro-phenyl)-1-(3,5-dimethoxy-4-methyl-benzoyl)-pyrrolidin-3-yl]-ethyl] -4-phenyl-piperidine-4-carboxylic acid amide 73.1 Synthesis of 1-[2-[3-(3,4-dichloro-phenyl)-1-(3,5-dimethoxy-4-methyl-benzoyl)-pyrrolidin-3-yl]-ethyl]-4-phenyl-piperidine-4-carboxylic acid amide Prepare by the method of example 70.5 using 1-[3-(3,4-dichloro-phenyl)-pyrrolidin-3-yl]-ethyl]-4-phenyl-piperidine-4-carboxylic acid amide hydrochloride (240 mg, 0.5 mmol) and 3,5-di-methoxy-4-methyl-benzoic acid (0.22 g, 0.55 mmol) to give a residue. Chromatograph the residue on silica gel eluting sequentially with 50% ethyl acetate/hexane and then 6% methanol/dichloromethane to give the title compound: $R_f$=0.43 (silica gel, 10% methanol/dichloromethane).

PREPARATION 3

Synthesis of 4-phenyl-piperidine-4-carboxylic acid amide hydrochloride

4-Phenyl-4-cyano-piperidine hydrochloride (10 g, 44.9 mmol), Benzyl bromide (5.4 mL, 45.4 mmol), and potassium carbonate (25.2g, 182.3 mmol) were combined in THF/water (80 mL/20 mL). After 18 hours the reaction mixture was partitioned between water and dichloromethane. The organic layer was separated and extracted with water, dried over $MgSO_4$, filtered and evaporated in vacuo to give a residue. The residue was recrystallized from hexane to give 4-phenyl-4-cyano-1-benzyl-piperidine as a solid: mp=73°–74° C.

Synthesis of 4-phenyl-1-benzyl-piperidine-4-carboxylic acid amide N-oxide

4-Phenyl-4-cyano-1-benzyl-piperidine (535 g, 1940 mmol) was combined with aqueous sodium hydroxide (85 mL, 50% by weight) and ethanol (5 L) and the mixture was heated to 50° C. The heating was removed, and a solution of hydrogen peroxide (856 mL, 30% by weight in water) was added at such a rate that the temperature of the reaction mixture does not rise above 50° C. The reaction mixture was then stirred at 50° C. for 20 hours. The reaction mixture was diluted with water (3 L) and the ethanol was removed in vacuo at 35° C. Cooling the reaction mixture to ambient temperature gave a solid which was collected by filtration, rinsed with water, and air dried to give 4-phenyl-1-benzyl-piperidine-4-carboxylic acid amide N-oxide.

Synthesis of 4-phenyl-piperidine-4-carboxylic acid amide hydrochloride

4-Phenyl-1-benzyl-piperidine-4-carboxylic acid amide n-oxide (529 g, 1700 mmol) and 10% palladium-on-carbon (25 g) and acetic acid (5 L) were combined in an autoclave. The autoclave was flushed with nitrogen and then was charged with 255 psi of hydrogen. Stirring was initiated, and the autoclave was recharged with hydrogen as required to maintain the pressure above 100 psi. When hydrogen consumption stopped the autoclave was flushed with nitrogen and the catalyst was removed by filtration. The filtrate was evaporated in vacuo to give a residue. The residue was dissolved in ethyl acetate (5 L), acidified by the addition of 12M aqueous hydrochloric acid solution (150 mL), and heated to reflux for 15 minutes. The mixture was cooled to 5° C. to give a solid which was collected by filtration, rinsed with ethyl acetate, and air dried to give the title compound.

PREPARATION 4

Synthesis of N,N-bis(2-chloroethyl)-N-benzylamine hydrochloride

Thionyl chloride (25.4 g, 130 mmol) and chloroform (20 mL) are combined. A solution of N,N-bis(2-hydroxyethyl)-N-benzylamine (25.4 g, 130 mmol) in chloroform (20 mL) is added dropwise over 1 hour. When the addition is complete the reaction mixture is refluxed for 1 hour. The reaction mixture is cooled to ambient temperature and diethyl ether was added to form a solid which is collected by filtration, rinsed with diethyl ether, and dried to give the title compound.

EXAMPLE 74

Synthesis of 1-[2-[3-(3,4-dichloro-phenyl)-1-(3,4,5-trimethoxy-benzoyl)-pyrrolidin-3-yl]-ethyl]-4-(4-fluoro-phenyl)-piperidine-4-carboxylic acid amide 74.1 Synthesis of 1-benzyl-4-(4-fluoro-phenyl)-4-cyano-piperidine hydrochloride 4-Fluorophenyl-acetonitrile (5.89 g, 40 mmol), and aqueous sodium hydroxide solution (60 mL, 50% by weight) are combined and then N,N-Bis(2-chloroethyl)-N-benzylamine hydrochloride (11.28 g, 42 mmol) and hexadecyltriethyl phosphonium bromide (1.02 g, 2 mmol) were added. The reaction mixture was heated to 100° C. and stirred vigorously for 1 hour. The reaction mixture is cooled to ambient temperature and water was added. The diluted reaction mixture was acidified with 6M hydrochloric acid solution and extracted with diethyl ether. The aqueous layer is then made basic with solid potassium hydroxide and extracted with ethyl acetate. The organic layer was separated, dried over $MgSO_4$, filtered, and evaporated in vacuo to give a residue. The residue was added to a solution of hydrochloric acid in methanol and the solution was evaporated in vacuo to give a solid. The solid was recrystallized from methanol/ethyl acetate to the title compound: mp=263–264.

Analysis: calculated for $C_{19}H_{19}FN_2 \cdot HCl$ C 68.98; H 6.09; N 8.47; Found C 68.79; H 6.12; N 8.40.

74.2 Synthesis of 1-benzyl-4-(4-fluoro-phenyl)-piperidine-4-carboxylic acid amide N-oxide 1-Benzyl-4-(4-fluoro-phenyl)-4-cyano-piperidine hydrochloride (7.8 g, 26.5 mmol) was combined with aqueous sodium hydroxide (1.2 mL, 50% by weight) and ethanol (130 mL) and the mixture was heated to 50° C. The heating was removed, and a solution of hydrogen peroxide (12.11 mL, 30% by weight in water, 106 mmol) was added at such a rate that the temperature of the reaction mixture does not rise above 50° C. The reaction mixture was then stirred at 50° C. for 4 hours. The reaction mixture was diluted with water (100 mL) and most of the solvent was removed in vacuo before adding water (200 mL) to form a solid which was collected by filtration, rinsed with water, and dried in vacuo to give the title compound.

74.3 Synthesis of 4-(4-fluoro-phenyl)-piperidine-4-carboxylic acid amide hydrochloride 1-Benzyl-4-(4-fluoro-phenyl)-piperidine-4-carboxylic acid amide N-oxide (5.3 g, 16.3 mmol) and 10% palladium-on-carbon (0.6 g) and acetic acid (100 mL) were combined in a pressure vessel. The reaction mixture was treated with hydrogen on a Parr apparatus at an initial pressure of 53 psi of hydrogen. When hydrogen consumption stopped the catalyst was removed by filtration. The filtrate was evaporated in vacuo to give a residue. The residue was dissolved in ethyl acetate (150 mL), acidified by the addition of 12M aqueous hydrochloric acid solution (5 mL), and heated to reflux for 10 minutes. The mixture was cooled to ambient temperature to give a solid which was collected by filtration, rinsed with ethyl acetate, recrystallized from methanol/ethyl acetate to give the title compound.

74.4 Synthesis of 1-[2-[3-(3,4-dichloro-phenyl)-1-(3,4,5-trimethoxy-benzoyl)-pyrrolidin-3-yl]-ethyl]-4-(4-fluoro-phenyl)-piperidine-4-carboxylic acid amide Prepare by the method of example 27.3.1 using 2-[3-(3,4-dichloro-phenyl)-1-(3-methoxy-benzoyl)-pyrrolidin-3-yl]-ethyl-methanesulfonate (1.65 g, 3.1 mmol) and 4-(4-fluoro-phenyl)-piperidine-4-carboxylic acid amide hydrochloride (1.1 g, 4.25 mmol) to give the title compound: $R_f$=0.27 (silica gel, 10% methanol/chloroform).

EXAMPLE 75

Synthesis of 1-[2-[3-(3,4-dichloro-phenyl)-1-(3,4,5-trimethoxy-benzoyl)-pyrrolidin-3-yl]-ethyl]-4-(3-methoxy-phenyl)-piperidine-4-carboxylic acid amide 75.1 Synthesis of 1-benzyl-4-(3-methoxy-phenyl)-4-cyano-piperidine hydrochloride Prepare by the method of example 74.1 using 3-methoxyphenyl-acetonitrile (3.68 g, 25 mmol) and N,N-bis(2-chloroethyl)-N-benzylamine hydrochloride (7.05 g, 26.25 mmol) to the title compound.

75.2 Synthesis of 1-benzyl-4-(3-methoxy-phenyl)-piperidine-4-carboxylic acid amide N-oxide Prepare by the method of example 74.2 using 1-benzyl-4-(3-methoxy-phenyl)-4-cyano-piperidine hydrochloride (2.5 g, 8.16 mmol) to give the title compound.

75.3 Synthesis of 4-(3-methoxy-phenyl)-piperidine-4-carboxylic acid amide hydrochloride Prepare by the method of example 74.3 using 1-benzyl-4-(3-methoxy-phenyl)-piperidine-4-carboxylic acid amide N-oxide (2.5 g, 16. mmol) to give the title compound.

75.4 Synthesis of 1-[2-[3-(3,4-dichloro-phenyl)-1-(3,4,5-trimethoxy-benzoyl)-pyrrolidin-3-yl]-ethyl]-4-(3-methoxy-phenyl)-piperidine-4-carboxylic acid amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (0.75 g, 1.4 mmol) and 4-(3-methoxy-phenyl)-piperidine-4-carboxylic acid amide hydrochloride (0.5 g, 1.85 mmol) to give the title compound: $R_f$=0.43 (silica gel, 10%methanol/chloroform).

EXAMPLE 76

Synthesis of 1-[2-[3-(3,4-dichloro-phenyl)-1-(3,4,5-trimethoxy-benzoyl)-pyrrolidin-3-yl]-ethyl]-4-(4-methyl-phenyl)-piperidine-4-carboxylic acid amide 76.1 Synthesis of 1-benzyl-4-(4-methyl-phenyl)-4-cyano-piperidine 4-Methylphenyl-acetonitrile (1.66 g, 12.6 mmol), sodium iodide (0.25 g), and sodium hydride (50.4 mmol) were combined in dimethylformamide (50 mL) and stirred until gas evolution ceases. A solution of N,N-bis(2-chloroethyl)-N-benzylamine hydrochloride (2.8 g, 12.6 mmol) in dimethylformamide (50 mL) was added dropwise. After 24 hours, the reaction mixture was heated to 70° C. and stirred for 2 days. The solvent was removed by evaporation in vacuo to give a residue and the residue was partitioned between water and dichloromethane. The organic layer was separated, dried over MgSO$_4$, filtered and evaporated in vacuo to give a residue which was chromatographed on silica gel eluting with 2/1 hexane/ethyl acetate to give the title compound.

76.2 Synthesis of 1-benzyl-4-(4-methyl-phenyl)-piperidine-4-carboxylic acid amide N-oxide Prepare by the method of example 74.2 using 1-benzyl-4-(4-methyl-phenyl)-4-cyano-piperidine (5 mmol) to give the title compound.

76.2 Synthesis of 4-(4-methyl-phenyl)-piperidine-4-carboxylic acid amide hydrochloride Prepare by the method of example 74.3 using 1-benzyl-4-(4-methyl-phenyl)-piperidine-4-carboxylic acid amide N-oxide (5 mmol) to give the title compound.

76.4 Synthesis of 1-[2-[3-(3,4-dichloro-phenyl)-1-(3,4,5-trimethoxy-benzoyl)-pyrrolidin-3-yl]-ethyl]-4-(4-methyl-phenyl)-piperidine-4-carboxylic acid amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (0.75 g, 1.4 mmol) and 4-(methyl-phenyl)-piperidine-4-carboxylic acid amide hydrochloride (1.85 mmol) to give the title compound.

EXAMPLE 77

Synthesis of 1-[2-[3-(3,4-dichloro-phenyl)-1-(3,4,5-trimethoxy-benzoyl)-pyrrolidin-3-yl]-ethyl]-4-(4-chloro-phenyl)-piperidine-4-carboxylic acid amide 77.1 Synthesis of 1-benzyl-4-(4-chloro-phenyl)-4-cyano-piperidine Prepare by the method of example 76.1 using 4-chlorophenyl-acetonitrile (1.0 g, 6.6 mmol) and N,N-bis(2-chloroethyl)-N-benzylamine hydrochloride (1.5 g, 6.6 mmol) to give the title compound.

77.2 Synthesis of 1-benzyl-4-(4-chloro-phenyl)-piperidine-4-carboxylic acid amide N-oxide Prepare by the method of example 74.2 using 1-benzyl-4-(4-chloro-phenyl)-4-cyano-piperidine (5 mmol) to give the title compound.

77.3 Synthesis of 4-(4-chloro-phenyl)-piperidine-4-carboxylic acid amide hydrochloride A mixture of 1/9 by volume of formic acid/methanol (50 mL) was carefully added to platinum black (2.2 g). A solution of 1-benzyl-4-(4-chloro-phenyl)-piperidine-4-carboxylic acid amide N-oxide (2.6 g) in methanol (10 mL) was added. After 18 hours, the reaction mixture was filtered through a bed of celite and the filtrate was evaporated in vacuo to give a residue. The residue was dissolved in ethyl acetate (10 mL) and a 1M solution of hydrochloric acid in methanol (4 mL) added. The reaction mixture was evaporated in vacuo to give a residue which was dissolved in methanol and treated with diethyl ether to give a solid. The solid was collected by filtration and dried to give the title compound.

77.4 Synthesis of 1-[2-[3-(3,4-dichloro-phenyl)-1-(3,4,5-trimethoxy-benzoyl)-pyrrolidin-3-yl]-ethyl]-4-(4-chloro-phenyl)-piperidine-4-carboxylic acid amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (0.75 g, 1.4 mmol) and 4-(chloro-phenyl)-piperidine-4-carboxylic acid amide hydrochloride (1.85 mmol) to give the title compound.

EXAMPLE 78

Synthesis of 1-[2-[3-(3,4-dichloro-phenyl)-1-(3,4,5-trimethoxy-benzoyl)-pyrrolidin-3-yl]-ethyl]-4-(4-trifluoromethyl-phenyl)-piperidine-4-carboxylic acid amide 78.1 Synthesis of 1-benzyl-4-(4-trifluoromethyl-phenyl)-4-cyano-piperidine Prepare by the method of example 76.1 using 4-trifluoromethylphenyl-acetonitrile (1.5 g, 8.1 mmol) and N,N-bis(2-chloroethyl)-N-benzylamine hydrochloride (1.9 g, 8.1 mmol) to give the title compound.

78.2 Synthesis of 1-benzyl-4-(4-trifluoromethyl-phenyl)-piperidine-4-carboxylic acid amide N-oxide Prepare by the method of example 74.2 using 1-benzyl-4-(4-trifluoromethyl-phenyl)-4-cyano-piperidine (5 mmol) to give the title compound.

78.3 Synthesis of 4-(4-trifluoromethyl-phenyl)-piperidine-4-carboxylic acid amide hydrochloride Prepare by the method of example 77.3 using 1-benzyl-4-(4-trifluoromethyl-phenyl)-piperidine-4-carboxylic acid amide N-oxide (4 mmol) to give the title compound.

78.4 Synthesis of 1-[2-[3-(3,4-dichloro-phenyl)-1-(3,4,5-trimethoxy-benzoyl)-pyrrolidin-3-yl]-ethyl]-4-(4-trifluoromethyl-phenyl)-piperidine-4-carboxylic acid amide Prepare by the method of example 27.3.1 using 2-[3-(3,4-dichloro-phenyl)-1-(3,4,5-trimethoxy-benzoyl)-pyrrolidin-3-yl]-ethyl-methanesulfonate (0.75 g, 1.4 mmol) and 4-(trifluoromethyl-phenyl)-piperidine-4-carboxylic acid amide hydrochloride (1.85 mmol) to give the title compound.

EXAMPLE 79

Synthesis of 1-[2-[3-(3,4-dichloro-phenyl)-1-(3,5-dimethoxy-4-difluoromethoxy-benzoyl)-pyrrolidin-3-yl]-ethyl]-4-phenyl-piperidine-4-carboxylic acid amide 79.1 Synthesis of methyl 3,5-dimethoxy-4-difluoromethoxy-benzoate Sodium hydride (0.144 g, 6 mmol) was added portionwise to a solution of methyl 3,5-dimethoxy-4-hydroxy-benzoate (0.21 g, 1 mmol) in tetrahydrofuran (20 mL) cooled to 0° C. After 2 hours, chlorodifluoromethane (gas) was introduced by sparge for 10 minutes every 2 hours (5 times). After 18 hours, an additional portion of sodium hydride (0.048 g, 2 mmol) was added followed by chlorodifluoromethane (gas) sparge for 10 minutes. The reaction mixture was sealed and stirred for 3 weeks. The reaction mixture was cooled to −78° C. and methanol (5 mL) was added. The reaction mixture was partitioned between ethyl acetate and water. The organic layer was separated, dried over MgSO$_4$, filtered, and evaporated in vacuo to give the title compound.

79.2 Synthesis of 3,5-dimethoxy-4-difluoromethoxy-benzoic acid

Methyl 3,5-dimethoxy-4-difluoromethoxy-benzoate (92.8 mg, 0.35 mmol) was combined with 1M sodium hydroxide solution (20 mL) and methanol (10 mL). After 4 hours, the reaction was acidified with 1M hydrochloric acid solution and extracted with ethyl acetate. The organic layer was dried over MgSO$_4$, filtered, and evaporated in vacuo to give the title compound: R$_f$=0.48 (silica gel, 10% methanol/dichloromethane).

79.3 Synthesis of 1-[2-[3-(3,4-dichloro-phenyl)-1-(3,5-dimethoxy-4-difluoromethoxy-benzoyl)-pyrrolidin-3-yl]-ethyl]-4-phenyl-piperidine-4-carboxylic acid amide Prepare by the method of example 70.5 using 3,5-dimethoxy-4-difluoromethoxy-benzoic acid (85 mg, 0.34 mmol) and 1-[3-(3,4-dichloro-phenyl)-pyrrolidin-3-yl]-ethyl]-4-phenyl-piperidine-4-carboxylic acid amide hydrochloride (241 mg, 0.5 mmol). Purify be chromatography on silica gel eluting sequentially with 50% ethyl acetate/hexane and then 6% methanol/dichloromethane to give the title compound: R$_f$=0.48 (silica gel, 10% methanol/dichloromethane).

EXAMPLE 80

Synthesis of 1-[2-[3-(3,4-dichloro-phenyl)-1-(3,5-dimethoxy-4-hydroxy-benzoyl)-pyrrolidin-3-yl]-ethyl]-4-phenyl-piperidine-4-carboxylic acid amide 80.1 Synthesis of 1-[2-[3-(3,4-dichloro-phenyl)-1-(3,5-dimethoxy-4-hydroxy-benzoyl)-pyrrolidin-3-yl]-ethyl]-4-phenyl-piperidine-4-carboxylic acid amide Prepare by the method of example 70.5 using 3,5-dimethoxy-4-hydroxy-benzoic acid (99 mg, 0.5 mmol) and 1-[3-(3,4-dichloro-phenyl)-pyrrolidin-3-yl]-ethyl]-4-phenyl-piperidine-4-carboxylic acid amide hydrochloride (241 mg, 0.5 mmol). Purify be chromatography on silica gel eluting sequentially with 50% ethyl acetate/hexane and then 6% methanol/dichloromethane to give the title compound: R$_f$=0.38 (silica gel, 10% methanol/dichloromethane).

EXAMPLE 81

Synthesis of 1-[2-[3-(3,4-dichloro-phenyl)-1-(3,5-dimethoxy-4-(2-diethylamino-ethyl)-benzoyl)-pyrrolidin-3-yl]-ethyl]-4-phenyl-piperidine-4-carboxylic acid amide 81.1 Synthesis of 1-[2-[3-(3,4-dichloro-phenyl)-1-(3,5-dimethoxy-4-(2-diethylamino-ethyl)-benzoyl)-pyrrolidin-3-yl]-ethyl]-4-phenyl-piperidine-4-carboxylic acid amide Combine 1-[2-[3-(3,4-dichloro-phenyl)-1-(3,5-dimethoxy-4-hydroxy-benzoyl)-pyrrolidin-3-yl]-ethyl]-4-phenyl-piperidine-4-carboxylic acid amide (1 mmol) and sodium hydride (2 mmol) in tetrahydrofuran (10 mL). Add diethylaminoethylchloride hydrochloride (1 mmol). After 24 hours, partition the the reaction mixture between water and ethyl acetate. Separate the organic layer, dry over MgSO$_4$, filter, and evaporate in vacuo to give the title compound.

EXAMPLE 82

Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide N-oxide 82.1 Synthesis of 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide N-oxide Combine 1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide (1.0 mmol) and dichloromethane (10 mL). Cool to 0° C. Add portionwise, m-chloroperbenzoic acid (1.0 mmol). After the addition is complete, warm to ambient temperature. After 18 hours, extract the reaction mixture with water. Separate the organic layer, dry over MgSO$_4$, filter, and evaporate in vacuo to give a residue. Purify the residue by chromatography to give the title compound.

The compounds of the present invention are useful in their pharmacological activities such as tachykinin antagonism, especially substance P and neurokinin A antagonism, and the like. One object of the present invention is to provide new and useful antagonists of tachykinins, especially substance P and neurokinin A. A particular object of the present invention are those compounds that exhibit both NK$_1$ and NK$_2$ receptor antagonism. For some compounds, significant antagonism of NK$_3$ receptors may additionally be useful.

The compounds of the present invention are believed to exert their therapeutic effect through antagonism of NK$_1$ and NK$_2$ receptors and thereby provide relief for diseases and conditions associated with inflammation, pain, and the central nervous system. However, it is understood that the present invention is not limited by any particular theory or proposed mechanism to explain its effectiveness in an end-use application.

A further object of the present invention is to provide compounds, stereoisomers, or pharmaceutically acceptable salts thereof, for the treatment and prevention of various diseases in a patient in need thereof. Because the compounds of the present invention are tachykinin antagonists, they are potentially useful in the treatment of conditions associated with inflammation, including asthma, allergies, bronchitis, rhinitis, Crohn's disease, ulcerative colitis, rheumatoid arthritis, osteoarthritis, migraine, cystitis and hypersensitivity reactions. Tachykinin antagonism may also be appropriate therapy for the treatment of cough, emesis, pain, peripheral neuropathy, post-herpetic neuralgia, adverse immunological reactions, blood flow disorders due to vasodilation, ophthalmic diseases, such as conjuctivitis and cutaneous diseases such as contact dermatitis, atopic dermatitis, urticaria and the like. Various central nervous system disorders including anxiety, depression, psychosis, schizophrenia and dementia may also be amenable to treatment with tachykinin antagonists.

The compounds of formula (1) are believed to exert their inhibitory effect through antagonism of NK$_1$ and NK$_2$ receptors and thereby provide relief for neurogenic inflammatory diseases including but not limited to asthma and other inflammatory conditions of the lung. Additionally, compounds of the present invention are also believed to be useful for conditions associated with rhinitis, cough, and pain.

Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (1).

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling diseases and conditions associated with inflammation, pain, and the central nervous system. The term "controlling" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with inflammation, pain, and the central nervous system.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with the diseases and conditions described above, a compound of formula (1) can be administered in any form or mode which makes the compound bioavailable in a therapeutically effective amount, including oral, inhalation, and parenteral routes. For example, compounds of formula (1) can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the the compounds of the present invention or a formulation thereof. Formulations for administration by inhalation of compounds of formula (1) may be delivered in single phase, bi-phasic, or tri-phasic systems. A variety of systems are available for the administration by aerosols of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosols and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE 14

ANTAGONISM OF IODINATED TACHYKININ BINDING TO $NK_1$ AND $NK_2$ RECEPTORS BY PUTATIVE ANTAGONISTS

The $NK_1$ receptor affinity of proposed tachykinin antagonists was evaluated in guinea pig lungs (Keystone Biologicals, Cleveland, Ohio), affinity for the $NK_2$ receptor evaluated in HSKR-1 cells (which are mouse 3T3 fibroblasts expressing the human jejunal $NK_2$ receptor) and NK-3 receptor affinity was evaluated in freshly collected guinea pig cerebral cortex. Tissues or cells were homogenized with a Polytron in 15 volumes of 50 mM Tris-HCl buffer (pH 7.4, 4° C.) and centrifuged. The pellet was resuspended in Tris-HCl buffer and was centrifuged; the pellet was washed twice by resuspension. The final pellet was resuspended at a concentration of 40 mg/ml for tissues (guinea pig lung and cerebral cortex) and 20 mg/ml for cells in incubation buffer and remained at room temperature for at least 15 min prior to use. Receptor binding was initiated by addition of 250 ul membrane preparation in duplicate to 0.1 nM of the following radioligands: $^{125}$I-Bolton Hunter Lys-3 labeled substance P; $^{125}$iodohistidyl-1-neurokinin A; and $^{125}$I-Bolton Hunter labeled Lys-4 eledoisin in a final volume of 500 ul of buffer containing 50 mM Tris-HCl (pH 7.4 at room temperature), 0.1% bovine serum albumin, 2 mM $MnCl_2$, 40 ug/ml bacitracin, 4 pg/ml leupeptin and chymostatin, 1 μM thiorphan and various doses of the putative tachykinin antagonists. Incubations were performed at room temperature for 90 min ($NK_1$ receptor assays) or 2 hr ($NK_2$ and $NK_3$ receptor assays); binding was terminated by addition of 50 mM Tris-HCl buffer (pH 7.4, 4° C.) and filtration under vacuum through GF/B filters presoaked with 0.1% polyethyleneimine ($NK_1$ receptor assays) or 0.5% bovine serum albumin ($NK_2$ and $NK_3$ receptor assays). Filter bound radioactivity was quantitated in a gamma counter. Nonspecific binding was defined as binding in the presence of 1 μM substance P, neurokinin A, or eledoisin. Specific binding was calculated by subtracting nonspecific binding from total binding. Competition of iodinated SP, NKA, or eledoisin binding by test compounds or standards was expressed as a percentage of this maximum competition. $IC_{50}$ values (concentration required to inhibit 50% of receptor binding) were generated for each of the test compounds by nonlinear regression using an iterative curve fitting program (GraphPAD Inplot, San Diego, Calif.).

$IC_{50}$ values for the compounds in question are found in Table 2 and represent the mean of several experiments. Several of the compounds presented, e.g. Example 3 exhibits high affinity for both $NK_1$, and $NK_2$ receptors as well as for $NK_3$ receptors.

TABLE 2

| EXAMPLE | STRUCTURE | NK-2 $IC_{50}$(nM) | NK-1 $IC_{50}$(nM) | NK-3 $IC_{50}$(nM) |
|---|---|---|---|---|
| 2 | [structure] | 34 | 131 | 65 |

TABLE 2-continued

| EXAMPLE | STRUCTURE | NK-2 IC$_{50}$(nM) | NK-1 IC$_{50}$(nM) | NK-3 IC$_{50}$(nM) |
|---|---|---|---|---|
| 13 | 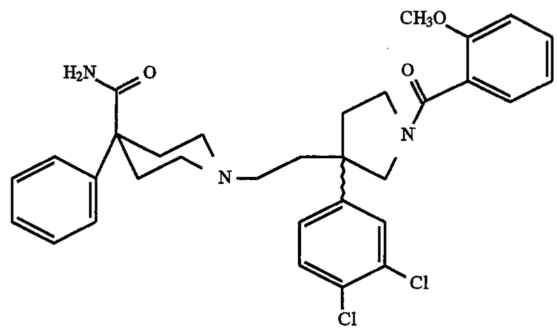 | 14 | 74 | |
| 4 | 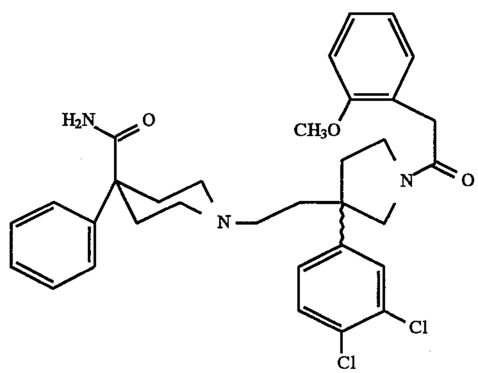 | 74 | 48 | 41 |
| 5 | 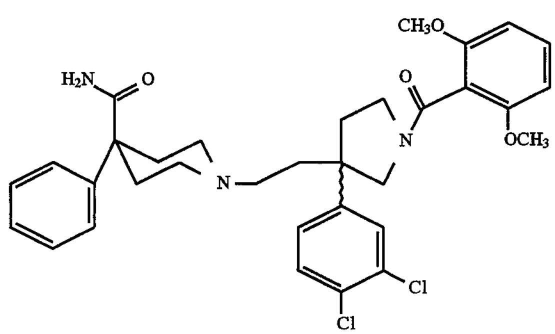 | 41 | 20 | 65 |
| 3 | 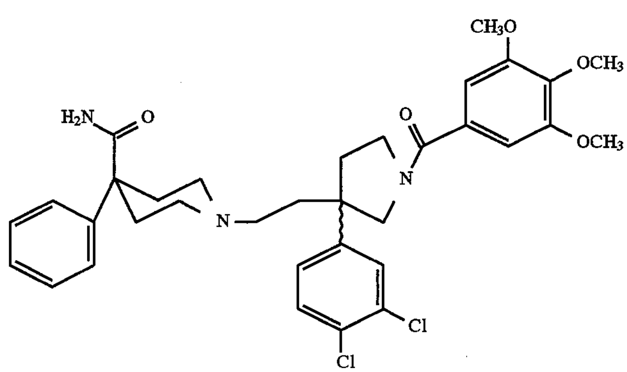 | 15 | 5 | — |

TABLE 2-continued
| EXAMPLE | STRUCTURE | NK-2 IC$_{50}$(nM) | NK-1 IC$_{50}$(nM) | NK-3 IC$_{50}$(nM) |
|---|---|---|---|---|
| 1 | 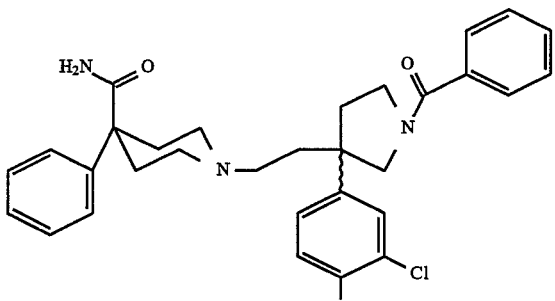 | 7 | 270 | 162 |
| 10 | 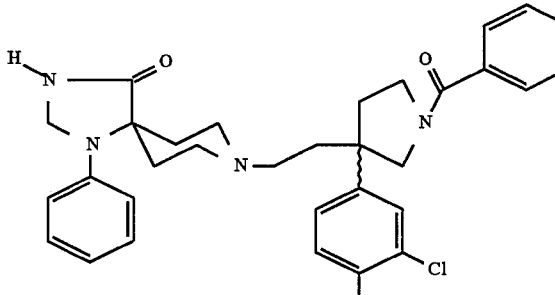 | 11 | 255 | 1191 |
| 11 | 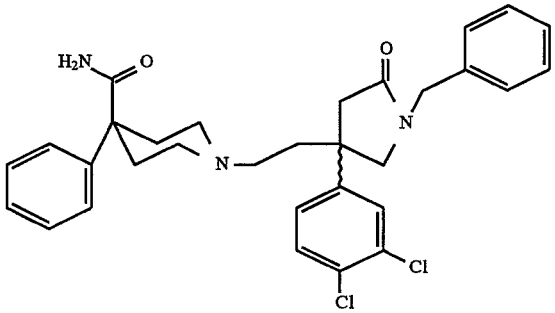 | 127 | 196 | 203 |
| 9 | 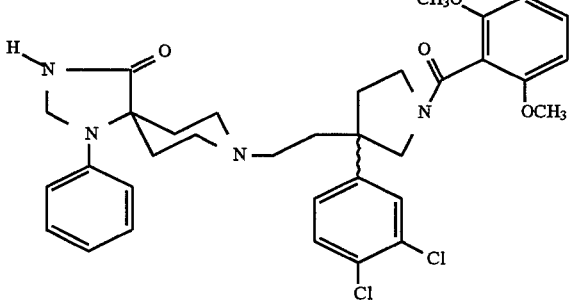 | 118 | 49 | 183 |

TABLE 2-continued
| EXAMPLE | STRUCTURE | NK-2 IC$_{50}$(nM) | NK-1 IC$_{50}$(nM) | NK-3 IC$_{50}$(nM) |
|---|---|---|---|---|
| 6 | 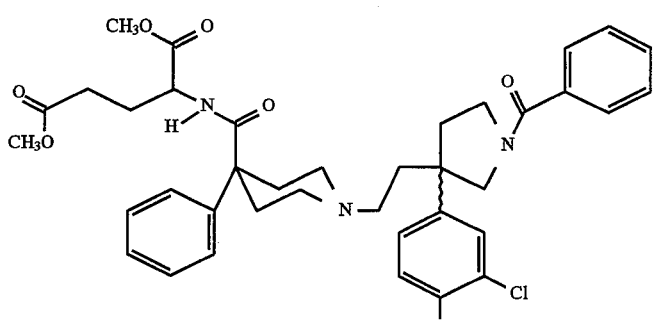 | 15 | 182 | — |
| 7 | 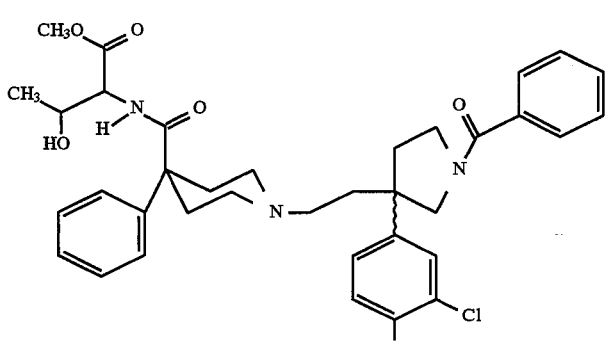 | 10 | 240 | 202 |
| 12 | 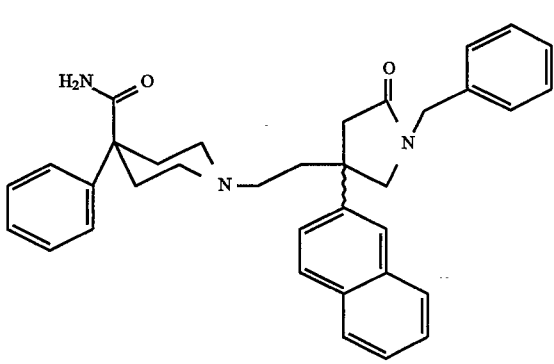 | 179 | 810 | — |
| 8 | 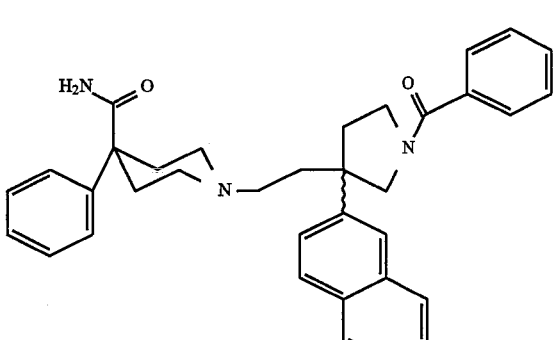 | 94 | 1480 | — |

TABLE 2-continued
| EXAMPLE | STRUCTURE | NK-2 IC₅₀(nM) | NK-1 IC₅₀(nM) | NK-3 IC₅₀(nM) |
|---|---|---|---|---|
| 23 | 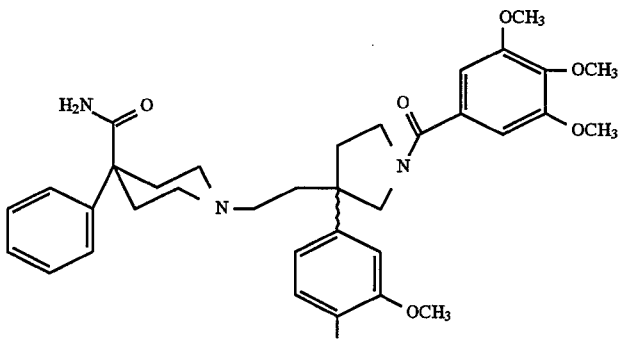 | 2683 | 20.0 | — |
| 21 | 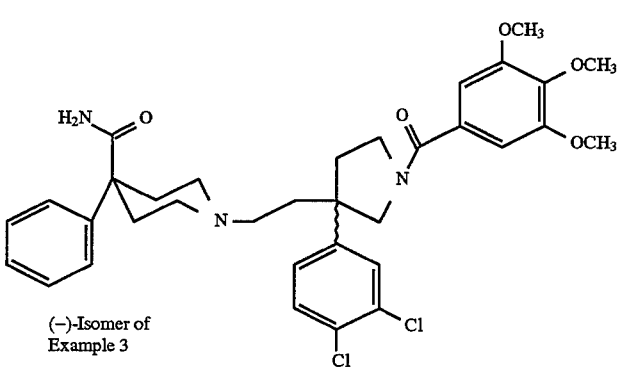<br>(−)-Isomer of Example 3 | 760 | 183 | 2304 |
| 22A | 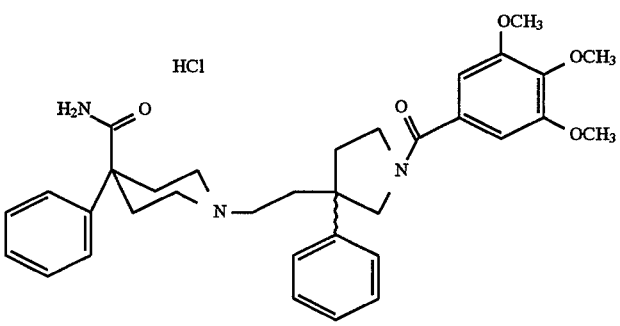 | 1187 | 17.4 | — |
| 20 | 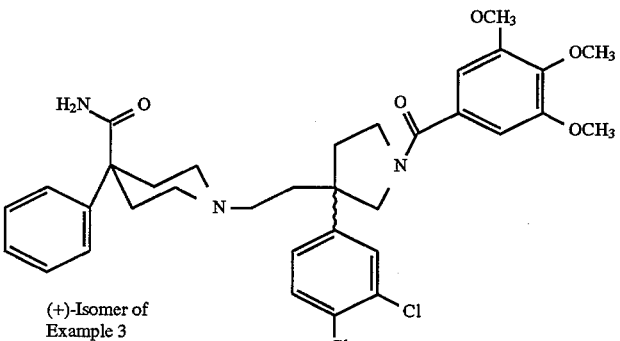<br>(+)-Isomer of Example 3 | 8.40 | 4.65 | 21 |

TABLE 2-continued

| EXAMPLE | STRUCTURE | NK-2 IC$_{50}$(nM) | NK-1 IC$_{50}$(nM) | NK-3 IC$_{50}$(nM) |
|---|---|---|---|---|
| 20A | 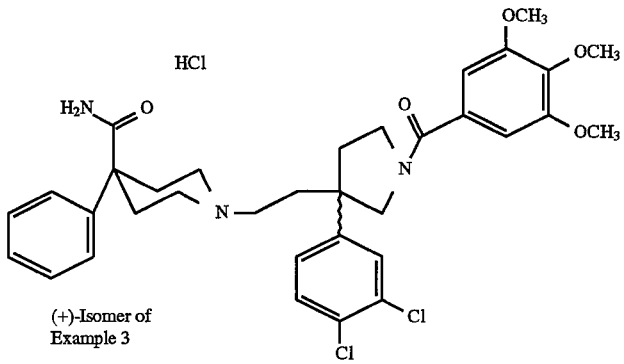 (+)-Isomer of Example 3 | 7.93 | 2.99 | — |
| 3A | 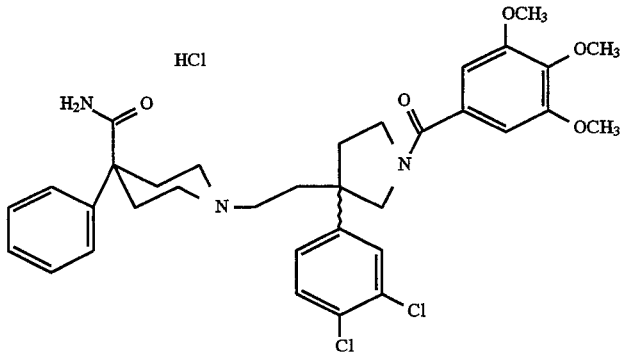 | 21 | 5.97 | 54.2 |
| 5A | 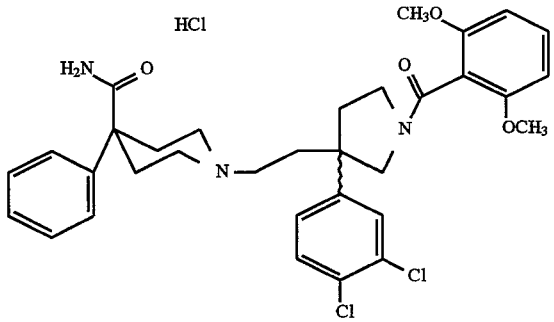 | 40 | 20 | — |

EXAMPLE 15

ANTAGONISM OF NK$_1$ AND NK$_2$ RECEPTOR MEDIATED PHOSPHATIDYLINOSITOL TURNOVER

Tachykinin-mediated inositol phosphate accumulation was measured in UC11 or SKLKB82#3 cells in the presence and absence of NK$_1$ or NK$_2$ receptor antagonists, respectively. Tissues were incubated in Krebs-Henseleit buffer at 37° C. with 95% O$_2$-5% CO$_2$ gassing. Tissues were then incubated with fresh buffer containing 100 µCi of myo-[2-$^3$H(N)] inositol at 37° C. for 60 min with gentle gassing. After washing twice in 5 ml room temperature buffer containing 10 mM LiCl, tissues were incubated for 30 min at room temperature with a buffer change at 15 min. Buffer was removed and Krebs-Henseleit buffer (containing 40 µg/ml bacitracin, 4 µg/ml each of leupeptin and chymostatin, 0.1% bovine serum albumin and 10 mM each of thiorphan and LiCl) added. After 15 min, SP was added to UC11 cells or NKA to SKLKB82#3 cells at various concentrations to start the reaction. After incubation for 60 min at room temperature the reaction was terminated by addition of 930 µl chloroform: methanol (1:2 by volume) to each tube, followed by 310 µl chloroform and 310 µl doubly distilled water. Samples were vortexed, centrifuged, and 0.9 ml of the aqueous (top) phase removed and added to 2 ml ddH$_2$O. The mixture was vortexed and loaded onto a 50% Bio-Rad AG 1-X8 (formate form, 100–200 mesh) exchange column (Bio-Rad Laboratories, Hercules, Calif.). The columns were washed, in order, with: 1) 10 ml doubly distilled water, 2) 5 ml of 5 mM disodium tetraborate/60 mM sodium formate, and 3) 5 ml of 1M ammonium formate/0.1M formic acid. The third elution was collected and 1 ml counted in 7 ml scintillation fluid. A 50 µl aliquot of the organic (bottom) phase was removed, dried in a scintillation vial and counted in 7 ml scintillation fluid.

The ratio of DPM in the aqueous phase aliquot (total inositol phosphates) to the DPM in the 50 µl organic phase aliquot (total [$^3$H]inositol incorporated) was calculated for each sample. Data are expressed as a percent of agonist-induced accumulation of [$^3$H]-inositol phosphates over basal levels. The ratios in the presence of test compound and/or standards were compared to the ratios for control samples (i.e. no stimulating agonist). Dose-response graphs were constructed and the abilities of the test compounds to inhibit tachykinin-induced phosphatidyinositol turnover determined with the aid of a computer program. FIG. 1 illustrates the ability of Example 3 to produce dose related antagonism of the receptor mediated SP or NKA induced PI turnover in UC11 (FIG. 1a) or SKLKB82#3 cells (FIG. 1b), respectively. Data is expressed as percent stimulation of total inositol phosphate accumulation over basal levels and normalized to the maximum response produced by SP. These data suggest Example 3 has no agonist activity and antagonizes both $NK_1$ (on UC11 cells) and $NK_2$ (on SKLKB82#3) receptors in a dose-dependent manner. Schild analysis is performed using dose response curves (such as those presented in FIGS. 1a and 1b) to obtain a value indicative of the strength of a competitive antagonist and is expressed as the $pA_2$, which is the negative logarithm of the molar concentration of antagonist which reduces the effect of a dose of agonist to one-half of that expected at the dose of agonist. Table 3 contains data demonstrating the ability of the componds of Example 3A; Example 5A; and Example 20 to functionally antagonize the effects of SP or NKA in vitro. These compounds antagonized both $NK_1$ and $NK_2$ receptors by nearly equivalent amounts. It is further important to note that none of the compounds alone stimulated PI turnover suggesting an absence of agonist activity.

TABLE 3

Apparent Affinities of Compounds for Tachykinin Receptors

| COMPOUND | NK-1 RECEPTOR | | NK-2 RECEPTOR | |
|---|---|---|---|---|
| | pA$_2$ | −SLOPE | pA$_2$ | −SLOPE |
| EXAMPLE 3A | 7.91 | 0.90 | 8.75 | 0.73 |
| | (7.71–8.23) | (0.65–1.15) | (7.78–9.72) | (0.49–0.97) |
| EXAMPLE 5A | 7.32 | 1.17 | 7.35 | 1.11 |
| | (4.84–9.80) | (0.41–1.93) | (6.93–7.77) | (0.99–1.23) |
| EXAMPLE 20 | 8.19 | 1.03 | 8.67 | 1.00 |
| | (7.37–9.00) | (0.78–1.28) | (8.20–9.14) | (0.63–1.37) |

Values are mean (95% confidence limits) derived from Schild analysis of 2–3 experiments per compound per receptor.

EXAMPLE 16

ANTAGONISM OF SP-INDUCED PLASMA PROTEIN EXTRAVASATION IN GUINEA PIG TRACHEA

SP-induced protein leakage through postcapillary venules was assessed by measuring Evans Blue dye accumulation in guinea pig trachea. Animals were anesthetized with pentobarbital then injected with Evans Blue dye (20 mg/kg, i.v., prepared in 0.9% NaCl solution). One minute after dye administration, the antagonist was administered (i.v.) followed by SP (0.3 nmole/kg, i.v.) and, after 5 min, excess dye removed from the circulation by transcardiac perfusion with 50 ml 0.9% NaCl solution. The trachea and primary bronchi were removed, blotted dry and weighed. Dye quantitation was performed spectrophotometrically (620 nM) after extracting tissues in formamide for 24 hr at 50° C. Values were subtracted from background (dye only, no agonist). $ED_{50}$ (dose of compound which inhibits SP-induced plasma protein extravasation by 50%) was calculated from linear regression analysis.

FIG. 2 illustrates the ability of Example 3 to produce a dose related antagonism of SP-induced plasma protein extravasation in guinea pig trachea. These data suggest that Example 3 acts as an antagonist of $NK_1$ receptors in vivo.

Table 4, "Antagonism of SP-Induced Plasma Protein Extravasation in Guinea Pig Airways", contains data for the compound of Example 3 and its (+)-enantiomer the compound of Example 20A. These compounds are equipotent NK-1 receptor antagonists in this system.

TABLE 4

Antagonism of SP-induced Plasma Protein Extravasation in Guinea Pig Trachea

| COMPOUND | ED$_{50}$ (mg/kg) |
|---|---|
| Example 3A | 0.17(0.004–0.274) |
| Example 20A | 0.20(0.004–0.31) |

Values are mean (95% confidence limits). Compounds were injected intravenously 2 min prior to SP administration.
ED$_{50}$ values are based on at least 3 doses; at least 4 animals were used per dose.

EXAMPLE 17

ANTAGONISM OF NKA AND CAPSAICIN INDUCED RESPIRATORY EFFECTS IN CONSCIOUS GUINEA PIGS

In vivo experiments were performed using male Duncan Hartley guinea pigs (250–350 g). Changes in conscious breathing patterns were monitored in four animals simultaneously using modified whole body plethysmography consisting of four small plexiglass boxes each connected to a reference box via Validyne DP 45-16 differential pressure transducers. The 4 boxes were equipped with an air supply line (also used for aerosol delivery) and an exhaust air line. Supply and exhaust lines were of the same length and narrow bore and arose from a common supply chamber and vented to a common exhaust chamber. This system was used to ensure that fluctuations in supply air and atmospheric pressure would remain in phase and be eliminated from the net signal by the differential pressure transducers. The analog pressure signals were digitalized via a Data Translation DT2821 A to D board. Data were collected at a rate of 100 samples/second/animal. Each cycle of pressure change was analyzed using the following parameters: rising and falling slope determined between minimum and maximum pressures, the ratio of rising over falling slope, and the magnitude of the change between initial trough pressure and peak cycle pressure. Using these values (and observing the animals) the pressure cycles were characterized into normal breaths, forced exhalations (apparent by abdominal heaving), significant respiratory events (SREs; usually coughs, less often sneezes or gasps which were characterized by transient, extremely large pressure increases which were distinguishable from noise) and movement/noise with a PCAT 286 running a System V UNIX operating system. Dyspnea was defined as a significant, sustained increase in plethysmograph pressure which was associated with an observable shift to labored breathing in the animal.

During the course of a typical experiment in which airway responsiveness to various bronchoconstricting agents was examined, aerosols were delivered for 19 min (0.33 ml/min) using a DeVilbiss Ultraneb 99 ultrasonic nebulizer and animals monitored during this time. Prior to nebulization, 1 min of resting breathing was collected to establish a baseline pressure. In preliminary experiments, various concentrations of the bronchoconstrictive agents were evaluated and the concentration chosen which maximized the number of animals exhibiting dyspnea but minimized the severity of the response. Hence, neurokinin A was delivered at a final concentration of 0.05%, and capsaicin, 0.001%. The vehicle for nebulization of all bronchoconstrictive agents was phosphate buffered saline (pH 7.4) which elicited no respiratory effects itself. Putative tachykinin antagonists were administered either (i.v.) 20 min prior to onset of aerosol exposure or orally 1 hour prior to onset (to guinea pigs after an overnight fast).

"Antagonism of NKA-Induced Respiratory Effects in Conscious Guinea Pigs"

Table 6 illustrates the effects of the compounds of Example 3; Example 20A; and Example 5A on respiratory effects induced by NKA aerosol. All compounds reduced the effects of NKA aerosol as suggested by a decrease in the number of animals exhibiting dyspnea in response to the tachykinin or an increase in the period of time (or amount of aerosol) required to elicit the dyspnea response. These effects were dose dependent i.e. the higher the dose of compound, the greater attenuation of NKA-mediated effects. These data indicate that these compounds are capable of producing $NK_2$ receptor antagonism in guinea pigs in vivo.

TABLE 6

Modulation of Respiratory Effects Produced by NKA Aerosol in Conscious Guinea Pigs

| TREATMENT | DYSPNEA INCIDENCE | DYSPNEA ONSET (sec) |
|---|---|---|
| VEHICLE Example 3 | 100% (37/37) | 397 ± 29.5 |
| 5 mg/kg | 86% (6/7) | 394 ± 32 |
| 10 mg/kg | 60% (6/10) | 801 ± 104 |
| Example 20A | | |
| 1 mg/kg | 100% (10/10) | 451 ± 30 |
| 5 mg/kg | 90% (9/10) | 706 ± 82 |
| 10 mg/kg | 70% (7/10) | 829 ± 105 |
| Example 5A | | |
| 5 mg/kg | 60% (3/5) | 654 ± 37 |
| 10 mg/kg | 54% (7/13) | 608 ± 65 |

Compounds were administered 20 min prior to initiation of NKA aerosol (0.05%). Values for each treatment represent the mean and SEM of data from 5–37 animals per dose.

Capsaicin aerosol is known to promote release of the tachykinins SP and NKA from sensory nerves in the airways of guinea pigs which may then act upon $NK_1$ and $NK_2$ receptors, respectively to elicit respiratory effects. The ability of the compounds of Example 3A; and Example 20A to attenuate capsaicin-induced respiratory effects, shown in Table 7a, is inferred from their ability to reduce incidence of dyspnea, prolong the onset of the response and reduce the number of coughs/gasps which occur during aerosol exposure. The compound of Example 3A as well as the compound of Example 5 also antagonize the effects of capsaicin aerosol when administered orally as shown in Table 7b. These data suggest that the compounds of Example 3A; Example 20A; and Example 5 inhibit the endogenous tachykinins released by capsaicin aerosol which produce respiratory alterations in conscious guinea pigs in vivo.

TABLE 7a

Modulation of Respiratory Effects Produced by Capsaicin Aerosol in Conscious Guinea Pigs: Intravenous Administration of Putative Tachykinin Antagonists

| TREATMENT | DYSPNEA INCIDENCE | DYSPNEA ONSET (sec) | MAXIMUM PRESSURE INCREASE (mmH$_2$O) | SRE NUMBER* |
|---|---|---|---|---|
| Vehicle Example 3A | 100% (60/60) | 286 ± 14.3 | 1.09 ± 0.05 | 10.4 ± 0.88 |
| 10 mg/kg Example 20A | 89% (7/8) | 480 ± 80 | 0.83 ± 0.18 | 8.50 ± 1.9 |
| 1 mg/kg | 77.8% (7/9) | 331 ± 22 | 1.0 ± 0.1 | 9.9 ± 2.7 |
| 2.5 mg/kg | 100% (10/10) | 426 ± 57 | 0.6 ± 0.1 | 8.3 ± 1.6 |
| 5 mg/kg | 44.4% (4/9) | 597 ± 186 | 0.8 ± 0.06 | 4.4 ± 1.9 |
| 10 mg/kg | 55.6% (5/9) | 592 ± 71 | 0.8 ± 0.1 | 3.3 ± 1.1 |

Values are mean and SEM of data derived from number of animals indicated in parenthesis. Putative tachykinin antagonists were administered intravenously 20 min prior to initiation of capsaicin aerosol (0.001%). *SRE number indicates the number of coughs/gasps which occurred during the 19 min capsaicin exposure period.

TABLE 7b

Modulation of Respiratory Effects Produced by Capsaicin Aerosol in Conscious Guinea Pigs: Oral Administration of Putative Tachykinin Antagonists

| TREATMENT | DYSPNEA INCIDENCE | DYSPNEA ONSET (sec) | MAXIMUM PRESSURE INCREASE (mmH$_2$O) | SRE NUMBER* |
|---|---|---|---|---|
| Vehicle Example 3A | 100% (28/28) | 335 ± 32 | 0.8 ± 0.0 | 7.9 ± 1.1 |
| 25 mg/kg | 80% (8/10) | 424 ± 120 | 0.7 ± 0.2 | 4.6 ± 1.0 |
| 50 mg/kg | 70% (7/10) | 434 ± 152 | 0.4 ± 0.1 | 2.8 ± 0.8 |
| 100 mg/kg Example 5 | 50% (5/10) | 360 ± 120 | 0.4 ± 0.1 | 2.1 ± 0.5 |
| 25 mg/kg | 66.7% (6/9) | 253 ± 47 | 0.7 ± 0.1 | 4.4 ± 1.2 |
| 50 mg/kg | 85.7% (6/7) | 384 ± 85 | 0.5 ± 0.1 | 4.9 ± 1.9 |

Values are mean and SEM of data derived from number of animals indicated in parenthesis. Putative tachykinin antagonists were administered by oral gavage 1 hr prior to initiation of capsaicin aerosol (0.001%). *SRE number indicates the number of coughs/gasps which occurred during the 19 min capsaicin exposure period.

What is claimed is:

1. A method for treating asthma in a patient in need thereof comprising administering to said patient a therapeutically effective amount of a compound of the formula

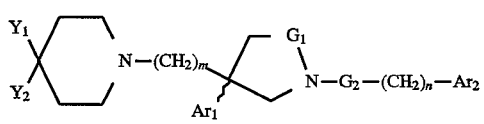

wherein $G_1$ is —$CH_2$— or —$C(O)$—;

$G_2$ is —$CH_2$— or —$C(O)$—;

m is 2 or 3;

n is 0 or 1;

143

Ar₁ is a radical chosen from the group:

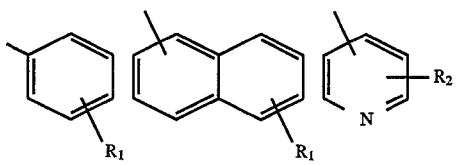

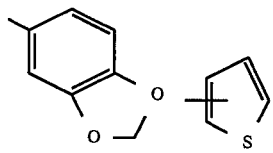

wherein

R₁ is from 1 to 3 substituents each independently chosen from the group consisting of hydrogen, halogen, hydroxy, CF₃, C₁–C₆ alkyl, and C₁–C₆ alkoxy;

R₂ is from 1 to 2 substituents each independently chosen from the group consisting of hydrogen, halogen, C₁–C₆ alkyl, and C₁–C₆ alkoxy;

Ar₂ is a radical chosen from the group

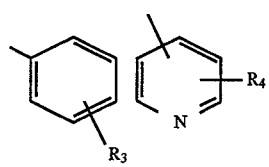

wherein

R₃ is from 1 to 3 substituents each independently chosen from the group consisting of hydrogen, halogen, C₁–C₆ alkoxy, hydroxy, —O—C(O)O—CH₂—CH₃, —OC(O)CH₃, —CF₂H, —(CH₂)$_q$NR₆R₇, and —(CH₂)$_q$NR₈R₉ wherein q is 2 or 3, R₆ is C₁–C₆ alkyl, R₇ is C₁–C₆ alkyl, R₈ and R₉ taken together with the bonded nitrogen form a morpholine ring, piperidine ring, 4-methylpiperazine ring, or pyrrolidine ring;

R₄ is from 1 to 2 substituents each independently chosen from the group consisting of hydrogen, halogen, C₁–C₆ alkyl, and C₁–C₆ alkoxy;

Y₁ is —C(O)NHR₅,—C(O)NR₆R₇, or —C(O)NR₈R₉ wherein

R₅ is chosen from the group consisting of hydrogen, 3-hydroxy-2-butyryl-C₁–C₆ alkyl ester, 2-glutaryl-C₁–C₆ alkyl ester, —(CH₂)$_q$NR₆R₇, and —(CH₂)$_q$NR₈R₉;

q is 2 or 3;

R₆ is C₁–C₆ alkyl;

R₇ is C₁–C₆ alkyl;

R₈ and R₉ taken together with the bonded nitrogen form a morpholine ring, piperidine ring, 4-methylpiperazine ring, or pyrrolidine ring;

Y₂ is a radical chosen from the group

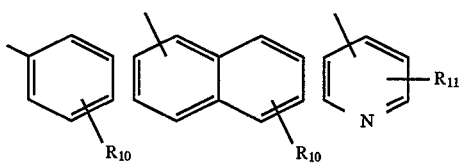

144

-continued

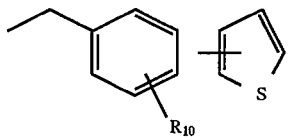

wherein

R₁₀ is from 1 to 3 substituents each independently chosen from the group consisting of hydrogen, halogen, CF₃, C₁–C₆ alkyl, and C₁–C₆ alkoxy;

R₁₁ is from 1 to 2 substituents each independently chosen from the group consisting of hydrogen, halogen, C₁–C₆ alkyl, and C₁–C₆ alkoxy;

or stereoisomers, or an N-oxide, or a pharmaceutically acceptable salt thereof.

2. A method of claim 1 wherein m is 2.

3. A method of claim 1 wherein G₁ is —CH₂— and G₂ is —C(O)—.

4. A method of claim 1 wherein G₁ is —C(O)— and G₂ is —CH₂—.

5. A method of claim 1 wherein the compound is (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide.

6. A method of claim 1 wherein the compound is (−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide.

7. A method of claim 1 wherein the compound is (+)- or (−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid 4-methylpiperazine-amide or a mixture thereof.

8. A method of claim 1 wherein the compound is (+)- or (−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid morpholine-amide or a mixture thereof.

9. A method of claim 1 wherein the compound is (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide hydrochloride.

10. A method of claim 1 wherein the compound is (+)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide citrate.

11. A method of claim 1 wherein the compound is (+)- or (−)-1-[2-[3-(3,4-dichloro-phenyl)-1-(3,4,5-trimethoxy-benzoyl)-pyrrolidin-3-yl]-ethyl]-4-phenyl-piperidine-4-carboxylic acid amide N-oxide or a mixture thereof.

12. A method for treating asthma in a patient in need thereof comprising administering to said patient a therapeutically effective amount of a compound of the formula

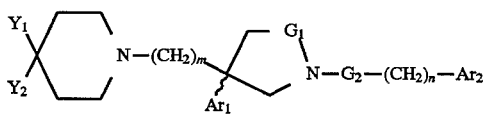

wherein

G₁ is —CH₂— or —C(O)—;

G₂ is —CH₂— or —C(O)—;

m is 2 or 3;

n is 0 or 1;

Ar₁ is a radical chosen from the group:

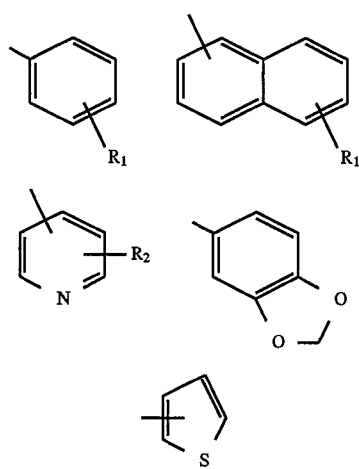

wherein $R_1$ is from 1 to 3 substituents each independently chosen from the group consisting of hydrogen, halogen, hydroxy, $CF_3$, $C_1$–$C_6$ alkyl, and $C_1$–$C_6$ alkoxy;

$R_2$ is from 1 to 2 substituents each independently chosen from the group consisting of hydrogen, halogen, $C_1$–$C_6$ alkyl, and $C_1$–$C_6$ alkoxy;

Ar₂ is a radical chosen from the group

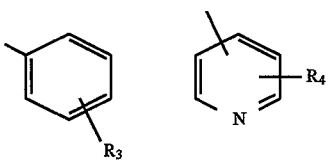

wherein $R_3$ is from 1 to 3 substituents each independently chosen from the group consisting of hydrogen, halogen, $C_1$–$C_6$ alkoxy, hydroxy, —O—C(O)O—CH₂—CH₃, —OC(O)CH₃, —CF₂H, —(CH₂)$_q$NR₆R₇, and —(CH₂)$_q$NR₈R₉ wherein q is 2 or 3, $R_6$ is $C_1$–$C_6$ alkyl, $R_7$ is $C_1$–$C_6$ alkyl, $R_8$ and $R_9$ taken together with the bonded nitrogen form a morpholine ring, piperidine ring, 4-methylpiperazine ring, or pyrrolidine ring;

$R_4$ is from 1 to 2 substituents each independently chosen from the group consisting of hydrogen, halogen, $C_1$–$C_6$ alkyl, and $C_1$–$C_6$ alkoxy;

$Y_1$ and $Y_2$ together with their attached carbon form a spirocyclic ring chosen from the group

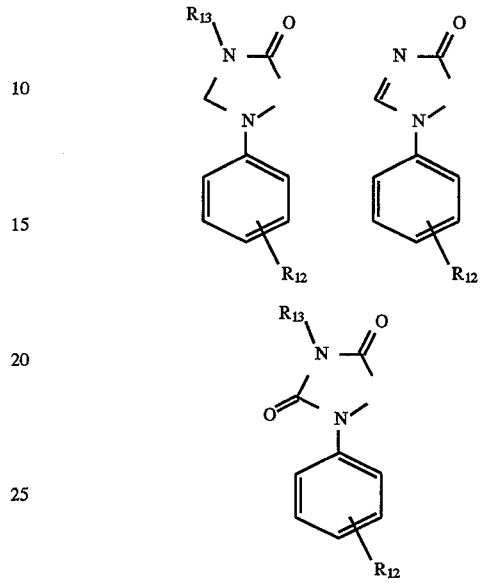

wherein $R_{12}$ is from 1 to 3 substituents each independently chosen from the group consisting of hydrogen, halogen, $CF_3$, $C_1$–$C_6$ alkyl, and $C_1$–$C_6$ alkoxy;

$R_{13}$ is hydrogen, $C_1$–$C_6$ alkyl, or benzyl;

or stereoisomers, or an N-oxide, or a pharmaceutically acceptable salt thereof.

13. A method of claim 12 wherein m is 2.

14. A method of claim 12 wherein $G_1$ is —CH₂— and $G_2$ is —C(O)—.

15. A method of claim 12 wherein $G_1$ is —C(O)— and $G_2$ is —CH₂—.

* * * * *